(12) United States Patent
Lücking et al.

(10) Patent No.: US 8,916,557 B2
(45) Date of Patent: Dec. 23, 2014

(54) SUBSTITUTED 4-ARYL-N-PHENYL-1,3,5-TRIAZIN-2-AMINES

(75) Inventors: Ulrich Lücking, Berlin (DE); Rolf Bohlmann, Berlin (DE); Arne Scholz, Berlin (DE); Gerhard Siemeister, Berlin (DE); Mark Jean Gnoth, Mettmann (DE); Ulf Bömer, Glienicke (DE); Gerd Rühter, Hamburg (DE); Carsten Schultz-Fademrecht, Dortmund (DE); Dirk Kosemund, Berlin (DE); Philip Lienau, Berlin (DE)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

(21) Appl. No.: 14/112,484

(22) PCT Filed: Apr. 18, 2012

(86) PCT No.: PCT/EP2012/057088
§ 371 (c)(1),
(2), (4) Date: Oct. 17, 2013

(87) PCT Pub. No.: WO2012/143399
PCT Pub. Date: Oct. 26, 2012

(65) Prior Publication Data
US 2014/0045852 A1    Feb. 13, 2014

(30) Foreign Application Priority Data

Apr. 19, 2011 (EP) .................................. 11162996
Aug. 17, 2011 (EP) .................................. 11177768
Sep. 5, 2011 (EP) .................................. 11180012

(51) Int. Cl.
*C07D 251/42* (2006.01)
*C07D 401/04* (2006.01)
*C07D 405/04* (2006.01)
*C07D 401/12* (2006.01)
*C07D 405/12* (2006.01)

(52) U.S. Cl.
CPC ............ *C07D 251/42* (2013.01); *C07D 401/12* (2013.01); *C07D 405/12* (2013.01); *C07D 405/04* (2013.01); *C07D 401/04* (2013.01)
USPC ............................ 514/245; 544/211; 544/212

(58) Field of Classification Search
USPC .................................. 514/245; 544/211, 212
See application file for complete search history.

*Primary Examiner* — Jeffrey H Murray
*Assistant Examiner* — Oluwafemi Masha

(57) ABSTRACT

The present invention relates to substituted 4-Aryl-N-phenyl-1,3,5-triazin-2-amines of general formula (I) as described and defined herein, and methods for their preparation, their use for the treatment and/or prophylaxis of disorders, in particular of hyper-proliferative disorders and/or virally induced infectious diseases and/or of cardiovascular diseases. The invention further relates to intermediate compounds useful in the preparation of said compounds of general formula (I).

15 Claims, No Drawings

SUBSTITUTED 4-ARYL-N-PHENYL-1,3,5-TRIAZIN-2-AMINES

The present invention relates to substituted 4-Aryl-N-phenyl-1,3,5-triazin-2-amines of general formula (I) or (Ia) as described and defined herein, and methods for their preparation, their use for the treatment and/or prophylaxis of disorders, in particular of hyper-proliferative disorders and/or virally induced infectious diseases and/or of cardiovascular diseases. The invention further relates to intermediate compounds useful in the preparation of said compounds of general formula (I) or (Ia).

The family of cyclin-dependent kinase (CDK) proteins consists of members that are key regulators of the cell division cycle (cell cycle CDK's), that are involved in regulation of gene transcription (transcriptional CDK's), and of members with other functions. CDKs require for activation the association with a regulatory cyclin subunit. The cell cycle CDKs CDK1/cyclin B, CDK2/cyclin A, CDK2/cyclinE, CDK4/cyclinD, and CDK6/cyclinD get activated in a sequential order to drive a cell into and through the cell division cycle. The transcriptional CDKs CDK9/cyclin T and CDK7/cyclin H regulate the activity of RNApolymerase II via phosphorylation of the carboxy-terminal domain (CTD). Positive transcription factor b (P-TEFb) is a heterodimer of CDK9 and one of four cyclin partners, cyclin T1, cyclin K, cyclin T2a or T2b.

Whereas CDK9 (NCBI GenBank Gene ID 1025) is exclusively involved in transcriptional regulation, CDK7 in addition participates in cell cycle regulation as CDK-activating kinase (CAK). Transcription of genes by RNA polymerase II is initiated by assembly of the pre-initiation complex at the promoter region and phosphorylation of Ser 5 and Ser 7 of the CTD by CDK7/cyclin H. For a major fraction of genes RNA polymerase II stops mRNA transcription after it moved 20-40 nucleotides along the DNA template. This promoter-proximal pausing of RNA polymerase II is mediated by negative elongation factors and is recognized as a major control mechanism to regulate expression of rapidly induced genes in response to a variety of stimuli (Cho et al., Cell Cycle 9, 1697, 2010). P-TEFb is crucially involved in overcoming promoter-proximal pausing of RNA polymerase II and transition into a productive elongation state by phosphorylation of Ser 2 of the CTD as well as by phosphorylation and inactivation of negative elongation factors.

Activity of P-TEFb itself is regulated by several mechanisms. About half of cellular P-TEFb exists in an inactive complex with 7SK small nuclear RNA (7SK snRNA), La-related protein 7 (LARP7/PIP7S) and hexamethylene bis-acetamide inducible proteins ½ (HEXIM1/2, He et al., Mol Cell 29, 588, 2008). The remaining half of P-TEFb exists in an active complex containing the bromodomain protein Brd4 (Yang et al., Mol Cell 19, 535, 2005). Brd4 recruits P-TEFb through interaction with acetylated histones to chromatin areas primed for gene transcription. Through alternately interacting with its positive and negative regulators, P-TEFb is maintained in a functional equilibrium: P-TEFb bound to the 7SK snRNA complex represents a reservoir from which active P-TEFb can be released on demand of cellular transcription and cell proliferation (Zhou & Yik, Microbiol Mol Biol Rev 70, 646, 2006). Furthermore, the activity of P-TEFb is regulated by posttranslational modifications including phosphorylation/de-phosphorylation, ubiquitination, and acetylation (reviewed in Cho et al., Cell Cycle 9, 1697, 2010).

Deregulated activity of CDK9 kinase activity of the P-TEFb heterodimer is associated with a variety of human pathological settings such as hyper-proliferative diseases (e.g. cancer), virally induced infectious diseases or cardiovascular diseases:

Cancer is regarded as a hyper-proliferative disorder mediated by a disbalance of proliferation and cell death (apoptosis). High levels of anti-apoptotic Bcl-2-family proteins are found in various human tumors and account for prolonged survival of tumor cells and therapy resistance Inhibition of P-TEFb kinase activity was shown to reduce transcriptional activity of RNA polymerase II leading to a decline of short-lived anti-apoptotic proteins, especially Mcl-1 and XIAP, reinstalling the ability of tumor cells to undergo apoptosis. A number of other proteins associated with the transformed tumor phenotype (such as Myc, NF-kB responsive gene transcripts, mitotic kinases) are either short-lived proteins or are encoded by short-lived transcripts which are sensitive to reduced RNA polymerase II activity mediated by P-TEFb inhibition (reviewed in Wang & Fischer, Trends Pharmacol Sci 29, 302, 2008).

Many viruses rely on the transcriptional machinery of the host cell for the transcription of their own genome. In case of HIV-1 RNA polymerase II gets recruited to the promoter region within the viral LTR's. The viral transcription activator (Tat) protein binds to nascent viral transcripts and overcomes promoter-proximal RNA polymerase II pausing by recruitment of P-TEFb which in turn promotes transcriptional elongation. Furthermore, the Tat protein increases the fraction of active P-TEFb by replacement of the P-TEFb inhibitory proteins HEXIM1/2 within the 7SK snRNA complex. Recent data have shown that inhibition of the kinase activity of P-TEFb is sufficient to block HIV-1 replication at kinase inhibitor concentrations that are not cytotoxic to the host cells (reviewed in Wang & Fischer, Trends Pharmacol Sci 29, 302, 2008). Similarly, recruitment of P-TEFb by viral proteins has been reported for other viruses such as B-cell cancer-associated Epstein-Barr virus, where the nuclear antigen EBNA2 protein interacts with P-TEFb (Bark-Jones et al., Oncogene, 25, 1775, 2006), and the human T-lymphotropic virus type 1 (HTLV-1), where the transcriptional activator Tax recruits P-TEFb (Zhou et al., J. Virol. 80, 4781, 2006).

Cardiac hypertrophy, the heart's adaptive response to mechanical overload and pressure (hemodynamic stress e.g. hypertension, myocardial infarction), can lead, on a long term, to heart failure and death. Cardiac hypertrophy was shown to be associated with increased transcriptional activity and RNA polymerase II CTD phosphorylation in cardiac muscle cells. P-TEFb was found to be activated by dissociation from the inactive 7SK snRNA/HEXIM1/2 complex. These findings suggest pharmacological inhibition of P-TEFb kinase activity as a therapeutic approach to treat cardiac hypertrophy (reviewed in Dey et al., Cell Cycle 6, 1856, 2007).

In summary, multiple lines of evidence suggest that selective inhibition of the CDK9 kinase activity of the P-TEFb heterodimer (=CDK9 and one of four cyclin partners, cyclin T1, cyclin K, cyclin T2a or T2b) represents an innovative approach for the treatment of diseases such as cancer, viral diseases, and/or diseases of the heart. CDK9 belongs to a family of at least 13 closely related kinases of which the subgroup of the cell cycle CDK's fulfills multiple roles in regulation of cell proliferation. Thus, co-inhibition of cell cycle CDK's (e.g. CDK1/cyclin B, CDK2/cyclin A, CDK2/cyclinE, CDK4/cyclinD, CDK6/cyclinD) and of CDK9, is expected to impact normal proliferating tissues such as intestinal mucosa, lymphatic and hematopoietic organs, and reproductive organs. To maximize the therapeutic margin of CDK9 kinase inhibitors molecules with high selectivity towards CDK9 are therefore required.

CDK inhibitors in general as well as CDK9 inhibitors are described in a number of different publications:

WO200812970 and WO200812971 both describe 2,4 disubstituted aminopyrimidines as CDK inhibitors in general. It is also asserted that some of these compounds may act as selective CDK9 inhibitors (WO200812970) and as CDK5 inhibitors (WO200812971), respectively, but no specific CDK9 IC50 (WO200812970) or CDK5 IC50 (WO200812971) data is presented.

WO2008129080 discloses 4,6 disubstituted aminopyrimidines and demonstrates that these compounds show an inhibitory effect on the protein kinase activity of various protein kinases, such as CDK1, CDK2, CDK4, CDK5, CDK6 and CDK9, with a preference for CDK9 inhibition (example 80).

EP1218360 B1, which corresponds to US2004116388A1, US7074789B2 and WO2001025220A1, describes triazin derivatives as kinase inhibitors, but does not disclose potent or selective CDK9 inhibitors.

WO2008079933 discloses aminopyridine and aminopyrimidine derivatives and their use as CDK1, CDK2, CDK3, CDK4, CDK5, CDK6, CDK7, CDK8 or CDK9 inhibitors.

WO2011012661 describes aminopyridine derivatives useful as CDK inhibitors.

Wang et al. (Chemistry & Biology 17, 1111-1121, 2010) describe 2-anilino-4-(thiazol-5-yl)pyrimidine transcriptional CDK inhibitors, which show anticancer activity in animal models.

WO2004009562 discloses substituted triazine kinase inhibitors. For selected compounds CDK1 and CDK 4 test data, but no CDK9 data is presented.

WO2004072063 describes heteroaryl (pyrimidine, triazine) substituted pyrroles as inhibitors of protein kinase such as ERK2, GSK3, PKA or CDK2.

WO2010009155 discloses triazine and pyrimidine derivatives as inhibitors of histone deacetylase and/or cyclin dependent kinases (CDKs). For selected compounds CDK2 test data is described.

WO2003037346 (corresponding to US7618968B2, US7291616B2, US2008064700A1, US2003153570A1) relates to aryl triazines and uses thereof, including to inhibit lysophosphatidic acid acyltransferase beta (LPAAT-beta) activity and/or proliferation of cells such as tumor cells.

WO2008025556 describes carbamoyl sulfoximides having a pyrimidine core, which are useful as kinase inhibitors. No CDK9 data is presented.

WO2002066481 describes pyrimidine derivatives as cyclin dependent kinase inhibitors CDK9 is not mentioned and no CDK9 data is presented.

WO2008109943 concerns phenyl aminopyri(mi)dine compounds and their use as kinase inhibitors, in particular as JAK2 kinase inhibitors. The specific examples focus on compounds having a pyrimidine core.

WO2009032861 describes substituted pyrimidinyl amines as JNK kinase inhibitors. The specific examples focus on compounds having a pyrimidine core.

WO2011046970 concerns amino-pyrimidine compounds as inhibitors of TBKL and/or IKK epsilon. The specific examples focus on compounds having a pyrimidine core.

Despite the fact that various inhibitors of CDK's are known, there remains a need for selective CDK9 inhibitors to be used for the treatment of diseases such as hyper-proliferative diseases, viral diseases, and/or diseases of the heart, which offer one or more advantages over the compounds known from prior art, such as:

improved activity and/or efficacy beneficial kinase selectivity profile according to the respective therapeutic need improved side effect profile, such as fewer undesired side effects, lower intensity of side effects, or reduced (cyto) toxicity improved pharmacokinetic properties, allowing e.g. for dose reduction or an easier dosing scheme A particular object of the invention is to provide CDK9 kinase inhibitors which, compared to the compounds known from prior art, show an increased selectivity for CDK9/Cyclin T1 as compared to CDK2/Cyclin E.

Another object of the invention is to provide CDK9 kinase inhibitors which show an increased potency to inhibit CDK9 activity (demonstrated by a lower 1050 value for CDK9/Cyc T1) compared to the compounds known from prior art.

Another object of the invention is to provide CDK9 kinase inhibitors, which show an improved anti-proliferative activity in tumor cell lines such as HeLa compared to the compounds known from prior art.

Another object of the invention is to provide CDK9 kinase inhibitors, which show improved pharmacokinetic properties, such as an increased apparent Caco-2 permeability (Papp A–B) across Caco-2 cell monolayers or such as a decreased efflux ratio (efflux ratio=Papp B–A/Papp A–B) from the basal to apical compartment across Caco-2 cell monolayers compared to the compounds known from the prior art.

Further, it is also an object of the present invention to provide CDK9 kinase inhibitors, which are highly selective for CDK9/Cyclin T1 as compared to CDK2/Cyclin E, and/or which show an increased potency to inhibit CDK9 activity (demonstrated by a lower 1050 value for CDK9/Cyc T1) and/or which show an improved anti-proliferative activity in tumor cell lines such as HeLa as compared to the compounds known from the prior art.

Further, it is also an object of the present invention to provide CDK9 kinase inhibitors, which are highly selective for CDK9/Cyclin T1 as compared to CDK2/Cyclin E, and/or which show an increased potency to inhibit CDK9 activity (demonstrated by a lower 1050 value for CDK9/Cyc T1) and/or which show an improved anti-proliferative activity in tumor cell lines such as HeLa and/or which show improved pharmacokinetic properties, such as an increased apparent Caco-2 permeability (Papp A–B) across Caco-2 cell monolayers or a decreased efflux ratio from the basal to apical compartment across Caco-2 cell monolayers compared to the compounds known from the prior art.

The present invention relates to compounds of general formula (I)

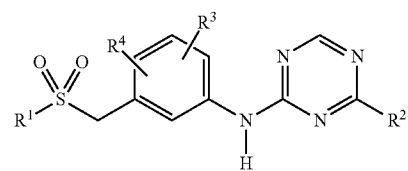

or of general formula (Ia)

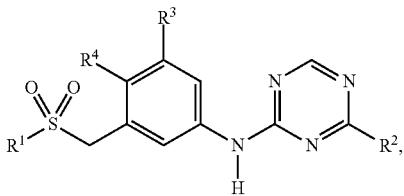

wherein $R^1$ represents a group selected from $C_1$-$C_6$-alkyl-, $C_3$-$C_7$-cycloalkyl-, heterocyclyl-, phenyl, heteroaryl, phenyl-$C_1$-$C_3$-alkyl- or heteroaryl-$C_1$-$C_3$-alkyl-, wherein said group is optionally substituted with one or two or three substituents, identically or differently, selected from the group consisting of hydroxy, cyano, halogen, halo-$C_1$-$C_3$-alkyl-, $C_1$-$C_6$-alkoxy-, $C_1$-$C_3$-fluoroalkoxy-, —$NH_2$, alkylamino-, dialkylamino-, acetylamino-, N-methyl-N-acetylamino-, cyclic amines;

$R^2$ represents a group selected from

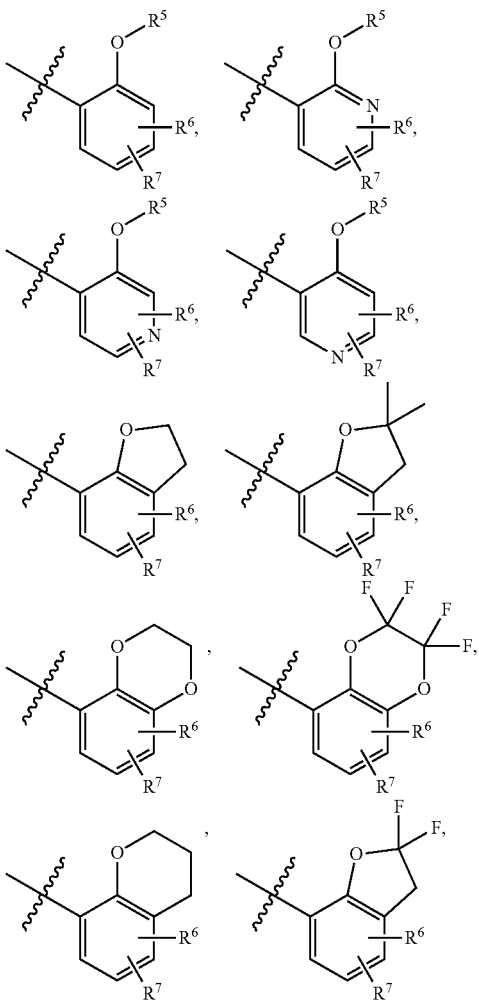

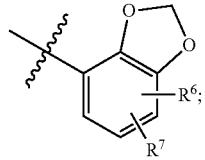

$R^3$, $R^4$ represent, independently from each other, a group selected from a hydrogen atom, fluoro atom, chloro atom, $C_1$-$C_3$-alkyl-, $C_1$-$C_3$-alkoxy-, halo-$C_1$-$C_3$-alkyl-, $C_1$-$C_3$-fluoroalkoxy-;

$R^5$ represents a group selected from a) a $C_1$-$C_{10}$-alkyl group, which is optionally substituted with one or two or three substituents, identically or differently, selected from the group consisting of halogen, hydroxy, —$NH_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-, $C_2$-$C_3$-alkenyl-, $C_2$-$C_3$-alkynyl-, $C_3$-$C_7$-cycloalkyl-, heterocycyl-, phenyl, heteroaryl, wherein said $C_3$-$C_7$-cycloalkyl-, heterocycyl-, phenyl or heteroaryl group is optionally substituted with one, two or three substituents, identically or differently, selected from halogen, hydroxy, $C_1$-$C_3$-alkyl-, $C_1$-$C_3$-alkoxy-, —$NH_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-;

b) a $C_3$-$C_7$-cycloalkyl- group, which is optionally substituted with one or two or three substituents, identically or differently, selected from the group consisting of halogen, hydroxy, —$NH_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-, $C_2$-$C_3$-alkenyl-, $C_2$-$C_3$-alkynyl-;

c) a heterocyclyl-group, which is optionally substituted with one or two or three substituents, identically or differently, selected from the group consisting of halogen, hydroxy, —$NH_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-, $C_2$-$C_3$-alkenyl-, $C_2$-$C_3$-alkynyl-;

d) a phenyl group, which is optionally substituted with one or two or three substituents, identically or differently, selected from the group consisting of halogen, hydroxy, —$NH_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-;

e) a heteroaryl group, which is optionally substituted with one or two or three substituents, identically or differently, selected from the group consisting of halogen, hydroxy, —$NH_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-;

f) a phenyl-$C_1$-$C_3$-alkyl- group, which is optionally substituted with one or two or three substituents, identically or differently, selected from the group consisting of halogen, hydroxy, —$NH_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-;

g) a heteroaryl-$C_1$-$C_3$-alkyl- group, which is optionally substituted with one or two or three substituents, identically or differently, selected from the group consisting of halogen, hydroxy, —$NH_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-;

$R^6$, $R^7$ represent, independently from each other, a group selected from a hydrogen atom, fluoro atom, chloro atom, $C_1$-$C_3$-alkyl-, $C_1$-$C_3$-alkoxy-, halo-$C_1$-$C_3$-alkyl-, $C_1$-$C_3$-fluoroalkoxy-;

or their salts, solvates or salts of solvates.

Compounds according to the invention are the compounds of the formula (I) or (Ia) and the salts, solvates and solvates of the salts thereof, the compounds of the hereinafter recited formula which are encompassed by formula (I) and the salts, solvates and solvates of the salts thereof, and the compounds which are encompassed by formula (I) or (Ia) and are mentioned hereinafter as exemplary embodiments and the salts, solvates and solvates of the salts thereof, where the compounds which are encompassed by formula (I) or (Ia) and are mentioned hereinafter are not already salts, solvates and solvates of the salts.

The compounds according to the invention may, depending on their structure, exist in stereoisomeric forms (enantiomers, diastereomers). The invention therefore relates to the enantiomers or diastereomers and respective mixtures thereof. The stereoisomerically pure constituents can be isolated in a known manner from such mixtures of enantiomers and/or diastereomers.

If the compounds according to the invention can be in tautomeric forms, the present invention encompasses all tautomeric forms.

Further, the compounds of the present invention can exist in free form, e.g. as a free base, or as a free acid, or as a zwitterion, or can exist in the form of a salt. Said salt may be any salt, either an organic or inorganic addition salt, particularly any physiologically acceptable organic or inorganic addition salt, customarily used in pharmacy.

Salts which are preferred for the purposes of the present invention are physiologically acceptable salts of the compounds according to the invention. However, salts which are not suitable for pharmaceutical applications per se, but which, for example, can be used for the isolation or purification of the compounds according to the invention, are also comprised.

The term "physiologically acceptable salt" refers to a relatively non-toxic, inorganic or organic acid addition salt of a compound of the present invention, for example, see S. M. Berge, et al. "Pharmaceutical Salts," J. Pharm. Sci. 1977, 66, 1-19.

Physiologically acceptable salts of the compounds according to the invention encompass acid addition salts of mineral acids, carboxylic acids and sulfonic acids, for example salts of hydrochloric acid, hydrobromic acid, hydroiodic, sulfuric acid, bisulfuric acid, phosphoric acid, nitric acid or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, persulfuric, 3-phenylpropionic, picric, pivalic, 2-hydroxyethanesulfonate, itaconic, sulfamic, trifluoromethanesulfonic, dodecylsulfuric, ethansulfonic, benzenesulfonic, para-toluenesulfonic, methansulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, hemisulfuric, or thiocyanic acid, for example.

Physiologically acceptable salts of the compounds according to the invention also comprise salts of conventional bases, such as, by way of example and by preference, alkali metal salts (for example sodium and potassium salts), alkaline earth metal salts (for example calcium and magnesium salts) and ammonium salts derived from ammonia or organic amines with 1 to 16 C atoms, such as, by way of example and by preference, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine, N-methylpiperidine, N-methylglucamine, dimethylglucamine, ethylglucamine, 1,6-hexadiamine, glucosamine, sarcosine, serinol, tris(hydroxymethyl)aminomethane, aminopropanediol, Sovak base, and 1-amino-2,3,4-butanetriol. Additionally, basic nitrogen containing groups may be quaternised with such agents as lower alkylhalides such as methyl-, ethyl-, propyl-, and butylchlorides, -bromides and -iodides; dialkylsulfates like dimethyl-, diethyl-, dibutyl- and diamylsulfates, long chain halides such as decyl-, lauryl-, myristyl- and stearylchlorides, -bromides and -iodides, aralkylhalides like benzyl- and phenethylbromides and others.

The present invention includes all possible salts of the compounds of the present invention as single salts, or as any mixture of said salts, in any ratio.

Solvates is the term used for the purposes of the invention for those forms of the compounds according to the invention which form a complex with solvent molecules by coordination in the solid or liquid state. Hydrates are a special form of solvates in which the coordination takes place with water. Hydrates are preferred as solvates within the scope of the present invention.

The invention also includes all suitable isotopic variations of a compound of the invention. An isotopic variation of a compound of the invention is defined as one in which at least one atom is replaced by an atom having the same atomic number but an atomic mass different from the atomic mass usually or predominantly found in nature. Examples of isotopes that can be incorporated into a compound of the invention include isotopes of hydrogen, carbon, nitrogen, oxygen, phosphorus, sulfur, fluorine, chlorine, bromine and iodine, such as $^2H$ (deuterium), $^3H$ (tritium), $^{13}C$, $^{14}C$, $^{15}N$, $^{17}O$, $^{18}O$ $^{32}P$, $^{33}P$, $^{33}S$, $^{34}S$, $^{35}S$, $^{36}S$, $^{18}F$, $^{36}Cl$, $^{82}Br$, $^{123}I$, $^{124}I$, $^{129}I$ and $^{131}I$, respectively. Certain isotopic variations of a compound of the invention, for example, those in which one or more radioactive isotopes such as $^3H$ or $^{14}C$ are incorporated, are useful in drug and/or substrate tissue distribution studies. Tritiated and carbon-14, i.e., $^{14}C$, isotopes are particularly preferred for their ease of preparation and detectability. Further, substitution with isotopes such as deuterium may afford certain therapeutic advantages resulting from greater metabolic stability, for example, increased in vivo half-life or reduced dosage requirements and hence may be preferred in some circumstances. Isotopic variations of a compound of the invention can generally be prepared by conventional procedures known by a person skilled in the art such as by the illustrative methods or by the preparations described in the examples hereafter using appropriate isotopic variations of suitable reagents.

In addition, the present invention also encompasses prodrugs of the compounds according to the invention. The term "prodrugs" encompasses compounds which themselves may be biologically active or inactive, but are converted (for example by metabolism or hydrolysis) to compounds according to the invention during their residence time in the body.

For the purposes of the present invention, the substituents have the following meaning, unless otherwise specified:

The term "halogen atom", "halogen" or "halo" represents fluorine, chlorine, bromine and iodine atoms, particularly chlorine or fluorine atoms, preferably fluorine atoms.

The term "alkyl" represents a linear or branched alkyl radical having the number of carbon atoms specifically indicated, e.g. $C_1$-$C_{10}$ one, two, three, four, five, six, seven, eight, nine or ten carbon atoms, e.g. methyl, ethyl, n-propyl, isopropyl, n-butyl, isobutyl, sec-butyl, tert-butyl, pentyl, isopentyl, hexyl, heptyl, octyl, nonyl-, decyl-, 2-methylbutyl, 1-methylbutyl, 1-ethylpropyl, 1,2-dimethylpropyl, neo-pentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl, or 1,2-dimethylbutyl. If the number of carbon atoms is not specifically indicated the term "alkyl" represents a linear or branched alkyl radical having, as a rule, 1 to 9, particularly 1 to 6, preferably 1 to 4 carbon atoms. Particularly, the alkyl group has 1, 2, 3, 4, 5 or 6 carbon atoms ("$C_1$-$C_6$-alkyl"), e.g. methyl, ethyl, n-propyl-, isopropyl, n-butyl, tert-butyl, pentyl, isopentyl, hexyl, 2-methylbutyl, 1-methylbutyl, 1-ethylpropyl, 1,2-dimethylpropyl, neo-pentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl, or 1,2-dimethylbutyl. Preferably, the alkyl group has 1, 2 or 3 carbon atoms ("$C_1$-$C_3$-alkyl"), methyl, ethyl, n-propyl or isopropyl.

The term "$C_2$-$C_3$-alkenyl" is to be understood as preferably meaning a linear or branched, monovalent hydrocarbon group, which contains one double bond, and which has 2 or 3 carbon atoms ("$C_2$-$C_3$-alkenyl"). Said alkenyl group is, for example, a vinyl, allyl, (E)-2-methylvinyl, (Z)-2-methylvinyl or isopropenyl group.

The term "$C_2$-$C_3$-alkynyl" is to be understood as preferably meaning a linear, monovalent hydrocarbon group which contains one triple bond, and which contains 2 or 3 carbon atoms. Said $C_2$-$C_3$-alkynyl group is, for example, ethynyl, prop-1-ynyl or prop-2-ynyl group.

The term "$C_3$-$C_7$-cycloalkyl" is to be understood as preferably meaning a saturated, monovalent, monocyclic hydrocarbon ring which contains 3, 4, 5, 6 or 7 carbon atoms. Said $C_3$-$C_7$-cycloalkyl group is for example, a monocyclic hydrocarbon ring, e.g. a cyclopropyl, cyclobutyl, cyclopentyl, cyclohexyl or cycloheptyl group. Said cycloalkyl ring can optionally contain one or more double bonds e.g. cycloalkenyl, such as a cyclopropenyl, cyclobutenyl, cyclopentenyl, cyclohexenyl or cycloheptenyl group, wherein the bond between said ring with the rest of the molecule may be to any carbon atom of said ring, be it saturated or unsaturated. Particularly, said cycloalkyl group is a $C_4$-$C_6$-cycloalkyl, a $C_5$-$C_6$-cycloalkyl or a cyclohexyl group.

The term "heterocyclyl" is to be understood as meaning a saturated or partially unsaturated, monovalent, mono- or bicyclic hydrocarbon ring which contains 3, 4, 5, 6, 7, 8 or 9 carbon atoms and further containing 1, 2 or 3 heteroatom-containing groups selected from oxygen, sulfur, nitrogen. Particularly, the term "heterocyclyl" is to be understood as meaning a "4- to 10-membered heterocyclic ring".

The term "a 4- to 10-membered heterocyclic ring" is to be understood as meaning a saturated or partially unsaturated, monovalent, mono- or bicyclic hydrocarbon ring which contains 3, 4, 5, 6, 7, 8 or 9 carbon atoms, and further containing 1, 2 or 3 heteroatom-containing groups selected from oxygen, sulfur, nitrogen. Said heterocyclic ring is for example, a monocyclic heterocyclic ring such as an oxetanyl, azetidinyl, tetrahydrofuranyl, pyrrolidinyl, 1,3-dioxolanyl, imidazolidinyl, pyrazolidinyl, oxazolidinyl, isoxazolidinyl, 1,4-dioxanyl, pyrrolinyl, tetrahydropyranyl, piperidinyl, morpholinyl, 1,3-dithianyl, thiomorpholinyl, piperazinyl, or chinuclidinyl group. Optionally, said heterocyciclic ring can contain one or more double bonds, e.g. 4H-pyranyl, 2H-pyranyl, 2,5-dihydro-1H-pyrrolyl, 1,3-dioxolyl, 4H-1,3,4-thiadiazinyl, 2,5-dihydrofuranyl, 2,3-dihydrofuranyl, 2,5-dihydrothienyl, 2,3-dihydrothienyl, 4,5-dihydrooxazolyl, 4,5-dihydroisoxazolyl, or 4H-1,4-thiazinyl group, or, it may be benzo fused.

Particularly, the term "heterocyclyl" is to be understood as being a heterocyclic ring which contains 3, 4 or 5 carbon atoms, and 1, 2 or 3 of the above-mentioned heteroatom-containing groups (a "4- to 7-membered heterocyclic ring"), more particularly said ring can contain 4 or 5 carbon atoms, and 1, 2 or 3 of the above-mentioned heteroatom-containing groups (a "5- to 7-membered heterocyclic ring"), more particularly said heterocyclic ring is a "6-membered heterocyclic ring", which is to be understood as containing 4 carbon atoms and 2 of the above-mentioned heteroatom-containing groups or 5 carbon atoms and one of the above-mentioned heteroatom-containing groups, preferably 4 carbon atoms and 2 of the above-mentioned heteroatom-containing groups.

The term "$C_1$-$C_6$-alkoxy-" is to be understood as preferably meaning a linear or branched, saturated, monovalent, hydrocarbon group of formula O-alkyl, in which the term "alkyl" is defined supra, e.g. a methoxy, ethoxy, n-propoxy, iso-propoxy, n-butoxy, iso-butoxy, tert-butoxy, sec-butoxy, pentyloxy, iso-pentyloxy, n-hexyloxy group, or an isomer thereof. Particularly, the "$C_1$-$C_6$-alkoxy-" group is a "$C_1$-$C_4$-alkoxy-", a "$C_1$-$C_3$-alkoxy-", a methoxy, ethoxy, or propoxy group, preferably a methoxy, ethoxy or propoxy group.

The term "$C_1$-$C_3$-fluoroalkoxy-" is to be understood as preferably meaning a linear or branched, saturated, monovalent, $C_1$-$C_3$-alkoxy- group, as defined supra, in which one or more of the hydrogen atoms is replaced, identically or differently, by one or more fluoro atoms. Said $C_1$-$C_3$-fluoroalkoxy-group is, for example a 1,1-difluoromethoxy-, a 1,1,1-trifluoromethoxy-, a 2-fluoroethoxy-, a 3-fluoropropoxy-, a 2,2,2-trifluoroethoxy-, a 3,3,3-trifluoropropoxy- particularly a "$C_1$-$C_2$-fluoroalkoxy-" group.

The term "alkylamino-" is to be understood as preferably meaning an alkylamino group with a linear or branched alkyl group as defined supra. ($C_1$-$C_3$)-alkylamino- for example means a monoalkylamino group with 1, 2 oder 3 carbon atoms, ($C_1$-$C_6$)-alkylamino- with 1, 2, 3, 4, 5 or 6 carbon atoms. The term "alkylamino-" comprises for example methylamino-, ethylamino-, n-propylamino-, isopropylamino-, tert.-butylamino-, n-pentylamino- or n-hexylamino-.

The term "dialkylamino-" is to be understood as preferably meaning an alkylamino group having two linear or branched alkyl groups as defined supra, which are independent from each other. ($C_1$-$C_3$)-dialkylamino- for example represents a dialkylamino group with two alkyl groups each of them having 1 to 3 carbon atoms per alkyl group. The term "dialkylamino-" comprises for example: N,N-Dimethylamino-, N,N-Diethylamino-, N-Ethyl-N-methylamino-, N-Methyl-N-n-propylamino-, N-Isopropyl-N-n-propylamino-, N-t-Butyl-N-methylamino-, N-Ethyl-N-n-pentylamino- and N-n-Hexyl-N-methylamino-.

The term "cyclic amine" is to be understood as preferably meaning a cyclic amine group. Suitable cyclic amines are especially azetidine, pyrrolidine, piperidine, piperazine, 1-methylpiperazine, morpholine, thiomorpholine, which could be optionally substituted by one or two methyl groups.

The term "halo-$C_1$-$C_3$-alkyl-" is to be understood as preferably meaning a linear or branched, saturated, monovalent hydrocarbon group in which the term "$C_1$-$C_3$-alkyl" is defined supra, and in which one or more hydrogen atoms is replaced by a halogen atom, identically or differently, i.e. one halogen atom being independent from another. Particularly, said halogen atom is fluorine. Said halo-$C_1$-$C_3$-alkyl- group is, for example, a halo-$C_1$-$C_2$-alkyl- group, —$CF_3$, —$CHF_2$, —$CH_2F$, —$CF_2CF_3$, or —$CH_2CF_3$, preferably it is —$CF_3$.

The term "phenyl-$C_1$-$C_3$-alkyl-" is to be understood as preferably meaning a phenyl group, in which one of the hydrogen atoms is replaced by a $C_1$-$C_3$-alkyl group, as defined supra, that links the phenyl-$C_1$-$C_3$-alkyl-group to the molecule. Particularly, the "phenyl-$C_1$-$C_3$-alkyl-" is a phenyl-$C_1$-$C_2$-alkyl-, preferably a benzyl-group.

The term "heteroaryl" is to be understood as preferably meaning a monovalent, aromatic, mono- or bicyclic aromatic ring system having 5, 6, 7, 8, 9, 10, 11, 12, 13 or 14 ring atoms (a "5- to 14-membered heteroaryl" group), particularly 5 (a "5-membered heteroaryl") or 6 (a "6-membered heteroaryl") or 9 (a "9-membered heteroaryl") or 10 ring atoms (a "10-membered heteroaryl"), and which contains at least one heteroatom which may be identical or different, said heteroatom being such as oxygen, nitrogen or sulfur, and can be monocyclic, bicyclic, or tricyclic, and in addition in each case can be benzo-condensed. Particularly, heteroaryl is selected from thienyl, furanyl, pyrrolyl, oxazolyl, thiazolyl, imidazolyl, pyrazolyl, isoxazolyl, isothiazolyl, oxadiazolyl, triazolyl, thiadiazolyl, tetrazolyl etc., and benzo derivatives thereof, such as, for example, benzofuranyl, benzothienyl, benzoxazolyl, benzisoxazolyl, benzimidazolyl, benzotriazolyl, indazolyl, indolyl, isoindolyl, etc.; or pyridyl, pyridazinyl, pyrimidinyl, pyrazinyl, triazinyl, etc., and benzo derivatives thereof, such as, for example, quinolinyl, quinazolinyl, isoquinolinyl, etc.; or azocinyl, indolizinyl, purinyl, etc., and benzo derivatives thereof; or cinnolinyl, phthalazinyl, quinazolinyl, quinoxalinyl, naphthyridinyl, pteridinyl, carbazolyl, acridinyl, phenazinyl, phenothiazinyl, phenoxazinyl, xanthenyl, or oxepinyl, 1,4-benzodioxanyl etc. Preferably, heteroaryl is selected from monocyclic heteroaryl, 5-membered heteroaryl or 6-membered heteroaryl.

The term "5-membered heteroaryl" is understood as preferably meaning a monovalent, aromatic, mono-aromatic ring system having 5 ring atoms and which contains at least one heteroatom which may be identical or different, said heteroatom being such as oxygen, nitrogen or sulfur. Particularly, "5 membered heteroaryl" is selected from thienyl, furanyl, pyrrolyl, oxazolyl, thiazolyl, imidazolyl, pyrazolyl, isoxazolyl, isothiazolyl, oxadiazolyl, triazolyl, thiadiazolyl, tetrazolyl.

The term "6-membered heteroaryl" is understood as preferably meaning a monovalent, aromatic, mono-aromatic ring system having 6 ring atoms and which contains at least one heteroatom which may be identical or different, said heteroatom being such as oxygen, nitrogen or sulfur. Particularly, "6 membered heteroaryl" is selected from pyridyl, pyridazinyl, pyrimidinyl, pyrazinyl, triazinyl.

The term "heteroaryl-$C_1$-$C_3$-alkyl-" is to be understood as preferably meaning a heteroaryl, a 5-membered heteroaryl or a 6-membered heteroaryl group, each as defined supra, in which one of the hydrogen atoms is replaced by a $C_1$-$C_3$-alkyl group, as defined supra, that links the heteroaryl-$C_1$-$C_3$-alkyl-group to the molecule. Particularly, the "heteroaryl-$C_1$-$C_3$-alkyl-" is a heteroaryl-$C_1$-$C_2$-alkyl-, a pyridinyl-$C_1$-$C_3$-alkyl-, a pyridinylmethyl-, a pyridinylethyl-, a pyridinylpropyl-, -a pyrimidinyl-$C_1$-$C_3$-alkyl-, a pyrimidinylmethyl-, a pyrimidinylethyl-, a pyrimidinylpropyl-, preferably a pyridinylmethyl- or a pyridinylethyl- or a pyrimidinylethyl- or a pyrimidinylpropyl- group.

The term "$C_1$-$C_{10}$", as used throughout this text, e.g. in the context of the definition of "$C_1$-$C_{10}$-alkyl" is to be understood as meaning an alkyl group having a finite number of carbon atoms of 1 to 10, i.e. 1, 2, 3, 4, 5, 6, 7, 8, 9 or 10 carbon atoms. It is to be understood further that said term "$C_1$-$C_{10}$" is to be interpreted as any sub-range comprised therein, e.g. $C_1$-$C_{10}$, $C_1$-$C_9$, $C_1$-$C_8$, $C_1$-$C_7$, $C_1$-$C_6$, $C_1$-$C_5$, $C_1$-$C_4$, $C_1$-$C_3$, $C_1$-$C_2$, $C_2$-$C_{10}$, $C_2$-$C_9$, $C_2$-$C_8$, $C_2$-$C_7$, $C_2$-$C_6$, $C_2$-$C_5$, $C_2$-$C_4$, $C_2$-$C_3$, $C_3$-$C_{10}$, $C_3$-$C_9$, $C_3$-$C_8$, $C_3$-$C_7$, $C_3$-$C_6$, $C_3$-$C_5$, $C_3$-$C_4$, $C_4$-$C_{10}$, $C_4$-$C_9$, $C_4$-$C_8$, $C_4$-$C_7$, $C_4$-$C_6$, $C_4$-$C_5$, $C_5$-$C_{10}$, $C_5$-$C_9$, $C_5$-$C_8$, $C_5$-$C_7$, $C_5$-$C_6$, $C_6$-$C_{10}$, $C_6$-$C_9$, $C_6$-$C_8$, $C_6$-$C_7$, $C_7$-$C_{10}$, $C_7$-$C_9$, $C_7$-$C_8$, $C_8$-$C_{10}$, $C_8$-$C_9$, $C_9$-$C_{10}$.

Similarly, as used herein, the term "$C_1$-$C_6$", as used throughout this text, e.g. in the context of the definition of "$C_1$-$C_6$-alkyl", "$C_1$-$C_6$-alkoxy" is to be understood as meaning an alkyl group having a finite number of carbon atoms of 1 to 6, i.e. 1, 2, 3, 4, 5 or 6 carbon atoms. It is to be understood further that said term "$C_1$-$C_6$" is to be interpreted as any sub-range comprised therein, e.g. $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, $C_5$-$C_6$.

Similarly, as used herein, the term "$C_1$-$C_3$", as used throughout this text, e.g. in the context of the definition of "$C_1$-$C_3$-alkyl", "$C_1$-$C_3$-alkoxy" or "$C_1$-$C_3$-fluoroalkoxy" is to be understood as meaning an alkyl group having a finite number of carbon atoms of 1 to 3, i.e. 1, 2 or 3 carbon atoms. It is to be understood further that said term "$C_1$-$C_3$" is to be interpreted as any sub-range comprised therein, e.g. $C_1$-$C_3$, $C_1$-$C_2$, $C_2$-$C_3$.

Further, as used herein, the term "$C_3$-$C_7$", as used throughout this text, e.g. in the context of the definition of "$C_3$-$C_7$-cycloalkyl", is to be understood as meaning a cycloalkyl group having a finite number of carbon atoms of 3 to 7, i.e. 3, 4, 5, 6 or 7 carbon atoms, particularly 3, 4, 5 or 6 carbon atoms. It is to be understood further that said term "$C_3$-$C_7$" is to be interpreted as any sub-range comprised therein, e.g. $C_3$-$C_7$, $C_3$-$C_6$, $C_3$-$C_5$, $C_3$-$C_4$, $C_4$-$C_7$, $C_4$-$C_6$, $C_4$-$C_5$, $C_5$-$C_7$, $C_5$-$C_6$, $C_6$-$C_7$.

A symbol  at a bond denotes the linkage site in the molecule.

As used herein, the term "one or more times", e.g. in the definition of the substituents of the compounds of the general formulae of the present invention, is understood as meaning one, two, three, four or five times, particularly one, two, three or four times, more particularly one, two or three times, even more particularly one or two times.

Where the plural form of the word compounds, salts, hydrates, solvates and the like, is used herein, this is taken to mean also a single compound, salt, isomer, hydrate, solvate or the like.

In another embodiment the present invention concerns compounds of general formula (I) or (Ia), wherein $R^1$ represents a group selected from $C_1$-$C_6$-alkyl-, $C_3$-$C_7$-cycloalkyl-, phenyl,
  wherein said group is optionally substituted with one substituent selected from the group consisting of hydroxy, $C_1$-$C_6$-alkoxy-;

R² represents a group selected from

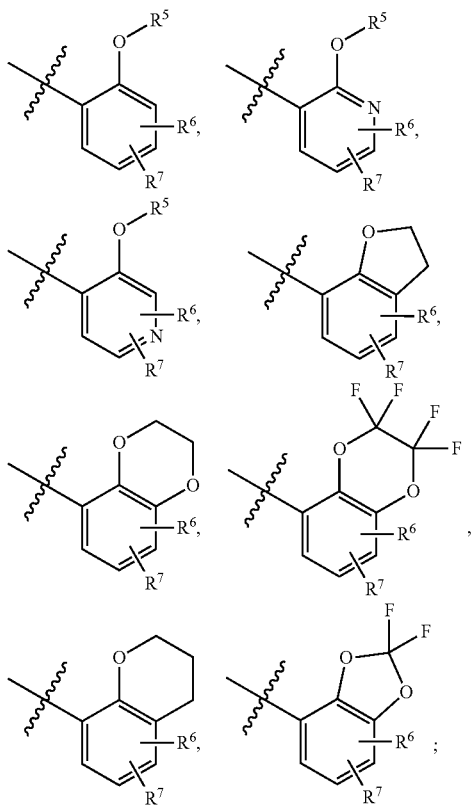

R³, R⁴ represent, independently from each other, a group selected from a hydrogen atom, fluoro atom, chloro atom;

R⁵ represents a group selected from
a) a $C_1$-$C_{10}$-alkyl- group, which is optionally substituted with one or two or three substituents, identically or differently, selected from the group consisting of halogen atom, $C_1$-$C_3$-alkyl-, $C_2$-$C_3$-alkynyl-, $C_1$-$C_3$-alkoxy-, $C_3$-$C_7$-cycloalkyl-, heterocycyl-, phenyl, wherein said $C_3$-$C_7$-cycloalkyl- or phenyl group is optionally substituted with one halogen substituent;
b) a $C_3$-$C_7$-cycloalkyl- group;
c) a phenyl-$C_1$-$C_3$-alkyl- group, which phenyl group is optionally substituted with one or two or three substituents, identically or differently, selected from the group consisting of halogen, cyano, halo-$C_1$-$C_3$-alkyl-, $C_1$-$C_3$-alkyl, $C_1$-$C_3$-alkoxy-;
d) a heteroaryl-$C_1$-$C_3$-alkyl- group, which is optionally substituted with one substituent selected from the group consisting of halogen, $C_1$-$C_3$-alkyl-;

R⁶, R⁷ represent, independently from each other, a group selected from a hydrogen atom or fluoro or chloro atom;

or its salts, solvates or salts of solvates.

In another embodiment the present invention concerns compounds of general formula (I) or (Ia), wherein R¹ represents a group selected from $C_1$-$C_6$-alkyl-, $C_3$-$C_7$-cycloalkyl-,
wherein said group is optionally substituted with one substituent selected from the group consisting of hydroxy, $C_1$-$C_6$-alkoxy-;

R² represents a group selected from

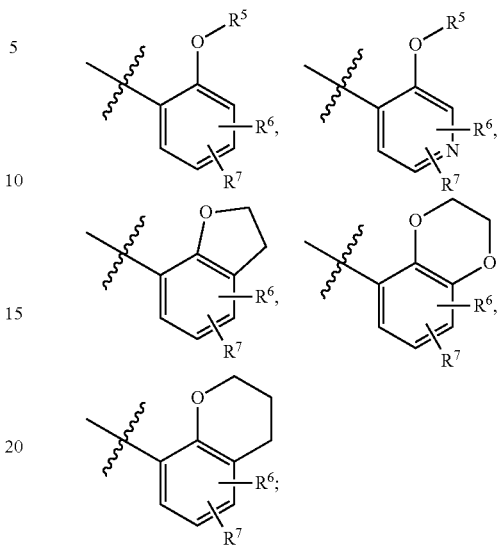

R³, R⁴ represent, independently from each other, a group selected from a hydrogen atom, fluoro atom, chloro atom;

R⁵ represents a group selected from
a) a $C_1$-$C_{10}$-alkyl- group, which is optionally substituted with one or two or three substituents, identically or differently, selected from the group consisting of halogen atom, $C_1$-$C_3$-alkyl-, $C_2$-$C_3$-alkynyl-, $C_3$-$C_7$-cycloalkyl-, heterocycyl-, phenyl, wherein said $C_3$-$C_7$-cycloalkyl- or phenyl group is optionally substituted with one halogen substituent;
b) a $C_3$-$C_7$-cycloalkyl- group;
c) a phenyl-$C_1$-$C_3$-alkyl- group, which phenyl group is optionally substituted with one or two or three substituents, identically or differently, selected from the group consisting of halogen, cyano, halo-$C_1$-$C_3$-alkyl-, $C_1$-$C_3$-alkyl, $C_1$-$C_3$-alkoxy-;
d) a heteroaryl-$C_1$-$C_3$-alkyl- group, which is optionally substituted with one substituent selected from the group consisting of halogen, $C_1$-$C_3$-alkyl-;

R⁶, R⁷ represent, independently from each other, a group selected from a hydrogen atom or fluoro or chloro atom;

or its salts, solvates or salts of solvates.

In another embodiment the present invention concerns compounds of general formula (I) or (Ia), wherein R¹ represents a group selected from $C_1$-$C_6$-alkyl-, $C_3$-$C_7$-cycloalkyl-,
wherein said group is optionally substituted with one substituent selected from the group consisting of hydroxy, $C_1$-$C_6$-alkoxy-;

R² represents a group selected from

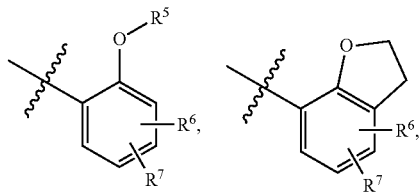

-continued

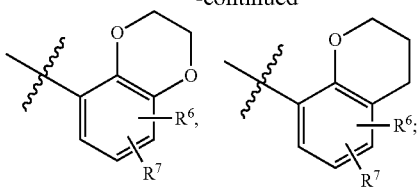

R³, R⁴ represent, independently from each other, a group selected from a hydrogen atom, fluoro atom, chloro atom;
R⁵ represents a group selected from
  a) a $C_1$-$C_{10}$-alkyl- group, which is optionally substituted with one or two or three substituents, identically or differently, selected from the group consisting of halogen atom, $C_1$-$C_3$-alkyl-, $C_2$-$C_3$-alkynyl-, $C_3$-$C_7$-cycloalkyl-, heterocycyl, phenyl, wherein said phenyl group is optionally substituted with one halogen substituent;
  b) a $C_3$-$C_7$-cycloalkyl- group;
  c) a phenyl-$C_1$-$C_3$-alkyl- group, which phenyl group is optionally substituted with one or two or three substituents, identically or differently, selected from the group consisting of halogen, cyano, halo-$C_1$-$C_3$-alkyl-, $C_1$-$C_3$-alkyl-;
  d) a heteroaryl-$C_1$-$C_3$-alkyl- group, which is optionally substituted with one substituent selected from the group consisting of halogen, $C_1$-$C_3$-alkyl-;
R⁶, R⁷ represent, independently from each other, a group selected from a hydrogen atom or fluoro or chloro atom;
or its salts, solvates or salts of solvates.

In another embodiment the present invention concerns compounds of general formula (I) or (Ia), wherein
R¹ represents a group selected from $C_1$-$C_6$-alkyl-, $C_3$-$C_7$-cycloalkyl-,
  wherein said group is optionally substituted with one substituent selected from the group consisting of hydroxy;
R² represents a group selected from

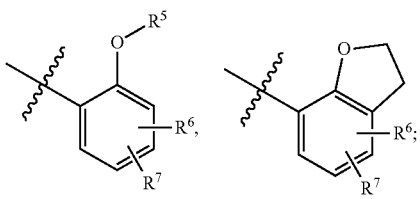

R³, R⁴ represent, independently from each other, a group selected from a hydrogen atom, fluoro atom, chloro atom;
R⁵ represents a group selected from
  a) a $C_1$-$C_{10}$-alkyl- group, which is optionally substituted with one substituent, selected from the group consisting of $C_2$-$C_3$-alkynyl-, phenyl, wherein said phenyl group is optionally substituted with one halogen substituent;
  b) a phenyl-$C_1$-$C_3$-alkyl- group, which phenyl group is optionally substituted with one or two substituents, identically or differently, selected from the group consisting of halogen;
  c) a heteroaryl-$C_1$-$C_3$-alkyl- group, which is optionally substituted with one substituent selected from the group consisting of halogen,
R⁶, R⁷ represent, independently from each other, a group selected from a hydrogen atom or fluoro atom;
or its salts, solvates or salts of solvates.

In another embodiment the present invention concerns compounds of general formula (I) or (Ia), wherein
R¹ represents $C_1$-$C_6$-alkyl- or cyclohexyl-,
R² represents a group selected from

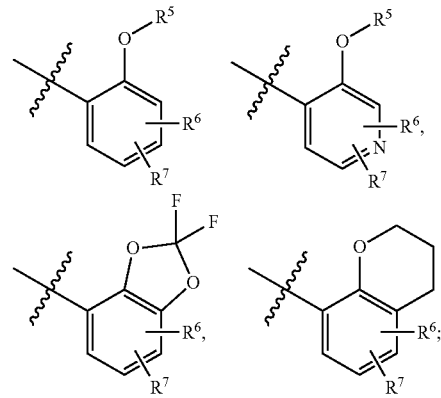

R³, R⁴ represent, independently from each other, a group selected from a hydrogen atom or a fluoro atom;
R⁵ represents a group selected from
  a) a $C_1$-$C_{10}$-alkyl- group, which is optionally substituted with one or two or three substituents, identically or differently, selected from the group consisting of halogen atom, $C_1$-$C_3$-alkyl-, phenyl;
  b) a phenyl-$C_1$-$C_3$-alkyl- group;
R⁶, R⁷ represent, independently from each other, a group selected from a hydrogen atom or a fluoro atom;
or their salts, solvates or salts of solvates.

In another embodiment the present invention concerns compounds of general formula (I) or (Ia), wherein
R¹ represents methyl or cyclohexyl,
R² represents a group selected from

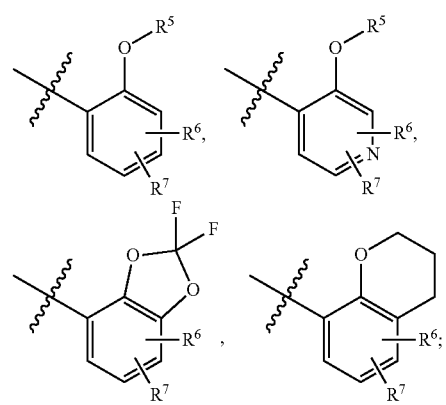

R³, R⁴ represent, independently from each other, a group selected from a hydrogen atom or fluoro atom,
R⁵ represents a group selected from methyl-, isopropyl-, benzyl-, trifluoromethyl-,
R⁶, R⁷ represent, independently from each other, a group selected from a hydrogen atom or fluoro atom;
or their salts, solvates or salts of solvates.

In another embodiment the present invention concerns compounds of general formula (I) or (Ia), wherein
R¹ represents a group selected from $C_1$-$C_6$-alkyl-, $C_3$-$C_7$-cycloalkyl-, phenyl, wherein said group is optionally substituted with one substituent selected from the group consisting of hydroxy, $C_1$-$C_6$-alkoxy-;

$R^2$ represents a group selected from

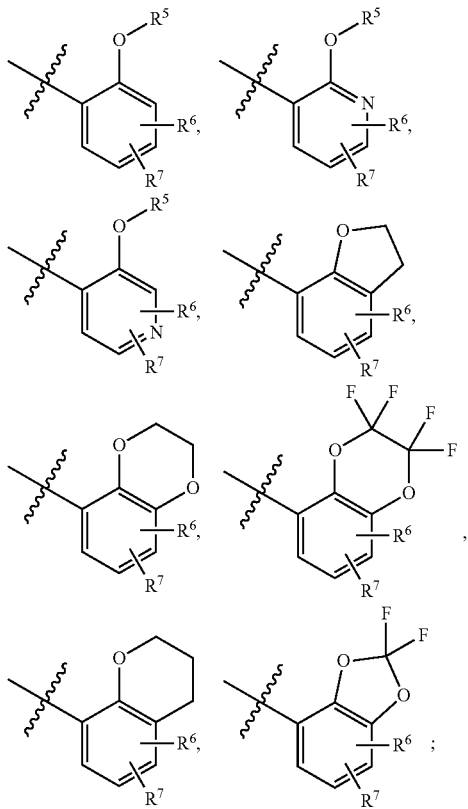

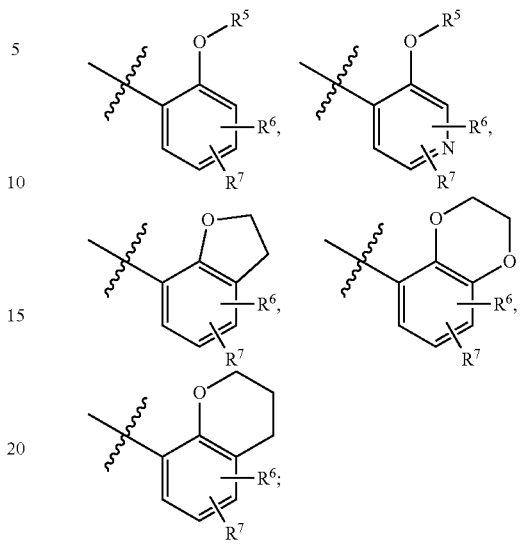

$R^3$, $R^4$ represent, independently from each other, a group selected from a hydrogen atom, fluoro atom, chloro atom;

$R^5$ represents a group selected from
  a) a $C_1$-$C_{10}$-alkyl- group, which is optionally substituted with one or two or three substituents, identically or differently, selected from the group consisting of halogen atom, $C_1$-$C_3$-alkyl-, heterocycyl-, phenyl, wherein said phenyl group is optionally substituted with one halogen substituent;
  b) a $C_3$-$C_7$-cycloalkyl- group;
  c) a phenyl-$C_1$-$C_3$-alkyl- group, which is optionally substituted with one substituent selected from the group consisting of halogen;

$R^6$, $R^7$ represent, independently from each other, a group selected from a hydrogen atom or fluoro or chloro atom;

or their salts, solvates or salts of solvates.

In another embodiment the present invention concerns compounds of general formula (I) or (Ia), wherein $R^1$ represents a group selected from $C_1$-$C_6$-alkyl-, $C_3$-$C_7$-cycloalkyl-,
  wherein said group is optionally substituted with one substituent selected from the group consisting of hydroxy, $C_1$-$C_6$-alkoxy-;

$R^2$ represents a group selected from $R^3$, $R^4$ represent, independently from each other, a group selected from a hydrogen atom, fluoro atom, chloro atom;

$R^5$ represents a group selected from
  a) a $C_1$-$C_{10}$-alkyl- group, which is optionally substituted with one substituent selected from the group consisting of $C_1$-$C_3$-alkyl-, phenyl, wherein said phenyl group is optionally substituted with one substituent selected from halogen;
  b) a $C_3$-$C_7$-cycloalkyl- group,
  c) a phenyl-$C_1$-$C_3$-alkyl- group, which is optionally substituted with one halogen substituent;

$R^6$, $R^7$ represent, independently from each other, a group selected from a hydrogen atom or fluoro or chloro atom;

or their salts, solvates or salts of solvates.

In another embodiment the present invention concerns compounds of general formula (I) or (Ia), wherein $R^1$ represents a $C_1$-$C_6$-alkyl- group;

$R^2$ represents a group selected from

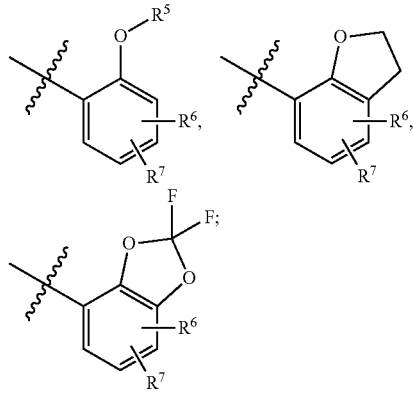

$R^3$, $R^4$ represent, independently from each other, a group selected from a hydrogen atom, fluoro atom;

$R^5$ represents a group selected from
  a) a $C_1$-$C_{10}$-alkyl- group, which is optionally substituted with one or two or three substituents, identically or differently, selected from the group consisting of $C_1$-$C_3$- alkyl-, phenyl, wherein said phenyl group is optionally substituted with one substituent selected from halogen;
c) a phenyl-$C_1$-$C_3$-alkyl- group, which is optionally substituted with one substituent selected from the group consisting of halogen;

$R^6$, $R^7$ represent, independently from each other, a group selected from a hydrogen atom or fluoro atom;

or their salts, solvates or salts of solvates.

In another embodiment the present invention concerns compounds of general formula (Ia),

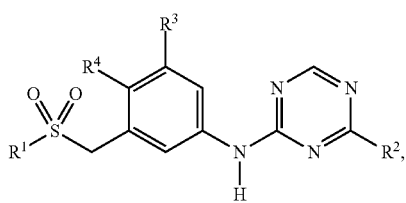

(Ia)

wherein $R^1$ represents a group selected from methyl, ethyl, tert.-butyl, propan-2-yl, cyclopropyl, cyclopentyl, cyclohexyl; phenyl, wherein said group is optionally substituted with one hydroxy or methoxy-substituent;

$R^2$ represents a group selected from
4,5-difluoro-2-methoxyphenyl-; 3,4-difluoro-2-methoxyphenyl-, 4-fluoro-2-methoxyphenyl-, 2-(benzyloxy)-4-fluorophenyl-, 4-fluoro-2-(propan-2-yloxy)phenyl-, 3-methoxypyridin-4-yl, 5-fluoro-2-methoxyphenyl-, 2-methoxypyridin-3-yl; 2-[(4-fluorobenzyl)oxy]phenyl-, 2-[(3-fluorobenzyl)oxy]phenyl-, 2-[(2-chlorobenzyl)oxy]phenyl-, 2-[(3-chlorobenzyl)oxy]phenyl-, 4-chloro-2-(cyclopentyloxy)phenyl-, 5-fluoro-2-[(2-fluorobenzyl)oxy]phenyl-, 5-fluoro-2-[(3-fluorobenzyl)oxy]phenyl-, 4-chloro-2-methoxyphenyl-, 2-(cyclopropyloxy)-4-fluorophenyl-, 2-ethoxy-4-fluorophenyl-, 4-fluoro-2-propoxyphenyl-, 2-butoxy-4-fluorophenyl-, 4-fluoro-2-(pentyloxy)phenyl-, 4-fluoro-2-(hexyloxy)phenyl-, 4-fluoro-2-[(4-methylpentyl)oxy]phenyl, 2-(2-cyclopropylethoxy)-4-fluorophenyl-, 4-fluoro-2-[(1-methylcyclopropyl)methoxy]phenyl-, 4-fluoro-2-(2-methoxyethoxy)phenyl-, 2-(2-ethoxyethoxy)-4-fluorophenyl-, 4-fluoro-2-(3-methylbutoxy)phenyl-, 2-(2-cyclopentylethoxy)-4-fluorophenyl-, 4-fluoro-2-(3-fluoropropoxy)phenyl-, 2-(cyclopropylmethoxy)-4-fluorophenyl-, 2-(cyclobutylmethoxy)-4-fluorophenyl-, 2-(cyclohexylmethoxy)-4-fluorophenyl-, 4-fluoro-2-(2-methylpropoxy)phenyl-, 4-fluoro-2-(4,4,4-trifluorobutoxy)phenyl-, 2-(2,2-difluoroethoxy)-4-fluorophenyl-, 4-fluoro-2-(2-fluoroethoxy)phenyl-, 2-(but-2-yn-1-yloxy)-4-fluorophenyl-, 2-(2-yyclohexylethoxy)-4-fluorophenyl-, 2-(cyclobutyloxy)-4-fluorophenyl-, 2-(cyclopentyloxy)-4-fluorophenyl-, 4-fluoro-2-[(1-fluorocyclohexyl)methoxy]phenyl-, 4-fluoro-2-[(1R)-1-(4-fluorophenyl)ethoxy]phenyl-, 4-fluoro-2-(1-phenylethoxy)phenyl-, 4-fluoro-2-{[3-(trifluoromethyl)benzyl]oxy}phenyl-, 4-fluoro-2-[(3-methoxybenzyl)oxy]phenyl-, 4-fluoro-2-[(2-fluorobenzyl)oxy]phenyl-, 4-fluoro-2-[(2,3,4-trifluorobenzyl)oxy]phenyl-, 4-fluoro-2-{[4-(trifluoromethyl)benzyl]oxy}phenyl-, 4-fluoro-2-(pyridin-3-ylmethoxy)phenyl-, 4-fluoro-2-[(2,4,5-trifluorobenzyl)oxy]phenyl-, 2-[(4-chlorobenzyl)oxy]-4-fluorophenyl-, 4-fluoro-2-[(4-methylbenzyl)oxy]phenyl-, 4-fluoro-2-{[3-fluoro-5-(trifluoromethyl)benzyl]oxy}phenyl-, 4-fluoro-2-[(1R)-1-phenylethoxy]phenyl-, 2-[(2,3-difluorobenzyl)-oxy]-4-fluorophenyl-, 2-[(2,5-difluorobenzyl)-oxy]-4-fluorophenyl-, 4-fluoro-2-[(2-fluoropyridin-4-yl)methoxy]phenyl-, 4-fluoro-2-[(3-methylbenzyl)oxy]phenyl-, 4-fluoro-2-[(2,3,5-trifluorobenzyl)oxy]phenyl-, 2-[(3-chlorobenzyl)oxy]-4-fluorophenyl-, 2-[(3,4-difluoro-benzyl)oxy]-4-fluorophenyl-, 4-fluoro-2-[(2-methylpyridin-4-yl)methoxy]-phenyl-, 2-[(2-chloropyridin-4-yl)methoxy]-4-fluorophenyl-, 4-fluoro-2-(pyridin-4-ylmethoxy)phenyl-, 2-[(4-cyanobenzyl)oxy]-4-fluorophenyl-;

$R^3$ represents a group selected from a hydrogen atom, chloro atom, fluoro atom;

$R^4$ represents a group selected from a hydrogen atom, fluoro atom;

or their salts, solvates or salts of solvates.

In a preferred embodiment the present invention concerns compounds of general formula (Ia), wherein $R^1$ represents a group selected from methyl, hydroxyethyl-, propan-2-yl-, cyclopropyl, cyclopentyl, cyclohexyl;

$R^2$ represents a group selected from
4,5-difluoro-2-methoxyphenyl-4-fluoro-2-methoxyphenyl-, 2-(benzyloxy)-4-fluorophenyl-, 3-methoxypyridin-4-yl, 2-[(4-fluorobenzyl)oxy]phenyl-, 2-[(3-fluorobenzyl)oxy]phenyl-, 2-[(3-chlorobenzyl)oxy]phenyl-, 4-chloro-2-(cyclopentyloxy)phenyl-, 5-fluoro-2-[(3-fluorobenzyl)oxy]phenyl-, 2-(cyclopropyloxy)-4-fluorophenyl-, 2-ethoxy-4-fluorophenyl-, 4-fluoro-2-propoxyphenyl-, 2-butoxy-4-fluorophenyl-, 4-fluoro-2-(pentyloxy)phenyl-, 4-fluoro-2-[(4-methylpentyl)oxy]phenyl, 2-(2-cyclopropylethoxy)-4-fluorophenyl-, 4-fluoro-2-[(1-methylcyclopropyl)methoxy]phenyl-, 4-fluoro-2-(3-methylbutoxy)phenyl-, 2-(2-cyclopentylethoxy)-4-fluorophenyl-, 4-fluoro-2-(3-fluoropropoxy)phenyl-, 2-(cyclopropylmethoxy)-4-fluorophenyl-, 2-(cyclobutylmethoxy)-4-fluorophenyl-, 2-(cyclohexylmethoxy)-4-fluorophenyl-, 4-fluoro-2-(4,4,4-trifluorobutoxy)phenyl-, 2-(2,2-difluoroethoxy)-4-fluorophenyl-, 4-fluoro-2-(2-fluoroethoxy)phenyl-, 2-(but-2-yn-1-yloxy)-4-fluorophenyl-, 4-fluoro-2-(1-phenylethoxy)phenyl-, 4-fluoro-2-{[3-(trifluoromethyl)benzyl]oxy}phenyl-, 4-fluoro-2-[(3-methoxybenzyl)oxy]phenyl-, 4-fluoro-2-[(2-fluorobenzyl)oxy]phenyl-, 4-fluoro-2-[(2,3,4-trifluorobenzyl)oxy]phenyl-, 4-fluoro-2-{[4-(trifluoromethyl)benzyl]oxy}phenyl-, 4-fluoro-2-(pyridin-3-ylmethoxy)phenyl-, 4-fluoro-2-[(2,4,5-trifluorobenzyl)oxy]phenyl-, 2-[(4-chlorobenzyl)oxy]-4-fluorophenyl-, 4-fluoro-2-[(4-methylbenzyl)oxy]phenyl-, 4-fluoro-2-{[3-fluoro-5-(trifluoromethyl)benzyl]oxy}phenyl-, 4-fluoro-2-[(1R)-1-phenylethoxy]phenyl-, 2-[(2,3-difluorobenzyl)-oxy]-4-fluorophenyl-, 2-[(2,5-difluorobenzyl)-oxy]-4-fluorophenyl-, 4-fluoro-2-[(3-methylbenzyl)oxy]phenyl-, 4-fluoro-2-[(2,3,5-trifluorobenzyl)oxy]phenyl-, 2-[(3-chlorobenzyl)oxy]-4-fluorophenyl-, 2-[(3,4-difluoro-benzyl)oxy]-4-fluorophenyl-, 4-fluoro-2-[(2-methylpyridin-4-yl)methoxy]-phenyl-, 2-[(2-chloropyridin-4-yl)methoxy]-4-fluorophenyl-, 4-fluoro-2-(pyridin-4-ylmethoxy)phenyl-, 2-[(4-cyanobenzyl)oxy]-4-fluorophenyl-;

$R^3$ represents a group selected from a hydrogen atom, chloro atom, fluoro atom;

$R^4$ represents a group selected from a hydrogen atom, fluoro atom;

or their salts, solvates or salts of solvates.

In a preferred embodiment the present invention concerns compounds of general formula (Ia), wherein
$R^1$ represents a group selected from methyl, ethanolyl (=hydroxyethyl-), propan-2-yl-, cyclopropyl;
$R^2$ represents a group selected from
4,5-difluoro-2-methoxyphenyl-4-fluoro-2-methoxyphenyl-, 2-(benzyloxy)-4-fluorophenyl-, 2-[(4-fluorobenzyl)oxy]phenyl-, 2-[(3-fluorobenzyl)oxy]phenyl-, 2-[(3-chlorobenzyl)oxy]phenyl-, 4-chloro-2-(cyclopentyloxy)phenyl-, 5-fluoro-2-[(3-fluorobenzyl)oxy]phenyl-, 2-(cyclopropyloxy)-4-fluorophenyl-, 2-ethoxy-4-fluorophenyl-, 2-butoxy-4-fluorophenyl-, 2-(cyclopropylmethoxy)-4-fluorophenyl-, 4-fluoro-2-(4,4,4-trifluorobutoxy)phenyl-, 4-fluoro-2-(2-fluoroethoxy)phenyl-, 2-(but-2-yn-1-yloxy)-4-fluorophenyl-, 4-fluoro-2-{[3-fluoro-5-(trifluoromethyl)benzyl]oxy}phenyl-, 4-fluoro-2-[(1R)-1-phenylethoxy]phenyl-, 2-[(2,3-difluorobenzyl)-oxy]-4-fluorophenyl-, 2-[(2,5-difluorobenzyl)-oxy]-4-fluorophenyl-, 4-fluoro-2-[(3-methylbenzyl)oxy]phenyl-, 4-fluoro-2-[(2,3,5-trifluorobenzyl)oxy]phenyl-, 2-[(3-chlorobenzyl)oxy]-4-fluorophenyl-, 2-[(3,4-difluoro-benzyl)oxy]-4-fluorophenyl-, 4-fluoro-2-[(2-methylpyridin-4-yl)methoxy]-phenyl-, 2-[(2-chloropyridin-4-yl)methoxy]-4-fluorophenyl-, 4-fluoro-2-(pyridin-4-ylmethoxy)phenyl-, 2-[(4-cyanobenzyl)oxy]-4-fluorophenyl-;
$R^3$ represents a group selected from a hydrogen atom, chloro atom, fluoro atom;
$R^4$ represents a group selected from a hydrogen atom, fluoro atom;
or their salts, solvates or salts of solvates.

In a preferred embodiment the present invention concerns compounds of general formula (Ia), wherein
$R^1$ represents a group selected from methyl, hydroxyethyl-, cyclopropyl-;
$R^2$ represents a group selected from
4,5-difluoro-2-methoxyphenyl-4-fluoro-2-methoxyphenyl-, 2-(benzyloxy)-4-fluorophenyl-, 3-methoxypyridin-4-yl, 2-[(4-fluorobenzyl)oxy]phenyl-, 2-[(3-fluorobenzyl)oxy]phenyl-, 5-fluoro-2-[(3-fluorobenzyl)oxy]phenyl-, 2-ethoxy-4-fluorophenyl-, 2-(but-2-yn-1-yloxy)-4-fluorophenyl-, 2-[(2-chloropyridin-4-yl)methoxy]-4-fluorophenyl-;
$R^3$ represents a group selected from a hydrogen atom, chloro atom, fluoro atom;
$R^4$ represents a group selected from a hydrogen atom, fluoro atom;
or their salts, solvates or salts of solvates.

In another embodiment the present invention concerns compounds of general formula (I) or (Ia), wherein
$R^1$ represents a group selected from methyl, ethyl, propan-2yl, tert-butyl, cyclopentyl, cyclohexyl, phenyl,
wherein said group is optionally substituted with one substituent selected from the group consisting of hydroxy, methoxy;
$R^2$ represents a group selected from

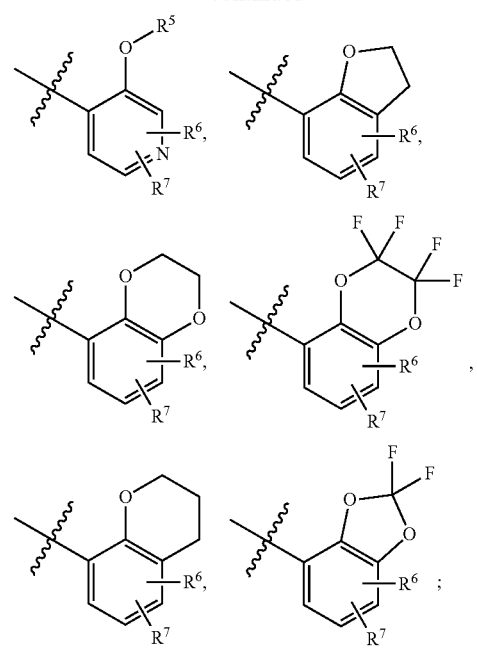

$R^3$, $R^4$ represent, independently from each other, a group selected from a hydrogen atom, fluoro atom, chloro atom;
$R^5$ represents a group selected from
a) methyl, propan-2-yl- which group is optionally substituted with one or two or three substituents, identically or differently, selected from the group consisting of a fluoro atom, tetrahydro-2H-pyran-4-yl, phenyl, wherein said phenyl group is optionally substituted with one substituent selected from fluoro or chloro atom;
b) ethyl, $(^2H_3)$methyl;
c) a cyclopentyl group;
d) a benzyl group, which is optionally substituted with one substituent selected from the group consisting of a fluoro or a chloro atom;
$R^6$, $R^7$ represent, independently from each other, a group selected from a hydrogen atom, fluoro or chloro atom;
or their salts, solvates or salts of solvates.

In another embodiment the present invention concerns compounds of general formula (I) or (Ia), wherein
$R^1$ represents a group selected from methyl, ethyl, propan-2yl, cyclohexyl, cyclopentyl,
wherein said group is optionally substituted with one substituent selected from the group consisting of hydroxy, methoxy-;
$R^2$ represents a group selected from

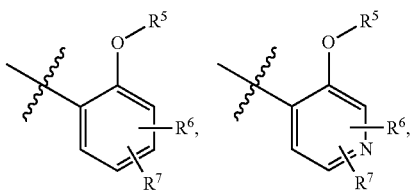

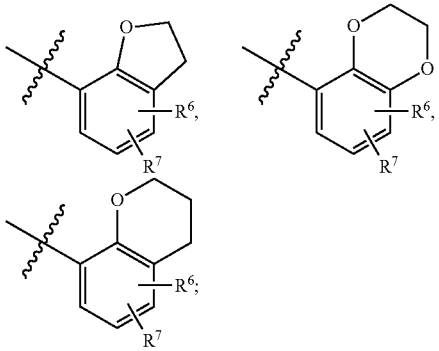

R³, R⁴ represent, independently from each other, a group selected from a hydrogen atom, fluoro atom, chloro atom;
R⁵ represents a group selected from
  a) methyl group, a propan-2-yl, which group is optionally substituted with one substituent selected from the group consisting of phenyl, wherein said phenyl group is optionally substituted with one substituent selected from a fluoro or a chloro atom;
  b) (²H₃)methyl;
  c) a cyclopentyl group;
  d) a benzyl group, which is optionally substituted with one substituent selected from a fluoro or a chloro atom;
R⁶, R⁷ represent, independently from each other, a group selected from a hydrogen atom or fluoro or chloro atom;
or their salts, solvates or salts of solvates.

In another embodiment the present invention concerns compounds of general formula (I) or (Ia), wherein
R¹ represents a methyl group;
R² represents a group selected from

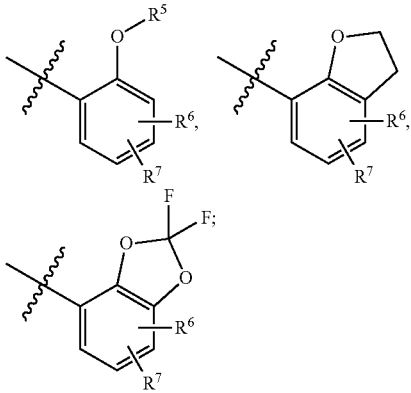

R³, R⁴ represent, independently from each other, a group selected from a hydrogen atom, fluoro atom;
R⁵ represents a group selected from
  a) methyl, propan-2-yl group, which group is optionally substituted with one substituent selected from the group consisting of phenyl, wherein said phenyl group is optionally substituted with one substituent selected from fluoro or chloro atom;
  b) a benzyl group, which is optionally substituted with one substituent selected from the group consisting of a fluoro or a chloro atom;
R⁶, R⁷ represent, independently from each other, a group selected from a hydrogen or fluoro atom;
or their salts, solvates or salts of solvates.

In another embodiment the present invention concerns compounds of general formula (I) or (Ia), wherein
R¹ represents a methyl group;
R² represents a group selected from

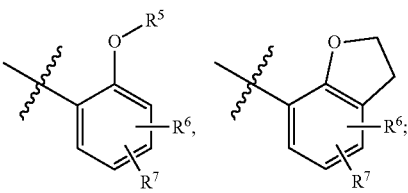

R³, R⁴ represent, independently from each other, a group selected from a hydrogen atom, fluoro atom;
R⁵ represents a group selected from
  a) methyl, propan-2-yl group, which group is optionally substituted with one substituent selected from the group consisting of phenyl, wherein said phenyl group is optionally substituted with one fluoro atom;
  b) a benzyl group, which is optionally substituted with one fluoro atom;
R⁶, R⁷ represent, independently from each other, a group selected from a hydrogen or fluoro atom; or their salts, solvates or salts of solvates.

In another embodiment the present invention concerns compounds of general formula (Ia),

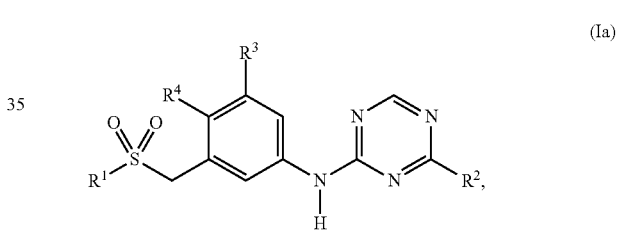

(Ia)

wherein
R¹ represents a group selected from methyl, ethyl, tert.-butyl, propan-2-yl-, cyclopentyl;
wherein said group is optionally substituted with one hydroxy substituent;
R² represents a group selected from
  4,5-difluoro-2-methoxyphenyl-; 3,4-difluoro-2-methoxyphenyl-, 4-fluoro-2-methoxyphenyl-, 2-(benzyloxy)-4-fluorophenyl-, 4-fluoro-2-(propan-2-yloxy)phenyl-, 3-methoxypyridin-4-yl, 5-fluoro-2-methoxyphenyl-, 2-methoxypyridin-3-yl; 2-[(4-fluorobenzyl)oxy]phenyl-, 2-[(3-fluorobenzyl)oxy]phenyl-, 2-[(2-chlorobenzyl)oxy]phenyl-, 2-[(3-chlorobenzyl)oxy]phenyl-, 4-chloro-2-(cyclopentyloxy)phenyl-, 5-fluoro-2-[(2-fluorobenzyl)oxy]phenyl-, 5-fluoro-2-[(3-fluorobenzyl)oxy]phenyl-, 4-chloro-2-methoxyphenyl-;
R³ represents a group selected from a hydrogen atom, chloro atom, fluoro atom;
R⁴ represents a group selected from a hydrogen atom, fluoro atom;
or their salts, solvates or salts of solvates.

In another embodiment the present invention concerns compounds of general formula (Ia), wherein
R¹ represents a group selected from methyl, ethanolyl (=hydroxyethyl-), propan-2-yl-, cyclopentyl;

$R^2$ represents a group selected from
- 4,5-difluoro-2-methoxyphenyl-; 4-fluoro-2-methoxyphenyl-, 2-(benzyloxy)-4-fluorophenyl-, 3-methoxypyridin-4-yl, 2-[(4-fluorobenzyl)oxy]phenyl-, 2-[(3-fluorobenzyl)oxy]phenyl-, 2-[(3-chlorobenzyl)oxy] phenyl-, 4-chloro-2-(cyclopentyloxy)phenyl-, 5-fluoro-2-[(3-fluorobenzyl)oxy]phenyl-;

$R^3$ represents a group selected from a hydrogen atom, chloro atom, fluoro atom;

$R^4$ represents a group selected from a hydrogen atom, fluoro atom;

or their salts, solvates or salts of solvates.

In another embodiment the present invention concerns compounds of general formula (Ia), wherein $R^1$ represents a group selected from methyl, ethanolyl (=hydroxyethyl-);

$R^2$ represents a group selected from
- 4,5-difluoro-2-methoxyphenyl-; 4-fluoro-2-methoxyphenyl-, 2-(benzyloxy)-4-fluorophenyl-, 3-methoxypyridin-4-yl, 2-[(4-fluorobenzyl)oxy]phenyl-, 2-[(3-fluorobenzyl)oxy]phenyl-, 5-fluoro-2-[(3-fluorobenzyl)oxy]phenyl-;

$R^3$ represents a group selected from a hydrogen atom, fluoro atom;

$R^4$ represents a group selected from a hydrogen atom, fluoro atom;

or their salts, solvates or salts of solvates.

In another embodiment the present invention concerns compounds of general formula (Ia), wherein $R^1$ represents a group selected from methyl, ethanol, propan-2-yl-;

$R^2$ represents a group selected from
- 4,5-difluoro-2-methoxyphenyl-; 4-fluoro-2-methoxyphenyl-, 2-(benzyloxy)-4-fluorophenyl-, 2-[(4-fluorobenzyl)oxy]phenyl-, 2-[(3-fluorobenzyl)oxy]phenyl-, 2-[(3-chlorobenzyl)oxy]phenyl-, 4-chloro-2-(cyclopentyloxy)phenyl-, 5-fluoro-2-[(3-fluorobenzyl)oxy]phenyl-;

$R^3$ represents a group selected from a hydrogen atom, chloro atom, fluoro atom;

$R^4$ represents a group selected from a hydrogen atom, fluoro atom; or their salts, solvates or salts of solvates.

In another embodiment the present invention concerns compounds of general formula (Ia), wherein $R^1$ represents a group selected from methyl, ethanolyl (=hydroxyethyl-);

$R^2$ represents a group selected from
- 4-fluoro-2-methoxyphenyl-, 2-(benzyloxy)-4-fluorophenyl-, 2-[(3-fluorobenzyl)oxy]phenyl-, 2-[(3-chlorobenzyl)oxy]phenyl-, 4-chloro-2-(cyclopentyloxy)phenyl-, 5-fluoro-2-[(3-fluorobenzyl)oxy]phenyl-;

$R^3$ represents a group selected from a hydrogen atom, chloro atom, fluoro atom;

$R^4$ represents a group selected from a hydrogen atom, fluoro atom;

or their salts, solvates or salts of solvates.

In another embodiment the present invention concerns compounds of general formula (Ia), wherein $R^1$ represents a group selected from methyl, ethanolyl (=hydroxyethyl-);

$R^2$ represents a group selected from
- 4-fluoro-2-methoxyphenyl-, 2-(benzyloxy)-4-fluorophenyl-, 2-[(3-fluorobenzyl)oxy]phenyl-, 4-chloro-2-(cyclopentyloxy)phenyl-, 5-fluoro-2-[(3-fluorobenzyl)oxy]phenyl-;

$R^3$ represents a group selected from a hydrogen atom, fluoro atom;

$R^4$ represents a group selected from a hydrogen atom, fluoro atom;

or its salts, solvates or salts of solvates.

In another embodiment the present invention concerns compounds of general formula (I) or (Ia), wherein $R^1$ represents a group selected from $C_1$-$C_6$-alkyl-, $C_3$-$C_7$-cycloalkyl-, heterocyclyl-, phenyl, heteroaryl, phenyl-$C_1$-$C_3$-alkyl- or heteroaryl-$C_1$-$C_3$-alkyl-, wherein said group is optionally substituted with one or two or three substituents, identically or differently, selected from the group consisting of hydroxy, cyano, halogen, halo-$C_1$-$C_3$-alkyl-, $C_1$-$C_6$-alkoxy-, $C_1$-$C_3$-fluoroalkoxy-, —$NH_2$, alkylamino-, dialkylamino-, acetylamino-, N-methyl-N-acetylamino-, cyclic amines;

$R^2$ represents a group selected from

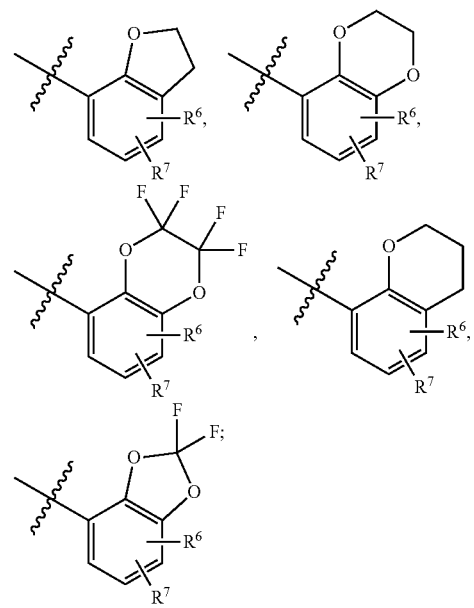

$R^3$, $R^4$ represent, independently from each other, a group selected from a hydrogen atom, fluoro atom, chloro atom, $C_1$-$C_3$-alkyl-, $C_1$-$C_3$-alkoxy-, halo-$C_1$-$C_3$-alkyl-, $C_1$-$C_3$-fluoroalkoxy-;

$R^6$, $R^7$ represent, independently from each other, a group selected from a hydrogen atom, fluoro atom, chloro atom, $C_1$-$C_3$-alkyl-, $C_1$-$C_3$-alkoxy-, halo-$C_1$-$C_3$-alkyl-, $C_1$-$C_3$-fluoroalkoxy-;

or their salts, solvates or salts of solvates.

In another embodiment the present invention concerns compounds of general formula (I) or (Ia), wherein $R^1$ represents a group selected from $C_1$-$C_6$-alkyl-;

$R^2$ represents a group selected from

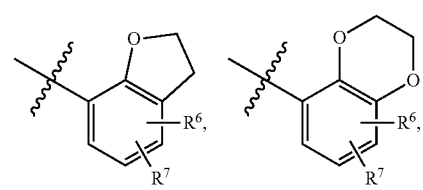

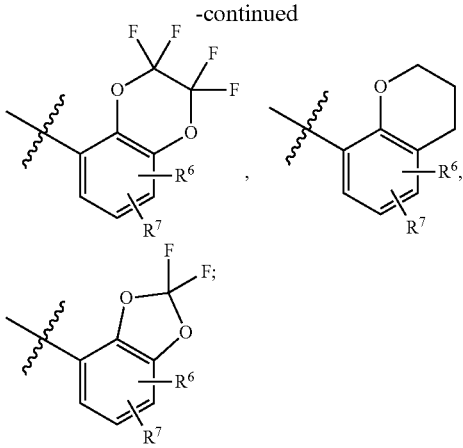

R³, R⁴ represent, independently from each other, a hydrogen atom;
R⁶, R⁷ represent, independently from each other, a hydrogen atom;
or their salts, solvates or salts of solvates.

In another embodiment the present invention concerns compounds of general formula (I) or (Ia), wherein
R¹ represents a group selected from $C_1$-$C_6$-alkyl-,
R² represents a group selected from

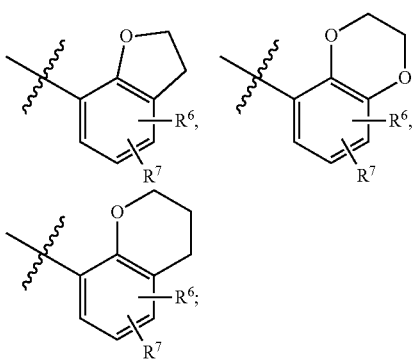

R³, R⁴ represent, independently from each other, a hydrogen atom;
R⁶, R⁷ represent, independently from each other, a hydrogen atom;
or their salts, solvates or salts of solvates.

In another embodiment the invention relates to compounds of formula (I), in which R¹ represents a $C_1$-$C_6$-alkyl-, a $C_3$-$C_7$-cycloalkyl-, a heterocyclyl-, a phenyl, a heteroraryl, a phenyl-$C_1$-$C_3$-alkyl- or a heteroaryl-$C_1$-$C_3$-alkyl- group,
wherein said group is optionally substituted with one or two or three substituents, identically or differently, selected from the group consisting of hydroxy, cyano, halogen, halo-$C_1$-$C_3$-alkyl-, $C_1$-$C_6$-alkoxy-, $C_1$-$C_3$-fluoroalkoxy-, —NH₂, alkylamino-, dialkylamino-, acetylamino-, N-methyl-N-acetylamino-, cyclic amines.

In another embodiment the invention relates to compounds of formula (I) or (Ia), in which R¹ represents a $C_1$-$C_3$-alkyl-, a $C_5$-$C_6$-cycloalkyl-, a 4- to 7-membered heterocyclic ring, a phenyl, a heteroaryl, a phenyl-$C_1$-$C_2$-alkyl- or a heteroaryl-$C_1$-$C_2$-alkyl- group,
wherein said group is optionally substituted with one or two or three substituents, identically or differently, selected from the group consisting of hydroxy, cyano, halogen, halo-$C_1$-$C_2$-alkyl-, $C_1$-$C_3$-alkoxy-, $C_1$-$C_2$-fluoroalkoxy-, —NH₂, alkylamino-, dialkylamino-, acetylamino-, N-methyl-N-acetylamino-, cyclic amines.

In another embodiment the invention relates to compounds of formula (I) or (Ia), in which R¹ represents a phenyl or a heteroraryl group,
wherein said group is optionally substituted with one or two or three substituents, identically or differently, selected from the group consisting of hydroxy, cyano, halogen, halo-$C_1$-$C_2$-alkyl-, $C_1$-$C_3$-alkoxy-, $C_1$-$C_2$-fluoroalkoxy-, —NH₂, alkylamino-, dialkylamino-, acetylamino-, N-methyl-N-acetylamino-, cyclic amines.

In another embodiment the invention relates to compounds of formula (I) or (Ia), in which R¹ represents a group selected from $C_1$-$C_6$-alkyl-, $C_3$-$C_7$-cycloalkyl-, phenyl, wherein said group is optionally substituted with one substituent selected from the group consisting of hydroxy, $C_1$-$C_6$-alkoxy-.

In a preferred embodiment the invention relates to compounds of formula (I) or (Ia), in which R¹ represents a group selected from $C_1$-$C_6$-alkyl-,
wherein said group is optionally substituted with one substituent selected from the group consisting of hydroxy, $C_1$-$C_6$-alkoxy-;

In another embodiment the invention relates to compounds of formula (I) or (Ia), in which R¹ represents a group selected from methyl, ethyl, propan-2-yl, cyclopropyl, tert-butyl, cyclopentyl, cyclohexyl or phenyl;
wherein said group is optionally substituted with one substituent selected from the group consisting of hydroxyl or methoxy.

In another embodiment the invention relates to compounds of formula (I) or (Ia), in which R¹ represents a group selected from methyl, ethyl, propan-2-yl, tert butyl, cyclopentyl, cyclohexyl or phenyl;
wherein said group is optionally substituted with one substituent selected from the group consisting of hydroxyl or methoxy.

In a preferred embodiment the invention relates to compounds of formula (I) or (Ia), in which R¹ represents a group selected from methyl, ethanolyl (=hydroxyethyl-), propan-2-yl-, cyclopropyl, cyclopentyl; cyclohexyl.

In another preferred embodiment the invention relates to compounds of formula (I) or (Ia), in which R¹ represents a group selected from methyl, ethanolyl (=hydroxyethyl-), propan-2-yl, cyclopentyl.

In another preferred embodiment the invention relates to compounds of formula (I) or (Ia), in which R¹ represents a group selected from methyl and ethanolyl (=hydroxyethyl-).

In another preferred embodiment the invention relates to compounds of formula (I) or (Ia), in which R¹ represents a methyl group.

In another embodiment the invention relates to compounds of formula (I) or (Ia), in which R² represents a group selected from

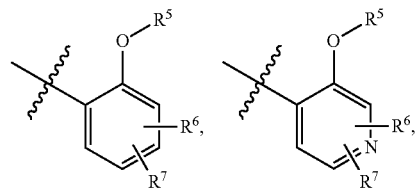

-continued

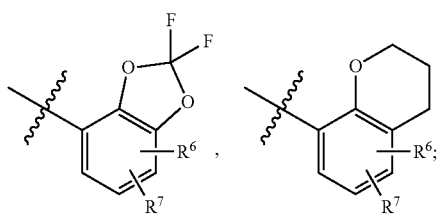

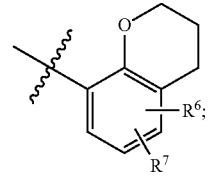

In another embodiment the invention relates to compounds of formula (I) or (Ia), in which $R^2$ represents a group selected from

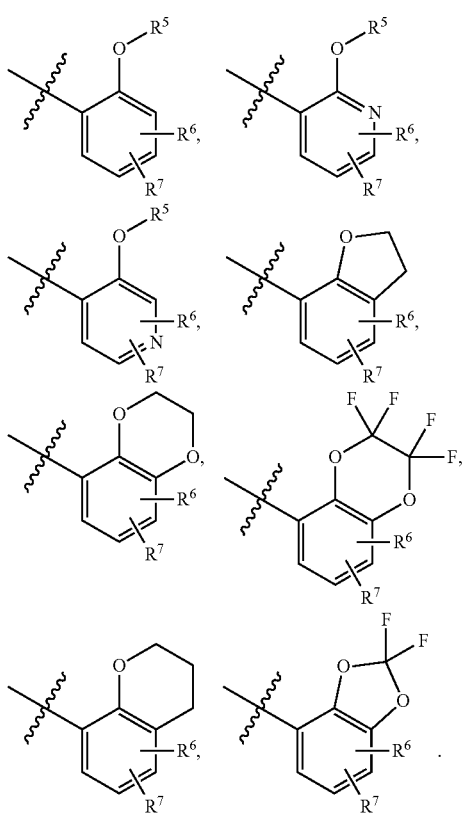

In another embodiment the invention relates to compounds of formula (I) or (Ia), in which $R^2$ represents

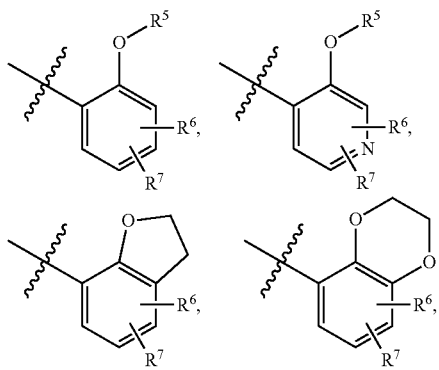

In another embodiment the invention relates to compounds of formula (I) or (Ia), in which $R^2$ represents

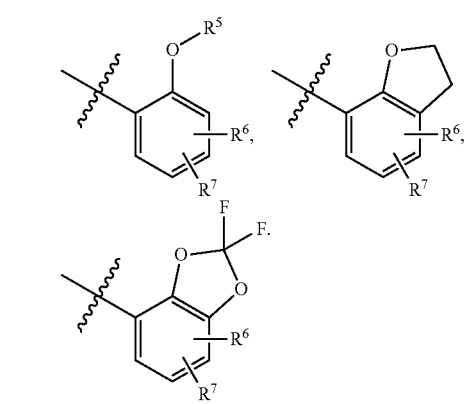

In another embodiment the invention relates to compounds of formula (I) or (Ia), in which $R^2$ represents

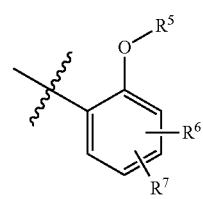

In a preferred embodiment the invention relates to compounds of formula (I) or (Ia), in which $R^2$ represents

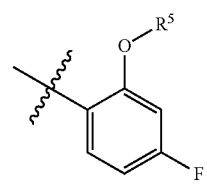

In another embodiment the invention relates to compounds of formula (I) or (Ia), in which $R^2$ represents

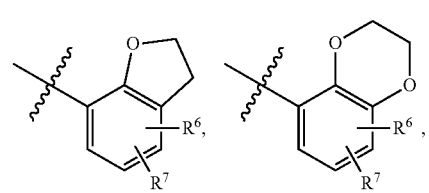

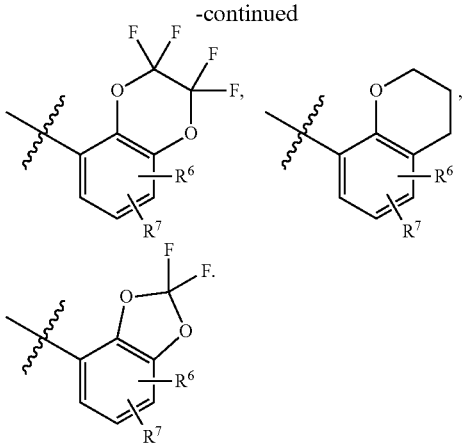

In another embodiment the invention relates to compounds of formula (I) or (Ia), in which R² represents

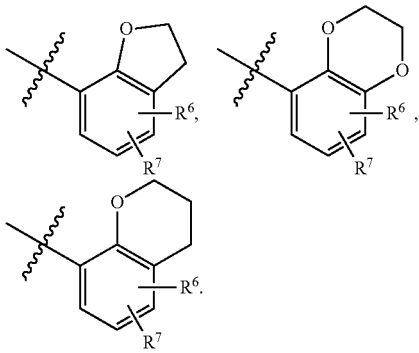

In another embodiment the invention relates to compounds of formula (I) or (Ia), in which R² represents

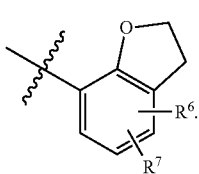

In a preferred embodiment the invention relates to compounds of formula (I) or (Ia), in which R² represents a group selected from 4,5-difluoro-2-methoxyphenyl-4-fluoro-2-methoxyphenyl-, 2-(benzyloxy)-4-fluorophenyl-, 2-[(4-fluorobenzyl)oxy]phenyl-, 2-[(3-fluorobenzyl)oxy]phenyl-, 2-[(3-chlorobenzyl)oxy]phenyl-, 4-chloro-2-(cyclopentyloxy)phenyl-, 5-fluoro-2-[(3-fluorobenzyl)oxy]phenyl-, 2-(cyclopropyloxy)-4-fluorophenyl-, 2-ethoxy-4-fluorophenyl-, 2-butoxy-4-fluorophenyl-, 2-(cyclopropylmethoxy)-4-fluorophenyl-, 4-fluoro-2-(4,4,4-trifluorobutoxy)phenyl-, 4-fluoro-2-(2-fluoroethoxy)phenyl-, 2-(but-2-yn-1-yloxy)-4-fluorophenyl-, 4-fluoro-2-{[3-fluoro-5-(trifluoromethyl)benzyl]oxy}phenyl-, 4-fluoro-2-[(1R)-1-phenylethoxy]phenyl-, 2-[(2,3-difluorobenzyl)-oxy]-4-fluorophenyl-, 2-[(2,5-difluorobenzyl)-oxy]-4-fluorophenyl-, 4-fluoro-2-[(3-methylbenzyl)oxy]phenyl-, 4-fluoro-2-[(2,3,5-trifluorobenzyl)oxy]phenyl-, 2-[(3-chlorobenzyl)oxy]-4-fluorophenyl-, 2-[(3,4-difluoro-benzyl)oxy]-4-fluorophenyl-, 4-fluoro-2-[(2-methylpyridin-4-yl)methoxy]phenyl-, 2-[(2-chloropyridin-4-yl)methoxy]-4-fluorophenyl-, 4-fluoro-2-(pyridin-4-ylmethoxy)phenyl-, 2-[(4-cyanobenzyl)oxy]-4-fluorophenyl-;

In another embodiment the invention relates to compounds of formula (I) or (Ia), in which R² represents a group selected from 4,5-difluoro-2-methoxyphenyl-; 3,4-difluoro-2-methoxyphenyl-, 4-fluoro-2-methoxyphenyl-, 2-(benzyloxy)-4-fluorophenyl-, 4-fluoro-2-(propan-2-yloxy)phenyl-, 3-methoxypyridin-4-yl, 5-fluoro-2-methoxyphenyl-, 2-methoxypyridin-3-yl-; 2-[(4-fluorobenzyl)oxy]phenyl-, 2-[(3-fluorobenzyl)oxy]phenyl-, 2-[(2-chlorobenzyl)oxy]phenyl-, 2-[(3-chlorobenzyl)oxy]phenyl-, 4-chloro-2-(cyclopentyloxy)phenyl-, 5-fluoro-2-[(2-fluorobenzyl)oxy]phenyl-, 5-fluoro-2-[(3-fluorobenzyl)oxy]phenyl-, 4-chloro-2-methoxyphenyl-.

In another embodiment the invention relates to compounds of formula (I) or (Ia), in which R² represents a group selected from 4,5-difluoro-2-methoxyphenyl-; 4-fluoro-2-methoxyphenyl-, 2-(benzyloxy)-4-fluorophenyl-, 3-methoxypyridin-4-yl-, 2-[(4-fluorobenzyl)oxy]phenyl-, 2-[(3-fluorobenzyl)oxy]phenyl-, 2-[(3-chlorobenzyl)oxy]phenyl-, 4-chloro-2-(cyclopentyloxy)phenyl-, 5-fluoro-2-[(3-fluorobenzyl)oxy]phenyl-.

In another embodiment the invention relates to compounds of formula (I) or (Ia), in which R² represents a group selected from 4,5-difluoro-2-methoxyphenyl-; 4-fluoro-2-methoxyphenyl-, 2-(benzyloxy)-4-fluorophenyl-, 3-methoxypyridin-4-yl-, 2-[(4-fluorobenzyl)oxy]phenyl-, 2-[(3-fluorobenzyl)oxy]phenyl-, 5-fluoro-2-[(3-fluorobenzyl)oxy]phenyl-.

In a preferred embodiment the invention relates to compounds of formula (I) or (Ia), in which R² represents a group selected from 4-fluoro-2-methoxyphenyl-, 2-(benzyloxy)-4-fluorophenyl-, 2-[(3-fluorobenzyl)oxy]phenyl-, 4-chloro-2-(cyclopentyloxy)phenyl-, 5-fluoro-2-[(3-fluorobenzyl)oxy]phenyl-.

In a preferred embodiment the invention relates to compounds of formula (I) or (Ia), in which R² represents a 4-fluoro-2-methoxyphenyl- group.

In another embodiment the invention relates to compounds of formula (I) or (Ia), in which R³ represents a group selected from a hydrogen atom, fluoro atom, chloro atom, $C_1$-$C_3$-alkyl-, $C_1$-$C_3$-alkoxy-, halo-$C_1$-$C_3$-alkyl-, $C_1$-$C_3$-fluoroalkoxy-.

In another embodiment the invention relates to compounds of formula (I) or (Ia), in which R³ represents a group selected from a hydrogen atom, fluoro atom, chloro atom, $C_1$-$C_2$-alkyl-, $C_1$-$C_2$-alkoxy-, halo-$C_1$-$C_2$-alkyl-, $C_1$-$C_2$-fluoroalkoxy-.

In another embodiment the invention relates to compounds of formula (I) or (Ia), in which R³ represents a group selected from a hydrogen, a fluoro or a chloro atom.

In another embodiment the invention relates to compounds of formula (I) or (Ia), in which R³ represents a fluoro or a chloro atom.

In another embodiment the invention relates to compounds of formula (I) or (Ia), in which R³ represents a group selected from a hydrogen atom or a fluoro atom.

In a preferred embodiment the invention relates to compounds of formula (I) or (Ia), in which R³ represents a hydrogen atom.

In another preferred embodiment the invention relates to compounds of formula (I) or (Ia), in which R³ represents a fluoro atom.

In another embodiment the invention relates to compounds of formula (I) or (Ia), in which R⁴ represents a group selected from a hydrogen atom, fluoro atom, chloro atom, $C_1$-$C_3$-alkyl-, $C_1$-$C_3$-alkoxy-, halo-$C_1$-$C_3$-alkyl-, $C_1$-$C_3$-fluoroalkoxy-.

In another embodiment the invention relates to compounds of formula (I) or (Ia), in which $R^4$ represents a group selected from a hydrogen atom, fluoro atom, chloro atom, $C_1$-$C_2$-alkyl-, $C_1$-$C_2$-alkoxy-, halo-$C_1$-$C_2$-30alkyl-, $C_1$-$C_2$-fluoroalkoxy-.

In another embodiment the invention relates to compounds of formula (I) or (Ia), in which $R^4$ represents a group selected from a hydrogen, a fluoro or a chloro atom.

In another embodiment the invention relates to compounds of formula (I) or (Ia), in which $R^4$ represents a fluoro or a chloro atom.

In another embodiment the invention relates to compounds of formula (I) or (Ia), in which $R^4$ represents a group selected from a hydrogen atom or fluoro atom.

In a preferred embodiment the invention relates to compounds of formula (I) or (Ia), in which $R^4$ represents a hydrogen atom.

In another preferred embodiment the invention relates to compounds of formula (I) or (Ia), in which $R^4$ represents a fluoro atom.

In a preferred embodiment the invention relates to compounds $R^5$ of formula (I) or (Ia), in which $R^5$ represents a group selected from
  a) a $C_1$-$C_{10}$-alkyl- group, which is optionally substituted with one or two or three substituents, identically or differently, selected from the group consisting of halogen atom, $C_1$-$C_3$-alkyl-, $C_2$-$C_3$-alkynyl-, $C_3$-$C_7$-cycloalkyl-, heterocycyl-, phenyl, wherein said phenyl group is optionally substituted with one halogen substituent;
  b) a $C_3$-$C_7$-cycloalkyl- group;
  c) a phenyl-$C_1$-$C_3$-alkyl- group, which phenyl group is optionally substituted with one or two substituents, identically or differently, selected from the group consisting of halogen, cyano, halo-$C_1$-$C_3$-alkyl-, $C_1$-$C_3$-alkyl;
  d) a heteroaryl-$C_1$-$C_3$-alkyl- group, which is optionally substituted with one substituent selected from the group consisting of halogen, $C_1$-$C_3$-alkyl-.

In another embodiment the invention relates to compounds of formula (I) or (Ia), in which $R^5$ represents a $C_1$-$C_6$-alkyl group, which is optionally substituted with one or two or three substituents, identically or differently, selected from the group consisting of halogen, hydroxy, —$NH_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-, $C_2$-$C_3$-alkenyl-, $C_2$-$C_3$-alkynyl-, $C_3$-$C_7$-cycloalkyl-, $C_3$-$C_7$-heterocycyl-, phenyl, heteroaryl,
  wherein said $C_3$-$C_7$-cycloalkyl-, $C_3$-$C_7$-heterocycyl-, phenyl or heteroaryl group is optionally substituted with one, two or three substituents, identically or differently, selected from halogen, hydroxy, $C_1$-$C_3$-alkyl-, $C_1$-$C_3$-alkoxy-, —$NH_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-.

In another embodiment the invention relates to compounds of formula (I) or (Ia), in which $R^5$ represents a $C_1$-$C_3$-alkyl group, which is optionally substituted with one or two or three substituents, identically or differently, selected from the group consisting of halogen, hydroxy, —$NH_2$, alkylamino-, dialkylamino-, acetylamino-, N-methyl-N-acetylamino-, cyclic amines, cyano, $C_1$-$C_3$-alkyl-, halo-$C_1$-$C_2$-alkyl-, $C_1$-$C_2$-fluoroalkoxy-, $C_1$-$C_2$-alkoxy-, $C_2$-$C_3$-alkenyl-, $C_2$-$C_3$-alkynyl-, $C_4$-$C_6$-cycloalkyl-, $C_3$-$C_7$-heterocycyl-, phenyl, heteroaryl,
  wherein said $C_3$-$C_7$-cycloalkyl-, $C_3$-$C_7$-heterocycyl-, phenyl or heteroaryl group is optionally substituted with one, two or three substituents, identically or differently, selected from halogen, hydroxy, $C_1$-$C_2$-alkyl-, $C_1$-$C_2$-alkoxy-, —$NH_2$, alkylamino-, dialkylamino-, acetylamino-, N-methyl-N-acetylamino-, cyclic amines, halo —$C_1$-$C_2$-alkyl-, $C_1$-$C_2$-fluoroalkoxy-.

In another embodiment the invention relates to compounds of formula (I) or (Ia), in which $R^5$ represents a $C_1$-$C_{10}$-alkyl- group, which is optionally substituted with one or two or three substituents, identically or differently, selected from the group consisting of halogen atom, $C_1$-$C_3$-alkyl-, heterocycyl-, phenyl, wherein said phenyl group is optionally substituted with one substituent selected from halogen.

In another embodiment the invention relates to compounds of formula (I) or (Ia), in which $R^5$ represents a $C_1$-$C_{10}$-alkyl- group, which is substituted with one or two or three substituents, identically or differently, selected from the group of a halogen atom.

In another embodiment the invention relates to compounds of formula (I) or (Ia), in which $R^5$ represents a $C_1$-$C_{10}$-alkyl- group, which is substituted with one or two or three substituents, identically or differently, selected from the group of a chloro or fluoro atom.

In another embodiment the invention relates to compounds of formula (I) or (Ia), in which $R^5$ represents a $C_1$-$C_{10}$-alkyl- group, which is substituted with one or two or three substituents selected from the group of a fluoro atom.

In another embodiment the invention relates to compounds of formula (I) or (Ia), in which $R^5$ represents a group selected from —$CF_3$, —$CH_2CF_3$, —$CHF2$, —$CH_2CH_2CF_3$, —$CH_2CH_2CF_2CF_3$.

In another embodiment the invention relates to compounds of formula (I) or (Ia), in which $R^5$ represents a group selected from —$CH_2CH_2CF_3$, —$CH_2CH_2CF_2CF_3$.

In another embodiment the invention relates to compounds of formula (I) or (Ia), in which $R^5$ represents a methyl, a ($^2H_3$)methyl group, a propan-2-yl group.

In another embodiment the invention relates to compounds of formula (I) or (Ia), in which $R^5$ represents a methyl group.

In another embodiment the invention relates to compounds of formula (I) or (Ia), in which $R^5$ represents a $C_5$-$C_6$-cycloalkyl- group, which is optionally substituted with one or two or three substituents, identically or differently, selected from the group consisting of halogen, hydroxy, —$NH_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-, $C_2$-$C_3$-alkenyl-, $C_2$-$C_3$-alkynyl-.

In another embodiment the invention relates to compounds of formula (I) or (Ia), in which $R^5$ represents a $C_5$-$C_6$-cycloalkyl- group, which is optionally substituted with one or two or three substituents, identically or differently, selected from the group consisting of fluoro, chloro, hydroxy, —$NH_2$, alkylamino-, dialkylamino-, acetylamino-, N-methyl-N-acetylamino-, cyclic amines, cyano, $C_1$-$C_2$-alkyl-, halo-$C_1$-$C_2$-alkyl-, $C_1$-$C_2$-fluoroalkoxy-, $C_1$-$C_2$-alkoxy-, $C_2$-$C_3$-alkenyl-, $C_2$-$C_3$-alkynyl-.

In another embodiment the invention relates to compounds of formula (I) or (Ia), in which $R^5$ represents a cyclopentyl group, which is optionally substituted with one or two or three substituents, identically or differently, selected from the group consisting of fluoro, chloro, hydroxy, —$NH_2$, alkylamino-, dialkylamino-, acetylamino-, N-methyl-N-acetylamino-, cyclic amines, cyano, $C_1$-$C_2$-alkyl-, halo-$C_1$-$C_2$-alkyl-, $C_1$-$C_2$-fluoroalkoxy-, $C_1$-$C_2$-alkoxy-, $C_2$-$C_3$-alkenyl-, $C_2$-$C_3$-alkynyl-.

In another embodiment the invention relates to compounds of formula (I) or (Ia), in which $R^5$ represents a cyclopentyl group.

In another embodiment the invention relates to compounds of formula (I) or (Ia), in which $R^5$ represents a $C_1$-$C_3$-alkyl group, which is optionally substituted with one or two or three substituents, identically or differently, selected from the group consisting of halogen, $C_1$-$C_3$-alkyl-, halo-$C_1$-$C_3$-alkyl-, $C_1$-$C_3$-fluoroalkoxy-, $C_3$-$C_7$-cycloalkyl, phenyl, wherein said $C_3$-$C_7$-cycloalkyl- or phenyl group is optionally substituted with one, two or three substituents, identically or differently, selected from halogen, $C_1$-$C_3$-alkyl-, $C_1$-$C_3$-alkoxy-, halo-$C_1$-$C_3$-alkyl-, $C_1$-$C_3$-fluoroalkoxy-.

In another embodiment the invention relates to compounds of formula (I) or (Ia), in which $R^5$ represents a $C_1$-$C_3$-alkyl group, which is optionally substituted with one or two or three substituents, identically or differently, selected from the group consisting of halogen, $C_1$-$C_3$-alkyl-, halo-$C_1$-$C_3$-alkyl-, $C_1$-$C_3$-fluoroalkoxy-, $C_3$-$C_7$-heterocycyl, heteroaryl, wherein said $C_3$-$C_7$-cycloalkyl- or phenyl group is optionally substituted with one, two or three substituents, identically or differently, selected from halogen, $C_1$-$C_3$-alkyl-, $C_1$-$C_3$-alkoxy-, halo-$C_1$-$C_3$-alkyl-, $C_1$-$C_3$-fluoroalkoxy-.

In another embodiment the invention relates to compounds of formula (I) or (Ia), in which $R^5$ represents a cyloalkyl-$CH_2$— group, which is optionally substituted with one or two or three substituents, identically or differently, selected from halogen, $C_1$-$C_3$-alkyl-, $C_1$-$C_3$-alkoxy-, halo-$C_1$-$C_3$-alkyl-, $C_1$-$C_3$-fluoroalkoxy-.

In another embodiment the invention relates to compounds of formula (I) or (Ia), in which $R^5$ represents a 4- to 7-membered heterocyclic ring, which is optionally substituted with one or two or three substituents, identically or differently, selected from the group consisting of halogen, hydroxy, —$NH_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-, $C_2$-$C_3$-alkenyl-, $C_2$-$C_3$-alkynyl-.

In another embodiment the invention relates to compounds of formula (I) or (Ia), in which $R^5$ represents a 4- to 7-membered heterocyclic ring, which is optionally substituted with one or two or three substituents, identically or differently, selected from the group consisting of halogen, hydroxy, —$NH_2$, alkylamino-, dialkylamino-, acetylamino-, N-methyl-N-acetylamino-, cyclic amines, cyano, $C_1$-$C_2$-alkyl-, halo-$C_1$-$C_2$-alkyl-, $C_1$-$C_2$-fluoroalkoxy-, $C_1$-$C_2$-alkoxy-, $C_2$-$C_3$-alkenyl-, $C_2$-$C_3$-alkynyl-.

In another embodiment the invention relates to compounds of formula (I) or (Ia), in which $R^5$ represents a phenyl group, which is optionally substituted with one or two or three substituents, identically or differently, selected from the group consisting of halogen, hydroxy, —$NH_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-.

In another embodiment the invention relates to compounds of formula (I) or (Ia), in which $R^5$ represents a phenyl group, which is optionally substituted with one or two or three substituents, identically or differently, selected from the group consisting of halogen, hydroxy, —$NH_2$, alkylamino-, dialkylamino-, acetylamino-, N-methyl-N-acetylamino-, cyclic amines, cyano, $C_1$-$C_2$-alkyl-, halo-$C_1$-$C_2$-alkyl-, $C_1$-$C_2$-fluoroalkoxy-, $C_1$-$C_2$-alkoxy-.

In another embodiment the invention relates to compounds of formula (I) or (Ia), in which $R^5$ represents a heteroaryl group, which is optionally substituted with one or two or three substituents, identically or differently, selected from the group consisting of halogen, hydroxy, —$NH_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-.

In another embodiment the invention relates to compounds of formula (I) or (Ia), in which $R^5$ represents a heteroaryl group, which is optionally substituted with one or two or three substituents, identically or differently, selected from the group consisting of halogen, hydroxy, —$NH_2$, alkylamino-, dialkylamino-, acetylamino-, N-methyl-N-acetylamino-, cyclic amines, cyano, $C_1$-$C_2$-alkyl-, halo-$C_1$-$C_2$-alkyl-, $C_1$-$C_2$-fluoroalkoxy-, $C_1$-$C_2$-alkoxy-.

In another embodiment the invention relates to compounds of formula (I) or (Ia), in which $R^5$ represents a phenyl-$C_1$-$C_2$-alkyl- group, which is optionally substituted with one or two or three substituents, identically or differently, selected from the group consisting of halogen, hydroxy, $NH_2$, alkylamino-, dialkylamino-, acetylamino-, N-methyl-N-acetylamino-, cyclic amines, cyano, $C_1$-$C_3$-alkyl-, halo —$C_1$-$C_3$-alkyl-, $C_1$-$C_3$-fluoroalkoxy-, $C_1$-$C_3$-alkoxy-.

In another embodiment the invention relates to compounds of formula (I) or (Ia), in which $R^5$ represents a phenyl-$C_1$-$C_2$-alkyl- group, which is optionally substituted with one or two or three substituents, identically or differently, selected from the group consisting of halogen, hydroxy, $NH_2$, alkylamino-, dialkylamino-, acetylamino-, N-methyl-N-acetylamino-, cyclic amines, cyano, $C_1$-$C_2$-alkyl-, halo —$C_1$-$C_2$-alkyl-, $C_1$-$C_2$-fluoroalkoxy-, $C_1$-$C_2$-alkoxy-.

In another embodiment the invention relates to compounds of formula (I) or (Ia), in which $R^5$ represents a benzyl group, which is optionally substituted with one or two or three substituents, identically or differently, selected from the group consisting of halogen, hydroxy, $NH_2$, alkylamino-, dialkylamino-, acetylamino-, N-methyl-N-acetylamino-, cyclic amines, cyano, $C_1$-$C_2$-alkyl-, halo-$C_1$-$C_2$-alkyl-, $C_1$-$C_2$-fluoroalkoxy-, $C_1$-$C_2$-alkoxy-.

In another embodiment the invention relates to compounds of formula (I) or (Ia), in which $R^5$ represents a benzyl group, which is optionally substituted with one or two or three substituents, identically or differently, selected from the group consisting of a fluoro atom, a methyl group hi another embodiment the invention relates to compounds of formula (I) or (Ia), in which $R^5$ represents a benzyl group, which is optionally substituted with one or two substituents, identically or differently, selected from the group consisting of a fluoro or a chloro atom.

In another embodiment the invention relates to compounds of formula (I) or (Ia), in which $R^5$ represents a benzyl group, which is optionally substituted with one fluoro atom.

In another embodiment the invention relates to compounds of formula (I) or (Ia), in which $R^5$ represents a benzyl, a 4-fluorobenzyl-, a 3-chlorobenzyl, a 2-fluorobenzyl or a 3-fluorobenzyl group.

In another embodiment the invention relates to compounds of formula (I) or (Ia), in which $R^5$ represents a phenyl-cyclopropyl- group, which phenyl is optionally substituted with one or two or three substituents, identically or differently, selected from the group consisting of halogen, hydroxy, $NH_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-.

In another embodiment the invention relates to compounds of formula (I) or (Ia), in which $R^5$ represents a phenyl-cyclopropyl- group, which phenyl is optionally substituted with one or two or three substituents, identically or differently, selected from the group consisting of a fluoro atom, a methyl group.

In another embodiment the invention relates to compounds of formula (I) or (Ia), in which $R^5$ represents a cycloalkyl-cyclopropyl- group, which cycloalkyl is optionally substituted with one or two or three substituents, identically or differently, selected from the group consisting of halogen, hydroxy, $NH_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoro alkoxy-, $C_1$-$C_3$-alkoxy-.

In another embodiment the invention relates to compounds of formula (I) or (Ia), in which $R^5$ represents a cycloalkyl-cyclopropyl- group, which phenyl is optionally substituted with one or two or three substituents, identically or differently, selected from the group consisting of a fluoro atom, a methyl group In another embodiment the invention relates to compounds of formula (I) or (Ia), in which $R^5$ represents a heteroaryl-$C_1$-$C_2$-alkyl- group, which is optionally substituted with one or two or three substituents, identically or differently, selected from the group consisting of halogen, hydroxy, $NH_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-.

In another embodiment the invention relates to compounds of formula (I) or (Ia), in which $R^5$ represents a heteroaryl-$C_1$-$C_2$-alkyl-, which is optionally substituted with one or two or three substituents, identically or differently, selected from the group consisting of halogen, hydroxy, $NH_2$, alkylamino-, dialkylamino-, acetylamino-, N-methyl-N-acetylamino-, cyclic amines, cyano, $C_1$-$C_2$-alkyl-, halo-$C_1$-$C_2$-alkyl-, $C_1$-$C_2$-fluoroalkoxy-, $C_1$-$C_2$-alkoxy-.

In another embodiment the invention relates to compounds of formula (I) or (Ia), in which $R^6$ represents a group selected from a hydrogen atom, fluoro atom, chloro atom, $C_1$-$C_3$-alkyl-, $C_1$-$C_3$-alkoxy-, halo-$C_1$-$C_3$-alkyl-, $C_1$-$C_3$-fluoro alkoxy-.

In another embodiment the invention relates to compounds of formula (I) or (Ia), in which $R^6$ represents a group selected from a hydrogen atom, fluoro atom, chloro atom, $C_1$-$C_2$-alkyl-, $C_1$-$C_2$-alkoxy-, halo-$C_1$-$C_2$-alkyl-, $C_1$-$C_2$-fluoroalkoxy-.

In another embodiment the invention relates to compounds of formula (I) or (Ia), in which $R^6$ represents a group selected from a hydrogen atom, fluoro atom, chloro atom.

In another embodiment the invention relates to compounds of formula (I) or (Ia), in which $R^6$ represents a hydrogen atom.

In another embodiment the invention relates to compounds of formula (I) or (Ia), in which $R^6$ represents a fluoro atom.

In a preferred embodiment the invention relates to compounds of formula (I) or (Ia), in which $R^6$ is in para position to the triazine and represents a fluoro atom.

In another embodiment the invention relates to compounds of formula (I) or (Ia), in which $R^7$ represents a group selected from a hydrogen atom, fluoro atom, chloro atom, $C_1$-$C_3$-alkyl-, $C_1$-$C_3$-alkoxy-, halo-$C_1$-$C_3$-alkyl-, $C_1$-$C_3$-fluoroalkoxy-.

In another embodiment the invention relates to compounds of formula (I) or (Ia), in which $R^7$ represents a group selected from a hydrogen atom, fluoro atom, chloro atom, $C_1$-$C_2$-alkyl-, $C_1$-$C_2$-alkoxy-, halo-$C_1$-$C_2$-alkyl-, $C_1$-$C_2$-fluoroalkoxy-.

In another embodiment the invention relates to compounds of formula (I) or (Ia), in which $R^7$ represents a group selected from a hydrogen atom, fluoro atom, chloro atom.

In another embodiment the invention relates to compounds of formula (I) or (Ia), in which $R^7$ represents a hydrogen atom.

In another embodiment the invention relates to compounds of formula (I) or (Ia), in which $R^6$ represents a fluoro atom and $R^7$ represents a hydrogen atom.

In another embodiment the invention relates to compounds of formula (I) or (Ia), in which $R^6$ is in para position to the triazine and represents a fluoro atom and $R^7$ represents a hydrogen atom.

It is to be understood that the present invention relates to any sub-combination within any embodiment of the present invention of compounds of formula (I) or (Ia), supra.

More particularly still, the present invention covers compounds of formula (I) or (Ia) which are disclosed in the Example section of this text, infra.

Very specially preferred are combinations of two or more of the abovementioned preferred ranges.

In particular, preferred subjects of the present invention are the compounds selected from:
4-(4,5-Difluoro-2-methoxyphenyl)-N-{3-[(methylsulfonyl)methyl]phenyl}-1,3,5-triazin-2-amine,
4-(3,4-Difluoro-2-methoxyphenyl)-N-{3-[(methylsulfonyl)methyl]phenyl}-1,3,5-triazin-2-amine,
4-(4-Fluoro-2-methoxyphenyl)-N-{3-[(methylsulfonyl)methyl]phenyl}-1,3,5-triazin-2-amine,
4-[2-(Benzyloxy)-4-fluorophenyl]-N-{3-[(methylsulfonyl)methyl]phenyl}-1,3,5-triazin-2-amine,
4-[4-Fluoro-2-(propan-2-yloxy)phenyl]-N-{3-[(methylsulfonyl)methyl]phenyl}-1,3,5-triazin-2-amine,
4-(2,2-Difluoro-1,3-benzodioxol-4-yl)-N-{3-[(methylsulfonyl)methyl]phenyl}-1,3,5-triazin-2-amine,
N-{3-[(Methylsulfonyl)methyl]phenyl}-4-[2-(trifluoromethoxy)phenyl]-1,3,5-triazin-2-amine,
4-(3-Methoxypyridin-4-yl)-N-{3-[(methylsulfonyl)methyl]phenyl}-1,3,5-triazin-2-amine,
N-{3-[(Cyclohexylsulfonyl)methyl]phenyl}-4-(4-fluoro-2-methoxyphenyl)-1,3,5-triazin-2-amine,
4-(4-Fluoro-2-methoxyphenyl)-N-{3-fluoro-5-[(methylsulfonyl)methyl]phenyl}-1,3,5-triazin-2-amine,
4-(5-Fluoro-2-methoxyphenyl)-N-{3-[(methylsulfonyl)methyl]phenyl}-1,3,5-triazin-2-amine,
4-(3,4-Dihydro-2H-chromen-8-yl)-N-{3-[(methylsulfonyl)methyl]phenyl}-1,3,5-triazin-2-amine,
4-(2,3-Dihydro-1-benzofuran-7-yl)-N-{3-[(methylsulfonyl)methyl]phenyl}-1,3,5-triazin-2-amine,
2-[(3-{[4-(4-Fluoro-2-methoxyphenyl)-1,3,5-triazin-2-yl]amino}benzyl)sulfonyl]ethanol,
4-[2-(Difluoromethoxy)-4-fluorophenyl]-N-{3-[(methylsulfonyl)methyl]phenyl}-1,3,5-triazin-2-amine,
N-{3-[(Methylsulfonyl)methyl]phenyl}-4-[2-(2,2,2-trifluoroethoxy)phenyl]-1,3,5-triazin-2-amine,
N-{3-[(tert-Butylsulfonyl)methyl]phenyl}-4-(4-fluoro-2-methoxyphenyl)-1,3,5-triazin-2-amine,
4-(2,3-Dihydro-1,4-benzodioxin-5-yl)-N-{3-[(methylsulfonyl)methyl]phenyl}-1,3,5-triazin-2-amine,
N-{3-[(Methylsulfonyl)methyl]phenyl}-4-(2,2,3,3-tetrafluoro-2,3-dihydro-1,4-benzodioxin-5-yl)-1,3,5-triazin-2-amine,
4-(2-Methoxypyridin-3-yl)-N-{3-[(methylsulfonyl)methyl]phenyl}-1,3,5-triazin-2-amine,
4-[5-Fluoro-2-(tetrahydro-2H-pyran-4-ylmethoxy)phenyl]-N-{3-[(methylsulfonyl)methyl]phenyl}-1,3,5-triazin-2-amine, 4-{2-[($^2$H$_3$)methyloxy]phenyl}-N-{3-[(methylsulfonyl)methyl]phenyl}-1,3,5-triazin-2-amine,
4-(4-Fluoro-2-methoxyphenyl)-N-(3-{[(2-methoxyethyl)sulfonyl]methyl}phenyl)-1,3,5-triazin-2-amine,
4-(4-Fluoro-2-methoxyphenyl)-N-{3-[(propan-2-ylsulfonyl)methyl]phenyl}-1,3,5-triazin-2-amine,
4-{2-[(4-Fluorobenzyl)oxy]phenyl}-N-{3-[(methylsulfonyl)methyl]phenyl}-1,3,5-triazin-2-amine,
4-{2-[(3-Fluorobenzyl)oxy]phenyl}-N-{3-[(methylsulfonyl)methyl]phenyl}-1,3,5-triazin-2-amine,
4-{2-[(2-Chlorobenzyl)oxy]phenyl}-N-{3-[(methylsulfonyl)methyl]phenyl}-1,3,5-triazin-2-amine,
4-{2-[(3-Chlorobenzyl)oxy]phenyl}-N-{3-[(methylsulfonyl)methyl]phenyl}-1,3,5-triazin-2-amine,
4-[4-Chloro-2-(cyclopentyloxy)phenyl]-N-{3-[(methylsulfonyl)methyl]phenyl}-1,3,5-triazin-2-amine,
4-{5-Fluoro-2-[(2-fluorobenzyl)oxy]phenyl}-N-{3-[(methylsulfonyl)methyl]phenyl}-1,3,5-triazin-2-amine,
4-{5-Fluoro-2-[(3-fluorobenzyl)oxy]phenyl}-N-{3-[(methylsulfonyl)methyl]phenyl}-1,3,5-triazin-2-amine,
4-(4-Chloro-2-methoxyphenyl)-N-{3-[(methylsulfonyl)methyl]phenyl}-1,3,5-triazin-2-amine,
4-(4-Fluoro-2-methoxyphenyl)-N-{4-fluoro-3-[(methylsulfonyl)methyl]phenyl}-1,3,5-triazin-2-amine,
4-{2-[(3-Chlorobenzyl)oxy]phenyl}-N-{3-[(propan-2-ylsulfonyl)methyl]phenyl}-1,3,5-triazin-2-amine,
4-(4-Fluoro-2-methoxyphenyl)-N-{3-[(phenylsulfonyl)methyl]phenyl}-1,3,5-triazin-2-amine,
N-{3-[(Cyclopentylsulfonyl)methyl]phenyl}-4-(4-fluoro-2-methoxyphenyl)-1,3,5-triazin-2-amine,
4-{2-[(4-Fluorobenzyl)oxy]phenyl}-N-{3-[(prop-2-ylsulfonyl)methyl]phenyl}-1,3,5-triazin-2-amine,
4-{5-Fluoro-2-[(3-fluorobenzyl)oxy]phenyl}-N-{3-[(prop-2-ylsulfonyl)methyl]phenyl}-1,3,5-triazin-2-amine,
N-{5-Chloro-3-[(methylsulfonyl)methyl]phenyl}-4-(4-fluoro-2-methoxyphenyl)-1,3,5-triazin-2-amine,
N-{3-[(Cyclopropylsulfonyl)methyl]phenyl}-4-(4-fluoro-2-methoxyphenyl)-1,3,5-triazin-2-amine,
4-[2-(Cyclopropyloxy)-4-fluorophenyl]-N-{3-[(methylsulfonyl)methyl]phenyl}-1,3,5-triazin-2-amine,
4-(2-Ethoxy-4-fluorophenyl)-N-{3-[(methylsulfonyl)-methyl]phenyl}-1,3,5-triazin-2-amine,
4-(4-Fluoro-2-propoxyphenyl)-N-{3-[(methylsulfonyl)-methyl]phenyl}-1,3,5-triazin-2-amine,
4-(2-Butoxy-4-fluorophenyl)-N-{3-[(methylsulfonyl)-methyl]phenyl}-1,3,5-triazin-2-amine,
4-[4-Fluoro-2-(pentyloxy)phenyl]-N-{3-[(methylsulfonyl)-methyl]phenyl}-1,3,5-triazin-2-amine,
4-[4-Fluoro-2-(hexyloxy)phenyl]-N-{3-[(methylsulfonyl)methyl]phenyl}-1,3,5-triazin-2-amine,
4-{4-Fluoro-2-[(4-methylpentyl)oxy]phenyl}-N-{3-[(methylsulfonyl)-methyl]phenyl}-1,3,5-triazin-2-amine,
4-[2-(2-Cyclopropylethoxy)-4-fluorophenyl]-N-{3-[(methylsulfonyl)methyl]phenyl}-1,3,5-triazin-2-amine,
4-{4-Fluoro-2-[(1-methylcyclopropyl)methoxy]phenyl}-N-{3-[(methylsulfonyl)-methyl]phenyl}-1,3,5-triazin-2-amine,
4-[4-Fluoro-2-(2-methoxyethoxy)phenyl]-N-{3-[(methylsulfonyl)methyl]-phenyl}-1,3,5-triazin-2-amine,
4-[2-(2-Ethoxyethoxy)-4-fluorophenyl]-N-{3-[(methylsulfonyl)methyl]phenyl}-1,3,5-triazin-2-amine,
4-[4-Fluoro-2-(3-methylbutoxy)phenyl]-N-{3-[(methylsulfonyl)methyl]phenyl}-1,3,5-triazin-2-amine,
4-[2-(2-Cyclopentylethoxy)-4-fluorophenyl]-N-{3-[(methylsulfonyl)methyl]phenyl}-1,3,5-triazin-2-amine,
4-[4-Fluoro-2-(3-fluoropropoxy)phenyl]-N-{3-[(methylsulfonyl)methyl]phenyl}-1,3,5-triazin-2-amine,
4-[2-(Cyclopropylmethoxy)-4-fluorophenyl]-N-{3-[(methylsulfonyl)methyl]phenyl}-1,3,5-triazin-2-amine,
4-[2-(Cyclobutylmethoxy)-4-fluorophenyl]-N-{3-[(methylsulfonyl)methyl]phenyl}-1,3,5-triazin-2-amine,
4-[2-(Cyclohexylmethoxy)-4-fluorophenyl]-N-{3-[(methylsulfonyl)methyl]phenyl}-1,3,5-triazin-2-amine,
4-[4-Fluoro-2-(2-methylpropoxy)phenyl]-N-{3-[(methylsulfonyl)methyl]phenyl}-1,3,5-triazin-2-amine,
4-[4-Fluoro-2-(4,4,4-trifluorobutoxy)phenyl]-N-{3-[(methylsulfonyl)methyl]phenyl}-1,3,5-triazin-2-amine,
4-[2-(2,2-Difluoroethoxy)-4-fluorophenyl]-N-{3-[(methylsulfonyl)methyl]phenyl}-1,3,5-triazin-2-amine,
4-[4-Fluoro-2-(2-fluoroethoxy)phenyl]-N-{3-[(methylsulfonyl)methyl]phenyl}-1,3,5-triazin-2-amine,
4-[2-(But-2-yn-1-yloxy)-4-fluorophenyl]-N-{3-[(methylsulfonyl)methyl]phenyl}-1,3,5-triazin-2-amine,
4-[2-(2-Cyclohexylethoxy)-4-fluorophenyl]-N-{3-[(methylsulfonyl)methyl]phenyl}-1,3,5-triazin-2-amine,
4-[2-(Cyclobutyloxy)-4-fluorophenyl]-N-{3-[(methylsulfonyl)methyl]phenyl}-1,3,5-triazin-2-amine,
4-[2-(Cyclopentyloxy)-4-fluorophenyl]-N-{3-[(methylsulfonyl)methyl]phenyl}-1,3,5-triazin-2-amine,
4-{4-Fluoro-2-[(1-fluorocyclohexyl)methoxy]phenyl}-N-{3-[(methylsulfonyl)methyl]phenyl}-1,3,5-triazin-2-amine,
4-{4-Fluoro-2-[(1R)-1-(4-fluorophenyl)ethoxy]phenyl}-N-{3-[(methylsulfonyl)-methyl]phenyl}-1,3,5-triazin-2-amine,
rac-4-[4-Fluoro-2-(1-phenylethoxy)phenyl]-N-{3-[(methylsulfonyl)methyl]phenyl}-1,3,5-triazin-2-amine,
4-(4-Fluoro-2-{[3-(trifluoromethyl)benzyl]oxy}-phenyl)-N-{3-[(methylsulfonyl)-methyl]phenyl}-1,3,5-triazin-2-amine,
4-{4-Fluoro-2-[(3-methoxybenzyl)oxy]phenyl}-N-{3-[(methylsulfonyl)-methyl]phenyl}-1,3,5-triazin-2-amine,
4-{4-Fluoro-2-[(2-fluorobenzyl)oxy]phenyl}-N-{3-[(methylsulfonyl)-methyl]phenyl}-1,3,5-triazin-2-amine,
4-{4-Fluoro-2-[(2,3,4-trifluorobenzyl)oxy]phenyl}-N-{3-[(methylsulfonyl)methyl]-phenyl}-1,3,5-triazin-2-amine,
4-(4-Fluoro-2-{[4-(trifluoromethyl)benzyl]oxy}-phenyl)-N-{3-[(methylsulfonyl)-methyl]phenyl}-1,3,5-triazin-2-amine,
4-[4-Fluoro-2-(pyridin-3-ylmethoxy)phenyl]-N-{3-[(methylsulfonyl)methyl]phenyl}-1,3,5-triazin-2-amine,
4-{4-Fluoro-2-[(2,4,5-trifluorobenzyl)oxy]phenyl}-N-{3-[(methylsulfonyl)-methyl]phenyl}-1,3,5-triazin-2-amine,
4-{2-[(4-Chlorobenzyl)oxy]-4-fluorophenyl}-N-{3-[(methylsulfonyl)methyl]phenyl}-1,3,5-triazin-2-amine,
4-{4-Fluoro-2-[(4-methylbenzyl)oxy]phenyl}-N-{3-[(methylsulfonyl)-methyl]phenyl}-1,3,5-triazin-2-amine,
4-(4-Fluoro-2-{[3-fluoro-5-(trifluoromethyl)benzyl]oxy}phenyl)-N-{3-[(methylsulfonyl)-methyl]-phenyl}-1,3,5-triazin-2-amine,
4-{4-Fluoro-2-[(1R)-1-phenylethoxy]phenyl}-N-{3-[(methylsulfonyl)methyl]phenyl}-1,3,5-triazin-2-amine,
4-{2-[(2,3-Difluorobenzyl)-oxy]-4-fluorophenyl}-N-{3-[(methylsulfonyl)-methyl]phenyl}-1,3,5-triazin-2-amine,
4-{2-[(2,5-Difluorobenzyl)-oxy]-4-fluorophenyl}-N-{3-[(methylsulfonyl)methyl]phenyl}-1,3,5-triazin-2-amine,
4-{4-Fluoro-2-[(2-fluoropyridin-4-yl)methoxy]phenyl}-N-{3-[(methylsulfonyl)-methyl]phenyl}-1,3,5-triazin-2-amine,
4-{4-Fluoro-2-[(3-methylbenzyl)oxy]phenyl}-N-{3-[(methylsulfonyl)-methyl]phenyl}-1,3,5-triazin-2-amine,
4-{4-Fluoro-2-[(2,3,5-trifluorobenzyl)oxy]phenyl}-N-{3-[(methylsulfonyl)methyl]-phenyl}-1,3,5-triazin-2-amine, 4-{2-[(3-Chlorobenzyl)oxy]-4-fluorophenyl}-N-{3-[(methylsulfonyl)methyl]phenyl}-1,3,5-triazin-2-amine, 4-{2-[(3,4-Difluoro-benzyl)oxy]-4-fluorophenyl}-N-{3-[(methylsulfonyl)-methyl]phenyl}-1,3,5-triazin-2-amine, 4-{4-Fluoro-2-[(2-methylpyridin-4-yl)methoxy]-phenyl}-N-{3-[(methylsulfonyl)methyl]phenyl}-1,3,5-triazin-2-amine, 4-{2-[(2-Chloropyridin-4-yl)methoxy]-4-fluorophenyl}-N-{3-[(methylsulfonyl)-methyl]phenyl}-1,3,5-triazin-2-amine, 4-[4-Fluoro-2-(pyridin-4-ylmethoxy)phenyl]-N-{3-[(methylsulfonyl)methyl]phenyl}-1,3,5-triazin-2-amine, 4-({5-Fluoro-2-[4-({3-[(methylsulfonyl)methyl]phenyl}amino)-1,3,5-triazin-2-yl]phenoxy}methyl)-benzonitrile, or their salts, solvates or salts of solvates.

The abovementioned definitions of radicals which have been detailed in general terms or in preferred ranges also apply to the end products of the formula (I) or (Ia) and, analogously, to the starting materials or intermediates required in each case for the preparation.

The invention furthermore relates to a process for the preparation of the compounds of formula (I) according to the invention, in which method an intermediate compound of formula (3),

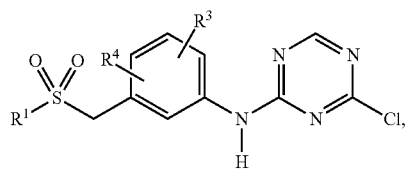

in which $R^1$, $R^3$ and $R^4$ are as defined for the compound of general formula (I),
is reacted with a compound of formula (4)

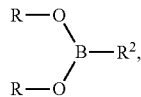

in which $R^2$ is as defined for the compound of general formula (I) according to the invention, and R represent, independently from each other, a hydrogen atom, or a $C_1$-$C_{10}$-alkyl- group or, alternatively, both R together form a R—R group, which is $C(CH_3)_2$—$C(CH_3)_2$, thus providing a compound of general formula (I) according to the invention and the resulting compounds of formula (I) according to the invention are optionally, if appropriate, reacted with the corresponding (i) solvents and/or (ii) bases or acids to the solvates, salts and/or solvates of the salts thereof.

Compounds of general formula (4) can be prepared analogously to known processes (review: D. G. Hall, Boronic Acids, 2005 WILEY-VCH Verlag GmbH & Co. KGaA, Weinheim, ISBN 3-527-30991-8 and references cited herein). Further, a wide variety of compounds of general formula (4) are commercially available.

The coupling reaction of compounds of formula (3) with compounds of formula (4) is catalyzed by Pd catalysts, e.g. by Pd(0) catalysts or by Pd(II) catalysts. Examples for Pd(0) catalysts are tetrakis(triphenylphosphine)palladium(0) [Pd(PPh₃)₄] or tris(dibenzylideneacetone)di-palladium(0) [Pd2(dba)₃], examples for Pd(II) catalysts dichlorobis(triphenylphosphine)-palladium(II) [Pd(PPh₃)₂C₁₂], palladium(II) acetate and triphenylphosphine or [1,1'-bis(diphenylphosphino)ferrocene]palladium dichloride (review: D. G. Hall, Boronic Acids, 2005 WILEY-VCH Verlag GmbH & Co. KGaA, Weinheim, ISBN 3-527-30991-8 and references cited therein).

This reaction is preferably carried out in aprotic or protic solvents, preferably in a mixture of aprotic and protic solvents, more preferably in solvents like, for example, 1,2-dimethoxyethane, dioxane, dimethlyformamid, tetrahydrofuran, or isopropanol with water (review: D. G. Hall, Boronic Acids, 2005 WILEY-VCH Verlag GmbH & Co. KGaA, Weinheim, ISBN 3-527-30991-8 and references cited therein).

Preferably the reaction is carried out in the presence of a suitable base, such as for example aqueous potassium carbonate, aqueous sodium bicarbonate or potassium phosphate (review: D. G. Hall, Boronic Acids, 2005 WILEY-VCH Verlag GmbH & Co. KGaA, Weinheim, ISBN 3-527-30991-8 and references cited therein).

The reaction is performed at temperatures ranging from room temperature (=20° C.) to the boiling point of the solvent. Further on, the reaction can be performed at temperatures above the boiling point using pressure tubes and a microwave oven. (review: D. G. Hall, Boronic Acids, 2005 WILEY-VCH Verlag GmbH & Co. KGaA, Weinheim, ISBN 3-527-30991-8 and references cited therein).

The reaction is preferably completed after 1 to 36 hours of reaction time.

Compounds of general formula (3) can be obtained as follows:

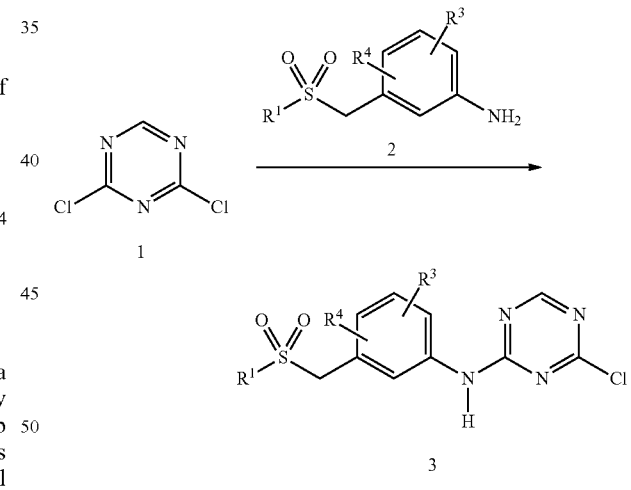

2,4-dichloro-1,3,5-triazine (1), which is known or can be prepared analogously to known processes, is reacted with suitable anilines (2) to give the corresponding 4-chloro-N-phenyl-1,3,5-triazin-2-amines (3).

This reaction can be carried out with one equivalent of the aniline (2) in an inert solvent like, for example, 1,2-dimethoxyethane, dioxane, dimethlyformamid, tetrahydrofuran, or an alcohol like, for example, isopropanol, or mixtures of such solvents. Preferably, the reaction is carried out at a temperature below 0° C. in such a way that the reaction mixture is kept homogenous. Preferred conditions use an additional base like for example triethylamine or N,N-diisopropylethylamine. The reaction is preferably completed after 1 to 6 hours.

A multitude of compounds of general formula (2) are commercially available. Further on, the compounds of formula (2) are known or can be prepared analogously to known processes. For example by reaction of suitable benzylchlorides or -bromides of formula (5) with suitable thiols of formula (6) under basic conditions the corresponding thioethers of formula (7) can be prepared (see for example. Sammond et al, Bioorg. Med. Chem. Lett. 2005, 15, 3519)

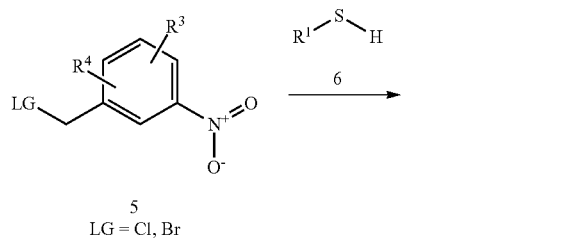

5
LG = Cl, Br

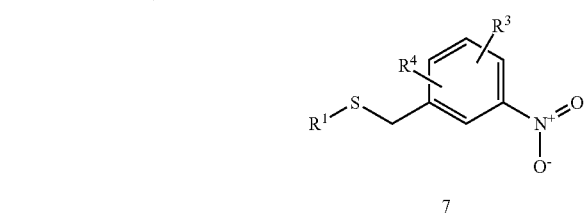

7

Oxidation of (7) gives the corresponding sulfones of formula (8). The oxidation can be carried out analogously to known processes (see for example: Sammond et al; Bioorg. Med. Chem. Lett. 2005, 15, 3519).

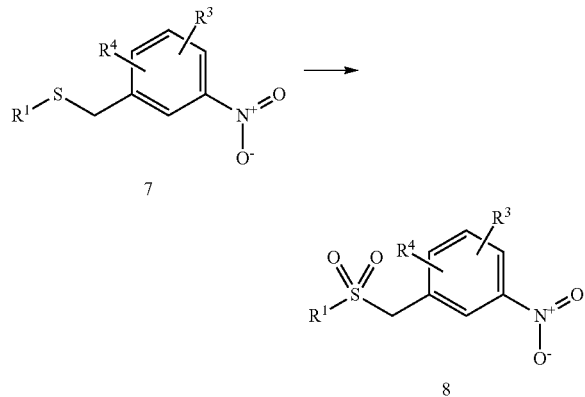

Finally, reduction of the nitro group gives the desired anilines of formula (2). The reduction can be carried out analogously to known processes (see for example: Sammond et al; Bioorg. Med. Chem. Lett. 2005, 15, 3519).

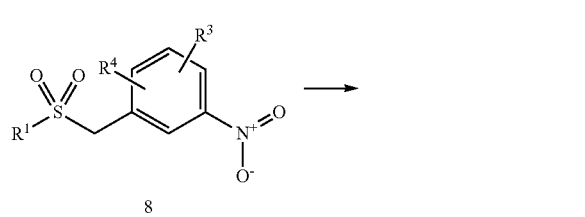

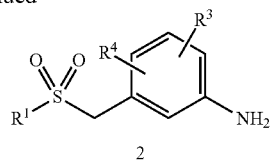

2

The preparation of the compounds of general formula (I) according to the invention can be illustrated by the following synthesis scheme:

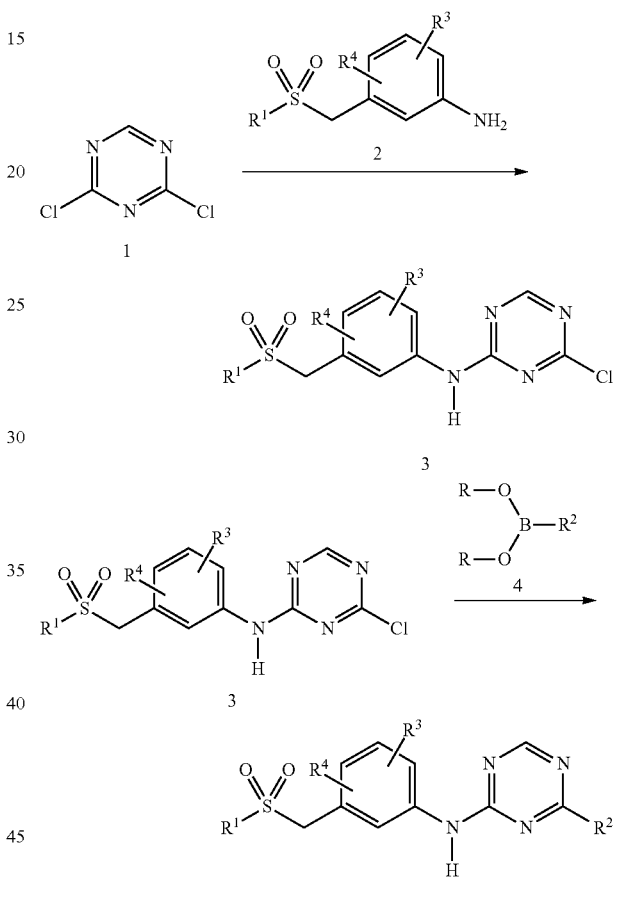

formula (I)

Compounds of general formula (Ia) can be prepared analogously.

In another embodiment the present invention concerns intermediate compounds of general formula (3)

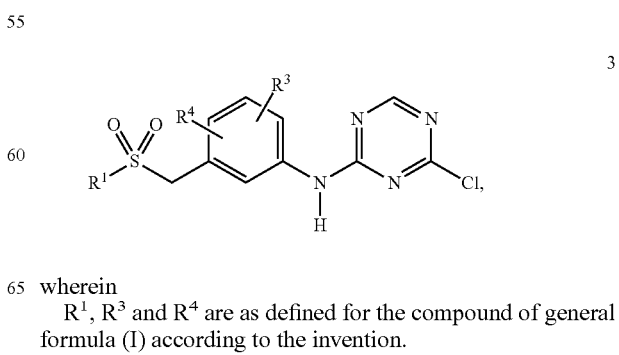

wherein
$R^1$, $R^3$ and $R^4$ are as defined for the compound of general formula (I) according to the invention.

In another embodiment the present invention concerns intermediate compounds of general formula (3a)

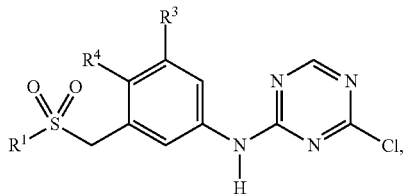

wherein
$R^1$, $R^3$ and $R^4$ are as defined for the compound of general formula (Ia) according to the invention.

The compounds according to the invention show a valuable pharmacological and pharmacokinetic spectrum of action which could not have been predicted.

They are therefore suitable for use as medicaments for the treatment and/or prophylaxis of disorders in humans and animals.

Within the scope of the present invention, the term "treatment" includes prophylaxis.

The pharmaceutical activity of the compounds according to the invention can be explained by their action as inhibitors of CDK9. Thus, the compounds according to the general formula (I) or (Ia) as well as pharmaceutically acceptable salts thereof are used as inhibitors for CDK9.

Furthermore, the compounds according to the invention show a particularly high potency (demonstrated by a low $IC_{50}$ value in the CDK9/CycT1 assay) for inhibiting CDK9 activity.

In context of the present invention, the $IC_{50}$ value with respect to CDK9 can be determined by the methods described in the method section below. Preferably, it is determined according to Method 1. ("CDK9/CycT1 kinase assay") described in the Materials and Method section below.

Surprisingly it turned out that the compounds according to the general formula (I) or (Ia) as well as pharmaceutically acceptable salts thereof selectively inhibit CDK9 in comparison to other cyclin-dependent protein kinases, preferably in comparison to CDK2. Thus, the compounds according to the general formula (I) or (Ia) as well as pharmaceutically acceptable salts thereof are preferably used as selective inhibitors for CDK9.

Compounds of the present invention according to general formula (I) or (Ia) show a significantly stronger CDK9 than CDK2 inhibition. Preferred compounds of the present invention show a CDK2 $IC_{50}$/CDK9 $IC_{50}$ ratio of more than 10, preferably of more than 20 and even more preferably of more than 30. The CDK9 $IC_{50}$ is determined according to Method 1., the CDK2 $IC_{50}$ according to Method 2, both described in more detail in the Materials and Method section below.

In context of the present invention, the $IC_{50}$ value with respect to CDK2 can be determined by the methods described in the method section below. Preferably, it is determined according to Method 2. ("CDK2/CycE kinase assay") described in the Materials and Method section below.

Further, preferred compounds of the present invention according to formula (I) or (Ia) mediate an anti-proliferative activity in tumor cell lines such as HeLa. In context of the present invention, the $IC_{50}$ values of the compounds with respect to this cell line is preferably determined according to Method 3. ("Proliferation Assay") described in the Materials and Method section below.

In addition, the compounds of the present invention according to formula (I) or (Ia) are characterized by improved pharmacokinetic properties, such as an increased apparent Caco-2 permeability ($P_{app}$ A-B) across Caco-2 cell monolayers, compared to the compounds known from the prior art.

Further, the compounds of the present invention according to formula (I) or (Ia) are characterized by improved pharmacokinetic properties, such as a decreased efflux ratio (efflux ratio=$P_{app}$ B-A/$P_{app}$ A-B) from the basal to apical compartment across Caco-2 cell monolayers, compared to the compounds known from the prior art.

In context of the present invention, the apparent Caco-2 permeability values from the basal to apical compartment ($P_{app}$ A-B) or the efflux ratio (defined as the ratio (($P_{app}$ B-A)/($P_{app}$ A-B)) are preferably determined according to Method 4. ("Caco-2 Permeation Assay") described in the Materials and Method section below.

A further subject matter of the present invention is the use of the compounds of general formula (I) or (Ia) according to the invention for the treatment and/or prophylaxis of disorders, preferably of disorders relating to or mediated by CDK9 activity, in particular of hyper-proliferative disorders, virally induced infectious diseases and/or of cardiovascular diseases, more preferably of hyper-proliferative disorders.

The compounds of the present invention may be used to inhibit the activity or expression of CDK9. Therefore, the compounds of formula (I) or (Ia) are expected to be valuable as therapeutic agents. Accordingly, in another embodiment, the present invention provides a method of treating disorders relating to or mediated by CDK9 activity in a patient in need of such treatment, comprising administering to the patient an effective amount of a compound of formula (I) or (Ia) as defined above. In certain embodiments, the disorders relating to CDK9 activity are hyper-proliferative disorders, virally induced infectious diseases and/or of cardiovascular diseases, more preferably hyper-proliferative disorders, particularly cancer.

The term "treating" or "treatment" as stated throughout this document is used conventionally, e.g., the management or care of a subject for the purpose of combating, alleviating, reducing, relieving, improving the condition of a disease or disorder, such as a carcinoma.

The term "subject" or "patient" includes organisms which are capable of suffering from a cell proliferative disorder or a disorder associated with reduced or insufficient programmed cell death (apoptosis) or who could otherwise benefit from the administration of a compound of the invention, such as human and non-human animals. Preferred humans include human patients suffering from or prone to suffering from a cell proliferative disorder or associated state, as described herein. The term "non-human animals" includes vertebrates, e.g., mammals, such as non-human primates, sheep, cow, dog, cat and rodents, e.g., mice, and non-mammals, such as chickens, amphibians, reptiles, etc.

The term "disorders relating to or mediated by CDK9" shall include diseases associated with or implicating CDK9 activity, for example the hyperactivity of CDK9, and conditions that accompany with these diseases. Examples of "disorders relating to or mediated by CDK9" include disorders resulting from increased CDK9 activity due to mutations in genes regulating CDK9 activity such as LARP7, HEXIM1/2 or 7sk snRNA, or disorders resulting from increased CDK9 activity due to activation of the CDK9/cyclinT/RNApolymerase II complex by viral proteins such as HIV-TAT or HTLV-TAX or disorders resulting from increased CDK9 activity due to activation of mitogenic signaling pathways.

The term "hyperactivity of CDK9" refers to increased enzymatic activity of CDK9 as compared to normal non-diseased cells, or it refers to increased CDK9 activity leading to unwanted cell proliferation, or to reduced or insufficient programmed cell death (apoptosis), or mutations leading to constitutive activation of CDK9.

The term "hyper-proliferative disorder" includes disorders involving the undesired or uncontrolled proliferation of a cell and it includes disorders involving reduced or insufficient programmed cell death (apoptosis). The compounds of the present invention can be utilized to prevent, inhibit, block, reduce, decrease, control, etc., cell proliferation and/or cell division, and/or produce apoptosis. This method comprises administering to a subject in need thereof, including a mammal, including a human, an amount of a compound of this invention, or a pharmaceutically acceptable salt, hydrate or solvate thereof which is effective to treat or prevent the disorder.

Hyper-proliferative disorders in the context of this invention include, but are not limited to, e.g., psoriasis, keloids and other hyperplasias affecting the skin, endometriosis, skeletal disorders, angiogenic or blood vessel proliferative disorders, pulmonary hypertension, fibrotic disorders, mesangial cell proliferative disorders, colonic polyps, polycystic kidney disease, benign prostate hyperplasia (BPH), and solid tumors, such as cancers of the breast, respiratory tract, brain, reproductive organs, digestive tract, urinary tract, eye, liver, skin, head and neck, thyroid, parathyroid, and their distant metastases. Those disorders also include lymphomas, sarcomas and leukemias.

Examples of breast cancer include, but are not limited to invasive ductal carcinoma, invasive lobular carcinoma, ductal carcinoma in situ, and lobular carcinoma in situ. Canine or feline mammary carcinoma.

Examples of cancers of the respiratory tract include, but are not limited to small-cell and non-small-cell lung carcinoma, as well as bronchial adenoma, pleuropulmonary blastoma, and mesothelioma.

Examples of brain cancers include, but are not limited to brain stem and hypophtalmic glioma, cerebellar and cerebral astrocytoma, glioblastoma, medulloblastoma, ependymoma, as well as neuroectodermal and pineal tumor.

Tumors of the male reproductive organs include, but are not limited to prostate and testicular cancer. Tumors of the female reproductive organs include, but are not limited to endometrial, cervical, ovarian, vaginal and vulvar cancer, as well as sarcoma of the uterus.

Tumors of the digestive tract include, but are not limited to anal, colon, colorectal, esophageal, gallbladder, gastric, pancreatic, rectal, small-intestine, and salivary gland cancers. Anal gland adenocarcinomas, mast cell tumors.

Tumors of the urinary tract include, but are not limited to bladder, penile, kidney, renal pelvis, ureter, urethral, and hereditary and sporadic papillary renal cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer. mast cell tumors. Head-and-neck cancers include, but are not limited to laryngeal, hypopharyngeal, nasopharyngeal, oropharyngeal cancer, lip and oral cavity cancer, and squamous cell cancer. Oral melanoma.

Lymphomas include, but are not limited to AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma. Malignant histiocytosis, fibrosarcoma, hemangiosarcoma, hemangiopericytoma, leiomyosarcoma.

Leukemias include, but are not limited to acute myeloid leukemia, acute lymphoblastic leukemia, chronic lymphocytic leukemia, chronic myelogenous leukemia, and hairy cell leukemia.

Fibrotic proliferative disorders, i.e. the abnormal formation of extracellular matrices, that may be treated with the compounds and methods of the present invention include lung fibrosis, atherosclerosis, restenosis, hepatic cirrhosis, and mesangial cell proliferative disorders, including renal diseases such as glomerulonephritis, diabetic nephropathy, malignant nephrosclerosis, thrombotic microangiopathy syndromes, transplant rejection, and glomerulopathies.

Other conditions in humans or other mammals that may be treated by administering a compound of the present invention include tumor growth, retinopathy, including diabetic retinopathy, ischemic retinal-vein occlusion, retinopathy of prematurity and age-related macular degeneration, rheumatoid arthritis, psoriasis, and bullous disorders associated with sub-epidermal blister formation, including bullous pemphigoid, erythema multiforme and dermatitis herpetiformis.

The compounds of the present invention may also be used to prevent and treat diseases of the airways and the lung, diseases of the gastrointestinal tract as well as diseases of the bladder and bile duct.

The disorders mentioned above have been well characterized in humans, but also exist with a similar etiology in other animals, including mammals, and can be treated by administering pharmaceutical compositions of the present invention.

In a further aspect of the present invention, the compounds according to the invention are used in a method for preventing and/or treating infectious diseases, in particular virally induced infectious diseases. The virally induced infectious diseases, including opportunistic diseases, are caused by retroviruses, hepadnaviruses, herpesviruses, flaviviridae, and/or adenoviruses. In a further preferred embodiment of this method, the retroviruses are selected from lentiviruses or oncoretroviruses, wherein the lentivirus is selected from the group comprising: HIV-1, HIV-2, FIV, BIV, SIVs, SHIV, CAEV, VMV or EIAV, preferably HIV-1 or HIV-2 and wherein the oncoretrovirus is selected from the group consisting of: HTLV-I, HTLV-II or BLV. In a further preferred embodiment of this method, the hepadnavirus is selected from HBV, GSHV or WHV, preferably HBV, the herpesivirus is selected from the group comprising: HSV I, HSV II, EBV, VZV, HCMV or HHV 8, preferably HCMV and the flaviviridae is selected from HCV, West nile or Yellow Fever.

The compounds according to general formula (I) or (Ia) are also useful for prophylaxis and/or treatment of cardiovascular diseases such as cardiac hypertrophy, adult congenital heart disease, aneurysm, stable angina, unstable angina, angina pectoris, angioneurotic edema, aortic valve stenosis, aortic aneurysm, arrhythmia, arrhythmogenic right ventricular dysplasia, arteriosclerosis, arteriovenous malformations, atrial fibrillation, Behcet syndrome, bradycardia, cardiac tamponade, cardiomegaly, congestive cardiomyopathy, hypertrophic cardiomyopathy, restrictive cardiomyopathy, cardiovascular disease prevention, carotid stenosis, cerebral hemorrhage, Churg-Strauss syndrome, diabetes, Ebstein's Anomaly, Eisenmenger complex, cholesterol embolism, bacterial endocarditis, fibromuscular dysplasia, congenital heart defects, heart diseases, congestive heart failure, heart valve diseases, heart attack, epidural hematoma, hematoma, subdural, Hippel-Lindau disease, hyperemia, hypertension, pulmonary hypertension, hypertrophic growth, left ventricular hypertrophy, right ventricular hypertrophy, hypoplastic left heart syndrome, hypotension, intermittent claudication, ischemic heart disease, Klippel-Trenaunay-Weber syndrome, lateral medullary syndrome, long QT syndrome mitral valve prolapse, moyamoya disease, mucocutaneous lymph node syndrome, myocardial infarction, myocardial ischemia, myocarditis, pericarditis, peripheral vascular diseases, phlebitis, polyarteritis nodosa, pulmonary atresia, Raynaud disease, restenosis, Sneddon syndrome, stenosis, superior vena cava syndrome, syndrome X, tachycardia, Takayasu's arteritis, hereditary hemorrhagic telangiectasia, telangiectasis, temporal arteritis, tetralogy of fallot, thromboangiitis obliterans, thrombosis, thromboembolism, tricuspid atresia, varicose veins, vascular diseases, vasculitis, vasospasm, ventricular fibrillation, Williams syndrome, peripheral vascular disease, varicose veins and leg ulcers, deep vein thrombosis, Wolff-Parkinson-White syndrome.

Preferred are cardiac hypertrophy, adult congenital heart disease, aneurysms, angina, angina pectoris, arrhythmias, cardiovascular disease prevention, cardiomyopathies, congestive heart failure, myocardial infarction, pulmonary hypertension, hypertrophic growth, restenosis, stenosis, thrombosis and arteriosclerosis.

A further subject matter of the present invention is the use of the compounds of general formula (I) or (Ia) according to the invention for the treatment and/or prophylaxis of disorders, in particular of the disorders mentioned above.

A further subject matter of the present invention are the compounds according to the invention for use in a method for the treatment and/or prophylaxis of the disorders mentioned above.

A further subject matter of the present invention is the use of the compounds according to the invention in the manufacture of a medicament for the treatment and/or prophylaxis of disorders, in particular the disorders mentioned above.

A further subject matter of the present invention is a method for the treatment and/or prophylaxis of disorders, in particular the disorders mentioned above, using an effective amount of the compounds according to the invention.

Another aspect of the present invention relates to pharmaceutical combinations comprising a compound of general formula (I) or (Ia) according to the invention in combination with at least one or more further active ingredients.

As used herein the term "pharmaceutical combination" refers to a combination of at least one compound of general formula (I) or (Ia) according to the invention as active ingredient together with at least one other active ingredient with or without further ingredients, carrier, diluents and/or solvents.

Another aspect of the present invention relates to pharmaceutical compositions comprising a compound of general formula (I) or (Ia) according to the invention in combination with an inert, nontoxic, pharmaceutically suitable adjuvant.

As used herein the term "pharmaceutical composition" refers to a galenic formulation of at least one pharmaceutically active agent together with at least one further ingredient, carrier, diluent and/or solvent.

Another aspect of the present invention relates to the use of the pharmaceutical combinations and/or the pharmaceutical compositions according to the invention for the treatment and/or prophylaxis of disorders, in particular of the disorders mentioned above.

Compounds of formula (I) or (Ia) may be administered as the sole pharmaceutical agent or in combination with one or more additional therapeutic agents where the combination causes no unacceptable adverse effects. This pharmaceutical combination includes administration of a single pharmaceutical dosage formulation which contains a compound of formula (I) or (Ia) and one or more additional therapeutic agents, as well as administration of the compound of formula (I) or (Ia) and each additional therapeutic agent in its own separate pharmaceutical dosage formulation. For example, a compound of formula (I) or (Ia) and a therapeutic agent may be administered to the patient together in a single oral dosage composition such as a tablet or capsule, or each agent may be administered in separate dosage formulations.

Where separate dosage formulations are used, the compound of formula (I) or (Ia) and one or more additional therapeutic agents may be administered at essentially the same time (e.g., concurrently) or at separately staggered times (e.g., sequentially).

In particular, the compounds of the present invention may be used in fixed or separate combination with other anti-tumor agents such as alkylating agents, anti-metabolites, plant-derived anti-tumor agents, hormonal therapy agents, topoisomerase inhibitors, camptothecin derivatives, kinase inhibitors, targeted drugs, antibodies, interferons and/or biological response modifiers, anti-angiogenic compounds, and other anti-tumor drugs. In this regard, the following is a non-limiting list of examples of secondary agents that may be used in combination with the compounds of the present invention:

Alkylating agents include, but are not limited to, nitrogen mustard N-oxide, cyclophosphamide, ifosfamide, thiotepa, ranimustine, nimustine, temozolomide, altretamine, apaziquone, brostallicin, bendamustine, carmustine, estramustine, fotemustine, glufosfamide, mafosfamide, bendamustin, and mitolactol; platinum-coordinated alkylating compounds include, but are not limited to, cisplatin, carboplatin, eptaplatin, lobaplatin, nedaplatin, oxaliplatin, and satraplatin;

Anti-metabolites include, but are not limited to, methotrexate, 6-mercaptopurine riboside, mercaptopurine, 5-fluorouracil alone or in combination with leucovorin, tegafur, doxifluridine, carmofur, cytarabine, cytarabine ocfosfate, enocitabine, gemcitabine, fludarabin, 5-azacitidine, capecitabine, cladribine, clofarabine, decitabine, eflornithine, ethynylcytidine, cytosine arabinoside, hydroxyurea, melphalan, nelarabine, nolatrexed, ocfosfite, disodium premetrexed, pentostatin, pelitrexol, raltitrexed, triapine, trimetrexate, vidarabine, vincristine, and vinorelbine;

Hormonal therapy agents include, but are not limited to, exemestane, Lupron, anastrozole, doxercalciferol, fadrozole, formestane, 11-beta hydroxysteroid dehydrogenase 1 inhibitors, 17-alpha hydroxylase/17,20 lyase inhibitors such as abiraterone acetate, 5-alpha reductase inhibitors such as finasteride and episteride, anti-estrogens such as tamoxifen citrate and fulvestrant, Trelstar, toremifene, raloxifene, lasofoxifene, letrozole, anti-androgens such as bicalutamide, flutamide, mifepristone, nilutamide, Casodex, and anti-progesterones and combinations thereof;

Plant-derived anti-tumor substances include, e.g., those selected from mitotic inhibitors, for example epothilones such as sagopilone, ixabepilone and epothilone B, vinblastine, vinflunine, docetaxel, and paclitaxel;

Cytotoxic topoisomerase inhibiting agents include, but are not limited to, aclarubicin, doxorubicin, amonafide, belotecan, camptothecin, 10-hydroxycamptothecin, 9-aminocamptothecin, diflomotecan, irinotecan, topotecan, edotecarin, epimbicin, etoposide, exatecan, gimatecan, lurtotecan, mitoxantrone, pirambicin, pixantrone, rubitecan, sobuzoxane, tafluposide, and combinations thereof;

Immunologicals include interferons such as interferon alpha, interferon alpha-2a, interferon alpha-2b, interferon beta, interferon gamma-1a and interferon gamma-nl, and other immune enhancing agents such as L19-IL2 and other IL2 derivatives, filgrastim, lentinan, sizofilan, TheraCys, ubenimex, aldesleukin, alemtuzumab, BAM-002, dacarbazine, daclizumab, denileukin, gemtuzumab, ozogamicin, ibritumomab, imiquimod, lenograstim, lentinan, melanoma vaccine (Corixa), molgramostim, sargramostim, tasonermin, tecleukin, thymalasin, tositumomab, Vimlizin, epratuzumab, mitumomab, oregovomab, pemtumomab, and Provenge; Merial melanoma vaccine Biological response modifiers are agents that modify defense mechanisms of living organisms or biological responses such as survival, growth or differentiation of tissue cells to direct them to have anti-tumor activity; such agents include, e.g., krestin, lentinan, sizofiran, picibanil, ProMune, and ubenimex;

Anti-angiogenic compounds include, but are not limited to, acitretin, aflibercept, angiostatin, aplidine, asentar, axitinib, recentin, bevacizumab, brivanib alaninat, cilengtide, combretastatin, DAST, endostatin, fenretinide, halofuginone, pazopanib, ranibizumab, rebimastat, removab, revlimid, sorafenib, vatalanib, squalamine, sunitinib, telatinib, thalidomide, ukrain, and vitaxin;

Antibodies include, but are not limited to, trastuzumab, cetuximab, bevacizumab, rituximab, ticilimumab, ipilimumab, lumiliximab, catumaxomab, atacicept, oregovomab, and alemtuzumab;

VEGF inhibitors such as, e.g., sorafenib, DAST, bevacizumab, sunitinib, recentin, axitinib, afli-bercept, telatinib, brivanib alaninate, vatalanib, pazopanib, and ranibizumab; Palladia EGFR (HER1) inhibitors such as, e.g., cetuximab, panitumumab, vectibix, gefitinib, erlotinib, and Zactima;

HER2 inhibitors such as, e.g., lapatinib, tratuzumab, and pertuzumab;

mTOR inhibitors such as, e.g., temsirolimus, sirolimus/Rapamycin, and everolimus;

c-Met inhibitors;

PI3K and AKT inhibitors;

CDK inhibitors such as roscovitine and flavopiridol;

Spindle assembly checkpoints inhibitors and targeted antimitotic agents such as PLK inhibitors, Aurora inhibitors (e.g. Hesperadin), checkpoint kinase inhibitors, and KSP inhibitors;

HDAC inhibitors such as, e.g., panobinostat, vorinostat, MS275, belinostat, and LBH589;

HSP90 and HSP70 inhibitors;

Proteasome inhibitors such as bortezomib and carfilzomib;

Serine/threonine kinase inhibitors including MEK inhibitors (such as e.g. RDEA 119) and Raf inhibitors such as sorafenib;

Farnesyl transferase inhibitors such as, e.g., tipifarnib;

Tyrosine kinase inhibitors including, e.g., dasatinib, nilotibib, DAST, bosutinib, sorafenib, bevacizumab, sunitinib, AZD2171, axitinib, aflibercept, telatinib, imatinib mesylate, brivanib alaninate, pazopanib, ranibizumab, vatalanib, cetuximab, panitumumab, vectibix, gefitinib, erlotinib, lapatinib, tratuzumab, pertuzumab, and c-Kit inhibitors; Palladia, masitinib Vitamin D receptor agonists;

Bcl-2 protein inhibitors such as obatoclax, oblimersen sodium, and gossypol;

Cluster of differentiation 20 receptor antagonists such as, e.g., rituximab;

Ribonucleotide reductase inhibitors such as, e.g., gemcitabine;

Tumor necrosis apoptosis inducing ligand receptor 1 agonists such as, e.g., mapatumumab;

5-Hydroxytryptamine receptor antagonists such as, e.g., rEV598, xaliprode, palonosetron hydro-chloride, granisetron, Zindol, and AB-1001;

Integrin inhibitors including alpha5-beta1 integrin inhibitors such as, e.g., E7820, JSM 6425, volociximab, and endostatin;

Androgen receptor antagonists including, e.g., nandrolone decanoate, fluoxymesterone, Android, Prost-aid, andromustine, bicalutamide, flutamide, apo-cyproterone, apo-flutamide, chlormadinone acetate, Androcur, Tabi, cyproterone acetate, and nilutamide;

Aromatase inhibitors such as, e.g., anastrozole, letrozole, testolactone, exemestane, amino-glutethimide, and formestane;

Matrix metalloproteinase inhibitors;

Other anti-cancer agents including, e.g., alitretinoin, ampligen, atrasentan bexarotene, bortezomib, bosentan, calcitriol, exisulind, fotemustine, ibandronic acid, miltefosine, mitoxantrone, I-asparaginase, procarbazine, dacarbazine, hydroxycarbamide, pegaspargase, pentostatin, tazaroten, velcade, gallium nitrate, canfosfamide, darinaparsin, and tretinoin.

The compounds of the present invention may also be employed in cancer treatment in conjunction with radiation therapy and/or surgical intervention.

Generally, the use of cytotoxic and/or cytostatic agents in combination with a compound or composition of the present invention will serve to:

(1) yield better efficacy in reducing the growth of a tumor or even eliminate the tumor as compared to administration of either agent alone, (2) provide for the administration of lesser amounts of the administered chemotherapeutic agents, (3) provide for a chemotherapeutic treatment that is well tolerated in the patient with fewer deleterious pharmacological complications than observed with single agent chemotherapies and certain other combined therapies, (4) provide for treating a broader spectrum of different cancer types in mammals, especially humans, (5) provide for a higher response rate among treated patients, (6) provide for a longer survival time among treated patients compared to standard chemotherapy treatments, (7) provide a longer time for tumor progression, and/or (8) yield efficacy and tolerability results at least as good as those of the agents used alone, compared to known instances where other cancer agent combinations produce antagonistic effects.

In a further embodiment of the present invention the compounds of the present invention may be used in fixed or separate combination with one or more other active ingredients such as: 131I-chTNT, abarelix, abiraterone, aclarubicin, aldesleukin, alemtuzumab, alitretinoin, altretamine, aminoglutethimide, amrubicin, amsacrine, anastrozole, arglabin, arsenic trioxide, asparaginase, azacitidine, basiliximab, BAY 80-6946, BAY 1000394, BAY 86-9766 (RDEA 119), belotecan, bendamustine, bevacizumab, bexarotene, bicalutamide, bisantrene, bleomycin, bortezomib, buserelin, busulfan, cabazitaxel, calcium folinate, calcium levofolinate, capecitabine, carboplatin, carmofur, carmustine, catumaxomab, celecoxib, celmoleukin, cetuximab, chlorambucil, chlormadinone, chlormethine, cisplatin, cladribine, clodronic acid, clofarabine, crisantaspase, cyclophosphamide, cyproterone, cytarabine, dacarbazine, dactinomycin, darbepoetin alfa, dasatinib, daunorubicin, decitabine, degarelix, denileukin diftitox, denosumab, deslorelin, dibrospidium chloride, docetaxel, doxifluridine, doxorubicin, doxorubicin+estrone, eculizumab, edrecolomab, elliptinium acetate, eltrombopag, endostatin, enocitabine, epirubicin, epitiostanol, epoetin alfa, epoetin beta, eptaplatin, eribulin, erlotinib, estradiol, estramustine, etoposide, everolimus, exemestane, fadrozole, filgrastim, fludarabine, fluorouracil, flutamide, formestane, fotemustine, fulvestrant, gallium nitrate, ganirelix, gefitinib, gemcitabine, gemtuzumab, glutoxim, goserelin, histamine dihydrochloride, histrelin, hydroxycarbamide, I-125 seeds, ibandronic acid, ibritumomab tiuxetan, idarubicin, ifosfamide, imatinib, imiquimod, improsulfan, interferon alfa, interferon beta, interferon gamma, ipilimumab, irinotecan, ixabepilone, lanreotide, lapatinib, lenalidomide, lenograstim, lentinan, letrozole, leuprorelin, levamisole, lisuride, lobaplatin, lomustine, lonidamine, masoprocol, medroxyprogesterone, megestrol, melphalan, mepitiostane, mercaptopurine, methotrexate, methoxsalen, Methyl aminolevulinate, methyltestosterone, mifamurtide, miltefosine, miriplatin, mitobronitol, mitoguazone, mitolactol, mitomycin, mitotane, mitoxantrone, nedaplatin, nelarabine, nilotinib, nilutamide, nimotuzumab, nimustine, nitracrine, ofatumumab, omeprazole, oprelvekin, oxaliplatin, p53 gene therapy, paclitaxel, palifermin, palladium-103 seed, pamidronic acid, panitumumab, pazopanib, pegaspargase, PEG-epoetin beta (methoxy PEG-epoetin beta), pegfilgrastim, peginterferon alfa-2b, pemetrexed, pentazocine, pentostatin, peplomycin, perfosfamide, picibanil, pirarubicin, plerixafor, plicamycin, poliglusam, polyestradiol phosphate, polysaccharide-K, porfimer sodium, pralatrexate, prednimustine, procarbazine, quinagolide, radium-223 chloride, raloxifene, raltitrexed, ranimustine, razoxane, regorafenib, risedronic acid, rituximab, romidepsin, romiplostim, sargramostim, sipuleucel-T, sizofiran, sobuzoxane, sodium glycididazole, sorafenib, streptozocin, sunitinib, talaporfin, tamibarotene, tamoxifen, tasonermin, teceleukin, tegafur, tegafur+gimeracil+oteracil, temoporfin, temozolomide, temsirolimus, teniposide, testosterone, tetrofosmin, thalidomide, thiotepa, thymalfasin, tioguanine, tocilizumab, topotecan, toremifene, tositumomab, trabectedin, trastuzumab, treosulfan, tretinoin, trilostane, triptorelin, trofosfamide, tryptophan, ubenimex, valrubicin, vandetanib, vapreotide, vemurafenib, vinblastine, vincristine, vindesine, vinflunine, vinorelbine, vorinostat, vorozole, yttrium-90 µlass microspheres, zinostatin, zinostatin stimalamer, zoledronic acid, zorubicin.

Furthermore, the compounds of formula (I) or (Ia) may be utilized, as such or in compositions, in research and diagnostics, or as analytical reference standards, and the like, which are well known in the art.

The compounds according to the invention can act systemically and/or locally. For this purpose, they can be administered in a suitable way, such as, for example, by the oral, parenteral, pulmonal, nasal, sublingual, lingual, buccal, rectal, dermal, transdermal, conjunctival or otic route, or as an implant or stent. For these administration routes, it is possible to administer the compounds according to the invention in suitable application forms.

Suitable for oral administration are administration forms which work as described in the prior art and deliver the compounds according to the invention rapidly and/or in modified form, which comprise the compounds according to the invention in crystalline and/or amorphous and/or dissolved form, such as, for example, tablets (coated or uncoated, for example tablets provided with enteric coatings or coatings whose dissolution is delayed or which are insoluble and which control the release of the compound according to the invention), tablets which rapidly decompose in the oral cavity, or films/wafers, films/lyophilizates, capsules (for example hard or soft gelatin capsules), sugar-coated tablets, granules, pellets, powders, emulsions, suspensions, aerosols or solutions.

Parenteral administration can take place with avoidance of an absorption step (for example intravenously, intraarterially, intracardially, intraspinally or intralumbally) or with inclusion of absorption (for example intramuscularly, subcutaneously, intracutaneously, percutaneously or intraperitoneally). Administration forms suitable for parenteral administration are, inter alia, preparations for injection and infusion in the form of solutions, suspensions, emulsions, lyophilizates or sterile powders.

Examples suitable for the other administration routes are pharmaceutical forms for inhalation (inter alia powder inhalers, nebulizers), nasal drops/solutions/sprays; tablets to be administered lingually, sublingually or buccally, films/wafers or capsules, suppositories, preparations for the eyes or ears, vaginal capsules, aqueous suspensions (lotions, shaking mixtures), lipophilic suspensions, ointments, creams, transdermal therapeutic systems (such as plasters, for example), milk, pastes, foams, dusting powders, implants or stents.

The compounds according to the invention can be converted into the stated administration forms. This can take place in a manner known per se by mixing with inert, nontoxic, pharmaceutically suitable adjuvants. These adjuvants include, inter alia, carriers (for example microcrystalline cellulose, lactose, mannitol), solvents (for example liquid polyethylene glycols), emulsifiers and dispersants or wetting agents (for example sodium dodecyl sulphate, polyoxysorbitan oleate), binders (for example polyvinylpyrrolidone), synthetic and natural polymers (for example albumin), stabilizers (for example antioxidants, such as, for example, ascorbic acid), colorants (for example inorganic pigments, such as, for example, iron oxides) and flavour- and/or odour-masking agents.

The present invention furthermore provides medicaments comprising at least one compound according to the invention, usually together with one or more inert, nontoxic, pharmaceutically suitable adjuvants, and their use for the purposes mentioned above.

When the compounds of the present invention are administered as pharmaceuticals, to humans or animals, they can be given per se or as a pharmaceutical composition containing, for example, 0.1% to 99.5% (more preferably 0.5% to 90%) of active ingredient in combination with one or more inert, nontoxic, pharmaceutically suitable adjuvants.

Regardless of the route of administration selected, the compounds of the invention of general formula (I) or (Ia) and/or the pharmaceutical composition of the present invention are formulated into pharmaceutically acceptable dosage forms by conventional methods known to those of skill in the art.

Actual dosage levels and time course of administration of the active ingredients in the pharmaceutical compositions of the invention may be varied so as to obtain an amount of the active ingredient which is effective to achieve the desired therapeutic response for a particular patient without being toxic to the patient.

Materials and Methods:

The percentage data in the following tests and examples are percentages by weight unless otherwise indicated; parts are parts by weight. Solvent ratios, dilution ratios and concentration data of liquid/liquid solutions are in each case based on volume.

Examples were tested in selected biological assays one or more times. When tested more than once, data are reported as either average values or as median values, wherein
- the average value, also referred to as the arithmetic mean value, represents the sum of the values obtained divided by the number of times tested, and
- the median value represents the middle number of the group of values when ranked in ascending or descending order. If the number of values in the data set is odd, the median is the middle value. If the number of values in the data set is even, the median is the arithmetic mean of the two middle values.

Examples were synthesized one or more times. When synthesized more than once, data from biological assays represent average values or median values calculated utilizing data sets obtained from testing of one or more synthetic batch.

The in vitro pharmacological properties of the compounds can be determined according to the following assays and methods.

1. CDK9/CycT1 Kinase Assay:

CDK9/CycT1-inhibitory activity of compounds of the present invention was quantified employing the CDK9/CycT1 TR-FRET assay as described in the following paragraphs:

Recombinant full-length His-tagged human CDK9 and CycT1, expressed in insect cells and purified by Ni-NTA affinity chromatography, were purchased from Invitrogen (Cat. No PV4131). As substrate for the kinase reaction biotinylated peptide biotin-Ttds-YISPLKSPYKISEG (C-terminus in amid form) was used which can be purchased e.g. form the company JERINI Peptide Technologies (Berlin, Germany). For the assay 50 nl of a 100fold concentrated solution of the test compound in DMSO was pipetted into a black low volume 384well microtiter plate (Greiner Bio-One, Frickenhausen, Germany), 2 µl of a solution of CDK9/CycT1 in aqueous assay buffer [50 mM Tris/HCl pH 8.0, 10 mM $MgCl_2$, 1.0 mM dithiothreitol, 0.1 mM sodium ortho-vanadate, 0.01% (v/v) Nonidet-P40 (Sigma)] were added and the mixture was incubated for 15 min at 22° C. to allow pre-binding of the test compounds to the enzyme before the start of the kinase reaction. Then the kinase reaction was started by the addition of 3 µl of a solution of adenosine-tri-phosphate (ATP, 16.7 µM=>final conc. in the 5 µl assay volume is 10 µM) and substrate (1.67 µM=>final conc. in the 5 µl assay volume is 1 µM) in assay buffer and the resulting mixture was incubated for a reaction time of 25 min at 22° C. The concentration of CDK9/CycT1 was adjusted depending of the activity of the enzyme lot and was chosen appropriate to have the assay in the linear range, typical concentrations were in the range of 1 µg/ml. The reaction was stopped by the addition of 5 µl of a solution of TR-FRET detection reagents (0.2 µM streptavidine-XL665 [Cisbio Bioassays, Codolet, France] and 1 nM anti-RB(pSer807/pSer811)-antibody from BD Pharmingen [#558389] and 1.2 nM LANCE EU-W1024 labeled anti-mouse IgG antibody [Perkin-Elmer, product no. AD0077]) in an aqueous EDTA-solution (100 mM EDTA, 0.2% (w/v) bovine serum albumin in 100 mM HEPES/NaOH pH 7.0).

The resulting mixture was incubated 1 h at 22° C. to allow the formation of complex between the phosphorylated biotinylated peptide and the detection reagents. Subsequently the amount of phosphorylated substrate was evaluated by measurement of the resonance energy transfer from the Eu-chelate to the streptavidine-XL. Therefore, the fluorescence emissions at 620 nm and 665 nm after excitation at 350 nm was measured in a HTRF reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 µM to 0.1 nM (20 µM, 5.9 µM, 1.7 µM, 0.51 µM, 0.15 µM, 44 nM, 13 nM, 3.8 nM, 1.1 nM, 0.33 nM and 0.1 nM, the dilution series prepared separately before the assay on the level of the 100fold concentrated solutions in DMSO by serial 1:3.4 dilutions) in duplicate values for each concentration and IC50 values were calculated by a 4 parameter fit.

2. CDK2/CycE Kinase Assay:

CDK2/CycE-inhibitory activity of compounds of the present invention was quantified employing the CDK2/CycE TR-FRET assay as described in the following paragraphs:

Recombinant fusion proteins of GST and human CDK2 and of GST and human CycE, expressed in insect cells (Sf9) and purified by Glutathion-Sepharose affinity chromatography, were purchased from ProQinase GmbH (Freiburg, Germany). As substrate for the kinase reaction biotinylated peptide biotin-Ttds-YISPLKSPYKISEG (C-terminus in amid form) was used which can be purchased e.g. form the company JERINI Peptide Technologies (Berlin, Germany).

For the assay 50 nl of a 100fold concentrated solution of the test compound in DMSO was pipetted into a black low volume 384well microtiter plate (Greiner Bio-One, Frickenhausen, Germany), 2 µl of a solution of CDK2/CycE in aqueous assay buffer [50 mM Tris/HCl pH 8.0, 10 mM $MgCl_2$, 1.0 mM dithiothreitol, 0.1 mM sodium ortho-vanadate, 0.01% (v/v) Nonidet-P40 (Sigma)] were added and the mixture was incubated for 15 mM at 22° C. to allow pre-binding of the test compounds to the enzyme before the start of the kinase reaction. Then the kinase reaction was started by the addition of 3 µl of a solution of adenosine-tri-phosphate (ATP, 16.7 µM=>final conc. in the 5 it assay volume is 10 µM) and substrate (1.25 µM=>final conc. in the 5 it assay volume is 0.75 µM) in assay buffer and the resulting mixture was incubated for a reaction time of 25 mM at 22° C. The concentration of CDK2/CycE was adjusted depending of the activity of the enzyme lot and was chosen appropriate to have the assay in the linear range, typical concentrations were in the range of 130 ng/ml. The reaction was stopped by the addition of 5 it of a solution of TR-FRET detection reagents (0.2 µM streptavidine-XL665 [Cisbio Bioassays, Codolet, France] and 1 nM anti-RB(pSer807/pSer811)-antibody from BD Pharmingen [#558389] and 1.2 nM LANCE EU-W1024 labeled anti-mouse IgG antibody [Perkin-Elmer, product no. AD0077]) in an aqueous EDTA-solution (100 mM EDTA, 0.2% (w/v) bovine serum albumin in 100 mM HEPES/NaOH pH 7.0).

The resulting mixture was incubated 1 h at 22° C. to allow the formation of complex between the phosphorylated biotinylated peptide and the detection reagents. Subsequently the amount of phosphorylated substrate was evaluated by measurement of the resonance energy transfer from the Eu-chelate to the streptavidine-XL. Therefore, the fluorescence emissions at 620 nm and 665 nm after excitation at 350 nm was measured in a TR-FRET reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 μM to 0.1 nM (20 μM, 5.9 μM, 1.7 μM, 0.51 μM, 0.15 μM, 44 nM, 13 nM, 3.8 nM, 1.1 nM, 0.33 nM and 0.1 nM, the dilution series prepared separately before the assay on the level of the 100fold concentrated solutions in DMSO by serial 1:3.4 dilutions) in duplicate values for each concentration and IC50 values were calculated by a 4 parameter fit.

3. Proliferation Assay:

Cultivated tumour cells (NCI-H460, human non-small cell lung carcinoma cells, ATCC HTB-177; DU 145, hormone-independent human prostate carcinoma cells, ATCC HTB-81; HeLa-MaTu, human cervical carcinoma cells, EPO-GmbH, Berlin; HeLa-MaTu-ADR, multidrug-resistant human cervical carcinoma cells, EPO-GmbH, Berlin; HeLa human cervical tumour cells, ATCC CCL-2; Caco-2 human colorectal carcinoma, ATCC HTB-37; B16F10 mouse melanoma cells, ATCC CRL-6475) were plated at a density of 5000 cells/well (DU145, HeLa-MaTu-ADR), 3000 cells/well (NCI-H460, HeLa-MaTu, HeLa), 1500 cells/well (Caco-2), or 1000 cells/well (B16F10) in a 96-well multititer plate in 200 μL of their respective growth medium supplemented 10% fetal calf serum. After 24 hours, the cells of one plate (zero-point plate) were stained with crystal violet (see below), while the medium of the other plates was replaced by fresh culture medium (200 μl), to which the test substances were added in various concentrations (0 μM, as well as in the range of 0.001-10 μM; the final concentration of the solvent dimethyl sulfoxide was 0.5%). The cells were incubated for 4 days in the presence of test substances. Cell proliferation was determined by staining the cells with crystal violet: the cells were fixed by adding 20 μl/measuring point of an 11% glutaric aldehyde solution for 15 minutes at room temperature. After three washing cycles of the fixed cells with water, the plates were dried at room temperature. The cells were stained by adding 100 μl/measuring point of a 0.1% crystal violet solution (pH 3.0). After three washing cycles of the stained cells with water, the plates were dried at room temperature. The dye was dissolved by adding 100 μl/measuring point of a 10% acetic acid solution. The extinction was determined by photometry at a wavelength of 595 nm. The change of cell number, in percent, was calculated by normalization of the measured values to the extinction values of the zero-point plate (=0%) and the extinction of the untreated (0 μm) cells (=100%). The IC50 values were determined by means of a 4 parameter fit.

4. Caco-2 Permeation Assay:

Caco-2 cells (purchased from DSMZ Braunschweig, Germany) were seeded at a density of 4.5×10⁴ cells per well on 24 well insert plates, 0.4 μm pore size, and grown for 15 days in DMEM medium supplemented with 10% fetal bovine serum, 1% GlutaMAX (100×, GIBCO), 100 U/ml penicillin, 100 μg/ml streptomycin (GIBCO) and 1% non essential amino acids (100×). Cells were maintained at 37° C. in a humified 5% CO2 atmosphere. Medium was changed every 2-3 day. Before running the permeation assay, the culture medium was replaced by a FCS-free hepes-carbonate transport buffer (pH 7.2). For assessment of monolayer integrity the transepithelial electrical resistance (TEER) was measured. Test compounds were predissolved in DMSO and added either to the apical or basolateral compartment in final concentration of 2 μM in transport buffer. Before and after 2 h incubation at 37° C. samples were taken from both compartments. Analysis of compound content was done after precipitation with methanol by LC/MS/MS analysis. Apparent permeability (Papp) was calculated in the apical to basolateral (Papp A→B) and basolateral to apical (Papp B→A) directions. The apparent permeability was calculated using following equation:

$$Papp=(Vr/Po)(1/S)(P2/t)$$

Where Vr is the volume of medium in the receiver chamber, Po is the measured peak area or height of the test drug in the donor chamber at t=o, S the surface area of the monolayer, P2 is the measured peak area of the test drug in the acceptor chamber after 2 h of incubation, and t is the incubation time. The efflux ratio basolateral (B) to apical (A) was calculated by dividing the Papp B-A by the Papp A-B. In addition the compound recovery was calculated. The following reference compounds were used for the classification of the permeability class: Antipyrine, Pyrazosin, Verapamil, Fluvastatin, Cimetidine, Ranitidine, Atenolol, Sulfasalazine.

PREPARATIVE EXAMPLES

Syntheses of Compounds

The syntheses of the inventive disubstituted triazines according to the present invention were preferably carried out according to the general synthetic sequence, shown in scheme 1.

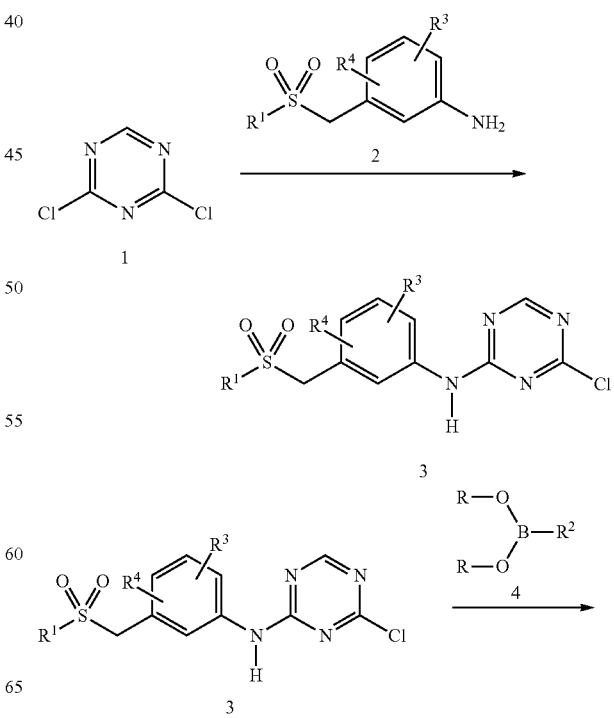

-continued

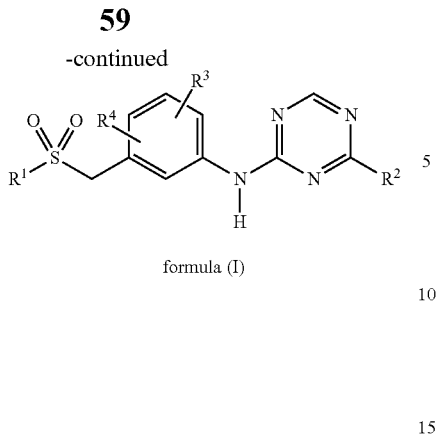

formula (I)

In the first step 2,4-dichloro-1,3,5-triazine (1) is reacted with suitable anilines (2) to give the corresponding 4-chloro-N-phenyl-1,3,5-triazin-2-amines (3). The reaction is carried out with one equivalent of the aniline (2) in an inert solvent like DMF, THF, DME, dioxane or an alcohol like isopropanol, or mixtures of such solvents. Preferably, the reaction is carried out at a temperature below 0° C. in such a way that the reaction mixture is kept homogenous. Preferred conditions use an additional base like triethylamine or N,N-diisopropylethylamine.

In the second step the intermediate 4-chloro-N-phenyl-1,3,5-triazin-2-amine (3) is reacted with a boronic acid derivative $R^2$—$B(OR)_2$ (4) to give compounds of formula (I) or (Ia). The boronic acid derivative (4) may be a boronic acid (R=H) or an ester of the boronic acid, e.g. its isopropyl ester (R=CH($CH_3$)$_2$), preferably an ester derived from pinacol in which the boronic acid intermediate forms a 2-aryl-4,4,5,5-tetramethyl-1,3,2-dioxaborolane (R—R=C($CH_3$)$_2$—C($CH_3$)$_2$—).

The coupling reaction is catalyzed by Pd catalysts, e.g. by Pd(0) catalysts like tetrakis(triphenylphosphine)palladium (0) [Pd(PPh$_3$)4], tris(dibenzylideneacetone)di-palladium(0) [Pd2(dba)$_3$], or by Pd(II) catalysts like dichlorobis(triphenylphosphine)-palladium(II) [Pd(PPh$_3$)$_2$Cl$_2$], palladium(II) acetate and triphenylphosphine or by [1,1'-bis(diphenylphosphino)ferrocene]palladium dichloride.

The reaction is preferably carried out in a mixture of a solvent like 1,2-dimethoxyethane, dioxane, DMF, DME, THF, or isopropanol with water and in the presence of a base like aqueous potassium carbonate, aqueous sodium bicarbonate or potassium phosphate.

Preparation of Compounds:

Abbreviations Used in the Description of the Chemistry and in the Examples that Follow are:

CDCl$_3$ (deuterated chloroform); cHex (cyclohexane); DCM (dichloromethane); DIPEA (di-iso-propylethylamine); DMF (dimethylformamide); DMSO (dimethyl sulfoxide); eq (equivalent); ES (electrospray); EtOAc (ethyl acetate); EtOH (ethanol); iPrOH (iso-propanol); MeOH (methanol); MS (mass spectrometry); NMR (nuclear magnetic resonance); Pd(dppf)C$_{12}$ ([1,1'-bis(diphenylphosphino)ferrocene] dichloro palladium(II) complex with dichloromethane); iPrOH (iso-propanol); RT (room temperature); sat. aq. (saturated aqueous); SiO$_2$ (silica gel); TFA (trifluoroacetic acid); THF (tetrahydrofuran).

The IUPAC names of the examples were generated using the program 'ACD/Name batch version 12.0' from ACD LABS.

Example 1

4-(4,5-Difluoro-2-methoxyphenyl)-N-{3-[(methylsulfonyl)methyl]phenyl}-1,3,5-triazin-2-amine

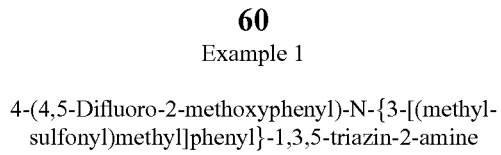

Preparation of Intermediate 1.1:
1-[(Methylsulfanyl)methyl]-3-nitrobenzene

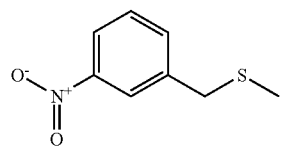

Sodium methanethiolate (13.5 g; 192 mmol) was added in two portions to a stirred solution of 1-(chloromethyl)-3-nitrobenzene (30.0 g; 175 mmol) in ethanol (360 ml) at −15° C. The cold bath was removed and the batch was stirred at room temperature for 3 hours. The batch was diluted with brine and extracted with ethyl acetate (2×). The combined organic phases were washed with water, dried (sodium sulfate), filtered and concentrated to give the desired product (32.2 g) that was used without further purification.

$^1$H NMR (400 MHz, CDCl$_3$, 300K) δ=8.18 (m, 1H), 8.11 (m, 1H), 7.66 (m, 1H), 7.50 (m, 1H), 3.75 (s, 2H), 2.01 (s, 3H).

Preparation of Intermediate 1.2:
1-[(Methylsulfonyl)methyl]-3-nitrobenzene

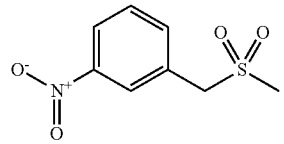

3-Chlorobenzenecarboperoxoic acid (77%; 26.9 g; 120 mmol) was added to a stirred solution of 1-[(methylsulfanyl) methyl]-3-nitrobenzene (10.0 g) in DCM (1305 ml) at 0° C. The batch was stirred at 0° C. for 30 minutes and then 2.5 hours at room temperature. The batch was diluted with water (300 ml) before sodium bicarbonate (11.0 g) was added. The batch was extracted with DCM (2×). The combined organic phases were filtered using a Whatman filter and concentrated. The residue was purified by chromatography (DCM/ethanol 95:5) and finally recrystallized from ethyl acetate to give the desired product (6.2 g; 28.9 mmol)

$^1$H NMR (400 MHz, d$_6$-DMSO, 300K) δ=8.28 (m, 1H), 8.22 (m, 1H), 7.83 (m, 1H), 7.69 (m, 1H), 4.68 (s, 2H), 2.93 (s, 3H).

Preparation of Intermediate 1.3:
3-[(Methylsulfonyl)methyl]aniline

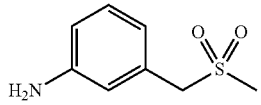

Titanium(III)chloride solution (about 15%) in about 10% hydrochloric acid (MERCK (MDA) INCL SCHUCHARDT, 162 ml) was added to a stirred solution of 1-[(methylsulfonyl)methyl]-3-nitrobenzene (5.1 g; 23.8 mmol) in THF (250 ml) at room temperature and the batch was stirred for 16 hours. By adding 1N sodium hydroxide solution the pH value of the reaction mixture was raised to 10 before the batch was extracted with ethyl acetate (2×). The combined organic phases were washed with brine, filtered using a Whatman filter and concentrated to give the desired product (4.5 g) that was used without further purification.

$^1$H NMR (400 MHz, $d_6$-DMSO, 300K) δ=6.97 (m, 1H), 6.51 (m, 3H), 5.13 (br, 2H), 4.23 (s, 2H), 2.83 (s, 3H).

Preparation of Intermediate 1.4: 4-Chloro-N-{3-[(methylsulfonyl)methyl]phenyl}-1,3,5-triazin-2-amine

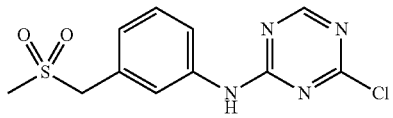 [SMILES: CS(=O)(=O)Cc1cccc(Nc2ncnc(Cl)n2)c1]

DIPEA (3.7 ml; 21.3 mmol) was added to a stirred solution of 2,4-dichloro-1,3,5-triazine (1.60 g; 10.7 mmol; ABCR GmbH & CO. KG) in THF/i-PrOH (1:1; 20 ml) at −40° C. Then a suspension of 3-[(methylsulfonyl)methyl]aniline (1.97 g; 10.7 mmol) in THF/i-PrOH (1:1; 10 ml) was added at this temperature. Under stirring the temperature of the reaction mixture was slowly raised over 3 hours to 0° C. The batch was concentrated in vacuo to give the crude product (5.2 g) that was used without further purification.

| System: | Waters Acquity UPLC-MS: Binary Solvent Manager, Sample Manager/Organizer, Column Manager, PDA, ELSD, SQD 3001 |
|---|---|
| Column: | Acquity UPLC BEH C18 1.7 50 × 2.1 mm |
| Solvent: | A1 = $H_2O$ + 0.1% HCOOH |
| | B1 = Acetonitrile |
| Gradient: | 0-1.6 min 1-99% B, 1.6-2.0 min 99% B |
| Flow: | 0.8 mL/min |
| Temperatuer: | 60° C. |
| Injektion: | 2.0 µl |
| Detection: | DAD scan range 210-400 nm –> Peaktable ELSD |
| Method: | MS ESI+, ESI– Switch |
| | A1 + B1 = C:\MassLynx\Mass__160__1000.flp |
| Retention: | 0.78 min |
| MS(ES+): | m/z = 299 [M + H] |

Preparation of End Product:

A batch with crude 4-chloro-N-{3-[(methylsulfonyl)methyl]phenyl}-1,3,5-triazin-2-amine (125 mg), (4,5-difluoro-2-methoxyphenyl)boronic acid (78 mg; 0.41 mmol; Aldrich Chemical Company Inc. Chemical Company Inc.) and tetrakis(triphenylphosphin)palladium(0) (73 mg; 0.06 mmol) in 1,2-dimethoxyethane (2.0 ml) and 2 M solution of potassium carbonate (0.42 ml) was degassed using argon. The batch was stirred under argon for 2.5 hours at 100° C. After cooling the batch was diluted with ethyl acetate and washed with brine. The organic phase was filtered using a Whatman filter and concentrated. The residue was purified by preparative HPLC to give the desired product (48 mg; 0.12 mmol).

| System: | Waters Autopurificationsystem: Pump 2545, Sample Manager 2767, CFO, DAD 2996, ELSD 2424, SQD 3001 |
|---|---|
| Column: | XBrigde C18 5 µm 100 × 30 mm |
| Solvent: | A = $H_2O$ + 0.1% HCOOH |
| | B = Acetonitrile |
| Gradient: | 0-1 min 1% B, 1-8 min 1-99% B, 8-10 min 99% B |
| Flow: | 50 mL/min |
| Temperatuer: | RT |
| Solution: | Max. 250 mg/max. 2.5 mL DMSO o. DMF |
| Injektion: | 1 × 2.5 mL |
| Detection: | DAD scan range 210-400 nm |
| | MS ESI+, ESI–, scan range 160-1000 m/z |

$^1$H NMR (400 MHz, $d_6$-DMSO, 300K) δ=10.40 (s, 1H), 8.78 (s, 1H), 7.80 (br, 3H), 7.34 (m, 2H), 7.09 (m, 1H), 4.42 (s, 2H), 3.83 (s, 3H), 2.88 (s, 3H).

Example 2

4-(3,4-Difluoro-2-methoxyphenyl)-N-{3-[(methylsulfonyl)methyl]phenyl}-1,3,5-triazin-2-amine

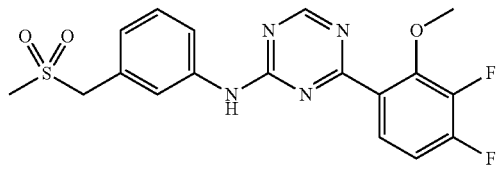 [SMILES: COc1c(-c2ncnc(Nc3cccc(CS(C)(=O)=O)c3)n2)ccc(F)c1F]

Example 2 was prepared under similar conditions as described in the preparation of Example 1 using crude 4-chloro-N-{3-[(methylsulfonyl)methyl]phenyl}-1,3,5-triazin-2-amine and (3,4-difluoro-2-methoxyphenyl)boronic acid (AOBChem USA). The batch was purified by preparative HPLC:

| System: | Waters Autopurificationsystem: Pump 254, Sample Manager 2767, CFO, DAD 2996, ELSD 2424, SQD 3001 |
|---|---|
| Column: | XBrigde C18 5 µm 100 × 30 mm |
| Solvent: | A = $H_2O$ + 0.1% HCOOH |
| | B = MeOH |
| Gradient: | 0-1 min 50% B, 1-8 min 50-90% B, 8-8.1 min 90-100% B, 8.1-10 min 100% B |
| Flow: | 50 mL/min |
| Temperature: | RT |
| Detektion: | DAD scan range 210-400 nm |
| | MS ESI+, ESI–, scan range 160-1000 m/z |
| | ELSD |
| Retention: | 7.6-7.9 min |

$^1$H NMR (400 MHz, $CDCl_3$, 300K) δ=8.83 (s, 1H), 7.87 (m, 1H), 7.71 (m, 2H), 7.43 (m, 1H), 7.35 (m, 1H), 7.18 (m, 1H), 7.02 (m, 1H), 4.28 (s, 2H), 4.02 (s, 3H), 2.81 (s, 3H).

Example 3

4-(4-Fluoro-2-methoxyphenyl)-N-{3-[(methylsulfonyl)methyl]phenyl}-1,3,5-triazin-2-amine

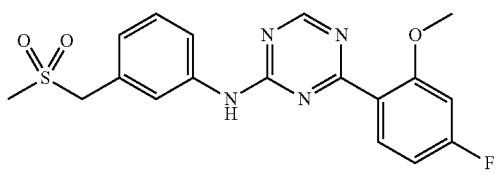 [SMILES: COc1cc(F)ccc1-c1ncnc(Nc2cccc(CS(C)(=O)=O)c2)n1]

Example 3 was prepared under similar conditions as described in the preparation of Example 1 using crude 4-chloro-N-{3-[(methylsulfonyl)methyl]phenyl}-1,3,5-triazin-2-amine and (4-fluoro-2-methoxyphenyl)boronic acid (Aldrich Chemical Company Inc.). The batch was purified by preparative HPLC:

| | |
|---|---|
| System: | Waters Autopurificationsystem: Pump 254, Sample Manager 2767, CFO, DAD 2996, ELSD 2424, SQD 3001 |
| Column: | XBrigde C18 5 µm 100 × 30 mm |
| Solvent: | A = H₂O + 0.1% HCOOH |
| | B = Acetonitril |
| Gradient: | 0-1 min 30% B, 1-8 min 30-70% B |
| Flow: | 50 mL/min |
| Temperature: | RT |
| Detektion: | DAD scan range 210-400 nm |
| | MS ESI+, ESI−, scan range 160-1000 m/z |
| | ELSD |
| Retention: | 5.8-6.2 min |

$^1$H NMR (400 MHz, CDCl$_3$, 300K) δ=8.82 (s, 1H), 7.96 (br, 1H), 7.76 (m, 2H), 7.42 (m, 2H), 7.16 (m, 1H), 6.77 (m, 2H), 4.27 (s, 2H), 3.94 (s, 3H), 2.80 (s, 3H).

Example 4

4-[2-(Benzyloxy)-4-fluorophenyl]-N-{3-[(methylsulfonyl)methyl]phenyl}-1,3,5-triazin-2-amine

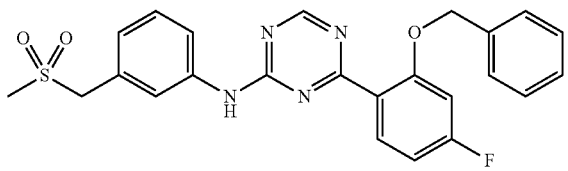 [SMILES: CS(=O)(=O)Cc1cccc(Nc2ncnc(-c3ccc(F)cc3OCc3ccccc3)n2)c1]

Example 4 was prepared under similar conditions as described in the preparation of Example 1 using crude 4-chloro-N-{3-[(methylsulfonyl)methyl]phenyl}-1,3,5-triazin-2-amine and [2-(benzyloxy)-4-fluorophenyl]boronic acid (ABCR GmbH & CO. KG). The batch was purified by preparative HPLC:

| | |
|---|---|
| System: | Waters Autopurificationsystem: Pump 254, Sample Manager 2767, CFO, DAD 2996, ELSD 2424, SQD 3001 |
| Column: | XBrigde C18 5 µm 100 × 30 mm |
| Solvent: | A = H₂O + 0.2% NH₃ |
| | B = Acetonitril |
| Gradient: | 0-1 min 30% B, 1-8 min 30-70% B |
| Flow: | 50 mL/min |
| Temperature: | RT |
| Detektion: | DAD scan range 210-400 nm |
| | MS ESI+, ESI−, scan range 160-1000 m/z |
| | ELSD |
| Retention: | 6.3-6.75 min |

$^1$H NMR (400 MHz, CDCl$_3$, 300K) δ=8.83 (s, 1H), 7.96 (m, 1H), 7.77 (br, 1H), 7.67 (m, 1H), 7.44 (m, 3H), 7.32 (m, 4H), 7.12 (m, 1H), 6.80 (m, 2H), 5.20 (s, 2H), 4.20 (s, 2H), 2.76 (s, 3H).

Example 5

4-[4-Fluoro-2-(propan-2-yloxy)phenyl]-N-{3-[(methylsulfonyl)methyl]phenyl}-1,3,5-triazin-2-amine

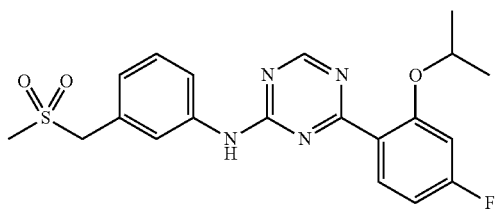 [SMILES: CC(C)Oc1cc(F)ccc1-c1ncnc(Nc2cccc(CS(C)(=O)=O)c2)n1]

Example 5 was prepared under similar conditions as described in the preparation of Example 1 using crude 4-chloro-N-{3-[(methylsulfonyl)methyl]phenyl}-1,3,5-triazin-2-amine and [4-fluoro-2-(propan-2-yloxy)phenyl]boronic acid (Aldrich Chemical Company Inc.). The batch was purified by preparative HPLC.

| | |
|---|---|
| System: | Waters Autopurificationsystem: Pump 254, Sample Manager 2767, CFO, DAD 2996, ELSD 2424, SQD 3001 |
| Column: | XBrigde C18 5 µm 100 × 30 mm |
| Solvent: | A = H₂O + 0.1% HCOOH |
| | B = MeOH |
| Gradient: | 0-1 min 50% B, 1-8 min 50-90% B, 8-8.1 min 90-100% B, 8.1-10 min 100% B |
| Flow: | 50 mL/min |
| Temperature: | RT |
| Detektion: | DAD scan range 210-400 nm |
| | MS ESI+, ESI−, scan range 160-1000 m/z |
| | ELSD |
| Retention: | 4.6-5.1 min |

$^1$H NMR (400 MHz, CDCl$_3$, 300K) δ=8.80 (s, 1H), 7.77 (m, 3H), 7.42 (m, 2H), 7.16 (m, 1H), 6.75 (m, 2H), 4.55 (m, 1H), 4.26 (s, 2H), 2.79 (s, 3H), 1.34 (d, 6H).

Example 6

4-(2,2-Difluoro-1,3-benzodioxol-4-yl)-N-{3-[(methylsulfonyl)methyl]phenyl}-1,3,5-triazin-2-amine

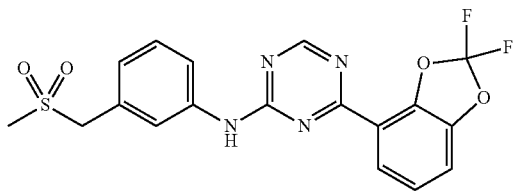 [SMILES: CS(=O)(=O)Cc1cccc(Nc2ncnc(-c3cccc4c3OC(F)(F)O4)n2)c1]

Example 6 was prepared under similar conditions as described in the preparation of Example 1 using crude 4-chloro-N-{3-[(methylsulfonyl)methyl]phenyl}-1,3,5-triazin-2-amine and (2,2-difluoro-1,3-benzodioxol-4-yl)boronic acid (Aalen Chemical Co., Ltd.). The batch was purified by preparative HPLC:

| System: | Waters Autopurificationsystem: Pump 2545, Sample Manager 2767, CFO, DAD 2996, ELSD 2424, SQD 3001 |
|---|---|
| Column: | XBrigde C18 5 µm 100 × 30 mm |
| Solvent: | A = H$_2$O + 0.1% HCOOH |
|  | B = Acetonitrile |
| Gradient: | 0-1 min 1% B, 1-8 min 1-99% B, 8-10 min 99% B |
| Flow: | 50 mL/min |
| Temperature: | RT |
| Solution: | Max. 250 mg/max. 2.5 mL DMSO o. DMF |
| Injektion: | 1 × 2.5 mL |
| Detection: | DAD scan range 210-400 nm |
|  | MS ESI+, ESI−, scan range 160-1000 m/z |

$^1$H NMR (400 MHz, CDCl$_3$, 300K) δ=8.86 (s, 1H), 8.14 (m, 1H), 7.85 (m, 2H), 7.45 (m, 2H), 7.27 (m, 1H), 7.23 (m, 2H), 4.30 (s, 2H), 2.81 (s, 3H).

Example 7

N-{3-[(Methylsulfonyl)methyl]phenyl}-4-[2-(trifluoromethoxy)phenyl]-1,3,5-triazin-2-amine

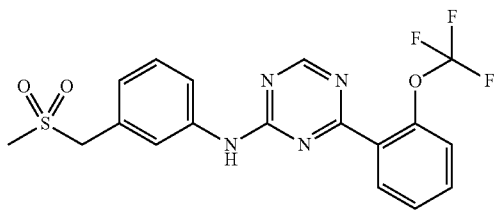 [SMILES: CS(=O)(=O)Cc1cccc(Nc2ncnc(-c3ccccc3OC(F)(F)F)n2)c1]

Example 7 was prepared under similar conditions as described in the preparation of Example 1 using crude 4-chloro-N-{3-[(methylsulfonyl)methyl]phenyl}-1,3,5-triazin-2-amine and [2-(trifluoromethoxy)phenyl]boronic acid (ABCR GmbH & CO. KG). The batch was purified by preparative HPLC:

| System: | Waters Autopurificationsystem: Pump 2545, Sample Manager 2767, CFO, DAD 2996, ELSD 2424, SQD 3001 |
|---|---|
| Column: | XBrigde C18 5 µm 100 × 30 mm |
| Solvent: | A = H$_2$O + 0.1% HCOOH |
|  | B = Acetonitrile |
| Gradient: | 0-1 min 1% B, 1-8 min 1-99% B, 8-10 min 99% B |
| Flow: | 50 mL/min |
| Temperature: | RT |
| Solution: | Max. 250 mg/max. 2.5 mL DMSO o. DMF |
| Injektion: | 1 × 2.5 mL |
| Detection: | DAD scan range 210-400 nm |
|  | MS ESI+, ESI−, scan range 160-1000 m/z |

$^1$H NMR (400 MHz, CDCl$_3$, 300K) δ=8.86 (s, 1H), 8.07 (m, 1H), 7.88 (m, 1H), 7.65 (m, 1H), 7.58 (m, 1H), 7.42 (m, 4H), 7.19 (m, 1H), 4.27 (s, 2H), 2.78 (s, 3H).

Example 8

4-(3-Methoxypyridin-4-yl)-N-{3-[(methylsulfonyl)methyl]phenyl}-1,3,5-triazin-2-amine

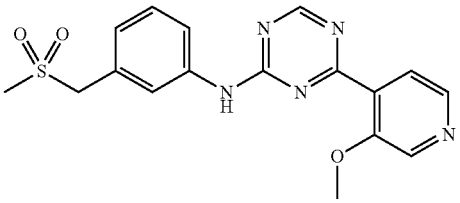 [SMILES: COc1cnccc1-c1ncnc(Nc2cccc(CS(C)(=O)=O)c2)n1]

Example 8 was prepared under similar conditions as described in the preparation of Example 1 using crude 4-chloro-N-{3-[(methylsulfonyl)methyl]phenyl}-1,3,5-triazin-2-amine and (3-methoxypyridin-4-yl)boronic acid (Combi-Blocks Inc.). The batch was purified by preparative HPLC:

| System: | Agilent: Prep 1200, 2 × Prep Pump, DLA, MWD, ELSD, Prep FC |
|---|---|
| Column: | XBrigde C18 5 µm 100 × 30 mm |
| Solvent: | A = H$_2$O + 0.1% formic acid |
|  | B = Acetonitrile |
| Gradient: | 0-17.5 min 10-40% B, 17.5-20 min 40-100% B |
| Flow: | 38 mL/min |
| Temperatur: | RT |
| Detektion: | MWD 210 nm/ELSD |
| Retention: | 6.9-7.9 min |

$^1$H NMR (400 MHz, CDCl$_3$, 300K) δ=8.87 (s, 1H), 8.52 (s, 1H), 8.42 (m, 1H), 7.75 (m, 3H), 7.52 (s, 1H), 7.44 (m, 1H), 7.18 (m, 1H), 4.27 (s, 2H), 4.04 (s, 3H), 2.80 (s, 3H).

Example 9

N-{3-[(Cyclohexylsulfonyl)methyl]phenyl}-4-(4-fluoro-2-methoxyphenyl)-1,3,5-triazin-2-amine

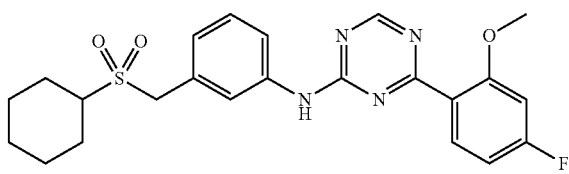 [SMILES: COc1cc(F)ccc1-c1ncnc(Nc2cccc(CS(=O)(=O)C3CCCCC3)c2)n1]

Preparation of Intermediate 9.1: 4-Chloro-N-{3-[(cyclohexylsulfonyl)methyl]phenyl}-1,3,5-triazin-2-amine

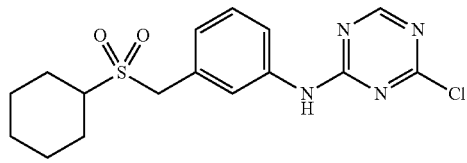 [SMILES: O=S(=O)(Cc1cccc(Nc2ncnc(Cl)n2)c1)C1CCCCC1]

DIPEA (0.7 ml; 3.95 mmol) was added to a stirred solution of 2,4-dichloro-1,3,5-triazine (296 mg; 1.97 mmol; ABCR GmbH & CO. KG) in THF/i-PrOH (1:1; 4 ml) at −40° C. Then a solution of 3-[(cyclohexylsulfonyl)methyl]aniline (500 mg; 1.97 mmol, BCH Research) in THF/i-PrOH (1:1; 3 ml) was added at this temperature. Under stirring the temperature of the reaction mixture was slowly raised over 4 hours to 0° C. The batch was concentrated in vacuo to give the crude product (1098 mg) that was used without further purification.

| System: | Waters Acquity UPLC-MS: Binary Solvent Manager, Sample Manager/Organizer, Column Manager, PDA, ELSD, SQD 3001 |
|---|---|
| Column: | Acquity UPLC BEH C18 1.7 50 × 2.1 mm |
| Solvent: | A1 = H$_2$O + 0.1% HCOOH |
| | B1 = Acetonitrile |
| Gradient: | 0-1.6 min 1-99% B, 1.6-2.0 min 99% B |
| Flow: | 0.8 mL/min |
| Temperatuer: | 60° C. |
| Injektion: | 2.0 μl |
| Detection: | DAD scan range 210-400 nm –> Peaktable ELSD |
| Method: | MS ESI+, ESI− Switch |
| | A1 + B1 = C:\MassLynx\Mass__160__1000.flp |
| Retention: | 1.10 min |
| MS(ES+): | m/z = 365 [M − H] |

Preparation of End Product:

Example 9 was prepared under similar conditions as described in the preparation of Example 1 using crude 4-chloro-N-{3-[(cyclohexylsulfonyl)methyl]phenyl}-1,3,5-triazin-2-amine and (4-fluoro-2-methoxyphenyl)boronic acid (Aldrich Chemical Company Inc.). The batch was purified by preparative HPLC:

| System: | Waters Autopurificationsystem: Pump 2545, Sample Manager 2767, CFO, DAD 2996, ELSD 2424, SQD 3001 |
|---|---|
| Column: | XBrigde C18 5 μm 100 × 30 mm |
| Solvent: | A = H$_2$O + 0.1% HCOOH |
| | B = Acetonitrile |
| Gradient: | 0-1 min 1% B, 1-8 min 1-99% B, 8-10 min 99% B |
| Flow: | 50 mL/min |
| Temperature: | RT |
| Solution: | Max. 250 mg/max. 2.5 mL DMSO o. DMF |
| Injektion: | 1 × 2.5 mL |
| Detection: | DAD scan range 210-400 nm |
| | MS ESI+, ESI−, scan range 160-1000 m/z |

$^1$H NMR (400 MHz, CDCl$_3$, 300K) δ=8.81 (s, 1H), 7.98 (br, 1H), 7.76 (m, 2H), 7.49 (m, 1H), 7.40 (m, 1H), 7.16 (m, 1H), 6.77 (m, 2H), 4.21 (s, 2H), 3.94 (s, 3H), 2.79 (m, 1H), 2.14 (m, 2H), 1.87 (br, 2H), 1.68 (m, 1H), 1.60 (m, 1H), 1.23 (m, 4H).

Example 10

4-(4-Fluoro-2-methoxyphenyl)-N-{3-fluoro-5-[(methylsulfonyl)methyl]phenyl}-1,3,5-triazin-2-amine

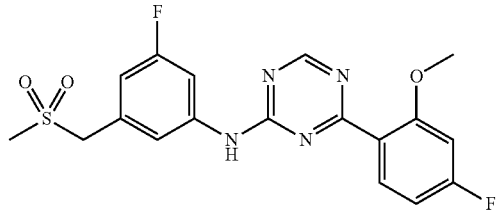 [SMILES: COc1cc(F)ccc1-c1ncnc(Nc2cc(F)cc(CS(C)(=O)=O)c2)n1]

Preparation of Intermediate 10.1: 1-Fluoro-3-[(methylsulfanyl)methyl]-5-nitrobenzene

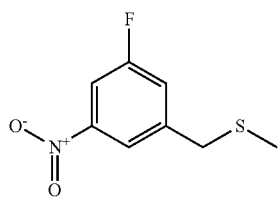

Sodium methanethiolate (1.22 g; 17.4 mmol) was added in three portions to a stirred solution of 1-(chloromethyl)-3-fluoro-5-nitrobenzene (3.00 g; 15.8 mmol, HE Chemical) in ethanol (33 ml) at 0° C. The ice bath was removed and the batch was stirred at room temperature for 18 hours. Further sodium methanethiolate (0.33 g; 4.7 mmol) was added and the batch was stirred for 5 additional hours at room temperature. The batch was diluted with brine and extracted with ethyl acetate (2×). The combined organic phases were washed with water, dried (sodium sulfate), filtered and concentrated to give the desired product (3.4 g) that was used without further purification. $^1$H NMR (400 MHz, CDCl$_3$, 300K) δ=8.00 (m, 1H), 7.81 (m, 1H), 7.42 (m, 1H), 3.74 (s, 2H), 2.02 (s, 3H).

Preparation of Intermediate 10.2:
1-Fluoro-3-[(methylsulfonyl)methyl]-5-nitrobenzene

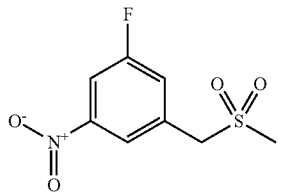

3-Chlorobenzenecarboperoxoic acid (77%; 3.68 g; 16.4 mmol) was added to a stirred solution of 1-fluoro-3-[(methylsulfanyl)methyl]-5-nitrobenzene (1.50 g) in DCM (178 ml) at 0° C. The batch was stirred at 0° C. for 30 minutes and then 2.5 hours at room temperature. The batch was diluted with water (450 ml) before sodium bicarbonate (1.50 g) was added. The batch was extracted with DCM (2×). The combinded organic phases were filtered using a Whatman filter and concentrated to give the crude product (3.33 g) that was used without further purification.

Preparation of Intermediate 10.3:
3-Fluoro-5-[(methylsulfonyl)methyl]aniline

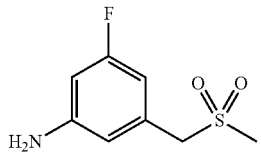

Titanium(III)chloride solution (about 15%) in about 10% hydrochloric acid (MERCK (MDA) INCL SCHUCHARDT; 29 ml) was added to a stirred solution of crude 1-fluoro-3-[(methylsulfonyl)methyl]-5-nitrobenzene (1.00 g) in THF (45 ml) at room temperature and the batch was stirred for 16 hours. The batch was cooled with an ice bath while 1N sodium hydroxide solution was added to raise the pH value of the reaction mixture to 8-9. It was stirred for 30 minutes at this temperature before the batch was extracted with ethyl acetate (2×). The combined organic phases were washed with brine, filtered using a Whatman filter and concentrated. The residue was purified by column chromatography (hexane/ethlyacetate 1:1 to ethyl acetate) to give the desired product (262 mg; 1.29 mmol)
$^1$H NMR (400 MHz, CDCl$_3$, 300K) δ=6.48 (m, 2H), 6.39 (m, 1H), 4.11 (s, 2H), 3.88 (br, 2H), 2.79 (s, 3H).

Preparation of Intermediate 10.4: 4-Chloro-N-{3-fluoro-5-[(methylsulfonyl)methyl]phenyl}-1,3,5-triazin-2-amin

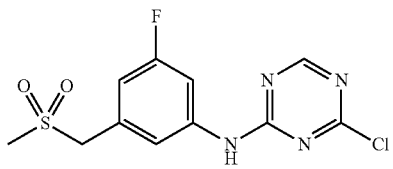

DIPEA (0.45 ml; 2.56 mmol) was added to a stirred solution of 2,4-dichloro-1,3,5-triazine (192 mg; 1.28 mmol) in THF/i-PrOH (1:1; 2.5 ml) at −40° C. Then a suspension of 3-fluoro-5-[(methylsulfonyl)methyl]aniline (260 mg; 1.28 mmol) in THF/i-PrOH (1:1; 1.3 ml) was added at this temperature. Under stirring the temperature of the reaction mixture was slowly raised over 2 hours to 0° C. The batch was concentrated to give the crude product (650 mg) that was used without further purification.

| System: | Waters Acquity UPLC-MS: Binary Solvent Manager, Sample Manager/Organizer, Column Manager, PDA, ELSD, SQD 3001 |
|---|---|
| Column: | Acquity UPLC BEH C18 1.7 50 × 2.1 mm |
| Solvent: | A2 = H$_2$O + 0.2% NH$_3$ |
| | B1 = Acetonitrile |
| Gradient: | 0-1.6 min 1-99% B, 1.6-2.0 min 99% B |
| Flow: | 0.8 mL/min |
| Temperatuer: | 60° C. |
| Injektion: | 2.0 μl |
| Detection: | DAD scan range 210-400 nm –> Peaktable ELSD |
| Method: | MS ESI+, ESI– Switch |
| | A2 + B1 = C:\MassLynx\NH3_Mass_100_1000.flp |
| System: | Waters Acquity UPLC-MS: Binary Solvent Manager, Sample Manager/Organizer, Column Manager, PDA, ELSD, SQD 3001 |
| Retention | 0.85 min |
| MS(ES+): | m/z = 317 [M + H] |

Preparation of End Product:

Example 10 was prepared under similar conditions as described in the preparation of Example 1 using crude 4-chloro-N-{3-fluoro-5-[(methylsulfonyl)methyl]phenyl}-1,3,5-triazin-2-amine and (4-fluoro-2-methoxyphenyl)boronic acid (Aldrich Chemical Company Inc.). The batch was purified by preparative HPLC:

| System: | Waters Autopurificationsystem: Pump 2545, Sample Manager 2767, CFO, DAD 2996, ELSD 2424, SQD 3001 |
|---|---|
| Column: | XBrigde C18 5 μm 100 × 30 mm |
| Solvent: | A = H$_2$O + 0.1% HCOOH |
| | B = Acetonitrile |
| Gradient: | 0-1 min 1% B, 1-8 min 1-99% B, 8-10 min 99% B |
| Flow: | 50 mL/min |
| Temperature: | RT |
| Solution: | Max. 250 mg/max. 2.5 mL DMSO o. DMF |
| Injektion: | 1 × 2.5 mL |
| Detection: | DAD scan range 210-400 nm |
| | MS ESI+, ESI–, scan range 160-1000 m/z |

$^1$H NMR (400 MHz, CDCl$_3$, 300K) δ=8.83 (s, 1H), 8.19 (br, 2H), 7.50 (m, 2H), 6.75 (m, 1H), 6.78 (m, 2H), 4.23 (s, 2H), 3.98 (s, 3H), 2.83 (s, 3H).

Example 11

4-(5-Fluoro-2-methoxyphenyl)-N-{3-[(methylsulfonyl)methyl]phenyl}-1,3,5-triazin-2-amine

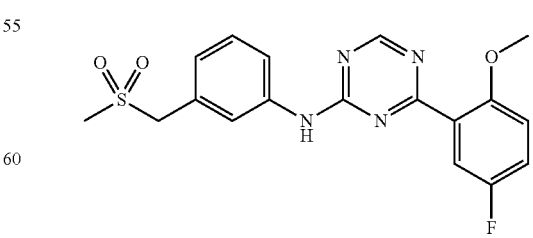

Example 11 was prepared under similar conditions as described in the preparation of Example 1 using crude 4-chloro-N-{3-[(methylsulfonyl)methyl]phenyl}-1,3,5-triazin-2-amine and (5-fluoro-2-methoxyphenyl)boronic acid (Aldrich Chemical Company Inc.). The batch was purified by preparative HPLC:

| System: | Waters Autopurificationsystem: Pump 2545, Sample Manager 2767, CFO, DAD 2996, ELSD 2424, SQD 3001 |
|---|---|
| Column: | XBrigde C18 5 μm 100 × 30 mm |
| Solvent: | A = $H_2O$ + 0.1% HCOOH |
| | B = Acetonitrile |
| Gradient: | 0-1 min 1% B, 1-8 min 1-99% B, 8-10 min 99% B |
| Flow: | 50 mL/min |
| Temperature: | RT |
| Solution: | Max. 250 mg/max. 2.5 mL DMSO o. DMF |
| Injektion: | 1 × 2.5 mL |
| Detection: | DAD scan range 210-400 nm |
| | MS ESI+, ESI−, scan range 160-1000 m/z |

$^1$H NMR (400 MHz, $CDCl_3$, 300K) δ=8.84 (s, 1H), 7.81 (m, 1H), 7.74 (br, 1H), 7.62 (m, 1H), 7.47 (br, 1H), 7.43 (m, 1H), 7.19 (m, 2H), 7.00 (m, 1H), 4.27 (s, 2H), 3.92 (s, 3H), 2.79 (s, 3H).

Example 12

4-(3,4-Dihydro-2H-chromen-8-yl)-N-{3-[(methylsulfonyl)methyl]phenyl}-1,3,5-triazin-2-amine

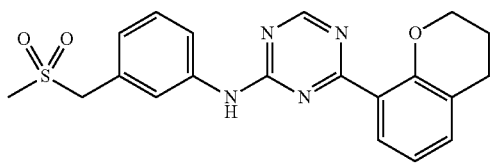 [SMILES: CS(=O)(=O)Cc1cccc(Nc2ncnc(-c3cccc4c3OCCC4)n2)c1]

Example 12 was prepared under similar conditions as described in the preparation of Example 1 using crude 4-chloro-N-{3-[(methylsulfonyl)methyl]phenyl}-1,3,5-triazin-2-amine and 3,4-dihydro-2H-chromen-8-ylboronic acid (Parkway Scientific LLC).

| System: | Waters Acquity UPLC-MS: Binary Solvent Manager, Sample Manager/Organizer, Column Manager, PDA, ELSD, SQD 3001 |
|---|---|
| Column: | Acquity UPLC BEH C18 1.7 50 × 2.1 mm |
| Solvent: | A2 = $H_2O$ + 0.2% $NH_3$ |
| | B1 = Acetonitrile |
| Gradient: | 0-1.6 min 1-99% B, 1.6-2.0 min 99% B |
| Flow: | 0.8 mL/min |
| Temperatuer: | 60° C. |
| Injektion: | 2.0 μl |
| Detection: | DAD scan range 210-400 nm −> Peaktable ELSD |
| Method: | MS ESI+, ESI− Switch |
| | A2 + B1 = C:\MassLynx\NH3_Mass_100_1000.flp |
| System: | Waters Acquity UPLC-MS: Binary Solvent Manager, Sample Manager/Organizer, Column Manager, PDA, ELSD, SQD 3001 |
| Retention: | 1.03 min |
| MS(ES+): | m/z = 397 [M + H] |

The batch was purified by preparative HPLC.

| System: | Waters Autopurificationsystem: Pump 254, Sample Manager 2767, CFO, DAD 2996, ELSD 2424, SQD 3001 |
|---|---|
| Column: | XBrigde C18 5 μm 100 × 30 mm |
| Solvent: | A = $H_2O$ + 0.1% HCOOH |
| | B = MeOH |
| Gradient: | 0-1 min 30% B, 1-8 min 30-70% B, 8-8.1 min 70-100% B, 8.1-10 min 100% B |
| Flow: | 50 mL/min |
| Temperature: | RT |
| Detection: | DAD scan range 210-400 nm |
| | MS ESI+, ESI−, scan range 160-1000 m/z |
| | ELSD |
| Retention: | 5.8-6.5 min |

$^1$H NMR (400 MHz, $CDCl_3$, 300K) δ=8.84 (s, 1H), 7.80 (m, 1H), 7.70 (m, 2H), 7.56 (m, 1H), 7.40 (m, 1H), 7.18 (m, 2H), 6.94 (m, 1H), 4.30 (m, 2H), 4.25 (s, 2H), 2.88 (m, 2H), 2.78 (s, 3H), 2.10 (m, 2H).

Example 13

4-(2,3-Dihydro-1-benzofuran-7-yl)-N-{3-[(methylsulfonyl)methyl]phenyl}-1,3,5-triazin-2-amine

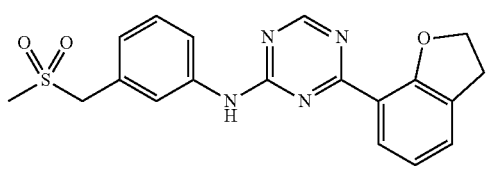 [SMILES: CS(=O)(=O)Cc1cccc(Nc2ncnc(-c3cccc4c3OCC4)n2)c1]

Example 13 was prepared under similar conditions as described in the preparation of Example 1 using crude 4-chloro-N-{3-[(methylsulfonyl)methyl]phenyl}-1,3,5-triazin-2-amine and 7-(4,4,5,5-tetramethyl-1,3,2-dioxaborolan-2-yl)-2,3-dihydro-1-benzofuran (ChemBridge Corporation). The batch was purified by preparative HPLC:

| System: | Waters Autopurificationsystem: Pump 2545, Sample Manager 2767, CFO, DAD 2996, ELSD 2424, SQD 3001 |
|---|---|
| Column: | XBrigde C18 5 μm 100 × 30 mm |
| Solvent: | A = $H_2O$ + 0.1% HCOOH |
| | B = Acetonitrile |
| Gradient: | 0-1 min 1% B, 1-8 min 1-99% B, 8-10 min 99% B |
| Flow: | 50 mL/min |
| Temperature: | RT |
| Solution: | Max. 250 mg/max. 2.5 mL DMSO o. DMF |
| Injektion: | 1 × 2.5 mL |
| Detection: | DAD scan range 210-400 nm |
| | MS ESI+, ESI−, scan range 160-1000 m/z |

$^1$H NMR (400 MHz, $CDCl_3$, 300K) δ=8.86 (s, 1H), 8.13 (m, 1H), 7.93 (br, 1H), 7.74 (m, 1H), 7.41 (m, 3H), 7.18 (m, 1H), 6.99 (m, 1H), 4.81 (m, 2H), 4.29 (s, 2H), 3.30 (m, 2H), 2.80 (s, 3H).

Example 14

2-[(3-{[4-(4-Fluoro-2-methoxyphenyl)-1,3,5-triazin-2-yl]amino}benzyl)sulfonyl]ethanol

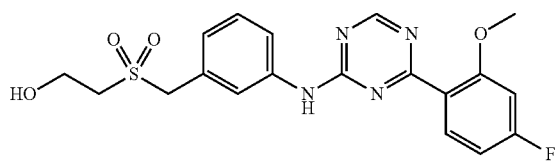 [SMILES: COc1cc(F)ccc1-c1ncnc(Nc2cccc(CS(=O)(=O)CCO)c2)n1]

Preparation of Intermediate 14.1: 2-[(3-Aminobenzyl)sulfonyl]ethanol

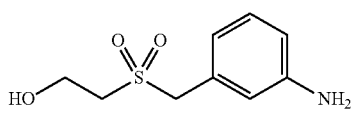 [SMILES: Nc1cccc(CS(=O)(=O)CCO)c1]

Titanium(III)chloride solution (about 15%) in about 10% hydrochloric acid (MERCK (MDA) INCL SCHUCHARDT, 114 ml) was added to a stirred solution of 2-[(3-nitrobenzyl)sulfonyl]ethanol (9.0 g; 36.7 mmol) in THF (384 ml) at room temperature and the batch was stirred for 18 hours. By adding aqueous sodium bicarbonate solution the pH value of the reaction mixture was raised to 7-8 before the batch was extracted with ethyl acetate (2×). The combined organic phases were washed with brine, dried (Sodium sulfate), filtered and concentrated. The residue was purified by column chromatography (DCM/ethanol 95:5) to give the desired product.

$^1$H NMR (400 MHz, $d_6$-DMSO, 300K) δ=6.97 (m, 1H), 6.52 (m, 3H), 5.13 (m, 3H), 4.23 (s, 2H), 3.75 (m, 2H), 3.10 (m, 2H).

Preparation of Intermediate 14.2: 2-({3-[(4-Chloro-1,3,5-triazin-2-yl)amino]benzyl}sulfonyl)ethanol

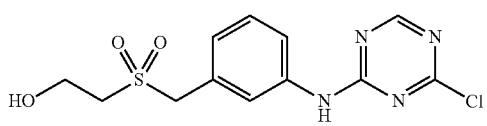 [SMILES: O=S(=O)(CCO)Cc1cccc(Nc2ncnc(Cl)n2)c1]

DIPEA (0.49 ml; 2.78 mmol) was added to a stirred solution of 2,4-dichloro-1,3,5-triazine (209 mg; 1.39 mmol) in THF/i-PrOH (1:1; 2.75 ml) at −40° C. 2-[(3-aminobenzyl)sulfonyl]ethanol (300 mg; 1.39 mmol) was added at this temperature. Under stirring the temperature of the reaction mixture was slowly raised over 90 minutes to 0° C. The batch was concentrated in vacuo to give the crude product (700 mg) that was used without further purification.

| | |
|---|---|
| System: | Waters Acquity UPLC-MS: Binary Solvent Manager, Sample Manager/Organizer, Column Manager, PDA, ELSD, SQD 3001 |
| Column: | Acquity UPLC BEH C18 1.7 50 × 2.1 mm |
| Solvent: | A2 = H$_2$O + 0.2% NH$_3$<br>B1 = Acetonitrile |
| Gradient: | 0-1.6 min 1-99% B, 1.6-2.0 min 99% B |
| Flow: | 0.8 mL/min |
| Temperatuer: | 60° C. |
| Injektion: | 2.0 µl |
| Detection: | DAD scan range 210-400 nm –> Peaktable<br>ELSD |
| Method: | MS ESI+, ESI– Switch<br>A2 + B1 = C:\MassLynx\NH3__Mass__100__1000.flp |
| System: | Waters Acquity UPLC-MS: Binary Solvent Manager, Sample Manager/Organizer, Column Manager, PDA, ELSD, SQD 3001 |
| Retention | 0.73 min |
| MS(ES+): | m/z = 329 [M + H] |

Preparation of End Product:

Example 14 was prepared under similar conditions as described in the preparation of Example 1 using crude 2-({3-[(4-chloro-1,3,5-triazin-2-yflamino]benzyl}sulfonyl)ethanol and (4-fluoro-2-methoxyphenyl)boronic acid (Aldrich Chemical Company Inc.). The batch was purified by preparative HPLC.

| | |
|---|---|
| System: | Waters Autopurificationsystem: Pump 2545, Sample Manager 2767, CFO, DAD 2996, ELSD 2424, SQD 3001 |
| Column: | XBrigde C18 5 µm 100 × 30 mm |
| Solvent: | A = H$_2$O + 0.1% HCOOH<br>B = Acetonitrile |
| Gradient: | 0-1 min 1% B, 1-8 min 1-99% B, 8-10 min 99% B |
| Flow: | 50 mL/min |
| Temperature: | RT |
| Solution: | Max. 250 mg/max. 2.5 mL DMSO o. DMF |
| Injektion: | 1 × 2.5 mL |
| Detection: | DAD scan range 210-400 nm<br>MS ESI+, ESI–, scan range 160-1000 m/z |

$^1$H NMR (400 MHz, CDCl$_3$, 300K) δ=8.82 (s, 1H), 7.96 (br, 1H), 7.77 (m, 2H), 7.49 (m, 1H), 7.42 (m, 1H), 7.21 (m, 1H), 6.77 (m, 2H), 4.37 (s, 2H), 4.08 (m, 2H), 3.94 (s, 3H), 3.11 (m, 2H).

Example 15

4-[2-(Difluoromethoxy)-4-fluorophenyl]-N-{3-[(methylsulfonyl)methyl]phenyl}-1,3,5-triazin-2-amine

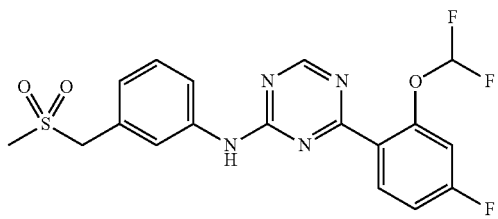 [SMILES: CS(=O)(=O)Cc1cccc(Nc2ncnc(-c3ccc(F)cc3OC(F)F)n2)c1]

Example 15 was prepared under similar conditions as described in the preparation of Example 1 using crude 4-chloro-N-{3-[(methylsulfonyl)methyl]phenyl}-1,3,5-triazin-2-amine and 2-[2-(difluoromethoxy)-4-fluorophenyl]-4,4,5,5-tetramethyl-1,3,2-dioxaborolane (Focus Synthesis LLC). The batch was purified by preparative HPLC:

| | |
|---|---|
| System: | Waters Autopurificationsystem: Pump 254, Sample Manager 2767, CFO, DAD 2996, ELSD 2424, SQD 3001 |
| Column: | XBrigde C18 5 µm 100 × 30 mm |
| Solvent: | A = H₂O + 0.1% HCOOH |
| | B = ACN |
| Gradient: | 0-1 min 30% B, 1-8 min 30-70% B, 8-8.1 min 70-100% B, 8.1-10 min 100% B |
| Flow: | 50 mL/min |
| Temperature: | RT |
| Detektion: | DAD scan range 210-400 nm |
| | MS ESI+, ESI−, scan range 160-1000 m/z |
| | ELSD |
| Retention: | 7.4-8.1 min |

$^1$H NMR (400 MHz, CDCl$_3$, 300K) δ=8.82 (s, 1H), 8.12 (m, 1H), 7.88 (m, 1H), 7.62 (m, 1H), 7.40 (m, 2H), 7.19 (m, 1H), 7.09 (m, 2H), 6.69 (tr, 1H), 4.28 (s, 2H), 2.81 (s, 3H).

Example 16

N-{3-[(Methylsulfonyl)methyl]phenyl}-4-[2-(2,2,2-trifluoroethoxy)phenyl]-1,3,5-triazin-2-amine

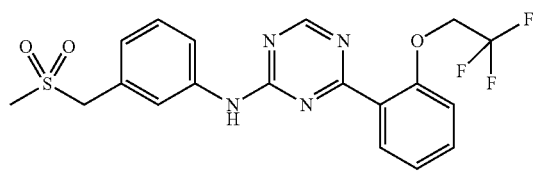 [SMILES: CS(=O)(=O)Cc1cccc(Nc2ncnc(-c3ccccc3OCC(F)(F)F)n2)c1]

Example 16 was prepared under similar conditions as described in the preparation of Example 1 using crude 4-chloro-N-{3-[(methylsulfonyl)methyl]phenyl}-1,3,5-triazin-2-amine and [2-(2,2,2-trifluoroethoxy)phenyl]boronic acid (Combi-Blocks Inc.). The batch was purified by preparative HPLC:

| | |
|---|---|
| System: | Waters Autopurificationsystem: Pump 2545, Sample Manager 2767, CFO, DAD 2996, ELSD 2424, SQD 3001 |
| Column: | XBrigde C18 5 µm 100 × 30 mm |
| Solvent: | A = H₂O + 0.1% HCOOH |
| | B = Acetonitrile |
| Gradient: | 0-1 min 1% B, 1-8 min 1-99% B, 8-10 min 99% B |
| Flow: | 50 mL/min |
| Temperature: | RT |
| Solution: | Max. 250 mg/max. 2.5 mL DMSO o. DMF |
| Injektion: | 1 × 2.5 mL |
| Detection: | DAD scan range 210-400 nm |
| | MS ESI+, ESI−, scan range 160-1000 m/z |

$^1$H NMR (400 MHz, CDCl$_3$, 300K) δ=8.83 (s, 1H), 7.92 (m, 1H), 7.83 (m, 1H), 7.65 (m, 1H), 7.52 (m, 2H), 7.41 (m, 1H), 7.23 (m, 1H), 7.18 (m, 1H), 7.09 (m, 1H), 4.44 (q, 2H), 4.26 (s, 2H), 2.78 (s, 3H).

Example 17

N-{3-[(tert-Butylsulfonyl)methyl]phenyl}-4-(4-fluoro-2-methoxyphenyl)-1,3,5-triazin-2-amine

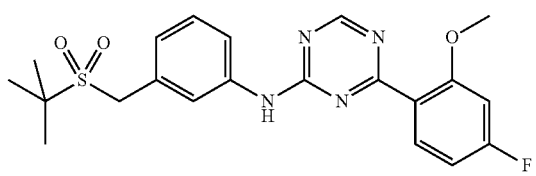 [SMILES: COc1cc(F)ccc1-c1ncnc(Nc2cccc(CS(=O)(=O)C(C)(C)C)c2)n1]

Preparation of Intermediate 17.1: N-{3-[(tert-Butyl-sulfonyl)methyl]phenyl}-4-chloro-1,3,5-triazin-2-amine

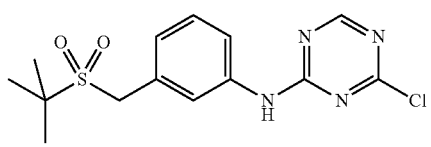 [SMILES: CC(C)(C)S(=O)(=O)Cc1cccc(Nc2ncnc(Cl)n2)c1]

DIPEA (0.46 ml; 2.64 mmol) was added to a stirred solution of 2,4-dichloro-1,3,5-triazine (198 mg; 1.32 mmol) in THF/i-PrOH (1:1; 2.6 ml) at −40° C. 3-[(tert-Butylsulfonyl)methyl]aniline (300 mg; 1.32 mmol, UkrOrgSynthesis Ltd.) was added at this temperature. Under stirring the temperature of the reaction mixture was slowly raised over 90 minutes to 0° C. The batch was concentrated in vacuo to give the crude product (700 mg) that was used without further purification.

| | |
|---|---|
| System: | Waters Acquity UPLC-MS: Binary Solvent Manager, Sample Manager/Organizer, Column Manager, PDA, ELSD, SQD 3001 |
| Column: | Acquity UPLC BEH C18 1.7 50 × 2.1 mm |
| Solvent: | A2 = H₂O + 0.2% NH₃ |
| | B1 = Acetonitrile |
| Gradient: | 0-1.6 min 1-99% B, 1.6-2.0 min 99% B |
| Flow: | 0.8 mL/min |
| Temperatuer: | 60° C. |
| Injektion: | 2.0 µl |
| Detection: | DAD scan range 210-400 nm −> Peaktable |
| | ELSD |
| Method: | MS ESI+, ESI− Switch |
| | A2 + B1 = C:\MassLynx\NH3_Mass_100_1000.flp |
| System: | Waters Acquity UPLC-MS: Binary Solvent Manager, Sample Manager/Organizer, Column Manager, PDA, ELSD, SQD 3001 |
| Retention | 0.96 min |
| MS(ES−): | m/z = 339 [M − H] |

Preparation of End Product:

Example 17 was prepared under similar conditions as described in the preparation of Example 1 using crude N-{3-[(tert-butylsulfonyl)methyl]phenyl}-4-chloro-1,3,5-triazin-2-amine and (4-fluoro-2-methoxyphenyl)boronic acid (Aldrich Chemical Company Inc.). The batch was purified by preparative HPLC:

| | |
|---|---|
| System: | Waters Autopurificationsystem: Pump 2545, Sample Manager 2767, CFO, DAD 2996, ELSD 2424, SQD 3001 |

| | |
|---|---|
| Column: | XBrigde C18 5 μm 100 × 30 mm |
| Solvent: | A = H₂O + 0.1% HCOOH |
| | B = Acetonitrile |
| Gradient: | 0-1 min 1% B, 1-8 min 1-99% B, 8-10 min 99% B |
| Flow: | 50 mL/min |
| Temperature: | RT |
| Solution: | Max. 250 mg/max. 2.5 mL DMSO o. DMF |
| Injektion: | 1 × 2.5 mL |
| Detection: | DAD scan range 210-400 nm |
| | MS ESI+, ESI−, scan range 160-1000 m/z |

$^1$H NMR (400 MHz, CDCl$_3$, 300K) δ=8.81 (s, 1H), 7.99 (br, 1H), 7.76 (m, 2H), 7.40 (m, 2H), 7.19 (m, 1H), 6.77 (m, 2H), 4.21 (s, 2H), 3.93 (s, 3H), 1.46 (s, 9H).

Example 18

4-(2,3-Dihydro-1,4-benzodioxin-5-yl)-N-{3-[(methylsulfonyl)methyl]phenyl}-1,3,5-triazin-2-amine

Example 18 was prepared under similar conditions as described in the preparation of Example 1 using crude 4-chloro-N-{3-[(methylsulfonyl)methyl]phenyl}-1,3,5-triazin-2-amine and 2,3-dihydro-1,4-benzodioxin-5-ylboronic acid (Combi-Blocks Inc.). The batch was purified by preparative HPLC.

| | |
|---|---|
| System: | Waters Autopurificationsystem: Pump 2545, Sample Manager 2767, CFO, DAD 2996, ELSD 2424, SQD 3001 |
| Column: | XBrigde C18 5 μm 100 × 30 mm |
| Solvent: | A = H₂O + 0.1% HCOOH |
| | B = Acetonitrile |
| Gradient: | 0-1 min 1% B, 1-8 min 1-99% B, 8-10 min 99% B |
| Flow: | 50 mL/min |
| Temperature: | RT |
| Solution: | Max. 250 mg/max. 2.5 mL DMSO o. DMF |
| Injektion: | 1 × 2.5 mL |
| Detection: | DAD scan range 210-400 nm |
| | MS ESI+, ESI−, scan range 160-1000 m/z |

$^1$H NMR (400 MHz, CDCl$_3$, 300K) δ=8.85 (s, 1H), 7.83 (m, 1H), 7.73 (m, 1H), 7.50 (m, 2H), 7.41 (m, 1H), 7.16 (m, 1H), 7.04 (m, 1H), 6.95 (m, 1H), 4.37 (m, 4H), 4.26 (s, 2H), 2.79 (s, 3H).

Example 19

N-{3-[(Methylsulfonyl)methyl]phenyl}-4-(2,2,3,3-tetrafluoro-2,3-dihydro-1,4-benzodioxin-5-yl)-1,3,5-triazin-2-amine

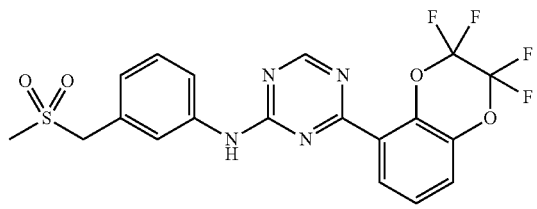 [SMILES: CS(=O)(=O)Cc1cccc(Nc2ncnc(-c3cccc4c3OC(F)(F)C(F)(F)O4)n2)c1]

A mixture of water/acetonitrile (2:1; 1.6 mL) was added to crude 4-chloro-N-{3-[(methylsulfonyl)methyl]phenyl}-1,3,5-triazin-2-amine (125 mg), potassium trifluoro(2,2,3,3-tetrafluoro-2,3-dihydro-1,4-benzodioxin-5-yl)borate(1−) (158 mg; 0.52 mmol; ABCR GmbH & CO. KG), tetrakis(triphenylphosphin)palladium(0) (10 mg; 0.008 mmol) and potassium carbonate (347 mg; 2.51 mmol) in a microwave tube under argon. The tube was sealed and the batch was heated under stirring for 5 minutes at 150° C. in a microwave oven. After cooling the batch was diluted with ethyl acetate and water. The batch was extracted with ethyl acetate (2×) and the combined organic phases were filtered using a Whatman filter and concentrated. The residue was purified by preparative HPLC to give the desired product (3 mg; 0.01 mmol).

| | |
|---|---|
| System: | Waters Autopurificationsystem: Pump 254, Sample Manager 2767, CFO, DAD 2996, ELSD 2424, SQD 3001 |
| Column: | XBrigde C18 5 μm 100 × 30 mm |
| Solvent: | A = H₂O + 0.1% HCOOH |
| | B = Acetonitrile |
| Gradient: | 0-1 min 30% B, 1-8 min 30-70% B, 8-8.1 min 70-100% B, 8.1-10 min 100% B |
| Flow: | 50 mL/min |
| Temperature: | RT |
| Detection: | DAD scan range 210-400 nm |
| | MS ESI+, ESI−, scan range 160-1000 m/z |
| | ELSD |
| Retention: | 6.8-7.2 min |

$^1$H NMR (400 MHz, d$_6$-DMSO, 300K) δ=10.57 (s, 1H), 8.91 (s, 1H), 7.97 (br, 2H), 7.69 (m, 2H), 7.51 (m, 1H), 7.36 (m, 1H), 7.15 (m, 1H), 4.47 (s, 2H), 2.92 (s, 3H).

Example 20

4-(2-Methoxypyridin-3-yl)-N-{3-[(methylsulfonyl)methyl]phenyl}-1,3,5-triazin-2-amine

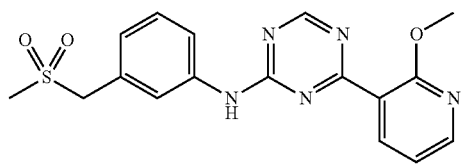

Example 20 was prepared under similar conditions as described in the preparation of Example 1 using crude 4-chloro-N-{3-[(methylsulfonyl)methyl]phenyl}-1,3,5-triazin-2-amine and (2-methoxypyridin-3-yl)boronic acid (Aldrich Chemical Company Inc.). The batch was purified by preparative HPLC.

| System: | Waters Autopurificationsystem: Pump 2545, Sample Manager 2767, CFO, DAD 2996, ELSD 2424, SQD 3001 |
|---|---|
| Column: | XBrigde C18 5 µm 100 × 30 mm |
| Solvent: | A = H$_2$O + 0.1% HCOOH |
| | B = Acetonitrile |
| Gradient: | 0-1 min 1% B, 1-8 min 1-99% B, 8-10 min 99% B |
| Flow: | 50 mL/min |
| Temperature: | RT |
| Solution: | Max. 250 mg/max. 2.5 mL DMSO o. DMF |
| Injektion: | 1 × 2.5 mL |
| Detection: | DAD scan range 210-400 nm |
| | MS ESI+, ESI−, scan range 160-1000 m/z |

$^1$H NMR (400 MHz, CDCl$_3$, 300K) δ=8.84 (s, 1H), 8.33 (m, 2H), 7.80 (m, 2H), 7.65 (s, 1H), 7.43 (m, 1H), 7.17 (m, 1H), 7.04 (m, 1H), 4.27 (s, 2H), 4.10 (s, 3H), 2.80 (s, 3H).

Example 21

4-[5-Fluoro-2-(tetrahydro-2H-pyran-4-ylmethoxy)phenyl]-N-{3-[(methylsulfonyl)methyl]phenyl}-1,3,5-triazin-2-amine

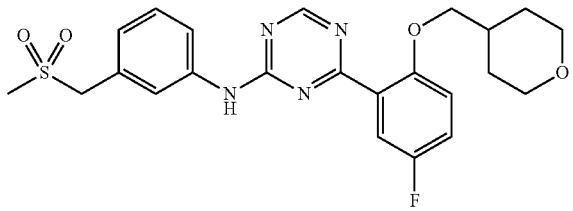 [SMILES: CS(=O)(=O)Cc1cccc(Nc2ncnc(-c3cc(F)ccc3OCC3CCOCC3)n2)c1]

Example 21 was prepared under similar conditions as described in the preparation of Example 1 using crude 4-chloro-N-{3-[(methylsulfonyl)methyl]phenyl}-1,3,5-triazin-2-amine and [5-fluoro-2-(tetrahydro-2H-pyran-4-ylmethoxy)phenyl]boronic acid (FCH Group Company). The batch was purified by preparative HPLC.

| System: | Waters Autopurificationsystem: Pump 254, Sample Manager 2767, CFO, DAD 2996, ELSD 2424, SQD 3001 |
|---|---|
| Column: | XBrigde C18 5 µm 100 × 30 mm |
| Solvent: | A = H$_2$O + 0.2% NH$_3$ |
| | B = MeOH |
| Gradient: | 0-1 min 50% B, 1-8 min 50-90% B, 8-8.1 min 90-100% B, 8.1-10 min 100% B |
| Flow: | 50 mL/min |
| Temperature: | RT |
| Detection: | DAD scan range 210-400 nm |
| | MS ESI+, ESI−, scan range 160-1000 m/z |
| | ELSD |
| Retention: | 4.0-4.5 min |

$^1$H NMR (400 MHz, CDCl$_3$, 300K) δ=8.83 (s, 1H), 7.85 (br, 1H), 7.68 (m, 3H), 7.42 (m, 1H), 7.16 (m, 2H), 6.94 (m, 1H), 4.27 (s, 2H), 4.02 (m, 2H), 3.92 (m, 2H), 3.41 (m, 2H), 2.80 (s, 3H), 2.03 (m, 1H), 1.65 (m, 4H).

Example 22

4-{2-[($^2$H$_3$)methyloxy]phenyl}-N-{3-[(methylsulfonyl)methyl]phenyl}-1,3,5-triazin-2-amine

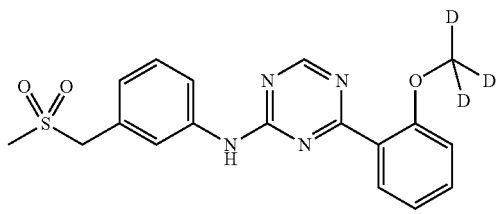 [SMILES: [2H]C([2H])([2H])Oc1ccccc1-c1ncnc(Nc2cccc(CS(C)(=O)=O)c2)n1]

Example 22 was prepared under similar conditions as described in the preparation of Example 1 using crude 4-chloro-N-{3-[(methylsulfonyl)methyl]phenyl}-1,3,5-triazin-2-amine and 2-[($^2$H$_3$)methyloxy]phenyl}boronic acid (CombiPhos Catalysts, Inc.). The batch was purified by preparative HPLC.

| System: | Waters Autopurificationsystem: Pump 254, Sample Manager 2767, CFO, DAD 2996, ELSD 2424, SQD 3001 |
|---|---|
| Column: | XBrigde C18 5 µm 100 × 30 mm |
| Solvent: | A = H$_2$O + 0.1% HCOOH |
| | B = MeOH |
| Gradient: | 0-1 min 30% B, 1-8 min 30-70% B, 8-8.1 min 70-100% B, 8.1-10 min 100% B |
| Flow: | 50 mL/min |
| Temperature: | RT |
| Detection: | DAD scan range 210-400 nm |
| | MS ESI+, ESI−, scan range 160-1000 m/z |
| | ELSD |
| Retention: | 4.5-5.5 min |

$^1$H NMR (400 MHz, CDCl$_3$, 300K) δ=8.84 (s, 1H), 7.84 (m, 2H), 7.72 (m, 1H), 7.59 (s, 1H), 7.44 (m, 2H), 7.16 (m, 1H), 7.05 (m, 2H), 4.26 (s, 2H), 2.77 (s, 3H).

Example 23

4-(4-Fluoro-2-methoxyphenyl)-N-(3-{[(2-methoxyethyl)sulfonyl]methyl}phenyl)-1,3,5-triazin-2-amine

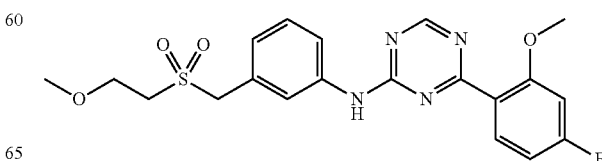

Preparation of Intermediate 23.1: N-(3-{[(2-Methoxyethyl)sulfonyl]methyl}phenyl)-4-chloro-1,3,5-triazin-2-amine

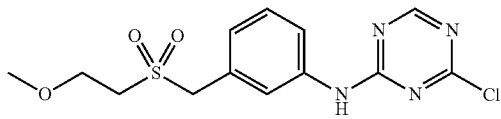 [SMILES: COCCS(=O)(=O)Cc1cccc(Nc2ncnc(Cl)n2)c1]

Intermediate 23.1 was prepared under similar conditions as described in the preparation of Intermediate 17.1 using 3-{[(2-methoxyethyl)sulfonyl]methyl}aniline (UkrOrnSynthesis Ltd.).

| | |
|---|---|
| System: | Waters Acquity UPLC-MS: Binary Solvent Manager, Sample Manager/Organizer, Column Manager, PDA, ELSD, SQD 3001 |
| Column: | Acquity UPLC BEH C18 1.7 50 × 2.1 mm |
| Solvent: | A2 = H$_2$O + 0.2% NH$_3$ |
| | B1 = Acetonitrile |
| Gradient: | 0-1.6 min 1-99% B, 1.6-2.0 min 99% B |
| Flow: | 0.8 mL/min |
| Temperatuer: | 60° C. |
| Injektion: | 2.0 μl |
| Detection: | DAD scan range 210-400 nm -> Peaktable ELSD |
| Method: | MS ESI+, ESI– Switch |
| | A2 + B1 = C:\MassLynx\NH3_Mass_100_1000.flp |
| System: | Waters Acquity UPLC-MS: Binary Solvent Manager, Sample Manager/Organizer, Column Manager, PDA, ELSD, SQD 3001 |
| Retention | 0.88 min |
| MS(ES–): | m/z = 343 [M – H] |

Preparation of End Product:

Example 23 was prepared under similar conditions as described in the preparation of Example 1 using crude N-(3-{[(2-methoxyethyl)sulfonyl]methyl}phenyl)-4-chloro-1,3,5-triazin-2-amine and (4-fluoro-2-methoxyphenyl)boronic acid (Aldrich Chemical Company Inc.). The batch was purified by preparative HPLC:

| | |
|---|---|
| System: | Waters Autopurificationsystem: Pump 2545, Sample Manager 2767, CFO, DAD 2996, ELSD 2424, SQD 3001 |
| Column: | XBrigde C18 5 μm 100 × 30 mm |
| Solvent: | A = H$_2$O + 0.1% HCOOH |
| | B = Acetonitrile |
| Gradient: | 0-1 min 1% B, 1-8 min 1-99% B, 8-10 min 99% B |
| Flow: | 50 mL/min |
| Temperature: | RT |
| Solution: | Max. 250 mg/max. 2.5 mL DMSO o. DMF |
| Injektion: | 1 × 2.5 mL |
| Detection: | DAD scan range 210-400 nm |
| | MS ESI+, ESI–, scan range 160-1000 m/z |

$^1$H NMR (400 MHz, CDCl$_3$, 300K) δ=8.81 (s, 1H), 7.97 (br, 1H), 7.83 (br, 1H), 7.70 (br, 1H), 7.48 (br, 1H), 7.40 (m, 1H), 7.21 (m, 1H), 6.76 (m, 2H), 4.34 (s, 2H), 3.93 (s, 3H), 3.82 (tr, 2H), 3.43 (s, 3H), 3.10 (tr, 2H).

Example 24

4-(4-Fluoro-2-methoxyphenyl)-N-{3-[(propan-2-ylsulfonyl)methyl]phenyl}-1,3,5-triazin-2-amine

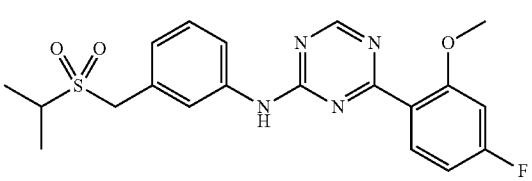 [SMILES: COc1cc(F)ccc1-c1ncnc(Nc2cccc(CS(=O)(=O)C(C)C)c2)n1]

Preparation of Intermediate 24.1: N-{3-[(Propan-2-ylsulfonyl)methyl]phenyl}-4-chloro-1,3,5-triazin-2-amine

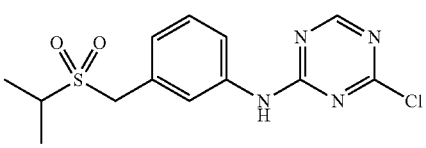 [SMILES: CC(C)S(=O)(=O)Cc1cccc(Nc2ncnc(Cl)n2)c1]

Intermediate 24.1 was prepared under similar conditions as described in the preparation of Intermediate 17.1 using 3-[(propan-2-ylsulfonyl)methyl]aniline (UkrOrgSynthesis Ltd.).

| | |
|---|---|
| System: | Waters Acquity UPLC-MS: Binary Solvent Manager, Sample Manager/Organizer, Column Manager, PDA, ELSD, SQD 3001 |
| Column: | Acquity UPLC BEH C18 1.7 50 × 2.1 mm |
| Solvent: | A2 = H$_2$O + 0.2% NH$_3$ |
| | B1 = Acetonitrile |
| Gradient: | 0-1.6 min 1-99% B, 1.6-2.0 min 99% B |
| Flow: | 0.8 mL/min |
| Temperatuer: | 60° C. |
| Injektion: | 2.0 μl |
| Detection: | DAD scan range 210-400 nm -> Peaktable ELSD |
| Method: | MS ESI+, ESI– Switch |
| | A2 + B1 = C:\MassLynx\NH3_Mass_100_1000.flp |
| System: | Waters Acquity UPLC-MS: Binary Solvent Manager, Sample Manager/Organizer, Column Manager, PDA, ELSD, SQD 3001 |
| Retention | 0.91 min |
| MS(ES–): | m/z = 327 [M – H] |

Preparation of End Product:

Example 24 was prepared under similar conditions as described in the preparation of Example 1 using crude N-{3-[(propan-2-ylsulfonyl)methyl]phenyl}-4-chloro-1,3,5-triazin-2-amine and (4-fluoro-2-methoxyphenyl)boronic acid (Aldrich Chemical Company Inc.). The batch was purified by preparative HPLC:

| | |
|---|---|
| System: | Waters Autopurificationsystem: Pump 2545, Sample Manager 2767, CFO, DAD 2996, ELSD 2424, SQD 3001 |
| Column: | XBrigde C18 5 μm 100 × 30 mm |
| Solvent: | A = H$_2$O + 0.1% HCOOH |
| | B = Acetonitrile |
| Gradient: | 0-1 min 1% B, 1-8 min 1-99% B, 8-10 min 99% B |
| Flow: | 50 mL/min |

| Temperature: | RT |
| --- | --- |
| Solution: | Max. 250 mg/max. 2.5 mL DMSO o. DMF |
| Injektion: | 1 × 2.5 mL |
| Detection: | DAD scan range 210-400 nm |
| | MS ESI+, ESI−, scan range 160-1000 m/z |

$^{1}$H NMR (400 MHz, CDCl$_3$, 300K) δ=8.81 (s, 1H), 7.96 (m, 1H), 7.75 (m, 2H), 7.51 (s, 1H), 7.40 (tr, 1H), 7.17 (m, 1H), 6.76 (m, 2H), 4.23 (s, 2H), 3.93 (s, 3H), 3.05 (m, 1H), 1.37 (d, 6H).

Example 25

4-{2-[(4-Fluorobenzypoxy]phenyl}-N-{3-[(methylsulfonyl)methyl]phenyl}-1,3,5-triazin-2-amine

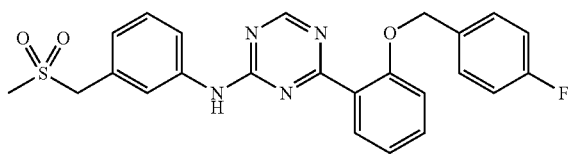 [SMILES: CS(=O)(=O)Cc1cccc(Nc2ncnc(-c3ccccc3OCc3ccc(F)cc3)n2)c1]

Example 25 was prepared under similar conditions as described in the preparation of Example 1 using crude 4-chloro-N-{3-[(methylsulfonyl)methyl]phenyl}-1,3,5-triazin-2-amine and {2-[(4-fluorobenzyl)oxy]phenyl}boronic acid (Aldrich Chemical Company Inc.). The batch was purified by preparative TLC.

$^{1}$H NMR (400 MHz, CDCl$_3$, 300K) δ=8.84 (s, 1H), 7.87 (m, 1H), 7.78 (br, 1H), 7.66 (m, 1H), 7.53 (s, 1H), 7.46 (m, 1H), 7.36 (m, 3H), 7.06 (m, 5H), 5.16 (s, 2H), 4.21 (s, 2H), 2.75 (s, 3H).

Example 26

4-{2-[(3-Fluorobenzyl)oxy]phenyl}-N-{3-[(methylsulfonyl)methyl]phenyl}-1,3,5-triazin-2-amine

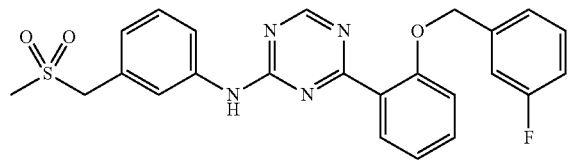 [SMILES: CS(=O)(=O)Cc1cccc(Nc2ncnc(-c3ccccc3OCc3cccc(F)c3)n2)c1]

Example 26 was prepared under similar conditions as described in the preparation of Example 1 using crude 4-chloro-N-{3-[(methylsulfonyl)methyl]phenyl}-1,3,5-triazin-2-amine and {2-[(3-fluorobenzyl)oxy]phenyl}boronic acid (Aldrich Chemical Company Inc.). The batch was purified by preparative HPLC.

| System: | Waters Autopurificationsystem: Pump 254, Sample Manager 2767, CFO, DAD 2996, ELSD 2424, SQD 3001 |
| --- | --- |
| Column: | XBrigde C18 5 µm 100 × 30 mm |
| Solvent: | A = H$_2$O + 0.2% NH$_3$ |
| | B = MeOH |
| Gradient: | 0-1 min 50% B, 1-8 min 50-90% B |
| Flow: | 50 mL/min |
| Temperature: | RT |
| Detection: | DAD scan range 210-400 nm |
| | MS ESI+, ESI−, scan range 160-1000 m/z |
| | ELSD |
| Retention: | 5.20-5.87 min |

$^{1}$H NMR (400 MHz, CDCl$_3$, 300K) δ=8.86 (s, 1H), 7.92 (m, 1H), 7.79 (s, 1H), 7.67 (m, 1H), 7.47 (m, 2H), 7.36 (m, 1H), 7.29 (m, 2H), 7.12 (m, 4H), 6.97 (m, 1H), 5.20 (s, 2H), 4.22 (s, 2H), 2.76 (s, 3H).

Example 27

4-{2-[(2-Chlorobenzyl)oxy]phenyl}-N-{3-[(methylsulfonyl)methyl]phenyl}-1,3,5-triazin-2-amine

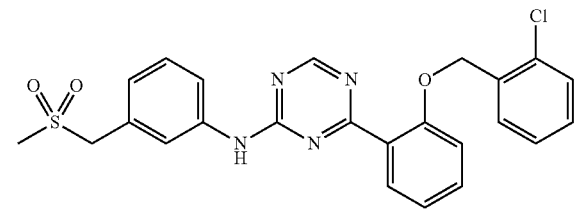 [SMILES: CS(=O)(=O)Cc1cccc(Nc2ncnc(-c3ccccc3OCc3ccccc3Cl)n2)c1]

Example 27 was prepared under similar conditions as described in the preparation of Example 1 using crude 4-chloro-N-{3-[(methylsulfonyl)methyl]phenyl}-1,3,5-triazin-2-amine and {2-[(2-chlorobenzyl)oxy]phenyl}boronic acid (Aldrich Chemical Company Inc.). The batch was purified by preparative HPLC.

| System: | Waters Autopurificationsystem: Pump 254, Sample Manager 2767, CFO, DAD 2996, ELSD 2424, SQD 3001 |
| --- | --- |
| Column: | XBrigde C18 5 µm 100 × 30 mm |
| Solvent: | A = H$_2$O + 0.2% NH$_3$ |
| | B = MeOH |
| Gradient: | 0-1 min 50% B, 1-8 min 50-90% B |
| Flow: | 50 mL/min |
| Temperature: | RT |
| Detection: | DAD scan range 210-400 nm |
| | MS ESI+, ESI−, scan range 160-1000 m/z |
| | ELSD |
| Retention: | 6.03-6.78 min |

$^{1}$H NMR (400 MHz, CDCl$_3$, 300K) δ=8.86 (s, 1H), 7.92 (m, 1H), 7.79 (br, 1H), 7.66 (m, 2H), 7.47 (m, 2H), 7.36 (m, 2H), 7.21 (m, 2H), 7.13 (m, 3H), 5.29 (s, 2H), 4.22 (s, 2H), 2.76 (s, 3H).

Example 28

4-{2-[(3-Chlorobenzyl)oxy]phenyl}-N-{3-[(methylsulfonyl)methyl]phenyl}-1,3,5-triazin-2-amine

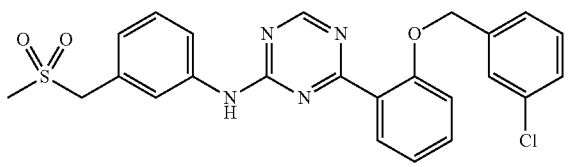

Example 28 was prepared under similar conditions as described in the preparation of Example 1 using crude 4-chloro-N-{3-[(methylsulfonyl)methyl]phenyl}-1,3,5-triazin-2-amine and {2-[(3-chlorobenzyl)oxy]phenyl}boronic acid (Aldrich Chemical Company Inc.). The batch was purified by preparative HPLC.

| System: | Waters Autopurificationsystem: Pump 254, Sample Manager 2767, CFO, DAD 2996, ELSD 2424, SQD 3001 |
|---|---|
| Column: | XBrigde C18 5 µm 100 × 30 mm |
| Solvent: | A = H₂O + 0.2% NH₃<br>B = MeOH |
| Gradient: | 0-1 min 50% B, 1-8 min 50-90% B |
| Flow: | 50 mL/min |
| Temperature: | RT |
| Detection: | DAD scan range 210-400 nm<br>MS ESI+, ESI−, scan range 160-1000 m/z<br>ELSD |
| Retention: | 5.91-6.30 min |

$^1$H NMR (400 MHz, d$_6$-DMSO, 300K) δ=10.35 (s, 1H), 8.81 (s, 1H), 7.75 (m, 3H), 7.54 (br, 1H), 7.47 (m, 1H), 7.32 (m, 4H), 7.18 (m, 1H), 7.07 (m, 2H), 5.21 (s, 2H), 4.40 (s, 2H), 2.86 (s, 3H).

Example 29

4-[4-Chloro-2-(cyclopentyloxy)phenyl]-N-{3-[(methylsulfonyl)methyl]phenyl}-1,3,5-triazin-2-amine

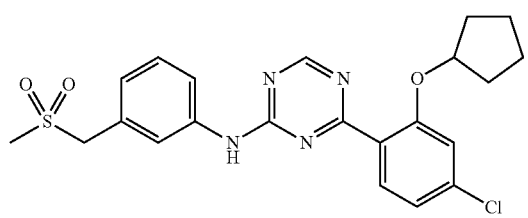 [SMILES: CS(=O)(=O)Cc1cccc(Nc2ncnc(-c3ccc(Cl)cc3OC3CCCC3)n2)c1]

A batch with crude crude 4-chloro-N-{3-[(methylsulfonyl)methyl]phenyl}-1,3,5-triazin-2-amine (175 mg), [4-chloro-2-(cyclopentyloxy)phenyl]boronic acid (141 mg; 0.59 mmol; Combi-Blocks Inc.) and [1,1'-bis(diphenylphosphino)ferrocene]palladium dichloride (72 mg; 0.09 mmol) in 1,2-dimethoxyethane (2.0 mL) and 2M solution of potassium carbonate (0.6 mL) was degassed using argon. The batch was stirred under argon for 60 minutes at 100° C. After cooling the batch was diluted with ethyl acetate. The organic phase was filtered using a Whatman filter and concentrated. The residue was purified by preparative HPLC.

| System: | Waters Autopurificationsystem: Pump 2545, Sample Manager 2767, CFO, DAD 2996, ELSD 2424, SQD 3001 |
|---|---|
| Column: | XBrigde C18 5 µm 100 × 30 mm |
| Solvent: | A = H₂O + 0.1% HCOOH<br>B = Acetonitrile |
| Gradient: | 0-1 min 1% B, 1-8 min 1-99% B, 8-10 min 99% B |
| Flow: | 50 mL/min |
| Temperature: | RT |
| Solution: | Max. 250 mg/max. 2.5 mL DMSO o. DMF |
| Injektion: | 1 × 2.5 mL |
| Detection: | DAD scan range 210-400 nm<br>MS ESI+, ESI−, scan range 160-1000 m/z |

$^1$H NMR (400 MHz, CDCl$_3$, 300K) δ=8.80 (s, 1H), 7.74 (m, 3H), 7.53 (s, 1H), 7.40 (m, 1H), 7.17 (m, 1H), 7.02 (m, 2H), 4.82 (m, 1H), 4.26 (s, 2H), 2.79 (s, 3H), 1.73 (m, 8H).

Example 30

4-{5-Fluoro-2-[(2-fluorobenzyl)oxy]phenyl}-N-{3-[(methylsulfonyl)methyl]phenyl}-1,3,5-triazin-2-amine

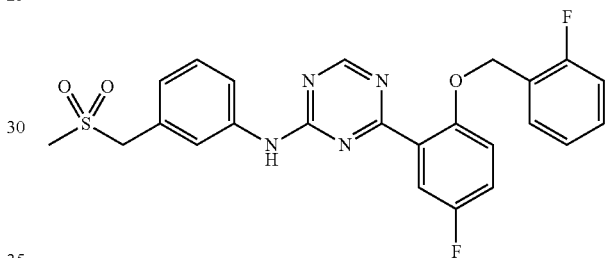

Example 30 was prepared under similar conditions as described in the preparation of Example 1 using crude 4-chloro-N-{3-[(methylsulfonyl)methyl]phenyl}-1,3,5-triazin-2-amine and {5-fluoro-2-[(2-fluorobenzyl)oxy]phenyl}boronic acid (Combi-Blocks Inc.). The batch was purified by preparative TLC. $^1$H NMR (400 MHz, CDCl$_3$, 300K) δ=8.84 (s, 1H), 7.79 (br, 1H), 7.63 (m, 2H), 7.48 (m, 2H), 7.37 (m, 1H), 7.27 (m, 1H), 7.09 (m, 5H), 5.22 (s, 2H), 4.23 (s, 2H), 2.78 (s, 3H).

Example 31

4-{5-Fluoro-2-[(3-fluorobenzyl)oxy]phenyl}-N-{3-[(methylsulfonyl)methyl]phenyl}-1,3,5-triazin-2-amine

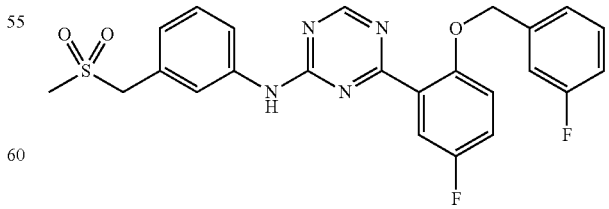

Example 31 was prepared under similar conditions as described in the preparation of Example 1 using crude 4-chloro-N-{3-[(methylsulfonyl)methyl]phenyl}-1,3,5-triazin-2-amine and {5-fluoro-2-[(3-fluorobenzyl)oxy]

phenyl}boronic acid (Combi-Blocks Inc.). The batch was purified by preparative TLC (DCM/EtOH 95:5).

¹H NMR (400 MHz, CDCl₃, 300K) δ=8.86 (s, 1H), 7.78 (s, 1H), 7.68 (m, 2H), 7.28 (m, 7H), 7.00 (m, 2H), 5.16 (s, 2H), 4.23 (s, 2H), 2.78 (s, 3H).

Example 32

4-(4-Chloro-2-methoxyphenyl)-N-{3-[(methylsulfonyl)methyl]phenyl}-1,3,5-triazin-2-amine

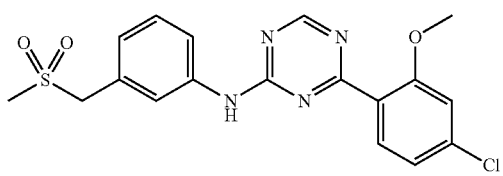 [SMILES: COc1cc(Cl)ccc1-c1ncnc(Nc2cccc(CS(C)(=O)=O)c2)n1]

Example 32 was prepared under similar conditions as described in the preparation of Example 30 using crude 4-chloro-N-{3-[(methylsulfonyl)methyl]phenyl}-1,3,5-triazin-2-amine and (4-chloro-2-methoxyphenyl)boronic acid (ABCR GmbH & CO. KG). The batch was purified by preparative HPLC.

| System: | Waters Autopurificationsystem: Pump 2545, Sample Manager 2767, CFO, DAD 2996, ELSD 2424, SQD 3001 |
|---|---|
| Column: | XBrigde C18 5 μm 100 × 30 mm |
| Solvent: | A = H₂O + 0.1% HCOOH |
| | B = Acetonitrile |
| Gradient: | 0-1 min 1% B, 1-8 min 1-99% B, 8-10 min 99% B |
| Flow: | 50 mL/min |
| Temperature: | RT |
| Solution: | Max. 250 mg/max. 2.5 mL DMSO o. DMF |
| Injektion: | 1 × 2.5 mL |
| Detection: | DAD scan range 210-400 nm |
| | MS ESI+, ESI−, scan range 160-1000 m/z |

¹H NMR (400 MHz, CDCl₃, 300K) δ=8.82 (s, 1H), 7.87 (m, 1H), 7.76 (m, 2H), 7.51 (s, 1H), 7.42 (m, 1H), 7.16 (m, 1H), 7.06 (m, 2H), 4.26 (s, 2H), 3.94 (s, 3H), 2.79 (s, 3H).

Example 33

4-(4-Fluoro-2-methoxyphenyl)-N-{4-fluoro-3-[(methylsulfonyl)methyl]phenyl}-1,3,5-triazin-2-amine

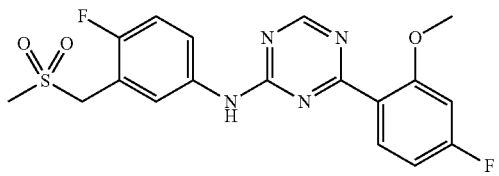 [SMILES: COc1cc(F)ccc1-c1ncnc(Nc2ccc(F)c(CS(C)(=O)=O)c2)n1]

Preparation of Intermediate 33.1:
1-Fluoro-2-[(methylsulfanyl)methyl]-4-nitrobenzene

A suspension of 2-bromomethyl-1-fluoro-4-nitrobenene (3.76 g) in ethanol (75 mL) at −15° C. was treated with sodiummethanethiolate (1.25 g) in 3 portions, during 3 hours the temperature was increased from −15° C. to 0° C. Then brine was added, extracted with ethyl acetate (3×), the combined organic phases were washed with water to neutrality, dried with sodium sulfate, filtered and concentrated. The title compound (3.25 g) was thus obtained and used without further purification.

Preparation of Intermediate 33.2:
1-Fluoro-2-[(methylsulfonyl)methyl]-4-nitrobenzene

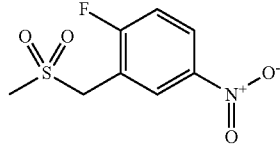

A solution of 1-fluoro-2-[(methylsulfanyl)methyl]-4-nitrobenzene (1.6 g) in DCM (55 mL) was treated at 0° C. with portions of 3-chloroperbenzoic acid (3.9 g, 77%). The mixture was stirred at 0° C. for further 30 minutes and then 2.5 hours at room temperature. The reaction mixture was diluted with DCM before sodium hydrogen sulfite and sodium bicarbonate solution was added and extracted with DCM (2×). The combinded organic phases were washed and concentrated. The residue was purified by chromatography (hexane/ethyl acetate 12% 100%) to give the title compound (1.7 g).

¹H-NMR (600 MHz, CDCl₃): δ=8.44 (dd, 1H), 8.33 (m, 1H), 7.34 (t, 1H), 4.41 (s, 2H), 2.93 (s, 3H).

Preparation of Intermediate 33.3:
4-Fluoro-3-[(methylsulfonyl)methyl]aniline

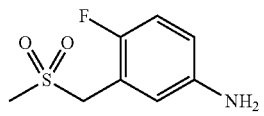

A solution of titanous chloride (about 15%) in about 10% hydrochloric acid (MERCK (MDA) INCL SCHUCHARDT, 71.5 mL) was added to a stirred solution of 1-fluoro-2-[(methylsulfonyl)methyl]-4-nitrobenzene (1.61 g) in THF (80 mL) at room temperature and stirred for 16 hours. By adding 1N sodium hydroxide solution the pH value of the reaction mixture was raised to 10 before it was extracted with ethyl acetate (2×). The combined organic phases were washed with brine, dried over sodium sulfate and concentrated to give the crude title compound (1.64 g) which crystallized from diethylether/Ethyl acetate (1.16 g).

$^1$H-NMR (600 MHz, CDCl$_3$): δ=6.92 (t, 1H), 6.76 (dd, 1H), 6.66 (m, 1H), 4.22 (s, 2H), 3.65 (br. s., 2H), 2.80 (s, 3H).

Preparation of Intermediate 33.4: 4-Chloro-N-{4-fluoro-3-[(methylsulfonyl)methyl]phenyl}-1,3,5-triazin-2-amine

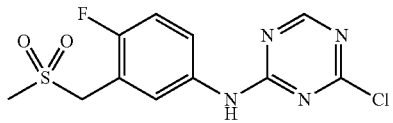 [SMILES: CS(=O)(=O)Cc1cc(Nc2ncnc(Cl)n2)ccc1F]

To a stirred solution of 2,4-dichloro-1,3,5-triazine (169 mg, ABCR GmbH & CO. KG) in THF/i-PrOH (1:1; 2 mL) DIPEA (0.38 mL) was added at −40° C. Then a suspension of 4-fluoro-3-[(methylsulfonyl)methyl]aniline (224 mg) in THF/i-PrOH (1:1, 10 mL) was added at this temperature. Under stirring the temperature of the reaction mixture was slowly raised over 3 hours to 0° C. The reaction mixture was then concentrated in vacuo to give the crude product (733 mg) which was used without further purification.

Preparation of End Product:

Example 33 was prepared under similar conditions as described for the preparation of Example 1 using crude 4-chloro-N-{4-fluoro-3-[(methylsulfonyl)methyl]phenyl}-1,3,5-triazin-2-amine (732 mg), (5-fluoro-2-methoxyphenyl)boronic acid (181 mg, Aldrich Chemical Company Inc.) and a 2 M aqueous solution of sodium carbonate (1.1 mL) as base. The crude product was purifed by flash chromatography on SiO$_2$ with hexane and ethyl acetate (12% 100%) to give the desired compound (56 mg).

$^1$H-NMR (400 MHz, DMSO-d$_6$): δ=10.39 (s, 1H), 8.79 (s, 1H), 7.80 (m, 3H), 7.29 (t, 1H), 7.09 (dd, 1H), 6.89 (td, 1H), 4.51 (s, 2H), 3.88 (br. s., 3H), 3.03 (m, 3H).

Example 34

4-{2-[(3-Chlorobenzyl)oxy]phenyl}-N-{3-[(propan-2-ylsulfonyl)methyl]phenyl}-1,3,5-triazin-2-amine

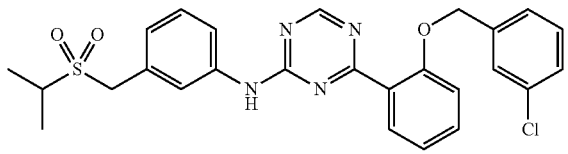 [SMILES: CC(C)S(=O)(=O)Cc1cccc(Nc2ncnc(-c3ccccc3OCc3cccc(Cl)c3)n2)c1]

Preparation of Intermediate 34.1: 1-Nitro-3-[(propan-2-ylsulfanyl)methyl]benzene

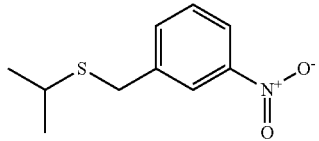

A solution of sodium methoxyde (15.5 mL, 25 wt % in methanol) was diluted with methanol (85 mL) and treated with 2-propanethiol (6.3 mL) at room temperature for 60 minutes, cooled to −15° C., treated with 3-nitrobenzylchloride (10 g) in 3 portions, kept for 2 hours at −15° C., then the temperature was increased to room temperature. The reaction mixture was concentrated in vacuo, treated with diethyl ether (300 mL), washed with water (2×100 mL) and brine (100 mL), dried with sodium sulfate and evaporated to dryness. The title compound (12.3 g) was thus obtained and used without further purification.

Preparation of Intermediate 34.2: 1-Nitro-3-[(propan-2-ylsulfonyl)methyl]benzene

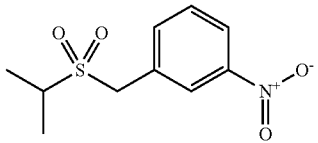 [SMILES: CC(C)S(=O)(=O)Cc1cccc([N+](=O)[O-])c1]

A solution of 1-nitro-3-[(propan-2-ylsulfonyl)methyl]benzene (4.0 g) in DCM (160 mL) was treated at 0° C. with portions of m-chloroperbenzoic acid (9.3 g, 77%). The mixture was stirred at 0° C. for further 30 minutes and then 18 hours at room temperature. The reaction mixture was diluted with DCM before sodium hydrogen sulfite and sodium bicarbonate solution was added and extracted with DCM (2×). The combinded organic phases were washed and concentrated. The residue was purified by chromatography (hexane/ethyl acetate 12% 100%) to give the title compound (4.5 g).

Preparation of Intermediate 34.3: N-{3-[(Propan-2-ylsulfonyl)methyl]phenyl}acetamide

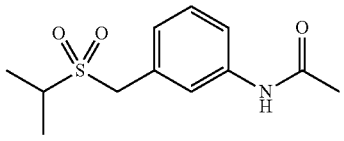 [SMILES: CC(=O)Nc1cccc(CS(=O)(=O)C(C)C)c1]

A suspension of crude 1-nitro-3-[(propan-2-ylsulfonyl)methyl]benzene (5.0 g) in acetic acid (58 mL) was treated with iron powder (4.7 g), heated for 22 hours at 110° C. bath temperature and cooled to room temperature. Then water (250 mL) and DCM (250 mL) were added, stirred, filtered, dried with sodium sulfate and condensed. An analytical sample (200 mg) of the crude title compound (5.6 g) was recrystallized from diethyl ether/ethanol (121 mg). Lit.:[Grohmann and Hathaway, Molbank 2006, M502].

$^1$H-NMR (600 MHz, CDCl$_3$): δ=7.61 (s, 1H), 7.50 (d, 1H), 7.37 (br. s., 1H), 7.32 (t, 1H), 7.14 (d, 1H), 4.20 (s, 2H), 3.05 (spt, 1H), 2.16 (s, 3H), 1.39 (d, 6H).

Preparation of Intermediate 34.4: 3-[(Propan-2-ylsulfonyl)methyl]anilinium chloride

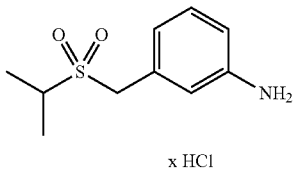

x HCl

A solution of N-{3-[(propan-2-ylsulfonyl)methyl]phenyl}acetamide (5.4 g) in ethanol (29.6 mL) was treated with concentrated hydrochloric acid (35.5 mL) and refluxed for 24 hours. The reaction mixture was condensed to dryness. The title compound (3.5 g) was obtained by crystallization from ethanol/ethyl acetate.

$^1$H-NMR (400 MHz, DMSO-d$_6$): δ=9.95 (br. s., 2H), 7.47 (m, 1H), 7.34 (m, 3H), 4.52 (s, 2H), 3.22 (spt, 1H), 1.29 (d, 6H).

Preparation of Intermediate 34.5: 4-Chloro-N-{3-[(propan-2-ylsulfonyl)methyl]phenyl}-1,3,5-triazin-2-amine

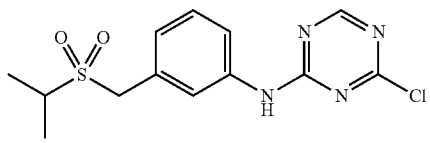 [SMILES: CC(C)S(=O)(=O)Cc1cccc(Nc2ncnc(Cl)n2)c1]

To a stirred solution of 2,4-dichloro-1,3,5-triazine (150 mg, ABCR GmbH & CO. KG) in THF/i-PrOH (1:1; 1.9 mL) DIPEA (0.52 mL) was added at −40° C. Then a suspension of 3-[(propan-2-ylsulfonyl)methyl]anilinium chloride (250 mg) in THF/i-PrOH (1:1, 0.94 mL) was added at this temperature. Under stirring the temperature of the reaction mixture was slowly raised over 3 hours to 0° C. The reaction mixture was then concentrated in vacuo to give the crude title compound (876 mg) which was used without further purification.

Preparation of End Product:

A suspension of crude 4-chloro-N-{3-[(propan-2-ylsulfonyl)methyl]phenyl}-1,3,5-triazin-2-amine (854 mg, 38% by weight) and [2-(3-chlorophenoxy)phenyl]boronic acid (263 mg) in 1,2-dimethoxyethane (3.1 mL) was treated with a 2 M solution of potassium carbonate (1.0 mL) and Pd(dppf)C$_{12}$ (82 mg) and then heated for 150 minutes at 80° C. and then for 90 minutes at 100° C. The reaction mixture was then allowed to cool to room temperature, taken up in ethyl acetate (100 mL) and water (50 mL), washed with saturated brine, dried over sodium sulfate, and condensed in vacuo to give the crude product that was purified by flash column chromatography on SiO$_2$ with DCM/acetone (5% 40%) to give analytically pure product (220 mg).

$^1$H-NMR (400 MHz, CDCl$_3$): δ=8.86 (s, 1H), 7.94 (dd, 1H), 7.79 (s, 1H), 7.69 (d, 1H), 7.60 (br. s., 1H), 7.47 (m, 1H), 7.37 (m, 2H), 7.26 (m, 3H), 7.15 (m, 2H), 7.07 (d, 1H), 5.18 (s, 2H), 4.21 (br. s., 2H), 3.04 (dt, 1H), 1.36 (d, 6H)

Example 35

4-(4-Fluoro-2-methoxyphenyl)-N-{3-[(phenylsulfonyl)methyl]phenyl}-1,3,5-triazin-2-amine

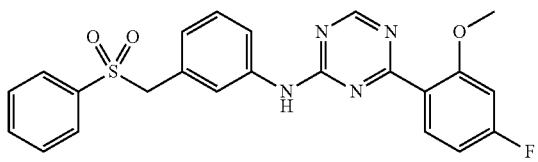 [SMILES: COc1cc(F)ccc1-c1ncnc(Nc2cccc(CS(=O)(=O)c3ccccc3)c2)n1]

Preparation of Intermediate 35.1: 1-Nitro-3-[(phenylsulfanyl)methyl]benzene

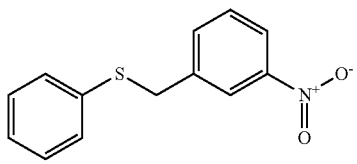 [SMILES: O=[N+]([O-])c1cccc(CSc2ccccc2)c1]

A solution of 3-nitrobenzyl chloride (10.0 g) in ethanol (120 mL) was cooled to 0° C., treated with sodium thiophenolate (9.1 g, 90%) in 3 portions, while the temperature was slowly increased to room temperature the mixture was stirred for 18 hours. The reaction mixture was then concentrated in vacuo, treated with diethyl ether (350 mL), washed with water (2×150 mL) and brine (100 mL), dried with sodium sulfate and evaporated to dryness. The title compound (14.6 g) was thus obtained and used without further purification.

Preparation of Intermediate 35.2: 1-Nitro-3-[(phenylsulfonyl)methyl]benzene

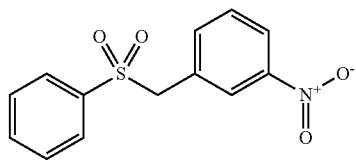 [SMILES: O=[N+]([O-])c1cccc(CS(=O)(=O)c2ccccc2)c1]

A solution of 1-nitro-3-[(phenylsulfanyl)methyl]benzene (4.5 g) in DCM (180 mL) was treated at 0° C. with portions of m-chloroperbenzenoic acid (9.0 g, 77%). The mixture was stirred at 0° C. for further 90 minutes and then 18 hours at room temperature. The reaction mixture was diluted with DCM before disodium sulfurothioate and sodium bicarbonate solution was added and extracted with DCM (2×). The combinded organic phases were washed and concentrated to obtain the crude title compound (5.2 g) which was used without further purification.

$^1$H-NMR (400 MHz, CDCl$_3$): δ=8.21 (m, 1H), 7.88 (t, 1H), 7.67 (m, 3H), 7.53 (m, 4H), 4.40 (s, 2H).

Preparation of Intermediate 35.3: 3-[(Phenylsulfonyl)methyl]aniline

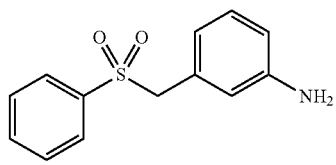 [SMILES: Nc1cccc(CS(=O)(=O)c2ccccc2)c1]

A solution of 1-nitro-3-[(phenylsulfonyl)methyl]benzene (5.15 g) in ethanol (55 mL) and water (11.4 mL) was treated with ammonium chlorid (4.99 g) at 0° C. Then zinc powder (6.10 g) was cautiously added in portions and stirred for 3 hours at RT. Then the mixture was filtered over Cellite, washed with ethanol, condensed to dryness, treated with ethyl acetate, washed with brine, dried with sodium sulfate and condensed to dryness. Crystallization of the crude product (5.20 g) from diethyl ether furnished the pure title compound (3.80 g).

$^1$H-NMR (500 MHz, CDCl$_3$): δ=7.67 (dd, 2H), 7.60 (m, 1H), 7.45 (m, 2H), 6.99 (t, 1H), 6.62 (m, 1H), 6.50 (t, 1H), 6.35 (d, 1H), 4.21 (s, 2H), 3.64 (br. s., 2H).

Preparation of Intermediate 35.4: 4-Chloro-N-{3-[(phenylsulfonyl)methyl]phenyl}-1,3,5-triazin-2-amine

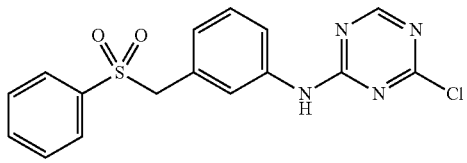 [SMILES: O=S(=O)(Cc1cccc(Nc2ncnc(Cl)n2)c1)c1ccccc1]

To a stirred solution of 2,4-dichloro-1,3,5-triazine (150 mg, ABCR GmbH & CO. KG) in THF/i-PrOH (1:1; 1.90 mL) DIPEA (0.35 mL) was added at −40° C. Then a suspension of 3-[(phenylsulfonyl)methyl]aniline (248 mg) in THF/i-PrOH (1:1, 0.94 mL) was added at this temperature. Under stirring the temperature of the reaction mixture was slowly raised over 2 hours to 0° C. The reaction mixture was then concentrated in vacuo to give the crude title compound (691 mg) which was used without further purification.

Preparation of End Product:

A suspension of crude 4-chloro-N-{3-[(phenylsulfonyl)methyl]phenyl}-1,3,5-triazin-2-amine (691 mg, 52% by weight) and (4-fluoro-2-methoxyphenyl)boronic acid (170 mg; Aldrich Chemical Company Inc.) was treated as described in example 34. One obtained pure product (135 mg).

$^1$H-NMR (400 MHz, CDCl$_3$): δ=8.78 (s, 1H), 7.97 (br. s., 1H), 7.77 (br. s., 1H), 7.68 (d, 2H), 7.58 (m, 1H), 7.45 (m, 3H), 7.28 (m, 2H), 6.79 (m, 3H), 4.32 (s, 2H), 3.94 (s, 3H).

Example 36

N-{3-[(Cyclopentylsulfonyl)methyl]phenyl}-4-(4-fluoro-2-methoxyphenyl)-1,3,5-triazin-2-amine

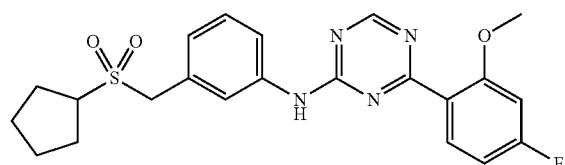

Preparation of Intermediate 36.1: 1-[(Cyclopentylsulfanyl)methyl]-3-nitrobenzene

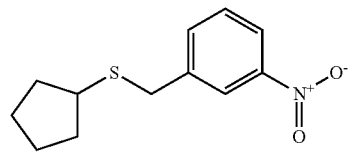 [SMILES: O=[N+]([O-])c1cccc(CSC2CCCC2)c1]

A solution of sodium methoxyde (15.5 mL, 25 wt % in methanol) was diluted with methanol (85 mL) and treated with cyclopentanethiol (7.3 mL) at room temperature for 60 minutes, cooled to −15° C., treated with 3-nitrobenzylchloride (10.0 g) in 3 portions, kept for 2 hours at −15° C., then the temperature was increased to room temperature. The reaction mixture was concentrated in vacuo, treated with diethyl ether (350 mL), washed with water (2×150 mL) and brine (100 mL), dried with sodium sulfate and evaporated to dryness. The title compound (14.9 g) was thus obtained and used without further purification.

Preparation of Intermediate 36.2: 1-[(Cyclopentylsulfonyl)methyl]-3-nitrobenzene

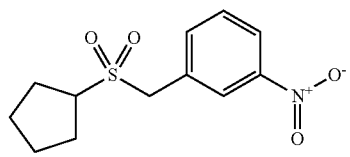 [SMILES: O=[N+]([O-])c1cccc(CS(=O)(=O)C2CCCC2)c1]

A solution of 1-[(cyclopentylsulfanyl)methyl]-3-nitrobenzene (4.5 g) in DCM (180 mL) was treated at 0° C. with portions of m-chloroperbenzoic acid (9.3 g, 77%). The mixture was stirred at 0° C. for further 90 minutes and then 18 hours at room temperature. The reaction mixture was diluted with DCM before disodium sulfurothioate and sodium bicarbonate solution was added and extracted with DCM (2×). The combined organic phases were washed and concentrated. The residue was purified by chromatography (hexane/ethyl acetate 12% 100%) to give the title compound (4.9 g).

$^1$H-NMR (400 MHz, CDCl$_3$): δ=8.27 (m, 2H), 7.80 (d, 1H), 7.62 (m, 1H), 4.29 (s, 2H), 3.29 (m, 1H), 2.14 (m, 2H), 1.99 (m, 2H), 1.85 (m, 2H), 1.68 (m, 2H).

Preparation of Intermediate 36.3: 3-[(Cyclopentylsulfonyl)methyl]aniline

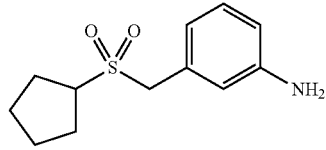 [SMILES: Nc1cccc(CS(=O)(=O)C2CCCC2)c1]

A solution of 1-[(cyclopentylsulfonyl)methyl]-3-nitrobenzene (4.9 g) in ethanol (37 mL) and water (11.1 mL) was treated with ammonium chloride (4.9 g) at 0° C. Then zinc powder (5.9 g) was cautiously added in portions and stirred for 3 hours at room temperature. Then the mixture was filtered over cellite, washed with ethanol, condensed to dryness, treated with ethyl acetate, washed with brine, dried with sodium sulfate and condensed to dryness. Crystallization of the crude product (4.5 g) from diethyl ether furnished the pure title compound (3.6 g).

$^1$H-NMR (500 MHz, CDCl$_3$): δ=7.15 (t, 1H), 6.76 (d, 1H), 6.73 (d, 1H), 6.68 (dd, 1H), 4.11 (s, 2H), 3.74 (br. s., 2H), 3.25 (m, 1H), 2.08 (m, 2H), 1.90 (m, 2H), 1.80 (m, 2H), 1.60 (m, 2H).

95

Preparation of Intermediate 36.4: 4-Chloro-N-{3-[(cyclopentylsulfonyl)methyl]phenyl}-1,3,5-triazin-2-amine

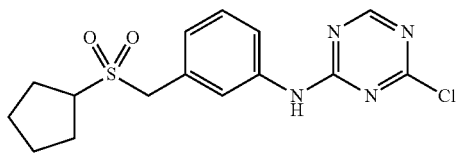 [SMILES: O=S(=O)(Cc1cccc(Nc2ncnc(Cl)n2)c1)C1CCCC1]

To a stirred solution of 2,4-dichloro-1,3,5-triazine (150 mg, ABCR GmbH & CO. KG) in THF/i-PrOH (1:1; 1.9 mL) DIPEA (0.35 mL) was added at −40° C. Then a suspension of 3-[(cyclopentylsulfonyl)methyl]aniline (240 mg) in THF/2-PrOH (1:1, 0.94 mL) was added at this temperature. Under stirring the temperature of the reaction mixture was slowly raised over 2 hours to 0° C. The reaction mixture was then concentrated in vacuo to give the crude title compound (726 mg) which was used without further purification.

Preparation of End Product:

A suspension of crude 4-chloro-N-{3-[(cyclopentylsulfonyl)methyl]phenyl}-1,3,5-triazin-2-amine (726 mg, 50% by weight) and (4-fluoro-2-methoxyphenyl)boronic acid (170 mg; Aldrich Chemical Company Inc.) was treated as described in example 34. One obtained pure product (170 mg).

$^1$H-NMR (400 MHz, CDCl$_3$): δ=8.81 (s, 1H), 7.96 (br. s., 1H), 7.80 (s, 1H), 7.75 (br. s., 1H), 7.41 (m, 2H), 7.17 (d, 1H), 6.78 (m, 2H), 4.22 (s, 2H), 3.94 (s, 3H), 3.26 (m, 1H), 2.08 (m, 2H), 1.93 (m, 2H), 1.79 (m, 2H), 1.58 (m, 2H).

Example 37

4-{2-[(4-Fluorobenzyl)oxy]phenyl}-N-{3-[(prop-2-ylsulfonyl)methyl]phenyl}-1,3,5-triazin-2-amine

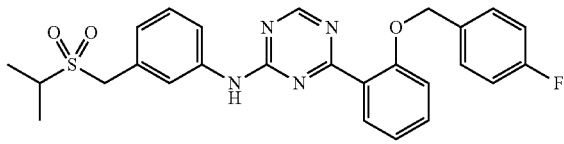 [SMILES: CC(C)S(=O)(=O)Cc1cccc(Nc2ncnc(-c3ccccc3OCc3ccc(F)cc3)n2)c1]

A suspension of crude 4-chloro-N-{3-[(prop-2-ylsulfonyl)methyl]phenyl}-1,3,5-triazin-2-amine (945 mg, 35% by weight) and (4-fluorobenzyl)oxy]phenyl)boronic acid (246 mg) was treated as described in example 34. One obtained pure product (137 mg).

$^1$H-NMR (500 MHz, CDCl$_3$): δ=8.83 (s, 1H), 7.88 (d, 1H), 7.78 (s, 1H), 7.68 (br. s., 1H), 7.45 (m, 1H), 7.37 (m, 4H), 7.16 (d, 1H), 7.11 (m, 1H), 7.07 (d, 1H), 7.00 (t, 2H), 5.17 (s, 2H), 4.20 (br. s., 2H), 3.03 (br. s., 1H), 1.36 (d, 6H).

96

Example 38

4-{5-Fluoro-2-[(3-fluorobenzyl)oxy]phenyl}-N-{3-[(prop-2-ylsulfonyl)methyl]phenyl}-1,3,5-triazin-2-amine

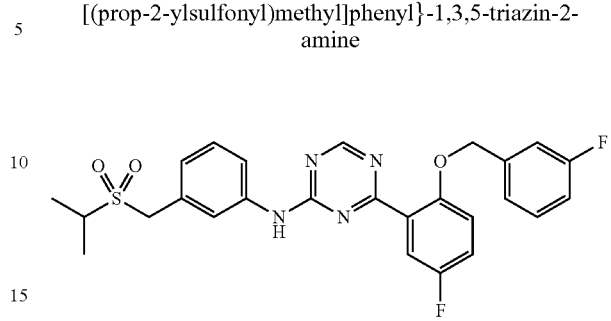

A suspension of crude 4-chloro-N-{3-[(prop-2-ylsulfonyl)methyl]phenyl}-1,3,5-triazin-2-amine (876 mg, 37% by weight) and {5-fluoro-2-[(3-fluorobenzyl)oxy]phenyl}boronic acid (264 mg) was treated as described in example 34. One obtained pure product (299 mg).

$^1$H-NMR (500 MHz, CDCl$_3$): δ=8.85 (s, 1H), 7.77 (br, 1H), 7.67 (m, 2H), 7.37 (m, 4H), 7.15 (m, 3H), 6.99 (m, 2H), 5.16 (s, 2H), 4.21 (s., 2H), 3.04 (br., 1H), 1.37 (br, 6H).

Example 39

N-{5-Chloro-3-[(methylsulfonyl)methyl]phenyl}-4-(4-fluoro-2-methoxyphenyl)-1,3,5-triazin-2-amine

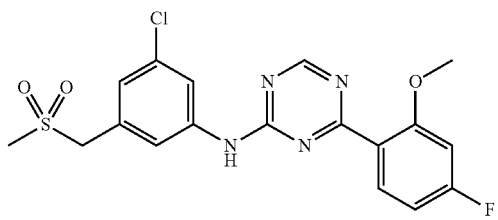

Preparation of Intermediate 39.1:
1-Chloro-3-[(methylsulfanyl)methyl]-5-nitrobenzene

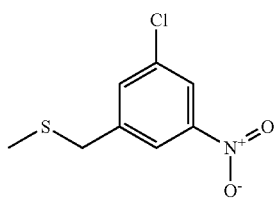

A solution of 1-(bromomethyl)-3-chloro-5-nitrobenzene (10.0 g) in ethanol (200 mL) was treated at −20° C. with portions of sodium methanthiolat (3.32 g) and stirred for 3 hours at room temperature. The reaction mixture was treated with brine (100 mL) extrakted with ethyl acetate (300 mL), washed with water (2×100 mL) and, dried with sodium sulfate and evaporated to dryness. One obtained the title compound (8.6 g) which was used without further purification.

Preparation of Intermediate 39.2:
1-Chloro-3-[(methylsulfonyl)methyl]-5-nitrobenzene

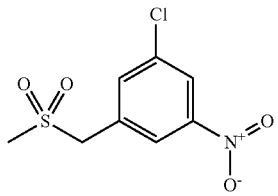

A solution of 1-chloro-3-[(methylsulfanyl)methyl]-5-nitrobenzene (4.26 g) in DCM (190 mL) was treated at 0° C. with portions of m-chloroperbenzoic acid (8.77 g, 77%). The mixture was stirred at 0° C. for further 30 minutes and then 17 hours at room temperature. The reaction mixture was diluted with DCM before disodium sulfurothioate and sodium bicarbonate solution was added and extracted with DCM (2×). The combinded organic phases were washed and concentrated. The residue was purified by chromatography (hexane/ethyl acetate 12% 100%) to give the title compound (4.80 g). An analytical sample was crystallized from acetone/hexan.

¹H-NMR (600 MHz, CDCl₃): δ=8.28 (t, 1H), 8.18 (t, 1H), 7.79 (t, 1H), 4.32 (s, 2H), 2.93 (s, 3H).

Preparation of Intermediate 39.3:
3-Chloro-5-[(methylsulfonyl)methyl]aniline

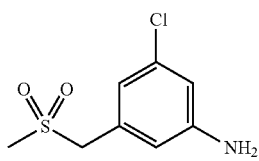

A solution of 1-chloro-3-[(methylsulfonyl)methyl]-5-nitrobenzene (4.6 g) in methanol (40 mL) was treated similarly as described in example 35.3. Crystallization of the crude product (4.6 g) from diethyl ether furnished the pure title compound (3.8 g)

¹H-NMR (600 MHz, CDCl₃): δ=6.72 (s, 1H), 6.69 (t, 1H), 6.62 (s, 1H), 4.10 (s, 2H), 3.85 (br., 2H), 2.79 (s, 3H).

Preparation of Intermediate 39.4: 4-Chloro-N-{3-chloro-5-[(methylsulfonyl)methyl]phenyl}-1,3,5-triazin-2-amine

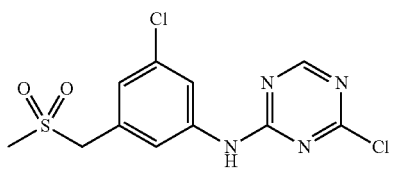 [SMILES: CS(=O)(=O)Cc1cc(Cl)cc(Nc2ncnc(Cl)n2)c1]

A solution of 2,4-dichlor-triazine (250 mg) in abs.THF (2.2 mL) and 2-propanol (2.2 mL) was treated at −40° C. with N,N-diisopropylethylamine (0.55 mL) and 1-chloro-3-[(methylsulfonyl)methyl]-5-nitrobenzene (348 mg) Under stirring the temperature of the reaction mixture was over 2 hours slowly raised to 0° C. The reaction mixture was then concentrated in vacuo to give the crude title compound (527 mg) which was used without further purification.

Preparation of End Product:

A suspension of crude 4-chloro-N-{5-chloro-3-[(methylsulfonyl)methyl]phenyl}-1,3,5-triazin-2-amine (898 mg, 59% by weight) and (4-fluoro-2-methoxyphenyl)boronic acid (269 mg; Aldrich Chemical Company Inc.) was similarly treated as described in example 34. Purification by flash column chromatography on SiO₂ with hexane/ethyl acetate (12% 100%) afforded the analytically pure product (330 mg).

¹H-NMR (500 MHz, CDCl₃): δ=8.84 (s, 1H), 8.08 (m, 2H), 7.60 (s, 1H), 7.48 (br, 1H), 7.13 (s, 1H), 6.79 (m, 2H), 4.21 (s, 2H), 3.96 (s, 3H), 2.84 (s, 3H).

Example 40

N-{3-[(Cyclopropylsulfonyl)methyl]phenyl}-4-(4-fluoro-2-methoxyphenyl)-1,3,5-triazin-2-amine

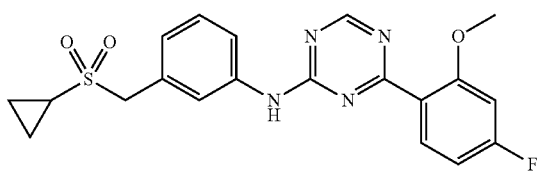 [SMILES: COc1cc(F)ccc1-c1ncnc(Nc2cccc(CS(=O)(=O)C3CC3)c2)n1]

Preparation of Intermediate 40.1:
1-[(Cyclopropylsulfonyl)methyl]-3-nitrobenzene

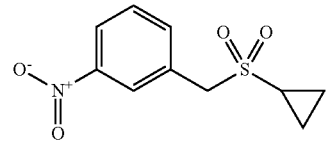 [SMILES: O=[N+]([O-])c1cccc(CS(=O)(=O)C2CC2)c1]

Sodium cyclopropanesulfinate (1.04 g; 8.1 mmol) was added to a stirred solution of 1-(bromomethyl)-3-nitrobenzene (1.17 g; 5.4 mmol) in acetonitrile (50 ml) at room temperature. The batch was stirred at 90° C. for 4 hours. After cooling, the batch was diluted with water and extracted with DCM (2×). The combined organic phases were filtered using a Whatman filter and concentrated to give the desired product (1.26 g) that was used without further purification. ¹H NMR (400 MHz, CDCl₃, 300K) δ=8.28 (m, 2H), 7.81 (m, 1H), 7.61 (m, 1H), 4.37 (s, 2H), 2.29 (m, 1H), 1.21 (m, 2H), 1.03 (m, 2H).

Preparation of Intermediate 40.2:
3-[(Cyclopropylsulfonyl)methyl]aniline

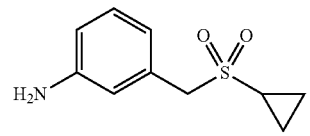 [SMILES: Nc1cccc(CS(=O)(=O)C2CC2)c1]

Intermediate 40.2 was prepared under similar conditions as described in the preparation of Intermediate 1.3 using 1-[(cyclopropylsulfonyl)methyl]-3-nitrobenzene.

$^1$H NMR (400 MHz, CDCl$_3$, 300K) δ=7.15 (m, 1H), 6.77 (m, 2H), 6.67 (m, 1H), 4.16 (s, 2H), 3.70 (br, 2H), 2.23 (m, 1H), 1.15 (m, 2H), 0.94 (m, 2H).

Preparation of Intermediate 40.3: 4-Chloro-N-{3-[(cyclopropylsulfonyl)methyl]phenyl}-1,3,5-triazin-2-amine

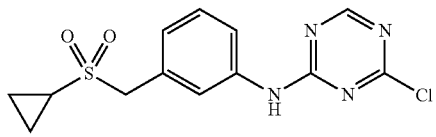 [SMILES: O=S(=O)(Cc1cccc(Nc2ncnc(Cl)n2)c1)C1CC1]

Intermediate 40.3 was prepared under similar conditions as described in the preparation of Intermediate 1.4 using 3-[(cyclopropylsulfonyl)methyl]aniline.

| | |
|---|---|
| System: | Waters Acquity UPLC-MS: Binary Solvent Manager, Sample Manager/Organizer, Column Manager, PDA, ELSD, SQD 3001 |
| Column: | Acquity UPLC BEH C18 1.7 50 × 2.1 mm |
| Solvent: | A1 = H$_2$O + 0.1% HCOOH |
| | B1 = Acetonitrile |
| Gradient: | 0-1.6 min 1-99% B, 1.6-2.0 min 99% B |
| Flow: | 0.8 mL/min |
| Temperatuer: | 60° C. |
| Injektion: | 2.0 µl |
| Detection: | DAD scan range 210-400 nm –> Peaktable ELSD |
| Method: | MS ESI+, ESI– Switch |
| Retention: | 0.89 min |
| MS(ES+): | m/z = 326 [M + H] |

Preparation of End Product:

Example 40 was prepared under similar conditions as described in the preparation of Example 34 using 4-chloro-N-{3-[(cyclopropylsulfonyl)methyl]phenyl}-1,3,5-triazin-2-amine and (4-fluoro-2-methoxy-phenyl)boronic acid.

$^1$H NMR (400 MHz, CDCl$_3$, 300K) δ=8.81 (s, 1H), 7.96 (br, 1H), 7.75 (m, 2H), 7.42 (m, 2H), 7.19 (m, 1H), 6.77 (m, 2H), 4.28 (s, 2H), 3.94 (s, 3H), 2.25 (m, 1H), 1.16 (m, 2H), 0.94 (m, 2H).

Example 41

4-[2-(Cyclopropyloxy)-4-fluorophenyl]-N-{3-[(methylsulfonyl)methyl]phenyl}-1,3,5-triazin-2-amine

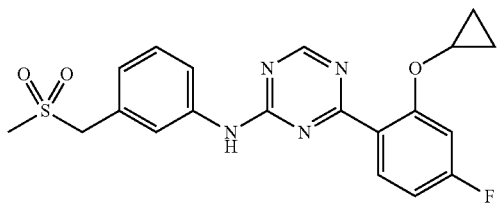

A mixture of 4-chloro-N-{3-[(methylsulfonyl)methyl]phenyl}-1,3,5-triazin-2-amine (134 mg), (Intermediate 1.4), 2-[2-(cyclopropyloxy)-4-fluorophenyl]-4,4,5,5-tetramethyl-1,3,2-dioxaborolane (150 mg; 0.539 mmol) and Pd(dppf)C$_{12}$ (55 mg; 0.06 mmol) in 1,2-dimethoxyethane (2.0 ml) and 2 M solution of potassium carbonate (0.45 ml) was degassed using argon. The batch was stirred under argon for 1 hour at 100° C. After cooling the batch was diluted with ethyl acetate (35 ml) and THF (35 ml). The organic phase was washed with brine, dried (sodium sulfate) and concentrated. The residue was purified by preparative HPLC to give the desired product (38 mg; 0.12 mmol).

| | |
|---|---|
| System: | Waters Autopurificationsystem: Pump 2545, Sample Manager 2767, CFO, DAD 2996, ELSD 2424, SQD 3001 |
| Column: | XBrigde C18 5 µm 100 × 30 mm |
| Solvent: | A = H$_2$O + 0.1% HCOOH |
| | B = Acetonitrile |
| Gradient: | 0-1 min 1% B, 1-8 min 1-99% B, 8-10 min 99% B |
| Flow: | 50 mL/min |
| Temperatuer: | RT |
| Solution: | Max. 250 mg/max. 2.5 mL DMSO o. DMF |
| Injektion: | 1 × 2.5 mL |
| Detection: | DAD scan range 210-400 nm |
| | MS ESI+, ESI–, scan range 160-1000 m/z |

$^1$H NMR (400 MHz, d$_6$-DMSO, 300K) δ=8.80 (s, 1H), 8.04-7.87 (m, 1H), 7.87-7.64 (m, 2H), 7.58 (br. s., 1H), 7.42 (t, 1H), 7.22-7.11 (m, 2H), 6.86-6.72 (m, 1H), 4.28 (s, 2H), 3.87 (br. s., 1H), 2.79 (s, 3H), 0.94-0.75 (m, 4H).

Example 42

4-(2-Ethoxy-4-fluorophenyl)-N-{3-[(methylsulfonyl)methyl]phenyl}-1,3,5-triazin-2-amine

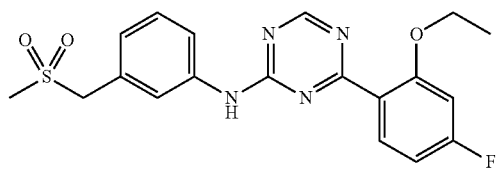 [SMILES: CCOc1cc(F)ccc1-c1ncnc(Nc2cccc(CS(C)(=O)=O)c2)n1]

Preparation of Intermediate 42.1: 4-(2,4-Difluorophenyl)-N-{3-[(methylsulfonyl)methyl]phenyl}-1,3,5-triazin-2-amine

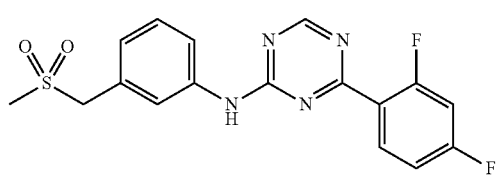 [SMILES: CS(=O)(=O)Cc1cccc(Nc2ncnc(-c3ccc(F)cc3F)n2)c1]

A mixture of crude 4-chloro-N-{3-[(methylsulfonyl)methyl]phenyl}-1,3,5-triazin-2-amine (Intermediate 1.4) (10.0 g, 61.7% by weight; 20.65 mmol), (2,4-difluorophenyl)boronic acid (4.03 g; 24.78 mmol) and Pd(dppf)C$_{12}$ (2.53 g; 3.1 mmol) in 1,2-dimethoxyethane (62 ml) and 2 M solution of potassium carbonate (20.6 ml) was degassed using argon. The mixture was stirred under argon for 90 min at 100° C. After cooling the mixture was poured into water (800 ml). The formed solid was filtered of, triturated with DCM (100 ml), washed with acetone (2×100 ml), and dried to yield intermediate 42.1 as a grey solid (6.87 g; 18 mmol).

$^1$H NMR (400 MHz, d$_6$-DMSO, 300 K) δ=10.47 (s, 1H), 8.85 (s, 1H), 8.27 (br. s, 1H), 7.84 (br. s., 1H), 7.79 (d, 1H), 7.48-7.34 (m, 2H), 7.26 (t, 1H), 7.15 (d, 1H), 4.48 (s, 2H), 2.94 (s, 3H).

Preparation of End Product:

A batch of 4-(2,4-difluorophenyl)-N-{3-[(methylsulfonyl)methyl]phenyl}-1,3,5-triazin-2-amine (75 mg; 0.19 mmol), ethanol (46 µl; 0.789 mmol), and sodium hydride (15.8 mg 60 percent in mineral oil) were placed in a microwave tube together with THF (3.75 ml). The mixture was irradiated in for 8 hours at 150° C. in a Biotage Initiator 60. The reaction mixture was diluted with ethyl acetate (70 ml), filtered using a Whatman filter and concentrated. The residue was purified by preparative HPLC to give the desired product (15.3 mg; 40 µmol).

| System: | Waters Autopurificationsystem: Pump 2545, Sample Manager 2767, CFO, DAD 2996, ELSD 2424, SQD |
|---|---|
| Column: | XBrigde C18 5 µm 100 × 30 mm |
| Solvent: | A = H2O + 0.1% Vol. HCOOH (99%) |
| | B = Acetonitril |
| Gradient: | 0-1 min 1% B, 1-8 min 1-99% B, 8-10 min 99% B |
| Flow: | 50 mL/min |
| Temperature: | RT |
| Injektion: | 1 × 2.5 mL |
| Detection: | DAD scan range 210-400 nm |
| | MS ESI+, ESI−, scan range 160-1000 m/z |

$^1$H NMR (400 MHz, d$_6$-DMSO, 300 K) δ=10.36 (s, 1H), 8.80 (s, 1H), 8.11-7.85 (m, 1H), 7.77 (br. s., 1H), 7.71 (br. s., 1H), 7.37 (t, 1H), 7.12 (d, 1H), 7.07 (dd, 1H), 6.88 (td, 1H), 4.45 (s, 2H), 4.14 (q, 2H), 2.92 (s, 3H), 1.28 (t, 3H).

Example 43

4-(4-Fluoro-2-propoxyphenyl)-N-{3-[(methylsulfonyl)methyl]phenyl}-1,3,5-triazin-2-amine

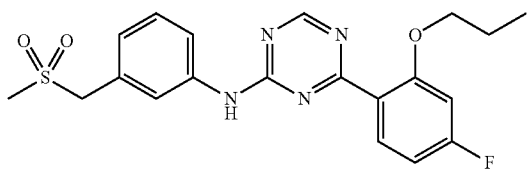 [SMILES: CCCOc1cc(F)ccc1-c1ncnc(Nc2cccc(CS(C)(=O)=O)c2)n1]

Starting with 4-(2,4-difluorophenyl)-N-{3-[(methylsulfonyl)methyl]phenyl}-1,3,5-triazin-2-amine (75 mg; 0.19 mmol), intermediate 42.1, and propan-1-ol (60 µl; 0.789 mmol), example 43 was prepared analogously to the procedure for the preparation of example 42.

$^1$H NMR (400 MHz, d$_6$-DMSO, 300 K) δ=10.34 (s, 1H), 8.80 (s, 1H), 8.02-7.82 (m, 1H), 7.82-7.66 (m, 2H), 7.36 (t, 1H), 7.12 (d, 1H), 7.07 (dd, 1H), 6.88 (td, 1H), 4.45 (s, 2H), 4.02 (t, 2H), 2.92 (s, 3H), 1.66 (sxt, 2H), 0.89 (t, 3H).

Example 44

4-(2-Butoxy-4-fluorophenyl)-N-{3-[(methylsulfonyl)-methyl]phenyl}-1,3,5-triazin-2-amine

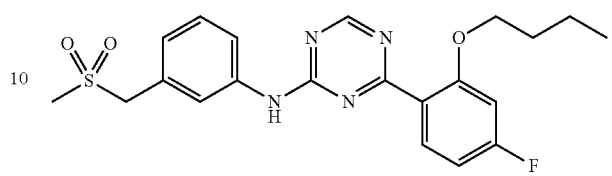

Starting with 4-(2,4-difluorophenyl)-N-{3-[(methylsulfonyl)methyl]phenyl}-1,3,5-triazin-2-amine (75 mg; 0.19 mmol), intermediate 42.1, and butan-1-ol (74 µl; 0.773 mmol), example 44 was prepared analogously to the procedure for the preparation of example 42.

$^1$H NMR (400 MHz, d$_6$-DMSO, 300 K) δ=10.34 (s, 1H), 8.79 (s, 1H), 8.03-7.81 (m, 1H), 7.73 (br. s., 2H), 7.37 (t, 1H), 7.12 (d, 1H), 7.07 (dd, 1H), 6.88 (td, 1H), 4.45 (s, 2H), 4.06 (t, 2H), 2.92 (s, 3H), 1.68-1.58 (m, 2H), 1.41-1.28 (m, 2H), 0.82 (t, 3H).

Example 45

4-[4-Fluoro-2-(pentyloxy)phenyl]-N-{3-[(methylsulfonyl)methyl]phenyl}-1,3,5-triazin-2-amine

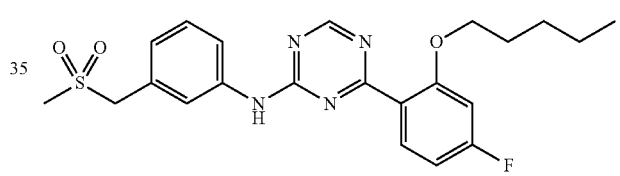

Starting with 4-(2,4-difluorophenyl)-N-{3-[(methylsulfonyl)methyl]phenyl}-1,3,5-triazin-2-amine (75 mg; 0.19 mmol), intermediate 42.1, and pentan-1-ol (87 µl; 0.773 mmol), example 45 was prepared analogously to the procedure for the preparation of example 42.

$^1$H NMR (400 MHz, d$_6$-DMSO, 300 K) δ=10.35 (s, 1H), 8.79 (s, 1H), 8.01-7.81 (m, 1H), 7.73 (br. s., 2H), 7.36 (t, 1H), 7.11 (d, 1H), 7.07 (dd, 1H), 6.88 (td, 1H), 4.45 (s, 2H), 4.05 (t, 2H), 2.91 (s, 3H), 1.70-1.59 (m, 2H), 1.36-1.26 (m, 2H), 1.27-1.16 (m, 2H), 0.79 (t, 3H).

Example 46

4-[4-Fluoro-2-(hexyloxy)phenyl]-N-{3-[(methylsulfonyl)methyl]phenyl}-1,3,5-triazin-2-amine

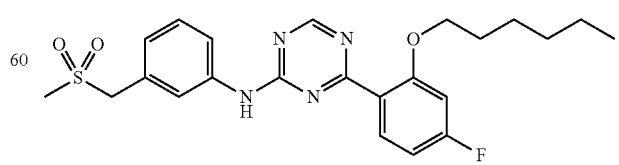

Starting with 4-(2,4-difluorophenyl)-N-{3-[(methylsulfonyl)methyl]phenyl}-1,3,5-triazin-2-amine (75 mg; 0.19 mmol), intermediate 42.1, and hexan-1-ol (100 μl; 0.781 mmol), example 46 was prepared analogously to the procedure for the preparation of example 42.

¹H NMR (400 MHz, d₆-DMSO, 300 K) δ=10.35 (s, 1H), 8.79 (s, 1H), 8.05-7.80 (m, 1H), 7.74 (br. s., 2H), 7.36 (t, 1H), 7.11 (d, 1H), 7.06 (dd, 1H), 6.87 (td, 1H), 4.45 (s, 2H), 4.05 (t, 2H), 2.91 (s, 3H), 1.69-1.58 (m, 2H), 1.40-1.25 (m, 2H), 1.25-1.09 (m, 4H), 0.83-0.72 (m, 3H).

Example 47

4-{4-Fluoro-2-[(4-methylpentyl)oxy]phenyl}-N-{3-[(methylsulfonyl)methyl]phenyl}-1,3,5-triazin-2-amine

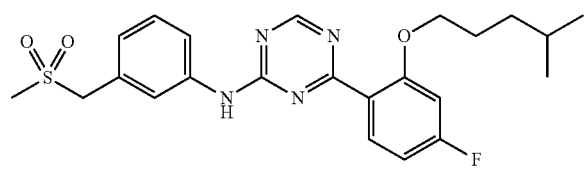 [SMILES: CC(C)CCCOc1cc(F)ccc1-c1ncnc(Nc2cccc(CS(C)(=O)=O)c2)n1]

Starting with 4-(2,4-difluorophenyl)-N-{3-[(methylsulfonyl)methyl]phenyl}-1,3,5-triazin-2-amine (75 mg; 0.19 mmol), intermediate 42.1, and 4-methylpentan-1-ol (100 μl; 0.789 mmol), example 47 was prepared analogously to the procedure for the preparation of example 42.

¹H NMR (400 MHz, d₆-DMSO, 300 K) δ=10.35 (s, 1H), 8.79 (s, 1H), 7.91 (br. s., 1H), 7.74 (br. s., 2H), 7.36 (t, 1H), 7.11 (d, 1H), 7.06 (dd, 1H), 6.88 (td, 1H), 4.45 (s, 2H), 4.04 (t, 2H), 2.91 (s, 3H), 1.69-1.59 (m, 2H), 1.52-1.39 (m, 1H), 1.28-1.17 (m, 2H), 0.77 (d, 6H).

Example 48

4-[2-(2-Cyclopropylethoxy)-4-fluorophenyl]-N-{3-[(methylsulfonyl)methyl]phenyl}-1,3,5-triazin-2-amine

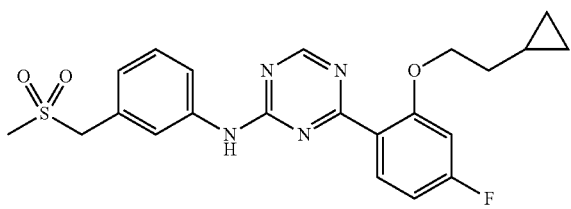 [SMILES: CS(=O)(=O)Cc1cccc(Nc2ncnc(-c3ccc(F)cc3OCCC3CC3)n2)c1]

Starting with 4-(2,4-difluorophenyl)-N-{3-[(methylsulfonyl)methyl]phenyl}-1,3,5-triazin-2-amine (75 mg; 0.19 mmol), intermediate 42.1, and 2-cyclopropylethanol (46.2 mg; 0.773 mmol), example 48 was prepared analogously to the procedure for the preparation of example 42.

¹H NMR (400 MHz, d₆-DMSO, 300 K) δ=10.34 (s, 1H), 8.79 (s, 1H), 7.86 (br. s., 1H), 7.72 (br. s., 2H), 7.36 (t, 1H), 7.14-7.03 (m, 2H), 6.88 (td, 1H), 4.45 (s, 2H), 4.10 (t, 2H), 2.91 (s, 3H), 1.55 (q, 2H), 0.75 (m, 1H), 0.31 (m, 2H), 0.02 (m, 2H).

Example 49

4-{4-Fluoro-2-[(1-methylcyclopropyl)methoxy]phenyl}-N-{3-[(methylsulfonyl)-methyl]-phenyl}-1,3,5-triazin-2-amine

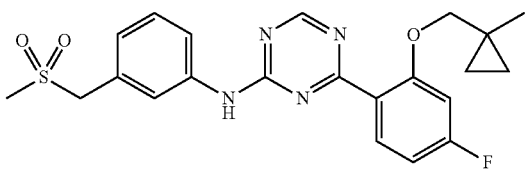

Starting with 4-(2,4-difluorophenyl)-N-{3-[(methylsulfonyl)methyl]phenyl}-1,3,5-triazin-2-amine (75 mg; 0.19 mmol), intermediate 42.1, and 1-methylcyclopropanmethanol (76.3 mg; 0.841 mmol), example 49 was prepared analogously to the procedure for the preparation of example 42.

¹H NMR (400 MHz, d₆-DMSO, 300 K) δ=10.34 (s, 1H), 8.80 (s, 1H), 7.87-7.78 (m, 1H), 7.78-7.67 (m, 2H), 7.37 (t, 1H), 7.11 (d, 1H), 7.01 (dd, 1H), 6.88 (td, 1H), 4.46 (s, 2H), 3.84 (s, 2H), 2.91 (s, 3H), 1.06 (br. s., 3H), 0.50-0.42 (m, 2H), 0.31-0.22 (m, 2H).

Example 50

4-[4-Fluoro-2-(2-methoxyethoxy)phenyl]-N-{3-[(methylsulfonyl)methyl]phenyl}-1,3,5-triazin-2-amine

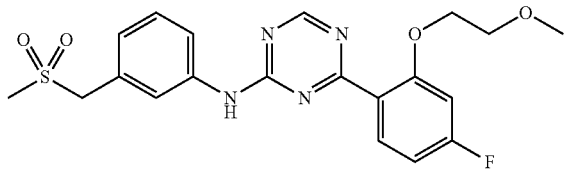

Starting with 4-(2,4-difluorophenyl)-N-{3-[(methylsulfonyl)methyl]phenyl}-1,3,5-triazin-2-amine (50 mg; 0.19 mmol), intermediate 42.1, and 2-methoxyethanol (42 μl; 0.515 mmol), example 50 was prepared analogously to the procedure for the preparation of example 42.

¹H NMR (400 MHz, d₆-DMSO, 300 K) δ=10.35 (s, 1H), 8.80 (s, 1H), 8.01-7.82 (m, 1H), 7.74 (br. s., 2H), 7.37 (t, 1H), 7.16-7.07 (m, 2H), 6.90 (td, 1H), 4.46 (s, 2H), 4.27-4.14 (m, 2H), 3.61 (br. s., 2H), 3.20 (s, 3H), 2.91 (s, 3H).

Example 51

4-[2-(2-Ethoxyethoxy)-4-fluorophenyl]-N-{3-[(methylsulfonyl)methyl]phenyl}-1,3,5-triazin-2-amine

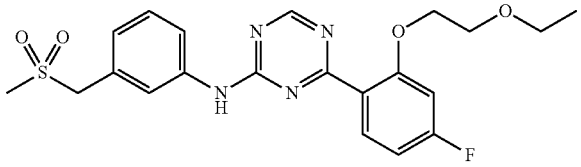 [SMILES: CCOCCOc1cc(F)ccc1-c1ncnc(Nc2cccc(CS(C)(=O)=O)c2)n1]

Starting with 4-(2,4-difluorophenyl)-N-{3-[(methylsulfonyl)methyl]phenyl}-1,3,5-triazin-2-amine (75 mg; 0.19 mmol), intermediate 42.1, and 2-ethoxyethanol (76 μl; 0.781 mmol), example 51 was prepared analogously to the procedure for the preparation of example 42.

¹H NMR (400 MHz, d₆-DMSO, 300 K) δ=10.36 (s, 1H), 8.80 (s, 1H), 8.01-7.81 (m, 1H), 7.75 (br. s., 2H), 7.37 (t, 1H), 7.18-7.06 (m, 2H), 6.90 (td, 1H), 4.46 (s, 2H), 4.19 (t, 2H), 3.64 (m., 2H), 3.39 (m, 2H), 2.92 (s, 3H), 0.99 (t, 3H).

Example 52

4-[4-Fluoro-2-(3-methylbutoxy)phenyl]-N-{3-[methylsulfonyl)methyl]phenyl}-1,3,5-triazin-2-amine

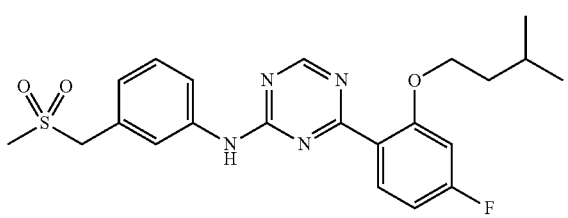 [SMILES: CC(C)CCOc1cc(F)ccc1-c1ncnc(Nc2cccc(CS(C)(=O)=O)c2)n1]

Starting with 4-(2,4-difluorophenyl)-N-{3-[(methylsulfonyl)methyl]phenyl}-1,3,5-triazin-2-amine (75 mg; 0.19 mmol), intermediate 42.1, and 3-methylbutan-1-ol (88 µl; 0.773 mmol), example 52 was prepared analogously to the procedure for the preparation of example 42.

¹H NMR (400 MHz, d₆-DMSO, 300 K) δ=10.34 (s, 1H), 8.79 (s, 1H), 8.00-7.81 (m, 1H), 7.72 (br. s., 2H), 7.36 (t, 1H), 7.15-7.05 (m, 2H), 6.88 (td, 1H), 4.45 (s, 2H), 4.07 (t, 2H), 2.91 (s, 3H), 1.69 (dt, 1H), 1.55 (q, 2H), 0.82 (d, 6H).

Example 53

4-[2-(2-Cyclopentylethoxy)-4-fluorophenyl]-N-{3-[(methylsulfonyl)methyl]phenyl}-1,3,5-triazin-2-amine

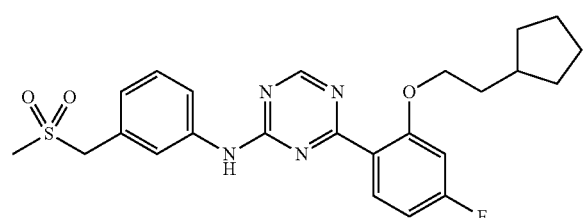

Starting with 4-(2,4-difluorophenyl)-N-{3-[(methylsulfonyl)methyl]phenyl}-1,3,5-triazin-2-amine (75 mg; 0.197 mmol), intermediate 42.1, and 2-cyclopentylethanol (101 µl; 0.789 mmol), example 53 was prepared analogously to the procedure for the preparation of example 42.

¹H NMR (400 MHz, d₆-DMSO, 300 K) δ=10.34 (s, 1H), 8.79 (s, 1H), 8.05-7.79 (m, 1H), 7.72 (br. s., 2H), 7.36 (t, 1H), 7.11 (d, 1H), 7.07 (dd, 1H), 6.87 (td, 1H), 4.45 (s, 2H), 4.06 (t, 2H), 2.91 (s, 3H), 1.90-1.77 (m, 1H), 1.66 (q, 4H), 1.56-1.46 (m, 2H), 1.46-1.31 (m, 2H), 1.12-0.95 (m, 2H).

Example 54

4-[4-Fluoro-2-(3-fluoropropoxy)phenyl]-N-{3-[(methylsulfonyl)methyl]phenyl}-1,3,5-triazin-2-amine

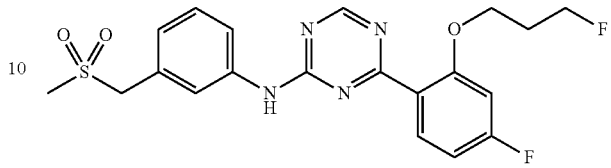

Starting with 4-(2,4-difluorophenyl)-N-{3-[(methylsulfonyl)methyl]phenyl}-1,3,5-triazin-2-amine (75 mg; 0.197 mmol), intermediate 42.1, and 3-fluoropropan-1-ol (59 mg; 0.736 mmol), example 54 was prepared analogously to the procedure for the preparation of example 42.

¹H NMR (400 MHz, d₆-DMSO, 300 K) δ=10.35 (s, 1H), 8.80 (s, 1H), 7.81 (d, 2H), 7.74 (br. s., 1H), 7.37 (t, 1H), 7.15-7.08 (m, 2H), 6.91 (td, 1H), 4.60 (br. s., 1H), 4.53-4.42 (m, 3H), 4.16 (t, 2H), 2.92 (s, 3H), 2.13-1.94 (m, 2H).

Example 55

4-[2-(Cyclopropylmethoxy)-4-fluorophenyl]-N-{3-[(methylsulfonyl)methyl]phenyl}-1,3,5-triazin-2-amine

Starting with 4-(2,4-difluorophenyl)-N-{3-[(methylsulfonyl)methyl]phenyl}-1,3,5-triazin-2-amine (75 mg; 0.193 mmol), intermediate 42.1, and cyclopropylmethanol (58 mg; 0.773 mmol), example 55 was prepared analogously to the procedure for the preparation of example 42.

¹H NMR (400 MHz, d₆-DMSO, 300 K) δ=10.36 (s, 1H), 8.81 (s, 1H), 8.05-7.81 (m, 1H), 7.72 (br. s., 2H), 7.37 (t, 1H), 7.12 (d, 1H), 7.06 (dd, 1H), 6.88 (td, 1H), 4.46 (s, 2H), 3.95 (d, 2H), 2.92 (s, 3H), 1.15 (br. s., 1H), 0.46 (d, 2H), 0.28 (d, 2H).

Example 56

4-[2-(Cyclobutylmethoxy)-4-fluorophenyl]-N-{3-[(methylsulfonyl)methyl]phenyl}-1,3,5-triazin-2-amine

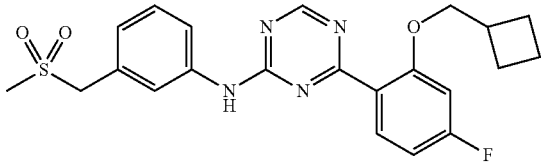 [SMILES: CS(=O)(=O)Cc1cccc(Nc2ncnc(-c3ccc(F)cc3OCC3CCC3)n2)c1]

Starting with 4-(2,4-difluorophenyl)-N-{3-[(methylsulfonyl)methyl]phenyl}-1,3,5-triazin-2-amine (50 mg; 0.129 mmol), intermediate 42.1, and cyclobutanemethanol (44.8 mg; 0.515 mmol), example 56 was prepared analogously to the procedure for the preparation of example 42.

$^1$H NMR (400 MHz, d$_6$-DMSO, 300 K) δ=10.33 (s, 1H), 8.79 (s, 1H), 7.74 (br. s., 3H), 7.37 (t, 1H), 7.12 (d, 1H), 7.07 (dd, 1H), 6.88 (td, 1H), 4.45 (s, 2H), 4.01 (d, 2H), 2.91 (s, 3H), 2.64 (dd, 1H), 1.91 (br. s., 2H), 1.85-1.67 (m, 4H).

Example 57

4-[2-(Cyclohexylmethoxy)-4-fluorophenyl]-N-{3-[(methylsulfonyl)methyl]phenyl}-1,3,5-triazin-2-amine

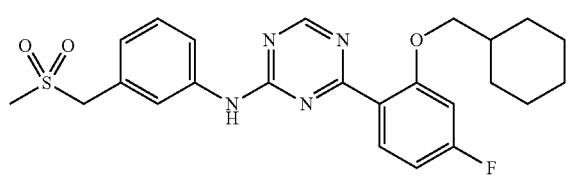 [SMILES: CS(=O)(=O)Cc1cccc(Nc2ncnc(-c3ccc(F)cc3OCC3CCCCC3)n2)c1]

Starting with 4-(2,4-difluorophenyl)-N-{3-[(methylsulfonyl)methyl]phenyl}-1,3,5-triazin-2-amine (50 mg; 0.129 mmol), intermediate 42.1, and cyclohexylmethanol (59.4 mg; 0.515 mmol), example 57 was prepared analogously to the procedure for the preparation of example 42.

$^1$H NMR (400 MHz, d$_6$-DMSO, 300 K) δ=10.32 (s, 1H), 8.79 (s, 1H), 7.89-7.79 (m, 1H), 7.74 (br. s., 2H), 7.36 (t, 1H), 7.12 (d, 1H), 7.04 (dd, 1H), 6.87 (td, 1H), 4.45 (s, 2H), 3.85 (d, 2H), 2.91 (s, 3H), 1.76-1.49 (m, 6H), 1.21-0.85 (m, 5H).

Example 58

4-[4-Fluoro-2-(2-methylpropoxy)phenyl]-N-{3-[(methylsulfonyl)methyl]phenyl}-1,3,5-triazin-2-amine

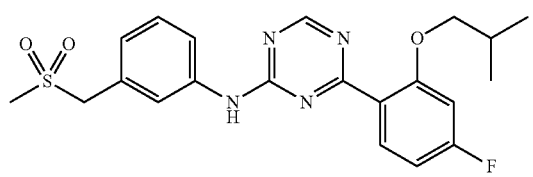

Starting with 4-(2,4-difluorophenyl)-N-{3-[(methylsulfonyl)methyl]phenyl}-1,3,5-triazin-2-amine (75 mg; 0.197 mmol), intermediate 42.1, and 2-methylpropan-1-ol (74 μl; 0.789 mmol), example 58 was prepared analogously to the procedure for the preparation of example 42.

$^1$H NMR (400 MHz, d$_6$-DMSO, 300 K) δ=10.33 (s, 1H), 8.80 (s, 1H), 7.90-7.78 (m, 1H), 7.74 (br. s., 2H), 7.36 (t, 1H), 7.11 (d, 1H), 7.05 (dd, 1H), 6.87 (td, 1H), 4.45 (s, 2H), 3.82 (d, 2H), 2.91 (s, 3H), 1.94 (dt, 1H), 0.89 (d, 6H).

Example 59

4-[4-Fluoro-2-(4,4,4-trifluorobutoxy)phenyl]-N-{3-[(methylsulfonyl)methyl]phenyl}-1,3,5-triazin-2-amine

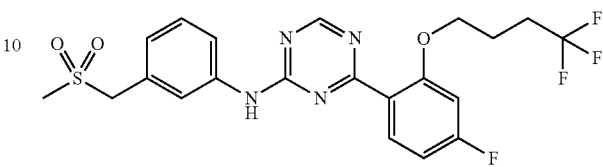

Starting with 4-(2,4-difluorophenyl)-N-{3-[(methylsulfonyl)methyl]phenyl}-1,3,5-triazin-2-amine (70 mg; 0.184 mmol), intermediate 42.1, and 4,4,4-trifluorobutan-1-ol (94.3 mg; 0.736 mmol), example 59 was prepared analogously to the procedure for the preparation of example 42.

$^1$H NMR (400 MHz, d$_6$-DMSO, 300 K) δ=10.36 (s, 1H), 8.78 (s, 1H), 7.82 (br. s., 2H), 7.76 (br. s., 1H), 7.37 (t, 1H), 7.15-7.06 (m, 2H), 6.92 (td, 1H), 4.46 (s, 2H), 4.14 (t, 2H), 2.92 (s, 3H), 2.40 (br. s., 2H), 1.93-1.83 (m, 2H).

Example 60

4-[2-(2,2-Difluoroethoxy)-4-fluorophenyl]-N-{3-[(methylsulfonyl)methyl]phenyl}-1,3,5-triazin-2-amine

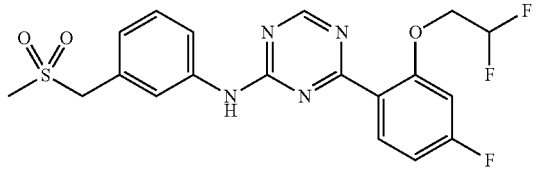 [SMILES: CS(=O)(=O)Cc1cccc(Nc2ncnc(-c3ccc(F)cc3OCC(F)F)n2)c1]

Starting with 4-(2,4-difluorophenyl)-N-{3-[(methylsulfonyl)methyl]phenyl}-1,3,5-triazin-2-amine (70 mg; 0.184 mmol), intermediate 42.1, and 2,2-difluoroethanol (48 μl; 0.736 mmol), example 60 was prepared analogously to the procedure for the preparation of example 42.

$^1$H NMR (400 MHz, d$_6$-DMSO, 300 K) δ=10.36 (s, 1H), 8.81 (s, 1H), 7.81 (br. s., 2H), 7.74 (br. s., 1H), 7.37 (t, 1H), 7.22 (dd, 1H), 7.13 (d, 1H), 6.99 (td, 1H), 6.50-6.04 (m, 1H), 4.51-4.37 (m, 4H), 2.92 (s, 3H).

Example 61

4-[4-Fluoro-2-(2-fluoroethoxy)phenyl]-N-{3-[(methylsulfonyl)methyl]phenyl}-1,3,5-triazin-2-amine

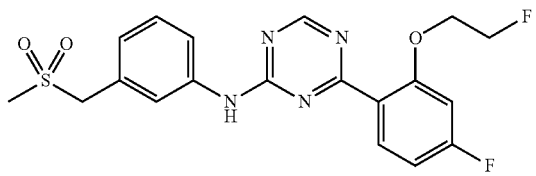 [SMILES: CS(=O)(=O)Cc1cccc(Nc2ncnc(-c3ccc(F)cc3OCCF)n2)c1]

Starting with 4-(2,4-difluorophenyl)-N-{3-[(methylsulfonyl)methyl]phenyl}-1,3,5-triazin-2-amine (70 mg; 0.184 mmol), intermediate 42.1, and 2-fluoroethanol (113.8 μl; 1.84 mmol), example 61 was prepared analogously to the procedure for the preparation of example 42.

$^1$H NMR (400 MHz, d$_6$-DMSO, 300 K) δ=10.36 (s, 1H), 8.81 (s, 1H), 7.98-7.83 (m, 1H), 7.79 (br. s., 1H), 7.73 (br. s., 1H), 7.37 (t, 1H), 7.18-7.09 (m, 2H), 6.94 (td, 1H), 4.73 (br. s., 1H), 4.62 (br. s., 1H), 4.46 (s, 2H), 4.43-4.37 (m, 1H), 4.37-4.29 (m, 1H), 2.92 (s, 3H).

Example 62

4-[2-(But-2-yn-1-yloxy)-4-fluorophenyl]-N-{3-[(methylsulfonyl)methyl]phenyl}-1,3,5-triazin-2-amine

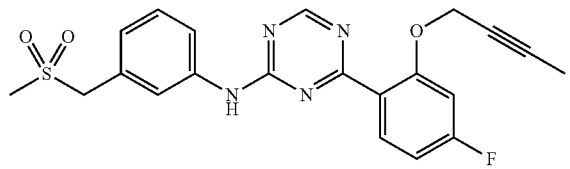 [SMILES: CC#CCOc1cc(F)ccc1-c1ncnc(Nc2cccc(CS(C)(=O)=O)c2)n1]

Starting with 4-(2,4-difluorophenyl)-N-{3-[(methylsulfonyl)methyl]phenyl}-1,3,5-triazin-2-amine (150 mg; 0.395 mmol), intermediate 42.1, and 2-butin-1-ol (112 mg; 1.578 mmol), example 62 was prepared analogously to the procedure for the preparation of example 42.

$^1$H NMR (400 MHz, d$_6$-DMSO, 300 K) δ=10.39 (s, 1H), 8.81 (s, 1H), 8.10-7.65 (m, 3H), 7.38 (t, 1H), 7.16-7.08 (m, 2H), 6.94 (td, 1H), 4.90 (br. s., 2H), 4.47 (s, 2H), 2.92 (s, 3H), 1.82 (s, 3H).

Example 63

4-[2-(2-Cyclohexylethoxy)-4-fluorophenyl]-N-{3-[(methylsulfonyl)methyl]phenyl}-1,3,5-triazin-2-amine

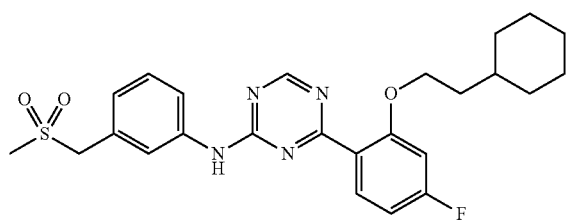 [SMILES: CS(=O)(=O)Cc1cccc(Nc2ncnc(-c3ccc(F)cc3OCCC3CCCCC3)n2)c1]

Starting with 4-(2,4-difluorophenyl)-N-{3-[(methylsulfonyl)methyl]phenyl}-1,3,5-triazin-2-amine (75 mg; 0.197 mmol), intermediate 42.1, and 2-cyclohexylethanol (111 µl; 0.789 mmol), example 63 was prepared analogously to the procedure for the preparation of example 43.

$^1$H NMR (400 MHz, d$_6$-DMSO, 300 K) δ=10.36 (s, 1H), 8.79 (s, 1H), 8.03-7.80 (m, 1H), 7.74 (br. s., 2H), 7.36 (t, 1H), 7.14-7.05 (m, 2H), 6.87 (td, 1H), 4.45 (s, 2H), 4.08 (t, 2H), 2.91 (s, 3H), 1.72-1.49 (m, 8H), 1.42-1.29 (m, 1H), 1.15-1.00 (m, 3H), 0.91-0.77 (m, 2H).

Example 64

4-[2-(Cyclobutyloxy)-4-fluorophenyl]-N-{3-[(methylsulfonyl)methyl]phenyl}-1,3,5-triazin-2-amine

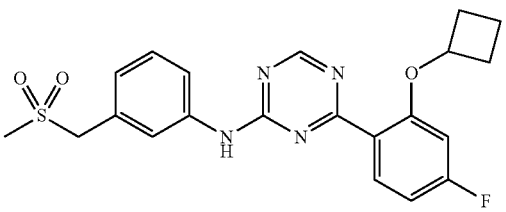 [SMILES: CS(=O)(=O)Cc1cccc(Nc2ncnc(-c3ccc(F)cc3OC3CCC3)n2)c1]

Starting with 4-(2,4-difluorophenyl)-N-{3-[(methylsulfonyl)methyl]phenyl}-1,3,5-triazin-2-amine (70 mg; 0.184 mmol), intermediate 42.1, and cyclobutanol (53.6 mg; 0.736 mmol), example 64 was prepared analogously to the procedure for the preparation of example 42.

$^1$H NMR (400 MHz, d$_6$-DMSO, 300 K) δ=10.37 (s, 1H), 8.81 (s, 1H), 8.32-7.88 (m, 1H), 7.79 (br. s., 1H), 7.66 (br. s., 1H), 7.37 (t, 1H), 7.12 (d, 1H), 6.93-6.78 (m, 2H), 4.81 (quin, 1H), 4.46 (s, 2H), 2.92 (s, 3H), 2.48-2.39 (m, 2H), 2.08-1.96 (m, 2H), 1.76 (q, 1H), 1.69-1.55 (m, 1H).

Example 65

4-[2-(Cyclopentyloxy)-4-fluorophenyl]-N-{3-[(methylsulfonyl)methyl]phenyl}-1,3,5-triazin-2-amine

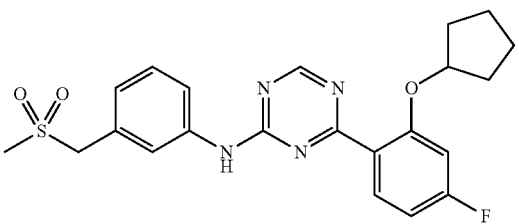 [SMILES: CS(=O)(=O)Cc1cccc(Nc2ncnc(-c3ccc(F)cc3OC3CCCC3)n2)c1]

Starting with 4-(2,4-difluorophenyl)-N-{3-[(methylsulfonyl)methyl]phenyl}-1,3,5-triazin-2-amine (75 mg; 0.197 mmol), intermediate 42.1, and cyclopentanol (67.3 mg; 0.781 mmol), example 65 was prepared analogously to the procedure for the preparation of example 42.

$^1$H NMR (400 MHz, d$_6$-DMSO, 300 K) δ=10.33 (s, 1H), 8.78 (s, 1H), 8.00-7.78 (m, 1H), 7.71 (br. s., 2H), 7.36 (t, 1H), 7.12 (d, 1H), 7.05 (dd, 1H), 6.86 (td, 1H), 4.95-4.88 (m, 1H), 4.46 (s, 2H), 2.92 (s, 3H), 1.94-1.78 (m, 2H), 1.76-1.42 (m, 6H).

Example 66

4-{4-Fluoro-2-[(1-fluorocyclohexyl)methoxy]phenyl}-N-{3-[(methylsulfonyl)-methyl]phenyl}-1,3,5-triazin-2-amine

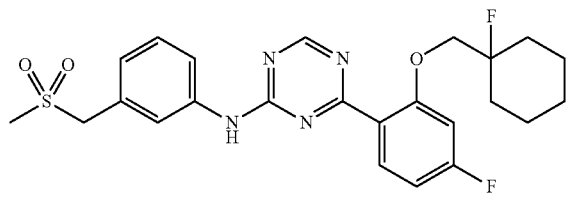 [SMILES: CS(=O)(=O)Cc1cccc(Nc2ncnc(-c3ccc(F)cc3OCC3(F)CCCCC3)n2)c1]

Starting with 4-(2,4-difluorophenyl)-N-{3-[(methylsulfonyl)methyl]phenyl}-1,3,5-triazin-2-amine (80 mg; 0.21 mmol), intermediate 42.1, and (1-fluorocyclohexyl)methanol (117 mg; 0.841 mmol), example 66 was prepared analogously to the procedure for the preparation of example 42.

¹H NMR (400 MHz, d₆-DMSO, 300 K) δ=10.33 (s, 1H), 8.80 (s, 1H), 7.84-7.70 (m, 3H), 7.36 (t, 1H), 7.17-7.09 (m, 2H), 6.91 (td, 1H), 4.45 (s, 2H), 4.09 (d, 2H), 2.91 (s, 3H), 1.83-1.68 (m, 2H), 1.64-1.33 (m, 7H), 1.27-1.08 (m, 1H).

Example 67

4-{4-Fluoro-2-[(1R)-1-(4-fluorophenyl)ethoxy]phenyl}-N-{3-[(methylsulfonyl)-methyl]phenyl}-1,3,5-triazin-2-amine

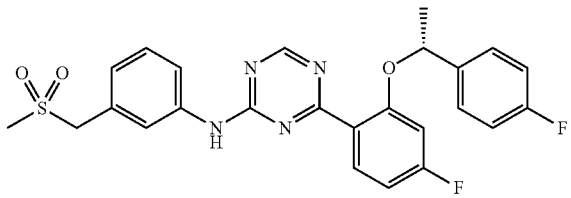 [SMILES: C[C@@H](Oc1cc(F)ccc1-c1ncnc(Nc2cccc(CS(C)(=O)=O)c2)n1)c1ccc(F)cc1]

Starting with 4-(2,4-difluorophenyl)-N-{3-[(methylsulfonyl)methyl]phenyl}-1,3,5-triazin-2-amine (50 mg; 0.129 mmol), intermediate 42.1, and (R)-4-fluoro-α-methylbenzyl alcohol (74.4 mg; 0.515 mmol), example 67 was prepared analogously to the procedure for the preparation of example 42.

¹H NMR (400 MHz, d₆-DMSO, 300 K) δ=10.36 (s, 1H), 8.86 (s, 1H), 8.00-7.81 (m, 1H), 7.81-7.62 (m, 2H), 7.56-7.41 (m, 2H), 7.41-7.26 (m, 1H), 7.17-7.05 (m, 3H), 6.94 (dd, 1H), 6.85 (td, 1H), 5.66 (q, 1H), 4.46 (s, 2H), 2.92 (s, 3H), 1.48 (d, 3H).

Example 68 rac-4-[4-Fluoro-2-(1-phenylethoxy)phenyl]-N-{3-[(methylsulfonyl)methyl]phenyl}-1,3,5-triazin-2-amine

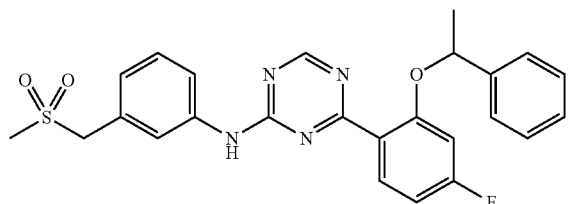

Starting with 4-(2,4-difluorophenyl)-N-{3-[(methylsulfonyl)methyl]phenyl}-1,3,5-triazin-2-amine (50 mg; 0.129 mmol), intermediate 42.1, and DL-1-phenylethanol (63 mg; 0.515 mmol), example 68 was prepared analogously to the procedure for the preparation of example 42.

¹H NMR (400 MHz, d₆-DMSO, 300 K) δ=10.37 (s, 1H), 8.86 (s, 1H), 8.08-7.81 (m, 1H), 7.73 (d, 2H), 7.44 (d, 2H), 7.38-7.27 (m, 3H), 7.27-7.19 (m, 1H), 7.11 (d, 1H), 6.90 (dd, 1H), 6.83 (td, 1H), 5.63 (q, 1H), 4.45 (s, 2H), 2.91 (s, 3H), 1.49 (d, 3H).

Example 69

4-(4-Fluoro-2-{[3-(trifluoromethyl)benzyl]oxy}phenyl)-N-{3-[(methylsulfonyl)-methyl]phenyl}-1,3,5-triazin-2-amine

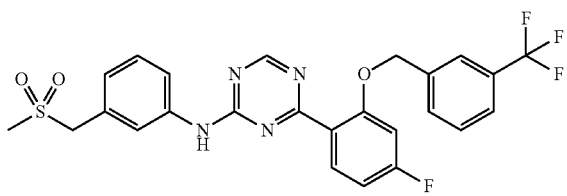 [SMILES: CS(=O)(=O)Cc1cccc(Nc2ncnc(-c3ccc(F)cc3OCc3cccc(C(F)(F)F)c3)n2)c1]

Starting with 4-(2,4-difluorophenyl)-N-{3-[(methylsulfonyl)methyl]phenyl}-1,3,5-triazin-2-amine (70 mg; 0.184 mmol), intermediate 42.1, and 3-(trifluoromethyl)benzyl alcohol (132 mg; 0.736 mmol), example 69 was prepared analogously to the procedure for the preparation of example 42.

¹H NMR (400 MHz, d₆-DMSO, 300 K) δ=10.39 (s, 1H), 8.81 (s, 1H), 7.97-7.84 (m, 2H), 7.84-7.69 (m, 3H), 7.67-7.60 (m, 1H), 7.57 (d, 1H), 7.38-7.23 (m, 1H), 7.19 (dd, 1H), 7.09 (d, 1H), 6.96 (td, 1H), 5.37 (s, 2H), 4.44 (br. s., 2H), 2.91 (s, 3H).

Example 70

4-{4-Fluoro-2-[(3-methoxybenzyl)oxy]phenyl}-N-{3-[(methylsulfonyl)methyl]phenyl}-1,3,5-triazin-2-amine

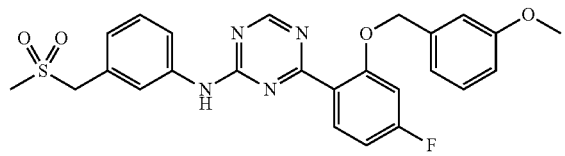

Starting with 4-(2,4-difluorophenyl)-N-{3-[(methylsulfonyl)methyl]phenyl}-1,3,5-triazin-2-amine (75 mg; 0.197 mmol), intermediate 42.1, and 3-methoxybenzyl alcohol (111 mg; 0.789 mmol), example 70 was prepared analogously to the procedure for the preparation of example 42.

¹H NMR (400 MHz, d₆-DMSO, 300 K) δ=10.38 (s, 1H), 8.83 (s, 1H), 7.95-7.77 (m, 2H), 7.77-7.67 (m, 1H), 7.38-7.26 (m, 1H), 7.23 (t, 1H), 7.18-7.07 (m, 2H), 7.07-7.02 (m, 1H), 7.00 (d, 1H), 6.92 (td, 1H), 6.82 (dd, 1H), 5.25 (s, 2H), 4.43 (br. s., 2H), 3.68 (s, 3H), 2.91 (s, 3H).

Example 71

4-{4-Fluoro-2-[(2-fluorobenzyl)oxy]phenyl}-N-{3-[(methylsulfonyl)methyl]phenyl}-1,3,5-triazin-2-amine

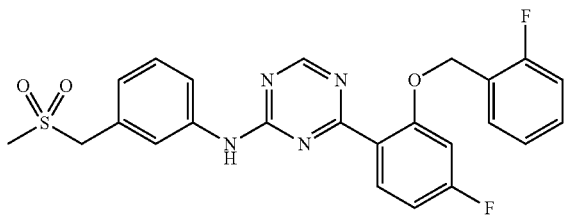 [SMILES: CS(=O)(=O)Cc1cccc(Nc2ncnc(-c3ccc(F)cc3OCc3ccccc3F)n2)c1]

Starting with 4-(2,4-difluorophenyl)-N-{3-[(methylsulfonyl)methyl]phenyl}-1,3,5-triazin-2-amine (70 mg; 0.184 mmol), intermediate 42.1, and 2-fluorobenzyl alcohol (94.8 mg; 0.736 mmol), example 710 was prepared analogously to the procedure for the preparation of example 42.

$^1$H NMR (400 MHz, d$_6$-DMSO, 300 K) δ=10.36 (s, 1H), 8.82 (s, 1H), 7.80 (d, 2H), 7.76-7.67 (m, 1H), 7.66-7.51 (m, 1H), 7.40-7.26 (m, 2H), 7.26-7.03 (m, 4H), 6.95 (td, 1H), 5.29 (s, 2H), 4.44 (br. s., 2H), 2.91 (s, 3H).

Example 72

4-{4-Fluoro-2-[(2,3,4-trifluorobenzyl)oxy]phenyl}-N-{3-[(methylsulfonyl)methyl]-phenyl}-1,3,5-triazin-2-amine

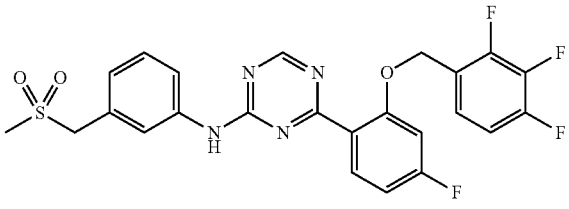 [SMILES: CS(=O)(=O)Cc1cccc(Nc2ncnc(-c3ccc(F)cc3OCc3ccc(F)c(F)c3F)n2)c1]

Starting with 4-(2,4-difluorophenyl)-N-{3-[(methylsulfonyl)methyl]phenyl}-1,3,5-triazin-2-amine (70 mg; 0.184 mmol), intermediate 42.1, and 2,3,4-trifluorobenzyl alcohol (119 mg; 0.736 mmol), example 72 was prepared analogously to the procedure for the preparation of example 42.

$^1$H NMR (400 MHz, d$_6$-DMSO, 300 K) δ=10.36 (s, 1H), 8.82 (s, 1H), 7.93-7.81 (m, 1H), 7.78 (d, 1H), 7.75-7.69 (m, 1H), 7.51-7.38 (m, 1H), 7.36-7.16 (m, 3H), 7.10 (d, 1H), 6.98 (td, 1H), 5.30 (s, 2H), 4.44 (s, 2H), 2.91 (s, 3H).

Example 73

4-(4-Fluoro-2-{[4-(trifluoromethyl)benzyl]oxy}phenyl)-N-{3-[(methylsulfonyl)-methyl]phenyl}-1,3,5-triazin-2-amine

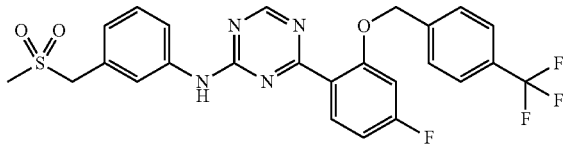 [SMILES: CS(=O)(=O)Cc1cccc(Nc2ncnc(-c3ccc(F)cc3OCc3ccc(C(F)(F)F)cc3)n2)c1]

Starting with 4-(2,4-difluorophenyl)-N-{3-[(methylsulfonyl)methyl]phenyl}-1,3,5-triazin-2-amine (70 mg; 0.184 mmol), intermediate 42.1, and 4-(trifluoromethyl)benzyl alcohol (132 mg; 0.736 mmol), example 73 was prepared analogously to the procedure for the preparation of example 42.

$^1$H NMR (400 MHz, d$_6$-DMSO, 300 K) δ=10.38 (s, 1H), 8.87 (s, 1H), 7.97-7.83 (m, 1H), 7.83-7.63 (m, 6H), 7.37-7.23 (m, 1H), 7.17 (dd, 1H), 7.09 (d, 1H), 6.95 (td, 1H), 5.37 (s, 2H), 4.43 (br. s., 2H), 2.90 (s, 3H).

Example 74

4-[4-Fluoro-2-(pyridin-3-ylmethoxy)phenyl]-N-{3-[(methylsulfonyl)methyl]phenyl}-1,3,5-triazin-2-amine

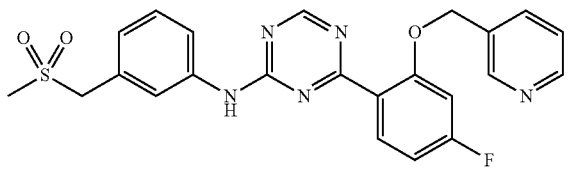

Starting with 4-(2,4-difluorophenyl)-N-{3-[(methylsulfonyl)methyl]phenyl}-1,3,5-triazin-2-amine (50 mg; 0.129 mmol), intermediate 42.1, and 3-(hydroxymethyl)-pyridine (57 mg; 0.515 mmol), example 74 was prepared analogously to the procedure for the preparation of example 42.

$^1$H NMR (400 MHz, d$_6$-DMSO, 300 K) δ=10.37 (s, 1H), 8.83 (s, 1H), 8.65 (s, 1H), 8.47 (d, 1H), 7.94-7.76 (m, 3H), 7.76-7.66 (m, 1H), 7.39-7.24 (m, 2H), 7.21 (dd, 1H), 7.09 (d, 1H), 6.95 (td, 1H), 5.31 (s, 2H), 4.44 (br. s., 2H), 2.91 (s, 3H).

Example 75

4-{4-Fluoro-2-[(2,4,5-trifluorobenzyl)oxy]phenyl}-N-{3-[(methylsulfonyl)-methyl]phenyl}-1,3,5-triazin-2-amine

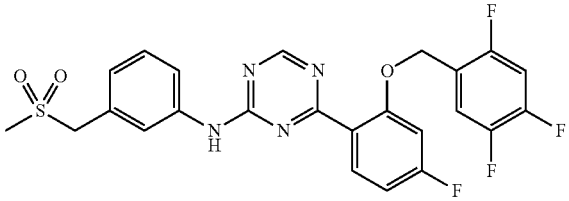 [SMILES: CS(=O)(=O)Cc1cccc(Nc2ncnc(-c3ccc(F)cc3OCc3cc(F)c(F)cc3F)n2)c1]

Starting with 4-(2,4-difluorophenyl)-N-{3-[(methylsulfonyl)methyl]phenyl}-1,3,5-triazin-2-amine (70 mg; 0.184 mmol), intermediate 42.1, and 2,4,5-trifluorobenzyl alcohol (123 mg; 0.736 mmol), example 75 was prepared analogously to the procedure for the preparation of example 42.

$^1$H NMR (400 MHz, d$_6$-DMSO, 300 K) δ=10.39 (s, 1H), 8.82 (s, 1H), 7.96-7.83 (m, 1H), 7.83-7.64 (m, 3H), 7.60-7.48 (m, 1H), 7.38-7.29 (m, 1H), 7.27 (dd, 1H), 7.10 (d, 1H), 6.98 (td, 1H), 5.26 (s, 2H), 4.44 (br. s., 2H), 2.91 (s, 3H).

Example 76

4-{2-[(4-Chlorobenzyl)oxy]-4-fluorophenyl}-N-{3-[(methylsulfonyl)methyl]phenyl}-1,3,5-triazin-2-amine

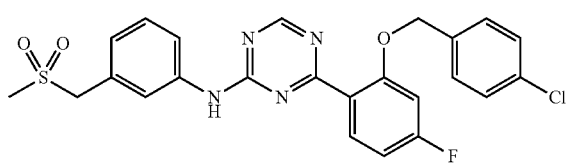 [SMILES: CS(=O)(=O)Cc1cccc(Nc2ncnc(-c3ccc(F)cc3OCc3ccc(Cl)cc3)n2)c1]

Starting with 4-(2,4-difluorophenyl)-N-{3-[(methylsulfonyl)methyl]phenyl}-1,3,5-triazin-2-amine (50 mg; 0.129 mmol), intermediate 42.1, and 4-chlorobenzyl alcohol (75 mg; 0.515 mmol), example 76 was prepared analogously to the procedure for the preparation of example 42.

$^1$H NMR (400 MHz, d$_6$-DMSO, 300 K) δ=10.37 (s, 1H), 8.84 (s, 1H), 7.81 (d, 2H), 7.78-7.70 (m, 1H), 7.48 (d, 2H), 7.43-7.24 (m, 3H), 7.17-7.06 (m, 2H), 6.93 (td, 1H), 5.25 (s, 2H), 4.44 (br. s., 2H), 2.91 (s, 3H).

Example 77

4-{4-Fluoro-2-[(4-methylbenzyl)oxy]phenyl}-N-{3-[(methylsulfonyl)methyl]phenyl}-1,3,5-triazin-2-amine

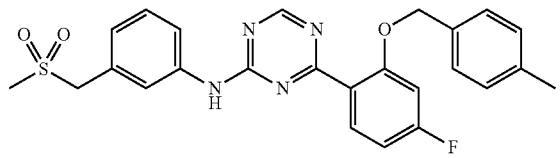

Starting with 4-(2,4-difluorophenyl)-N-{3-[(methylsulfonyl)methyl]phenyl}-1,3,5-triazin-2-amine (70 mg; 0.180 mmol), intermediate 42.1, and 4-methylbenzyl alcohol (90 mg; 0.721 0 mmol), example 77 was prepared analogously to the procedure for the preparation of example 42.

$^1$H NMR (400 MHz, d$_6$-DMSO, 300 K) δ=10.36 (s, 1H), 8.82 (s, 1H), 7.93-7.66 (m, 3H), 7.31 (d, 3H), 7.17-7.05 (m, 4H), 6.91 (td, 1H), 5.20 (s, 2H), 4.44 (br. s., 2H), 2.91 (br. s., 3H), 2.26 (s, 3H).

Example 78

4-(4-Fluoro-2-{[3-fluoro-5-(trifluoromethyl)benzyl]oxy}phenyl)-N-{3-[(methylsulfonyl)methyl]-phenyl}-1,3,5-triazin-2-amine

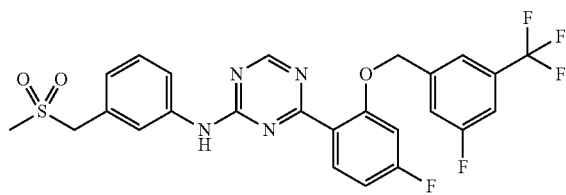 [SMILES: CS(=O)(=O)Cc1cccc(Nc2ncnc(-c3ccc(F)cc3OCc3cc(F)cc(C(F)(F)F)c3)n2)c1]

Starting with 4-(2,4-difluorophenyl)-N-{3-[(methylsulfonyl)methyl]phenyl}-1,3,5-triazin-2-amine (75 mg; 0.197 mmol), intermediate 42.1, and 3-fluoro-5-(trifluoromethyl)benzyl alcohol (158 mg; 0.789 mmol), example 78 was prepared analogously to the procedure for the preparation of example 42.

$^1$H NMR (400 MHz, d$_6$-DMSO, 300 K) δ=10.40 (s, 1H), 8.81 (s, 1H), 8.03-7.85 (m, 1H), 7.84-7.72 (m, 3H), 7.71-7.61 (m, 1H), 7.58 (d, 1H), 7.39-7.21 (m, 1H), 7.18 (dd, 1H), 7.14-7.03 (m, 1H), 6.98 (td, 1H), 5.39 (s, 2H), 4.44 (br. s., 2H), 2.91 (br. s., 3H).

Example 79

4-{4-Fluoro-2-[(1R)-1-phenylethoxy]phenyl}-N-{3-[(methylsulfonyl)methyl]phenyl}-1,3,5-triazin-2-amine

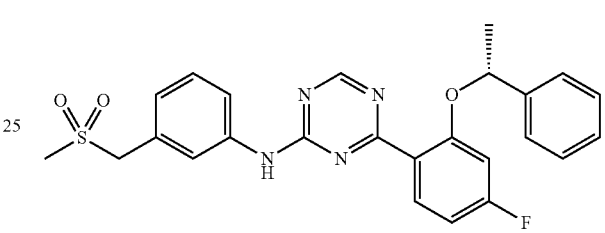

Starting with 4-(2,4-difluorophenyl)-N-{3-[(methylsulfonyl)methyl]phenyl}-1,3,5-triazin-2-amine (110 mg; 0.289 mmol), intermediate 42.1, and (R)-(+)-1-phenylethanol (143 mg; 1.157 mmol), example 79 was prepared analogously to the procedure for the preparation of example 42.

$^1$H NMR (400 MHz, d$_6$-DMSO, 300 K) δ=10.37 (s, 1H), 8.86 (s, 1H), 8.05-7.82 (m, 1H), 7.73 (d, 2H), 7.44 (d, 2H), 7.38-7.27 (m, 3H), 7.27-7.20 (m, 1H), 7.11 (d, 1H), 6.90 (dd, 1H), 6.83 (td, 1H), 5.63 (q, 1H), 4.45 (s, 2H), 2.91 (s, 3H), 1.53-1.46 (m, 3H).

Example 80

4-{2-[(2,3-Difluorobenzyl)oxy]-4-fluorophenyl}-N-{3-[(methylsulfonyl)-methyl]phenyl}-1,3,5-triazin-2-amine

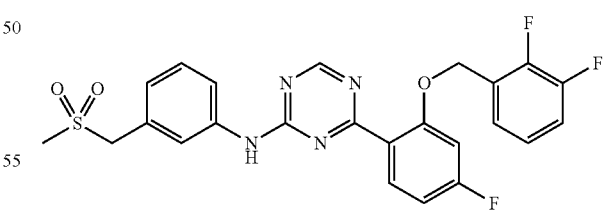

Starting with 4-(2,4-difluorophenyl)-N-{3-[(methylsulfonyl)methyl]phenyl}-1,3,5-triazin-2-amine (70 mg; 0.184 mmol), intermediate 42.1, and 2,3-difluorobenzyl alcohol (113 mg; 0.736 mmol), example 80 was prepared analogously to the procedure for the preparation of example 42.

$^1$H NMR (400 MHz, d$_6$-DMSO, 300 K) δ=10.36 (s, 1H), 8.82 (s, 1H), 7.92-7.82 (m, 1H), 7.79 (d, 1H), 7.76-7.68 (m, 1H), 7.48-7.23 (m, 4H), 7.20-7.04 (m, 2H), 6.97 (td, 1H), 5.34 (s, 2H), 4.44 (s, 2H), 2.91 (s, 3H).

Example 81

4-{2-[(2,5-Difluorobenzyl)oxy]-4-fluorophenyl}-N-{3-[(methylsulfonyl)methyl]-phenyl}-1,3,5-triazin-2-amine

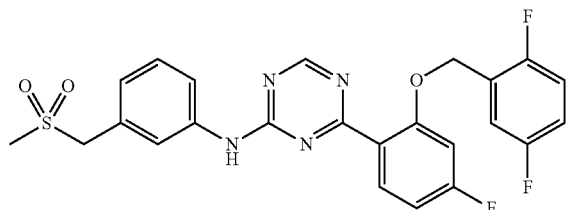

Starting with 4-(2,4-difluorophenyl)-N-{3-[(methylsulfonyl)methyl]phenyl}-1,3,5-triazin-2-amine (70 mg; 0.184 mmol), intermediate 42.1, and 2,5-difluorobenzyl alcohol (107 mg; 0.736 mmol), example 81 was prepared analogously to the procedure for the preparation of example 42.

$^1$H NMR (400 MHz, d$_6$-DMSO, 300 K) δ=10.39 (s, 1H), 8.82 (s, 1H), 7.94-7.82 (m, 1H), 7.82-7.72 (m, 2H), 7.55-7.40 (m, 1H), 7.37-7.22 (m, 3H), 7.22-7.12 (m, 1H), 7.09 (d, 1H), 6.97 (td, 1H), 5.30 (s, 2H), 4.44 (br. s., 2H), 2.91 (br. s., 3H).

Example 82

4-{4-Fluoro-2-[(2-fluoropyridin-4-yl)methoxy]phenyl}-N-{3-[(methylsulfonyl)-methyl]phenyl}-1,3,5-triazin-2-amine

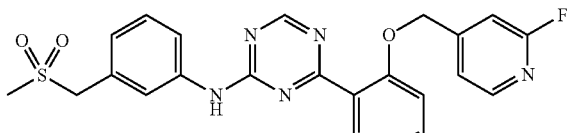

To mixture of 4-(2,4-difluorophenyl)-N-{3-[(methylsulfonyl)methyl]phenyl}-1,3,5-triazin-2-amine (75 mg; 0.197 mmol), intermediate 42.1, and 2-fluoro-4-pyridinemethanol (102 mg; 0.781 mmol) in THF (3.5 ml) a 1 M solution of sodium bis(trimethylsilyl)amide in THF (0.391 ml) was added. The batch was stirred under argon for 6 hours at 70° C. After cooling the batch was poored into saturated aqueous ammonium chloride solution. The organic phase was separated, washed with brine, dried (sodium sulfate) and concentrated. The residue was purified by preparative HPLC to give the desired product (38 mg; 0.08 mmol).

$^1$H NMR (400 MHz, d$_6$-DMSO, 300 K) δ=10.40 (s, 1H), 8.87 (s, 1H), 8.23-8.13 (m, 1H), 7.93 (br. s., 1H), 7.85-7.74 (m, 2H), 7.47-7.36 (m, 1H), 7.36-7.20 (m, 2H), 7.15 (dd, 1H), 7.09 (d, 1H), 6.98 (td, 1H), 5.39 (s, 2H), 4.44 (s, 2H), 2.91 (br. s., 3H).

Example 83

4-{4-Fluoro-2-[(3-methylbenzyl)oxy]phenyl}-N-{3-[(methylsulfonyl)methyl]phenyl}-1,3,5-triazin-2-amine

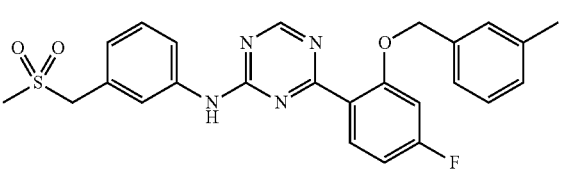

Starting with 4-(2,4-difluorophenyl)-N-{3-[(methylsulfonyl)methyl]phenyl}-1,3,5-triazin-2-amine (75 mg; 0.197 mmol), intermediate 42.1, and 3-methylbenzyl alcohol (99 mg; 0.789 mmol), example 83 was prepared analogously to the procedure for the preparation of example 42.

$^1$H NMR (400 MHz, d$_6$-DMSO, 300 K) δ=10.39 (s, 1H), 8.84 (s, 1H), 7.94-7.78 (m, 2H), 7.75 (br. s., 1H), 7.40-7.25 (m, 2H), 7.25-7.03 (m, 5H), 6.92 (td, 1H), 5.21 (s, 2H), 4.43 (br. s., 2H), 2.90 (br. s., 3H), 2.23 (s, 3H).

Example 84

4-{4-Fluoro-2-[(2,3,5-trifluorobenzyl)oxy]phenyl}-N-{3-[(methylsulfonyl)methyl]-phenyl}-1,3,5-triazin-2-amine

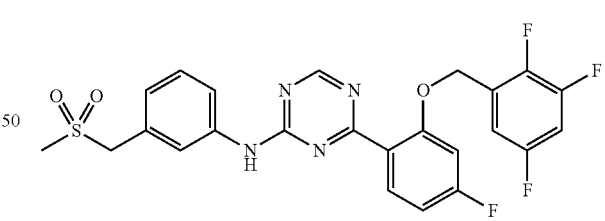

Starting with 4-(2,4-difluorophenyl)-N-{3-[(methylsulfonyl)methyl]phenyl}-1,3,5-triazin-2-amine (70 mg; 0.184 mmol), intermediate 42.1, and 2,3,5-trifluorobenzyl alcohol (119 mg; 0.736 mmol), example 84 was prepared analogously to the procedure for the preparation of example 42.

$^1$H NMR (400 MHz, d$_6$-DMSO, 300 K) δ=10.39 (s, 1H), 8.82 (s, 1H), 7.97-7.83 (m, 1H), 7.82-7.71 (m, 2H), 7.44 (d, 1H), 7.40-7.24 (m, 3H), 7.09 (d, 1H), 6.99 (td, 1H), 5.36 (s, 2H), 4.44 (br. s., 2H), 2.91 (s, 3H).

Example 85

4-{2-[(3-Chlorobenzyl)oxy]-4-fluorophenyl}-N-{3-[(methylsulfonyl)methyl]phenyl}-1,3,5-triazin-2-amine

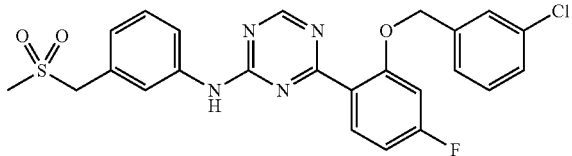 [SMILES: CS(=O)(=O)Cc1cccc(Nc2ncnc(-c3ccc(F)cc3OCc3cccc(Cl)c3)n2)c1]

Starting with 4-(2,4-difluorophenyl)-N-{3-[(methylsulfonyl)methyl]phenyl}-1,3,5-triazin-2-amine (75 mg; 0.197 mmol), intermediate 42.1, and 3-chlorobenzyl alcohol (115 mg; 0.789 mmol), example 85 was prepared analogously to the procedure for the preparation of example 42.

$^1$H NMR (400 MHz, $d_6$-DMSO, 300 K) δ=10.39 (s, 1H), 8.84 (s, 1H), 7.95-7.79 (m, 2H), 7.79-7.71 (m, 1H), 7.59 (br. s., 1H), 7.46-7.25 (m, 4H), 7.15 (dd, 1H), 7.10 (d, 1H), 6.95 (td, 1H), 5.28 (s, 2H), 4.44 (br. s., 2H), 2.91 (s, 3H).

Example 86

4-{2-[(3,4-Difluorobenzyl)oxy]-4-fluorophenyl}-N-{3-[(methylsulfonyl)methyl]-phenyl}-1,3,5-triazin-2-amine

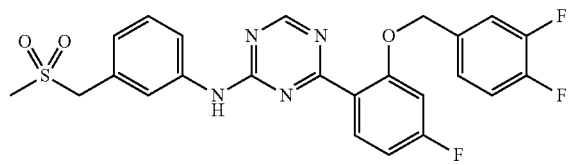 [SMILES: CS(=O)(=O)Cc1cccc(Nc2ncnc(-c3ccc(F)cc3OCc3ccc(F)c(F)c3)n2)c1]

Starting with 4-(2,4-difluorophenyl)-N-{3-[(methylsulfonyl)methyl]phenyl}-1,3,5-triazin-2-amine (70 mg; 0.184 mmol), intermediate 42.1, and 3,4-difluorobenzyl alcohol (108 mg; 0.736 mmol), example 86 was prepared analogously to the procedure for the preparation of example 42.

$^1$H NMR (400 MHz, $d_6$-DMSO, 300 K) δ=10.38 (s, 1H), 8.84 (s, 1H), 7.98-7.83 (m, 1H), 7.83-7.70 (m, 2H), 7.62-7.45 (m, 1H), 7.45-7.22 (m, 3H), 7.15 (dd, 1H), 7.10 (d, 1H), 6.95 (td, 1H), 5.25 (s, 2H), 4.44 (br. s., 2H), 2.91 (s, 3H).

Example 87

4-{4-Fluoro-2-[(2-methylpyridin-4-yl)methoxy]phenyl}-N-{3-[(methylsulfonyl)methyl]-phenyl}-1,3,5-triazin-2-amine

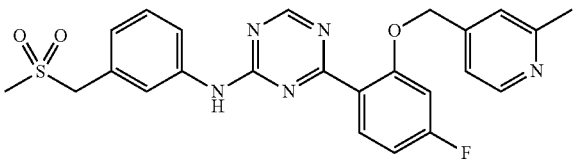

Starting with 4-(2,4-difluorophenyl)-N-{3-[(methylsulfonyl)methyl]phenyl}-1,3,5-triazin-2-amine (70 mg; 0.184 mmol), intermediate 42.1, and (2-methyl-pyridin-4-yl)-methanol (91 mg; 0.736 mmol), example 87 was prepared analogously to the procedure for the preparation of example 42.

$^1$H NMR (400 MHz, $d_6$-DMSO, 300 K) δ=10.41 (s, 1H), 8.87 (s, 1H), 8.35 (d, 1H), 7.95-7.86 (m, 1H), 7.83 (d, 1H), 7.80-7.73 (m, 1H), 7.39-7.26 (m, 2H), 7.26-7.18 (m, 1H), 7.14 (dd, 1H), 7.09 (d, 1H), 6.96 (td, 1H), 5.27 (s, 2H), 4.43 (s, 2H), 2.91 (s, 3H), 2.39 (s, 3H).

Example 88

4-{2-[(2-Chloropyridin-4-yl)methoxy]-4-fluorophenyl}-N-{3-[(methylsulfonyl)methyl]-phenyl}-1,3,5-triazin-2-amine

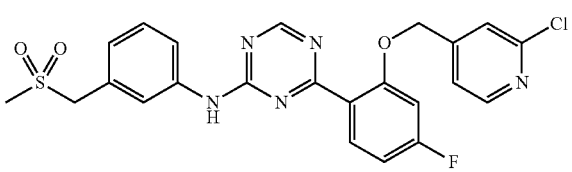 [SMILES: CS(=O)(=O)Cc1cccc(Nc2ncnc(-c3ccc(F)cc3OCc3ccnc(Cl)c3)n2)c1]

Starting with 4-(2,4-difluorophenyl)-N-{3-[(methylsulfonyl)methyl]phenyl}-1,3,5-triazin-2-amine (70 mg; 0.184 mmol), intermediate 42.1, and (2-chloro-pyridin-4-yl)-methanol (111 mg; 0.736 mmol), example 88 was prepared analogously to the procedure for the preparation of example 42.

$^1$H NMR (400 MHz, $d_6$-DMSO, 300 K) δ=10.41 (s, 1H), 8.87 (s, 1H), 8.39-8.28 (m, 1H), 8.01-7.86 (m, 1H), 7.85-7.73 (m, 2H), 7.70-7.60 (m, 1H), 7.51-7.39 (m, 1H), 7.37-7.24 (m, 1H), 7.15 (dd, 1H), 7.10 (d, 1H), 6.98 (td, 1H), 5.35 (s, 2H), 4.44 (br. s., 2H), 2.91 (s, 3H).

Example 89

4-[4-Fluoro-2-(pyridin-4-ylmethoxy)phenyl]-N-{3-[(methylsulfonyl)methyl]phenyl}-1,3,5-triazin-2-amine

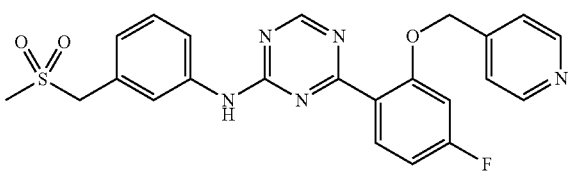 [SMILES: CS(=O)(=O)Cc1cccc(Nc2ncnc(-c3ccc(F)cc3OCc3ccncc3)n2)c1]

Starting with 4-(2,4-difluorophenyl)-N-{3-[(methylsulfonyl)methyl]phenyl}-1,3,5-triazin-2-amine (50 mg; 0.129 mmol), intermediate 42.1, and 3-(hydroxymethyl)-pyridine (57 mg; 0.515 mmol), example 89 was prepared analogously to the procedure for the preparation of example 42.

$^1$H NMR (400 MHz, $d_6$-DMSO, 300 K) δ=10.39 (s, 1H), 8.87 (s, 1H), 8.56-8.42 (m, 2H), 7.98-7.85 (m, 1H), 7.81 (d, 1H), 7.79-7.70 (m, 1H), 7.53-7.38 (m, 2H), 7.38-7.20 (m, 1H), 7.20-7.04 (m, 2H), 6.96 (td, 1H), 5.33 (s, 2H), 4.44 (br. s., 2H), 2.91 (s, 3H).

Example 90

4-({5-Fluoro-2-[4-({3-[(methylsulfonyl)methyl]phenyl}amino)-1,3,5-triazin-2-yl]phenoxy}methyl)benzonitrile

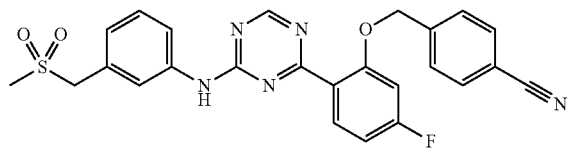 [SMILES: CS(=O)(=O)Cc1cccc(Nc2ncnc(-c3ccc(F)cc3OCc3ccc(C#N)cc3)n2)c1]

Starting with 4-(2,4-difluorophenyl)-N-{3-[(methylsulfonyl)methyl]phenyl}-1,3,5-triazin-2-amine (75 mg; 0.197 mmol), intermediate 42.1, and 4-hydroxymethyl-benzonitrile (107 mg; 0.789 mmol), example 90 was prepared analogously to the procedure for the preparation of example 42.

$^1$H NMR (400 MHz, $d_6$-DMSO, 300 K) δ=10.38 (s, 1H), 8.86 (s, 1H), 7.96-7.72 (m, 6H), 7.71-7.59 (m, 2H), 7.37-7.24 (m, 1H), 7.20-7.03 (m, 2H), 6.95 (td, 1H), 5.37 (s, 2H), 4.44 (br. s., 2H), 2.91 (s, 3H).

The following Table 1 provides an overview on the compounds of the invention:

TABLE 1

| Compound No. | Structure | Nomenclature |
|---|---|---|
| 1 | 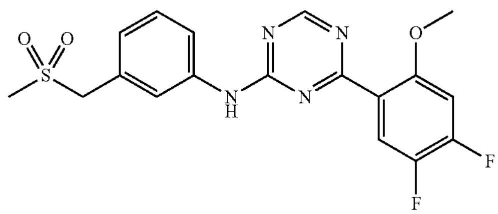 [SMILES: COc1cc(F)c(F)cc1-c1ncnc(Nc2cccc(CS(C)(=O)=O)c2)n1] | 4-(4,5-Difluoro-2-methoxyphenyl)-N-{3-[(methylsulfonyl)methyl]phenyl}-1,3,5-triazin-2-amine |
| 2 | 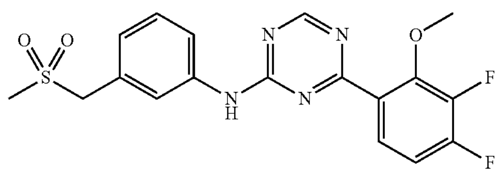 [SMILES: COc1c(-c2ncnc(Nc3cccc(CS(C)(=O)=O)c3)n2)ccc(F)c1F] | 4-(3,4-Difluoro-2-methoxyphenyl)-N-{3-[(methylsulfonyl)methyl]phenyl}-1,3,5-triazin-2-amine |
| 3 | 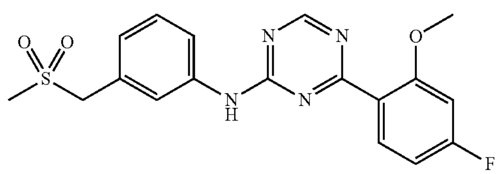 [SMILES: COc1cc(F)ccc1-c1ncnc(Nc2cccc(CS(C)(=O)=O)c2)n1] | 4-(4-Fluoro-2-methoxyphenyl)-N-{3-[(methylsulfonyl)methyl]phenyl}-1,3,5-triazin-2-amine |
| 4 | 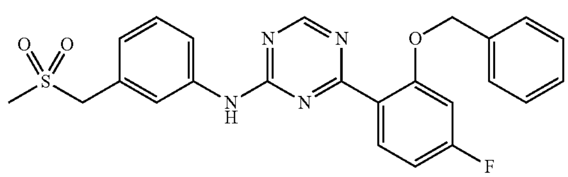 [SMILES: CS(=O)(=O)Cc1cccc(Nc2ncnc(-c3ccc(F)cc3OCc3ccccc3)n2)c1] | 4-[2-(Benzyloxy)-4-fluorophenyl]-N-{3-[(methylsulfonyl)methyl]phenyl}-1,3,5-triazin-2-amine |
| 5 | 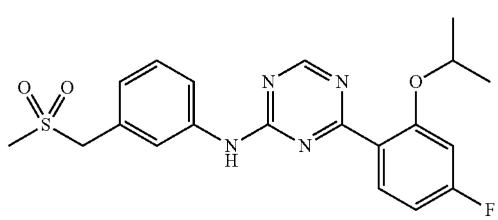 [SMILES: CC(C)Oc1cc(F)ccc1-c1ncnc(Nc2cccc(CS(C)(=O)=O)c2)n1] | 4-[4-Fluoro-2-(propan-2-yloxy)phenyl]-N-{3-[(methylsulfonyl)methyl]phenyl}-1,3,5-triazin-2-amine |
| 6 | 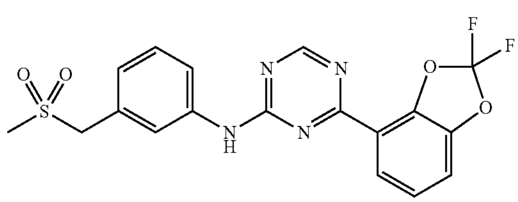 [SMILES: CS(=O)(=O)Cc1cccc(Nc2ncnc(-c3cccc4c3OC(F)(F)O4)n2)c1] | 4-(2,2-Difluoro-1,3-benzodioxol-4-yl)-N-{3-[(methylsulfonyl)methyl]phenyl}-1,3,5-triazin-2-amine |

TABLE 1-continued

| Compound No. | Structure | Nomenclature |
|---|---|---|
| 7 | 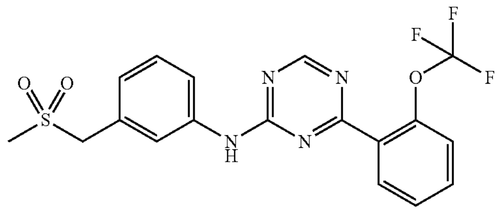 [SMILES: CS(=O)(=O)Cc1cccc(Nc2ncnc(-c3ccccc3OC(F)(F)F)n2)c1] | N-{3-[(Methylsulfonyl)methyl]phenyl}-4-[2-(trifluoromethoxy)phenyl]-1,3,5-triazin-2-amine |
| 8 | 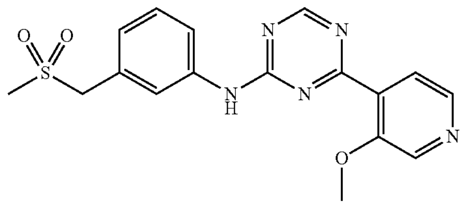 [SMILES: COc1cnccc1-c1ncnc(Nc2cccc(CS(C)(=O)=O)c2)n1] | 4-(3-Methoxypyridin-4-yl)-N-{3-[(methylsulfonyl)methyl]phenyl}-1,3,5-triazin-2-amine |
| 9 | 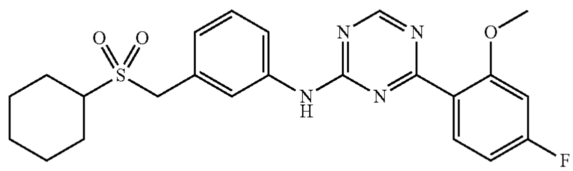 [SMILES: COc1cc(F)ccc1-c1ncnc(Nc2cccc(CS(=O)(=O)C3CCCCC3)c2)n1] | N-{3-[(Cyclohexylsulfonyl)methyl]phenyl}-4-(4-fluoro-2-methoxyphenyl)-1,3,5-triazin-2-amine |
| 10 | 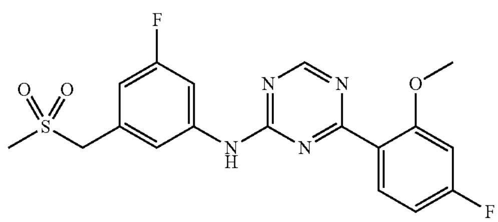 [SMILES: COc1cc(F)ccc1-c1ncnc(Nc2cc(F)cc(CS(C)(=O)=O)c2)n1] | 4-(4-Fluoro-2-methoxyphenyl)-N-{3-fluoro-5-[(methylsulfonyl)methyl]phenyl}-1,3,5-triazin-2-amine |
| 11 | 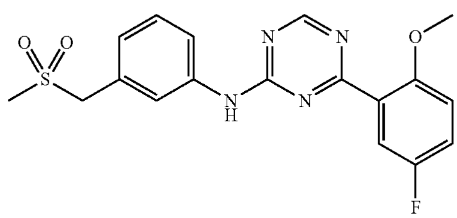 | 4-(5-Fluoro-2-methoxyphenyl)-N-{3-[(methylsulfonyl)methyl]phenyl}-1,3,5-triazin-2-amine |
| 12 | 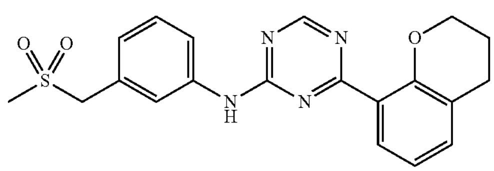 [SMILES: CS(=O)(=O)Cc1cccc(Nc2ncnc(-c3cccc4c3OCCC4)n2)c1] | 4-(3,4-Dihydro-2H-chromen-8-yl)-N-{3-[(methylsulfonyl)methyl]phenyl}-1,3,5-triazin-2-amine |
| 13 | 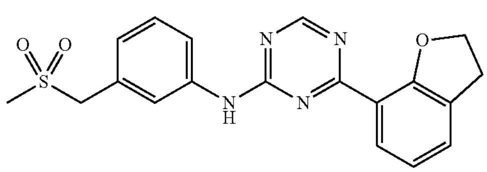 [SMILES: CS(=O)(=O)Cc1cccc(Nc2ncnc(-c3cccc4c3OCC4)n2)c1] | 4-(2,3-Dihydro-1-benzofuran-7-yl)-N-{3-[(methylsulfonyl)methyl]phenyl}-1,3,5-triazin-2-amine |
| 14 | 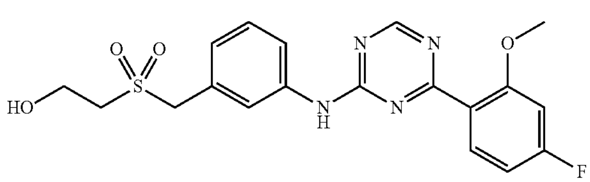 [SMILES: COc1cc(F)ccc1-c1ncnc(Nc2cccc(CS(=O)(=O)CCO)c2)n1] | 2-[(3-{[4-(4-Fluoro-2-methoxyphenyl)-1,3,5-triazin-2-yl]amino}benzyl)sulfonyl]ethanol |

TABLE 1-continued

| Compound No. | Structure | Nomenclature |
|---|---|---|
| 15 | 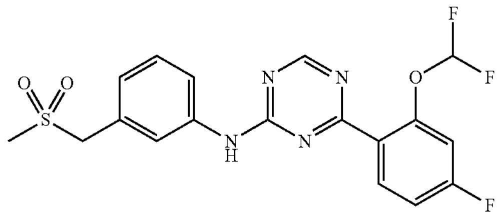 [SMILES: CS(=O)(=O)Cc1cccc(Nc2ncnc(-c3ccc(F)cc3OC(F)F)n2)c1] | 4-[2-(Difluoromethoxy)-4-fluorophenyl]-N-{3-[(methylsulfonyl)methyl]phenyl}-1,3,5-triazin-2-amine |
| 16 | 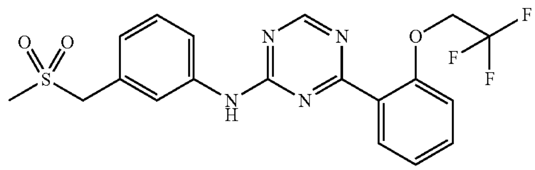 [SMILES: CS(=O)(=O)Cc1cccc(Nc2ncnc(-c3ccccc3OCC(F)(F)F)n2)c1] | N-{3-[(Methylsulfonyl)methyl]phenyl}-4-[2-(2,2,2-trifluoroethoxy)phenyl]-1,3,5-triazin-2-amine |
| 17 | 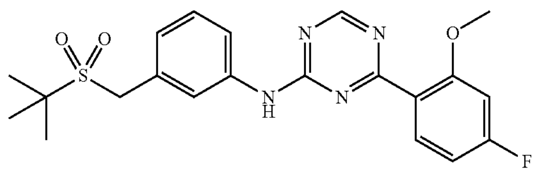 [SMILES: COc1cc(F)ccc1-c1ncnc(Nc2cccc(CS(=O)(=O)C(C)(C)C)c2)n1] | N-{3-[(tert-Butylsulfonyl)methyl]phenyl}-4-(4-fluoro-2-methoxyphenyl)-1,3,5-triazin-2-amine |
| 18 | 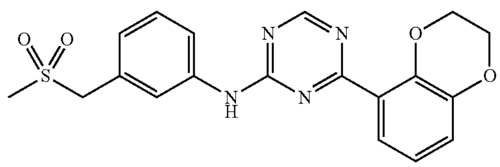 [SMILES: CS(=O)(=O)Cc1cccc(Nc2ncnc(-c3cccc4c3OCCO4)n2)c1] | 4-(2,3-Dihydro-1,4-benzodioxin-5-yl)-N-{3-[(methylsulfonyl)methyl]phenyl}-1,3,5-triazin-2-amine |
| 19 | 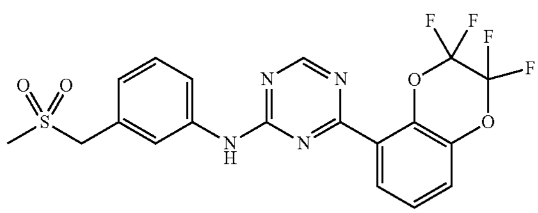 [SMILES: CS(=O)(=O)Cc1cccc(Nc2ncnc(-c3cccc4c3OC(F)(F)C(F)(F)O4)n2)c1] | N-{3-[(Methylsulfonyl)methyl]phenyl}-4-(2,2,3,3-tetrafluoro-2,3-dihydro-1,4-benzodioxin-5-yl)-1,3,5-triazin-2-amine |
| 20 | 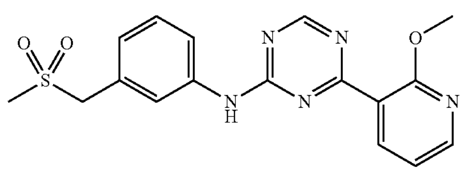 | 4-(2-Methoxypyridin-3-yl)-N-{3-[(methylsulfonyl)methyl]phenyl}-1,3,5-triazin-2-amine |
| 21 | 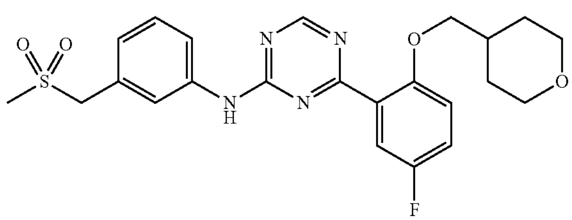 [SMILES: CS(=O)(=O)Cc1cccc(Nc2ncnc(-c3cc(F)ccc3OCC3CCOCC3)n2)c1] | 4-[5-Fluoro-2-(tetrahydro-2H-pyran-4-ylmethoxy)phenyl]-N-{3-[(methylsulfonyl)methyl]phenyl}-1,3,5-triazin-2-amine |
| 22 | 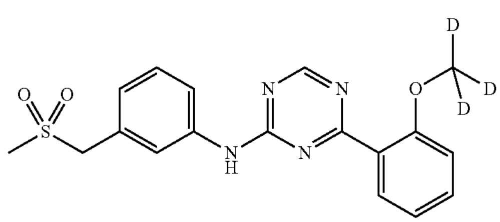 [SMILES: [2H]C([2H])([2H])Oc1ccccc1-c1ncnc(Nc2cccc(CS(C)(=O)=O)c2)n1] | 4-{2-[($^2$H$_3$)methyloxy]phenyl)-N-{3-[(methylsulfonyl)methyl]phenyl}-1,3,5-triazin-2-amine |

TABLE 1-continued

| Compound No. | Structure | Nomenclature |
|---|---|---|
| 23 | 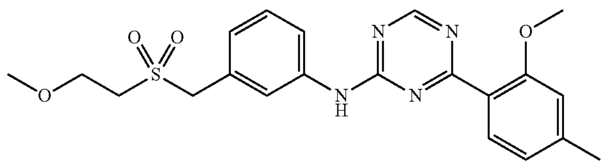 | 4-(4-Fluoro-2-methoxyphenyl)-N-(3-{[(2-methoxyethyl)sulfonyl]methyl}phenyl)-1,3,5-triazin-2-amine |
| 24 | 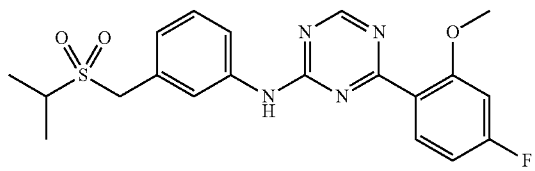 [SMILES: COc1cc(F)ccc1-c1ncnc(Nc2cccc(CS(=O)(=O)C(C)C)c2)n1] | 4-(4-Fluoro-2-methoxyphenyl)-N-{3-[(propan-2-ylsulfonyl)methyl]phenyl}-1,3,5-triazin-2-amine |
| 25 | 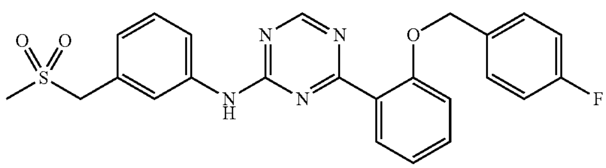 [SMILES: CS(=O)(=O)Cc1cccc(Nc2ncnc(-c3ccccc3OCc3ccc(F)cc3)n2)c1] | 4-{2-[(4-Fluorobenzyl)oxy]phenyl}-N-{3-[(methylsulfonyl)methyl]phenyl}-1,3,5-triazin-2-amine |
| 26 | 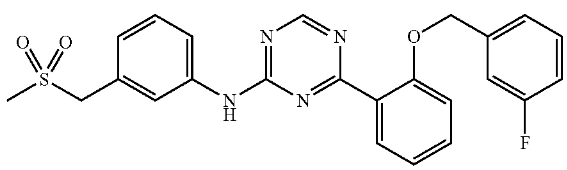 [SMILES: CS(=O)(=O)Cc1cccc(Nc2ncnc(-c3ccccc3OCc3cccc(F)c3)n2)c1] | 4-{2-[(3-Fluorobenzyl)oxy]phenyl}-N-{3-[(methylsulfonyl)methyl]phenyl}-1,3,5-triazin-2-amine |
| 27 | 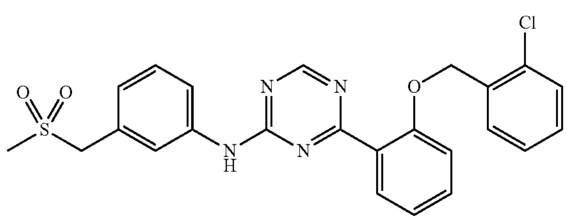 [SMILES: CS(=O)(=O)Cc1cccc(Nc2ncnc(-c3ccccc3OCc3ccccc3Cl)n2)c1] | 4-{2-[(2-Chlorobenzyl)oxy]phenyl}-N-{3-[(methylsulfonyl)methyl]phenyl}-1,3,5-triazin-2-amine |
| 28 | 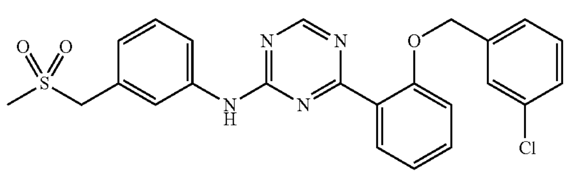 [SMILES: CS(=O)(=O)Cc1cccc(Nc2ncnc(-c3ccccc3OCc3cccc(Cl)c3)n2)c1] | 4-{2-[(3-Chlorobenzyl)oxy]phenyl}-N-{3-[(methylsulfonyl)methyl]phenyl}-1,3,5-triazin-2-amine |
| 29 | 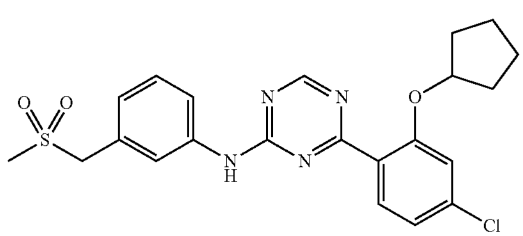 [SMILES: CS(=O)(=O)Cc1cccc(Nc2ncnc(-c3ccc(Cl)cc3OC3CCCC3)n2)c1] | 4-[4-Chloro-2-(cyclopentyloxy)phenyl]-N-{3-[(methylsulfonyl)methyl]phenyl}-1,3,5-triazin-2-amine |

TABLE 1-continued

| Compound No. | Structure | Nomenclature |
|---|---|---|
| 30 | 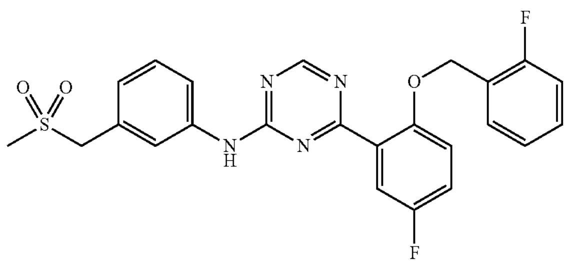 [SMILES: CS(=O)(=O)Cc1cccc(Nc2ncnc(-c3cc(F)ccc3OCc3ccccc3F)n2)c1] | 4-{5-Fluoro-2-[(2-fluorobenzyl)oxy]phenyl}-N-{3-[(methylsulfonyl)methyl]phenyl}-1,3,5-triazin-2-amine |
| 31 | 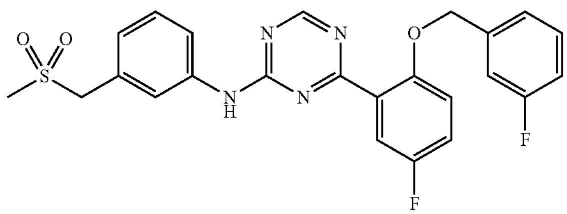 [SMILES: CS(=O)(=O)Cc1cccc(Nc2ncnc(-c3cc(F)ccc3OCc3cccc(F)c3)n2)c1] | 4-{5-Fluoro-2-[(3-fluorobenzyl)oxy]phenyl}-N-{3-[(methylsulfonyl)methyl]phenyl}-1,3,5-triazin-2-amine |
| 32 | 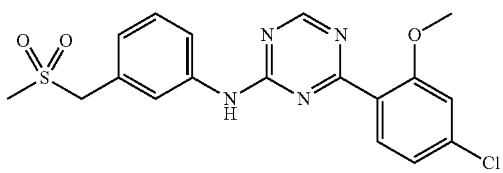 [SMILES: COc1cc(Cl)ccc1-c1ncnc(Nc2cccc(CS(C)(=O)=O)c2)n1] | 4-(4-Chloro-2-methoxyphenyl)-N-{3-[(methylsulfonyl)methyl]phenyl}-1,3,5-triazin-2-amine |
| 33 | 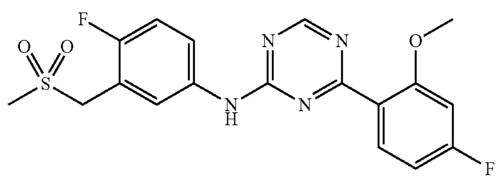 [SMILES: COc1cc(F)ccc1-c1ncnc(Nc2ccc(F)c(CS(C)(=O)=O)c2)n1] | 4-(4-Fluoro-2-methoxyphenyl)-N-{4-fluoro-3-[(methylsulfonyl)methyl]phenyl}-1,3,5-triazin-2-amine |
| 34 | 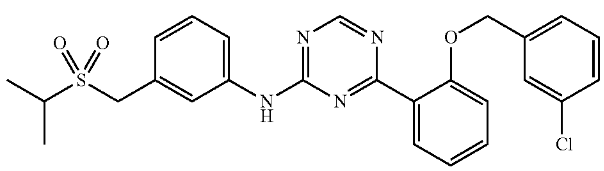 [SMILES: CC(C)S(=O)(=O)Cc1cccc(Nc2ncnc(-c3ccccc3OCc3cccc(Cl)c3)n2)c1] | 4-{2-[(3-Chlorobenzyl)oxy]phenyl}-N-{3-[(propan-2-ylsulfonyl)methyl]phenyl}-1,3,5-triazin-2-amine |
| 35 | 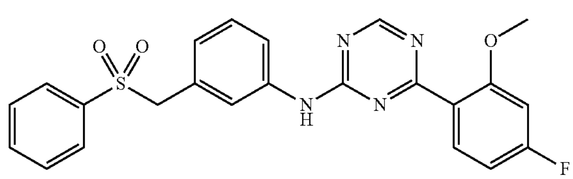 [SMILES: COc1cc(F)ccc1-c1ncnc(Nc2cccc(CS(=O)(=O)c3ccccc3)c2)n1] | 4-(4-Fluoro-2-methoxyphenyl)-N-{3-[(phenylsulfonyl)methyl]phenyl}-1,3,5-triazin-2-amine |
| 36 | 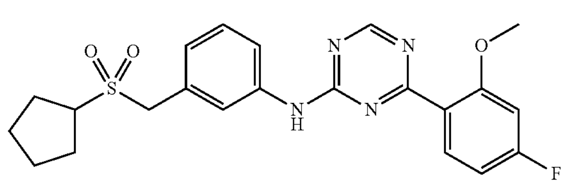 [SMILES: COc1cc(F)ccc1-c1ncnc(Nc2cccc(CS(=O)(=O)C3CCCC3)c2)n1] | N-{3-[(Cyclopentylsulfonyl)methyl]phenyl}-4-(4-fluoro-2-methoxyphenyl)-1,3,5-triazin-2-amine |
| 37 | 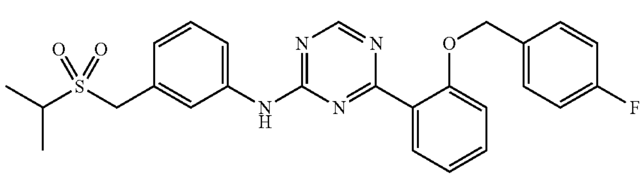 [SMILES: CC(C)S(=O)(=O)Cc1cccc(Nc2ncnc(-c3ccccc3OCc3ccc(F)cc3)n2)c1] | 4-{2-[(4-Fluorobenzyl)oxy]phenyl}-N-{3-[(prop-2-ylsulfonyl)methyl]phenyl}-1,3,5-triazin-2-amine |

TABLE 1-continued

| Compound No. | Structure | Nomenclature |
|---|---|---|
| 38 | 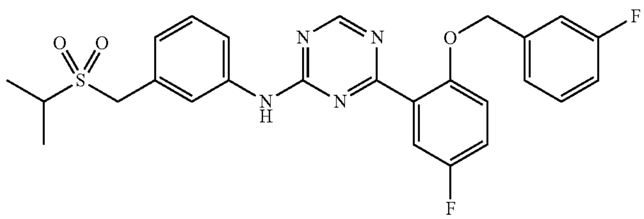 [SMILES: CC(C)S(=O)(=O)Cc1cccc(Nc2ncnc(-c3cc(F)ccc3OCc3cccc(F)c3)n2)c1] | 4-{5-Fluoro-2-[(3-fluorobenzyl)oxy]phenyl}-N-{3-[(prop-2-ylsulfonyl)methyl]phenyl}-1,3,5-triazin-2-amine |
| 39 | 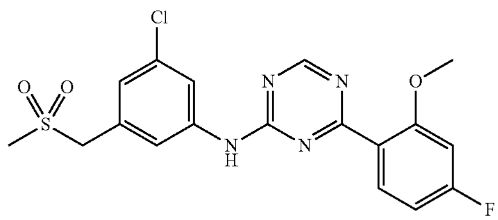 | N-{5-Chloro-3-[(methylsulfonyl)methyl]phenyl}-4-(4-fluoro-2-methoxyphenyl)-1,3,5-triazin-2-amine |
| 40 | 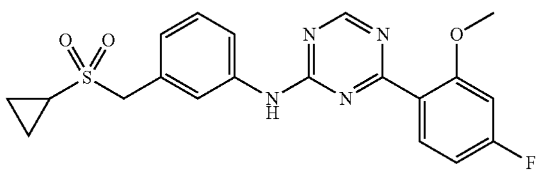 [SMILES: COc1cc(F)ccc1-c1ncnc(Nc2cccc(CS(=O)(=O)C3CC3)c2)n1] | N-{3-[(Cyclopropylsulfonyl)methyl]phenyl}-4-(4-fluoro-2-methoxyphenyl)-1,3,5-triazin-2-amine |
| 41 | 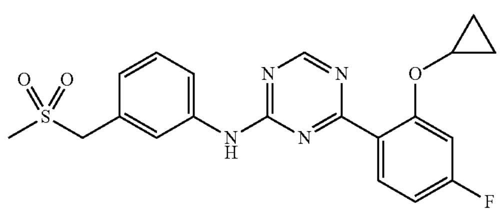 [SMILES: CS(=O)(=O)Cc1cccc(Nc2ncnc(-c3ccc(F)cc3OC3CC3)n2)c1] | 4-[2-(Cyclopropyloxy)-4-fluorophenyl]-N-{3-[(methylsulfonyl)methyl]phenyl}-1,3,5-triazin-2-amine |
| 42 | 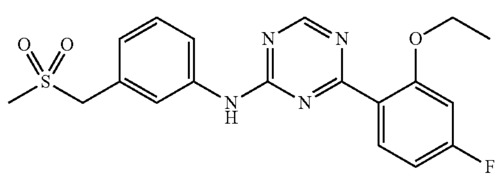 [SMILES: CCOc1cc(F)ccc1-c1ncnc(Nc2cccc(CS(C)(=O)=O)c2)n1] | 4-(2-Ethoxy-4-fluorophenyl)-N-{3-[(methylsulfonyl)-methyl]phenyl}-1,3,5-triazin-2-amine |
| 43 | 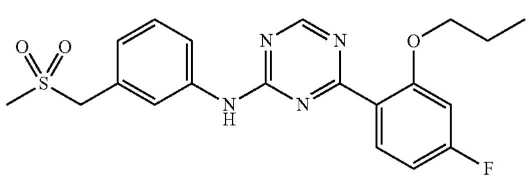 [SMILES: CCCOc1cc(F)ccc1-c1ncnc(Nc2cccc(CS(C)(=O)=O)c2)n1] | 4-(4-Fluoro-2-propoxyphenyl)-N-{3-[(methylsulfonyl)-methyl]phenyl}-1,3,5-triazin-2-amine |
| 44 | 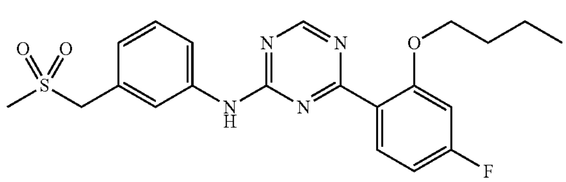 [SMILES: CCCCOc1cc(F)ccc1-c1ncnc(Nc2cccc(CS(C)(=O)=O)c2)n1] | 4-(2-Butoxy-4-fluorophenyl)-N-{3-[(methylsulfonyl)-methyl]phenyl}-1,3,5-triazin-2-amine |
| 45 | 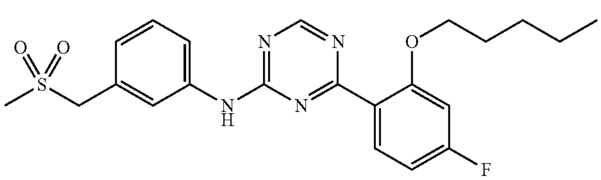 [SMILES: CCCCCOc1cc(F)ccc1-c1ncnc(Nc2cccc(CS(C)(=O)=O)c2)n1] | 4-[4-Fluoro-2-(pentyloxy)phenyl]-N-{3-[(methylsulfonyl)-methyl]phenyl}-1,3,5-triazin-2-amine |

TABLE 1-continued

| Compound No. | Structure | Nomenclature |
|---|---|---|
| 46 | 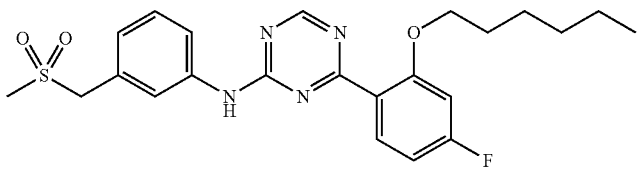 [SMILES: CCCCCCOc1cc(F)ccc1-c1ncnc(Nc2cccc(CS(C)(=O)=O)c2)n1] | 4-[4-Fluoro-2-(hexyloxy)phenyl]-N-{3-[(methylsulfonyl)methyl]phenyl}-1,3,5-triazin-2-amine |
| 47 | 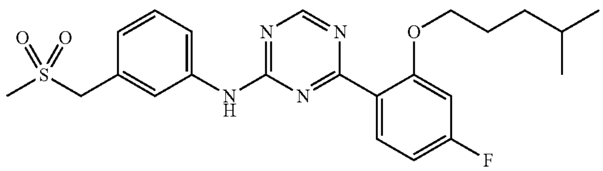 [SMILES: CC(C)CCCOc1cc(F)ccc1-c1ncnc(Nc2cccc(CS(C)(=O)=O)c2)n1] | 4-{4-Fluoro-2-[(4-methylpentyl)oxy]phenyl}-N-{3-[(methylsulfonyl)-methyl]phenyl}-1,3,5-triazin-2-amine |
| 48 | 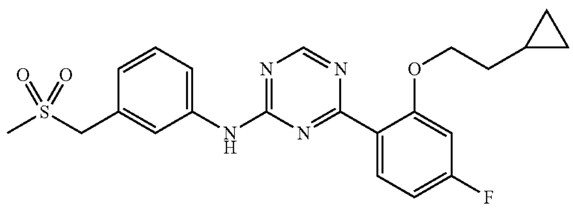 [SMILES: CS(=O)(=O)Cc1cccc(Nc2ncnc(-c3ccc(F)cc3OCCC3CC3)n2)c1] | 4-[2-(2-Cyclopropylethoxy)-4-fluorophenyl]-N-{3-[(methylsulfonyl)methyl]phenyl}-1,3,5-triazin-2-amine |
| 49 | 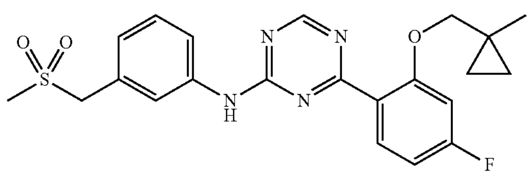 | 4-{4-Fluoro-2-[(1-methylcyclopropyl)methoxy]phenyl}-N-{3-[(methylsulfonyl)-methyl]phenyl}-1,3,5-triazin-2-amine |
| 50 | 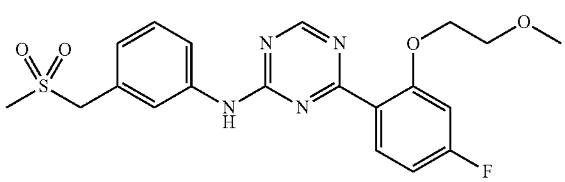 | 4-[4-Fluoro-2-(2-methoxyethoxy)phenyl]-N-{3-[(methylsulfonyl)methyl]-phenyl}-1,3,5-triazin-2-amine |
| 51 | 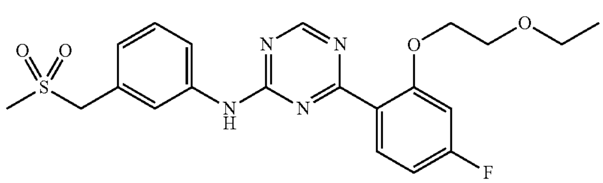 [SMILES: CCOCCOc1cc(F)ccc1-c1ncnc(Nc2cccc(CS(C)(=O)=O)c2)n1] | 4-[2-(2-Ethoxyethoxy)-4-fluorophenyl]-N-{3-[(methylsulfonyl)methyl]phenyl}-1,3,5-triazin-2-amine |
| 52 | 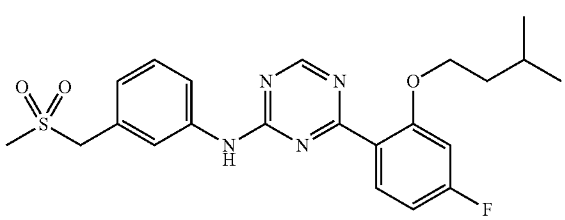 [SMILES: CC(C)CCOc1cc(F)ccc1-c1ncnc(Nc2cccc(CS(C)(=O)=O)c2)n1] | 4-[4-Fluoro-2-(3-methylbutoxy)phenyl]-N-{3-[(methylsulfonyl)methyl]phenyl}-1,3,5-triazin-2-amine |
| 53 | 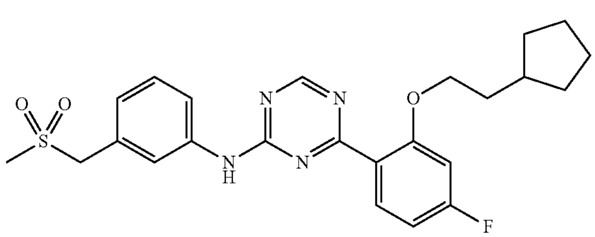 [SMILES: CS(=O)(=O)Cc1cccc(Nc2ncnc(-c3ccc(F)cc3OCCC3CCCC3)n2)c1] | 4-[2-(2-Cyclopentylethoxy)-4-fluorophenyl]-N-(3-[(methylsulfonyl)methyl]phenyl}-1,3,5-triazin-2-amine |

TABLE 1-continued

| Compound No. | Structure | Nomenclature |
|---|---|---|
| 54 | 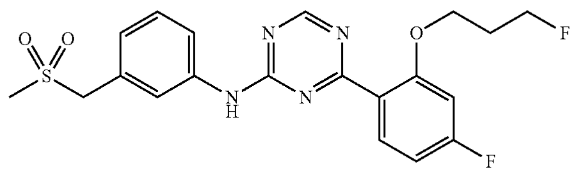 [SMILES: CS(=O)(=O)Cc1cccc(Nc2ncnc(-c3ccc(F)cc3OCCCF)n2)c1] | 4-[4-Fluoro-2-(3-fluoropropoxy)phenyl]-N-{3-[(methylsulfonyl)methyl]phenyl}-1,3,5-triazin-2-amine |
| 55 | 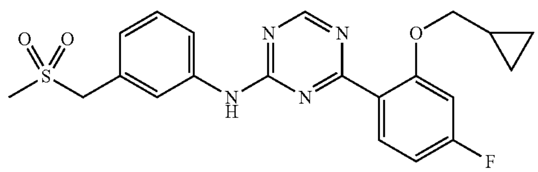 [SMILES: CS(=O)(=O)Cc1cccc(Nc2ncnc(-c3ccc(F)cc3OCC3CC3)n2)c1] | 4-[2-(Cyclopropylmethoxy)-4-fluorophenyl]-N-{3-[(methylsulfonyl)methyl]phenyl}-1,3,5-triazin-2-amine |
| 56 | 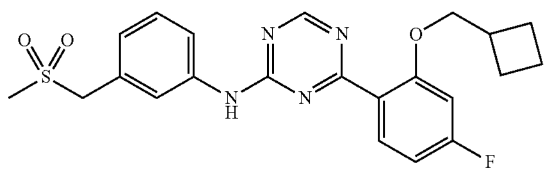 [SMILES: CS(=O)(=O)Cc1cccc(Nc2ncnc(-c3ccc(F)cc3OCC3CCC3)n2)c1] | 4-[2-(Cyclobutylmethoxy)-4-fluorophenyl]-N-{3-[(methylsulfonyl)methyl]phenyl}-1,3,5-triazin-2-amine |
| 57 | 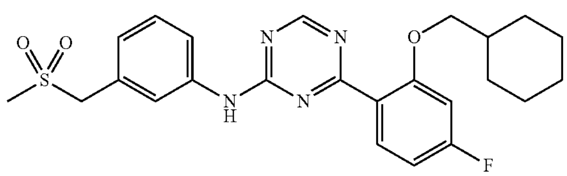 [SMILES: CS(=O)(=O)Cc1cccc(Nc2ncnc(-c3ccc(F)cc3OCC3CCCCC3)n2)c1] | 4-[2-(Cyclohexylmethoxy)-4-fluorophenyl]-N-{3-[(methylsulfonyl)methyl]phenyl}-1,3,5-triazin-2-amine |
| 58 | 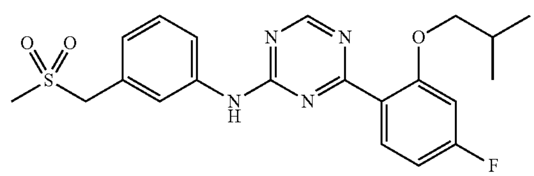 [SMILES: CC(C)COc1cc(F)ccc1-c1ncnc(Nc2cccc(CS(C)(=O)=O)c2)n1] | 4-[4-Fluoro-2-(2-methylpropoxy)phenyl]-N-{3-[(methylsulfonyl)methyl]phenyl}-1,3,5-triazin-2-amine |
| 59 | 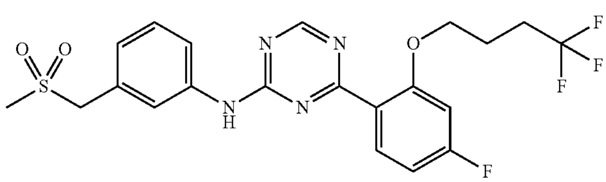 [SMILES: CS(=O)(=O)Cc1cccc(Nc2ncnc(-c3ccc(F)cc3OCCCC(F)(F)F)n2)c1] | 4-[4-Fluoro-2-(4,4,4-trifluorobutoxy)phenyl]-N-(3-[(methylsulfonyl)methyl]phenyl}-1,3,5-triazin-2-amine |
| 60 | 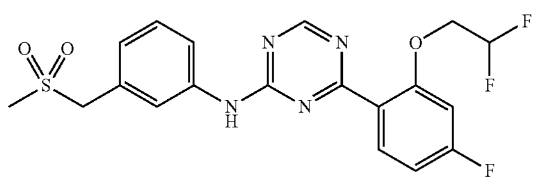 [SMILES: CS(=O)(=O)Cc1cccc(Nc2ncnc(-c3ccc(F)cc3OCC(F)F)n2)c1] | 4-[2-(2,2-Difluoroethoxy)-4-fluorophenyl]-N-{3-[(methylsulfonyl)methyl]phenyl}-1,3,5-triazin-2-amine |
| 61 | 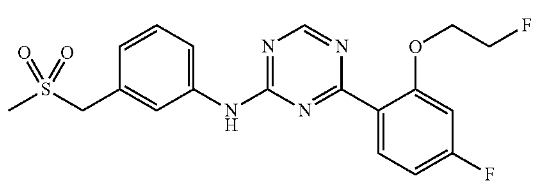 [SMILES: CS(=O)(=O)Cc1cccc(Nc2ncnc(-c3ccc(F)cc3OCCF)n2)c1] | 4-[4-Fluoro-2-(2-fluoroethoxy)phenyl]-N-{3-[(methylsulfonyl)methyl]phenyl}-1,3,5-triazin-2-amine |

TABLE 1-continued

| Compound No. | Structure | Nomenclature |
|---|---|---|
| 62 | 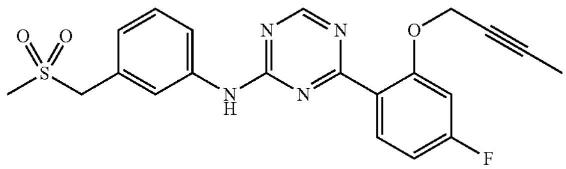 [SMILES: CC#CCOc1cc(F)ccc1-c1ncnc(Nc2cccc(CS(C)(=O)=O)c2)n1] | 4-[2-(But-2-yn-1-yloxy)-4-fluorophenyl]-N-{3-[(methylsulfonyl)methyl]phenyl}-1,3,5-triazin-2-amine |
| 63 | 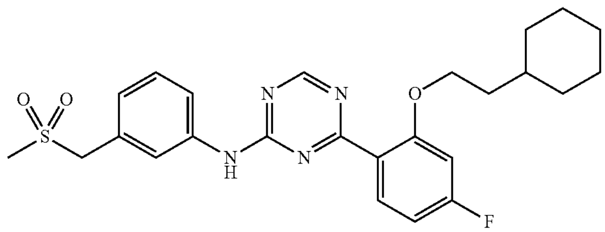 [SMILES: CS(=O)(=O)Cc1cccc(Nc2ncnc(-c3ccc(F)cc3OCCC3CCCCC3)n2)c1] | 4-[2-(2-Cyclohexylethoxy)-4-fluorophenyl]-N-{3-[(methylsulfonyl)methyl]phenyl}-1,3,5-triazin-2-amine |
| 64 | 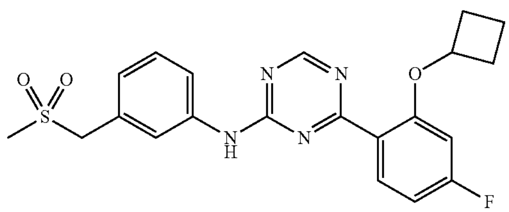 [SMILES: CS(=O)(=O)Cc1cccc(Nc2ncnc(-c3ccc(F)cc3OC3CCC3)n2)c1] | 4-[2-(Cyclobutyloxy)-4-fluorophenyl]-N-{3-[(methylsulfonyl)methyl]phenyl}-1,3,5-triazin-2-amine |
| 65 | 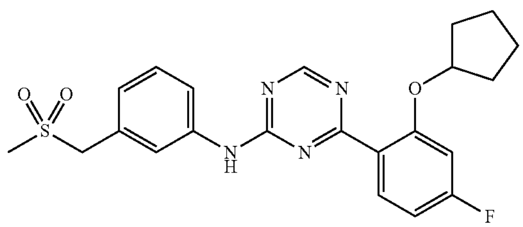 | 4-[2-(Cyclopentyloxy)-4-fluorophenyl]-N-{3-[(methylsulfonyl)methyl]phenyl}-1,3,5-triazin-2-amine |
| 66 | 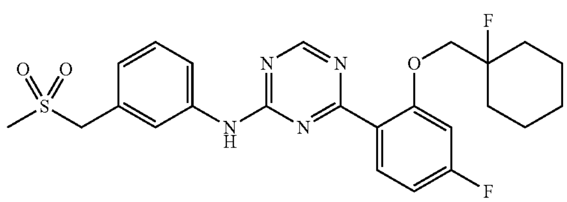 [SMILES: CS(=O)(=O)Cc1cccc(Nc2ncnc(-c3ccc(F)cc3OCC3(F)CCCCC3)n2)c1] | 4-{4-Fluoro-2-[(1-fluorocyclohexyl)methoxy]phenyl}-N-{3-[(methylsulfonyl)methyl]phenyl}-1,3,5-triazin-2-amine |
| 67 | 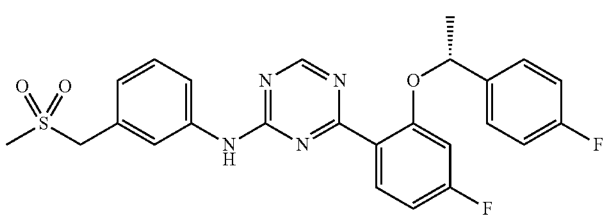 [SMILES: C[C@@H](Oc1cc(F)ccc1-c1ncnc(Nc2cccc(CS(C)(=O)=O)c2)n1)c1ccc(F)cc1] | 4-{4-Fluoro-2-[(1R)-1-(4-fluorophenyl)ethoxy]phenyl}-N-{3-[(methylsulfonyl)-methyl]phenyl}-1,3,5-triazin-2-amine |
| 68 | 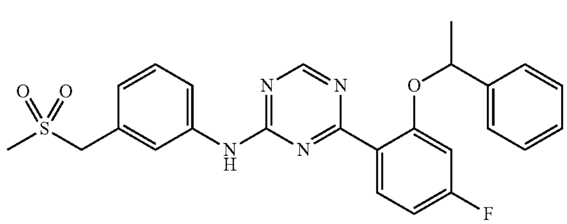 [SMILES: CC(Oc1cc(F)ccc1-c1ncnc(Nc2cccc(CS(C)(=O)=O)c2)n1)c1ccccc1] | rac-4-[4-Fluoro-2-(1-phenylethoxy)phenyl]-N-{3-[(methylsulfonyl)methyl]phenyl}-1,3,5-triazin-2-amine |

TABLE 1-continued

| Compound No. | Structure | Nomenclature |
|---|---|---|
| 69 | 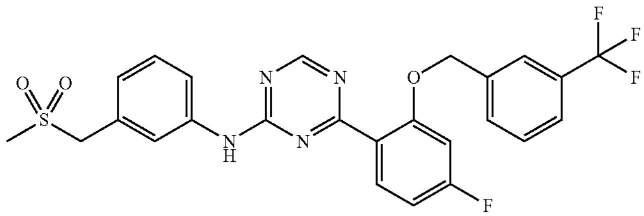 [SMILES: CS(=O)(=O)Cc1cccc(Nc2ncnc(-c3ccc(F)cc3OCc3cccc(C(F)(F)F)c3)n2)c1] | 4-(4-Fluoro-2-{[3-(trifluoromethyl)benzyl]oxy}phenyl)-N-{3-[(methylsulfonyl)-methyl]phenyl}-1,3,5-triazin-2-amine |
| 70 | 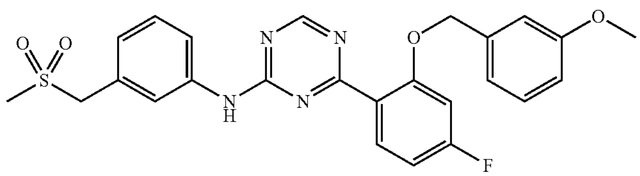 | 4-{4-Fluoro-2-[(3-methoxybenzyl)oxy]phenyl}-N-(3-[(methylsulfonyl)-methyl]phenyl}-1,3,5-triazin-2-amine |
| 71 | 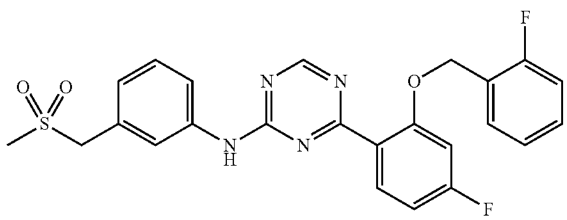 [SMILES: CS(=O)(=O)Cc1cccc(Nc2ncnc(-c3ccc(F)cc3OCc3ccccc3F)n2)c1] | 4-{4-Fluoro-2-[(2-fluorobenzyl)oxy]phenyl}-N-{3-[(methylsulfonyl)-methyl]phenyl}-1,3,5-triazin-2-amine |
| 72 | 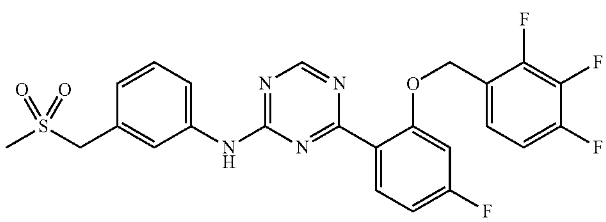 [SMILES: CS(=O)(=O)Cc1cccc(Nc2ncnc(-c3ccc(F)cc3OCc3ccc(F)c(F)c3F)n2)c1] | 4-{4-Fluoro-2-[(2,3,4-trifluorobenzyl)oxy]phenyl}-N-{3-[(methylsulfonyl)methyl]-phenyl}-1,3,5-triazin-2-amine |
| 73 | 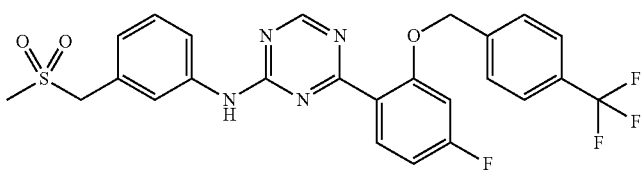 [SMILES: CS(=O)(=O)Cc1cccc(Nc2ncnc(-c3ccc(F)cc3OCc3ccc(C(F)(F)F)cc3)n2)c1] | 4-(4-Fluoro-2-{[4-(trifluoromethyl)benzyl]oxy}phenyl)-N-{3-[(methylsulfonyl)-methyl]phenyl}-1,3,5-triazin-2-amine |
| 74 | 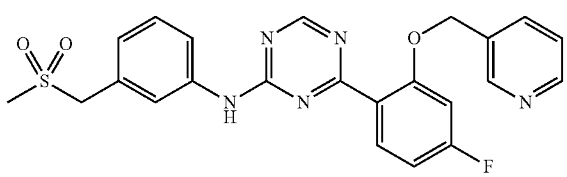 [SMILES: CS(=O)(=O)Cc1cccc(Nc2ncnc(-c3ccc(F)cc3OCc3cccnc3)n2)c1] | 4-[4-Fluoro-2-(pyridin-3-ylmethoxy)phenyl]-N-{3-[(methylsulfonyl)methyl]phenyl}-1,3,5-triazin-2-amine |
| 75 | 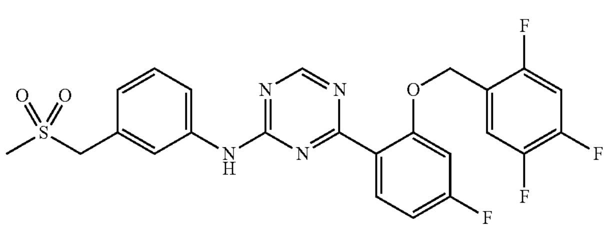 [SMILES: CS(=O)(=O)Cc1cccc(Nc2ncnc(-c3ccc(F)cc3OCc3cc(F)c(F)cc3F)n2)c1] | 4-{4-Fluoro-2-[(2,4,5-trifluorobenzyl)oxy]phenyl}-N-{3-[(methylsulfonyl)-methyl]phenyl}-1,3,5-triazin-2-amine |

TABLE 1-continued

| Compound No. | Structure | Nomenclature |
|---|---|---|
| 76 | 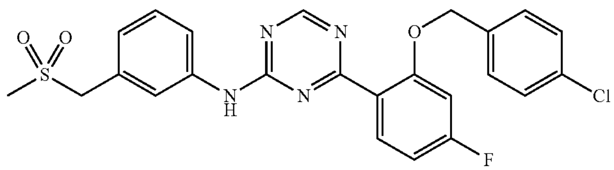 [SMILES: CS(=O)(=O)Cc1cccc(Nc2ncnc(-c3ccc(F)cc3OCc3ccc(Cl)cc3)n2)c1] | 4-{2-[(4-Chlorobenzyl)oxy]-4-fluorophenyl}-N-{3-[(methylsulfonyl)methyl]phenyl}-1,3,5-triazin-2-amine |
| 77 | 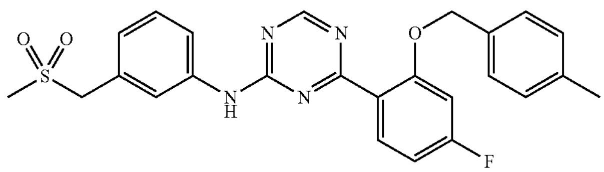 | 4-{4-Fluoro-2-[(4-methylbenzyl)oxy]phenyl}-N-{3-[(methylsulfonyl)-methyl]phenyl}-1,3,5-triazin-2-amine |
| 78 | 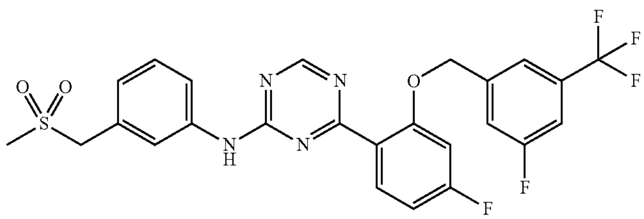 [SMILES: CS(=O)(=O)Cc1cccc(Nc2ncnc(-c3ccc(F)cc3OCc3cc(F)cc(C(F)(F)F)c3)n2)c1] | 4-(4-Fluoro-2-{[3-fluoro-5-(trifluoromethyl)benzyl]oxy}phenyl)-N-{3-[(methylsulfonyl)-methyl]-phenyl}-1,3,5-triazin-2-amine |
| 79 | 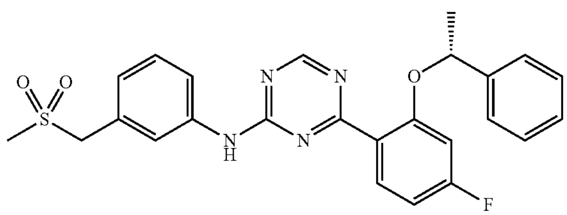 | 4-{4-Fluoro-2-[(1R)-1-phenylethoxy]phenyl}-N-{3-[(methylsulfonyl)methyl]phenyl}-1,3,5-triazin-2-amine |
| 80 | 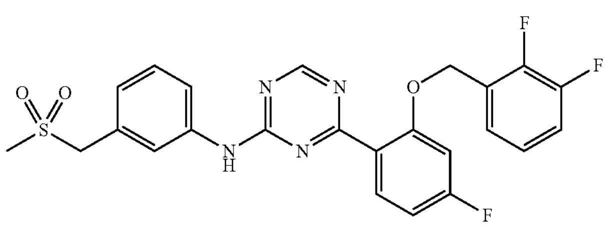 [SMILES: CS(=O)(=O)Cc1cccc(Nc2ncnc(-c3ccc(F)cc3OCc3cccc(F)c3F)n2)c1] | 4-{2-[(2,3-Difluorobenzyl)-oxy]-4-fluorophenyl}-N-{3-[(methylsulfonyl)-methyl]phenyl}-1,3,5-triazin-2-amine |
| 81 | 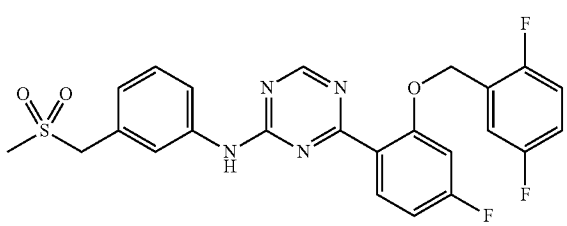 [SMILES: CS(=O)(=O)Cc1cccc(Nc2ncnc(-c3ccc(F)cc3OCc3cc(F)ccc3F)n2)c1] | 4-{2-[(2,5-Difluorobenzyl)-oxy]-4-fluorophenyl}-N-{3-[(methylsulfonyl)methyl]phenyl}-1,3,5-triazin-2-amine |
| 82 | 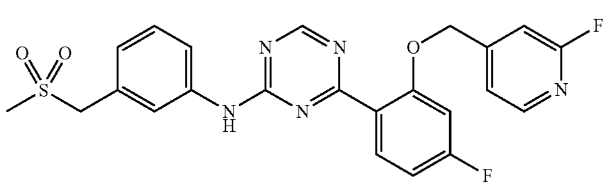 [SMILES: CS(=O)(=O)Cc1cccc(Nc2ncnc(-c3ccc(F)cc3OCc3ccnc(F)c3)n2)c1] | 4-{4-Fluoro-2-[(2-fluoropyridin-4-yl)methoxy]phenyl}-N-{3-[(methylsulfonyl)-methyl]phenyl}-1,3,5-triazin-2-amine |

TABLE 1-continued

| Compound No. | Structure | Nomenclature |
|---|---|---|
| 83 | 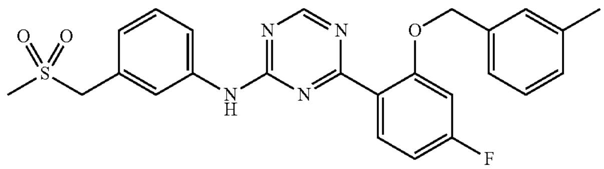 | 4-{4-Fluoro-2-[(3-methylbenzyl)oxy]phenyl}-N-{3-[(methylsulfonyl)-methyl]phenyl}-1,3,5-triazin-2-amine |
| 84 | 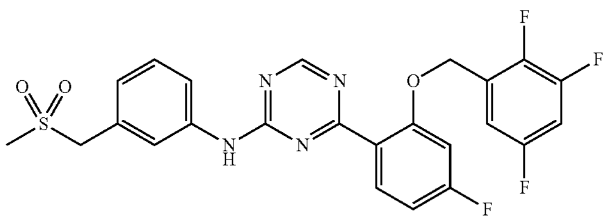 [SMILES: CS(=O)(=O)Cc1cccc(Nc2ncnc(-c3ccc(F)cc3OCc3cc(F)cc(F)c3F)n2)c1] | 4-{4-Fluoro-2-[(2,3,5-trifluorobenzyl)oxy]phenyl}-N-{3-[(methylsulfonyl)methyl]-phenyl}-1,3,5-triazin-2-amine |
| 85 | 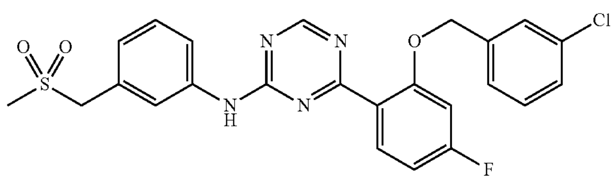 [SMILES: CS(=O)(=O)Cc1cccc(Nc2ncnc(-c3ccc(F)cc3OCc3cccc(Cl)c3)n2)c1] | 4-{2-[(3-Chlorobenzyl)oxy]-4-fluorophenyl}-N-{3-[(methylsulfonyl)methyl]phenyl}-1,3,5-triazin-2-amine |
| 86 | 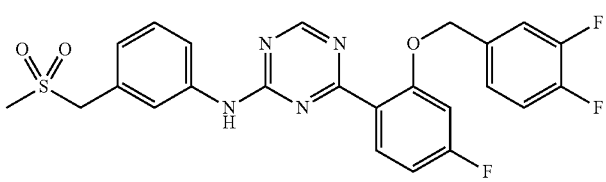 [SMILES: CS(=O)(=O)Cc1cccc(Nc2ncnc(-c3ccc(F)cc3OCc3ccc(F)c(F)c3)n2)c1] | 4-{2-[(3,4-Difluoro-benzyl)oxy]-4-fluorophenyl}-N-{3-[(methylsulfonyl)-methyl]phenyl}-1,3,5-triazin-2-amine |
| 87 | 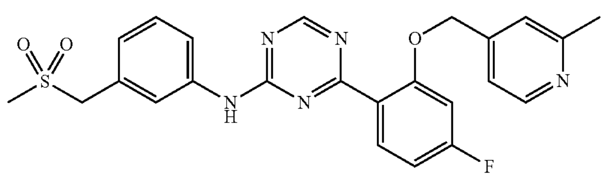 | 4-{4-Fluoro-2-[(2-methylpyridin-4-yl)methoxy]-phenyl}-N-{3-[(methylsulfonyl)methyl]phenyl}-1,3,5-triazin-2-amine |
| 88 | 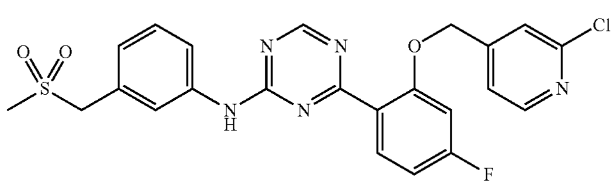 [SMILES: CS(=O)(=O)Cc1cccc(Nc2ncnc(-c3ccc(F)cc3OCc3ccnc(Cl)c3)n2)c1] | 4-{2-[(2-Chloropyridin-4-yl)methoxy]-4-fluorophenyl}-N-{3-[(methylsulfonyl)-methyl]phenyl}-1,3,5-triazin-2-amine |
| 89 | 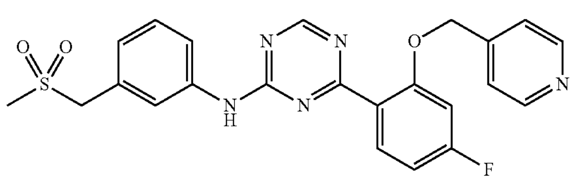 [SMILES: CS(=O)(=O)Cc1cccc(Nc2ncnc(-c3ccc(F)cc3OCc3ccncc3)n2)c1] | 4-[4-Fluoro-2-(pyridin-4-ylmethoxy)phenyl]-N-{3-[(methylsulfonyl)methyl]phenyl}-1,3,5-triazin-2-amine |
| 90 | 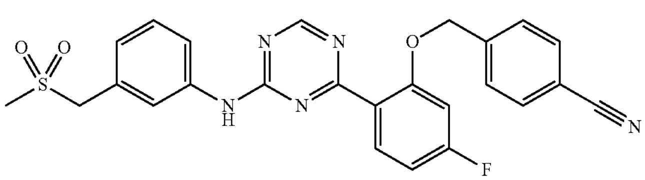 [SMILES: CS(=O)(=O)Cc1cccc(Nc2ncnc(-c3ccc(F)cc3OCc3ccc(C#N)cc3)n2)c1] | 4-({5-Fluoro-2-[4-({3-[(methylsulfonyl)methyl]phenyl}amino)-1,3,5-triazin-2-yl]phenoxy}methyl)-benzonitrile |

Results:

TABLE 2

Inhibition for CDK9 and CDK2 of compounds according to the present invention

| | Nomenclature | ② | ③ |
|---|---|---|---|
| 1 | 4-(4,5-Difluoro-2-methoxyphenyl)-N-{3-[(methylsulfonyl)methyl]phenyl}-1,3,5-triazin-2-amine | 14 nM | 640 nM |
| 2 | 4-(3,4-Difluoro-2-methoxyphenyl)-N-{3-[(methylsulfonyl)methyl]phenyl}-1,3,5-triazin-2-amine | 160 nM | 8600 nM |
| 3 | 4-(4-Fluoro-2-methoxyphenyl)-N-{3-[(methylsulfonyl)methyl]phenyl}-1,3,5-triazin-2-amine | 24 nM | 1600 nM |
| 4 | 4-[2-(Benzyloxy)-4-fluorophenyl]-N-{3-[(methylsulfonyl)methyl]phenyl}-1,3,5-triazin-2-amine | 3 nM | 89 nM |
| 5 | 4-[4-Fluoro-2-(propan-2-yloxy)phenyl]-N-{3-[(methylsulfonyl)methyl]phenyl}-1,3,5-triazin-2-amine | 25 nM | 1400 nM |
| 6 | 4-(2,2-Difluoro-1,3-benzodioxol-4-yl)-N-{3-[(methylsulfonyl)methyl]phenyl}-1,3,5-triazin-2-amine | 33 nM | 1300 nM |
| 7 | N-{3-[(Methylsulfonyl)methyl]phenyl}-4-[2-(trifluoromethoxy)phenyl]-1,3,5-triazin-2-amine | 330 nM | 5400 nM |
| 8 | 4-(3-Methoxypyridin-4-yl)-N-{3-[(methylsulfonyl)methyl]phenyl}-1,3,5-triazin-2-amine | 37 nM | 4700 nM |
| 9 | N-{3-[(Cyclohexylsulfonyl)methyl]phenyl}-4-(4-fluoro-2-methoxyphenyl)-1,3,5-triazin-2-amine | 10 nM | 560 nM |
| 10 | 4-(4-Fluoro-2-methoxyphenyl)-N-{3-fluoro-5-[(methylsulfonyl)methyl]phenyl}-1,3,5-triazin-2-amine | 6 nM | 320 nM |
| 11 | 4-(5-Fluoro-2-methoxyphenyl)-N-{3-[(methylsulfonyl)methyl]phenyl}-1,3,5-triazin-2-amine | 33 nM | 1300 nM |
| 12 | 4-(3,4-Dihydro-2H-chromen-8-yl)-N-{3-[(methylsulfonyl)methyl]phenyl}-1,3,5-triazin-2-amine | 7 nM | 510 nM |
| 13 | 4-(2,3-Dihydro-1-benzofuran-7-yl)-N-{3-[(methylsulfonyl)methyl]phenyl}-1,3,5-triazin-2-amine | 15 nM | 710 nM |
| 14 | 2-[(3-{[4-(4-Fluoro-2-methoxyphenyl)-1,3,5-triazin-2-yl]amino}benzyl)sulfonyl]ethanol | 12 nM | 610 nM |
| 15 | 4-[2-(Difluoromethoxy)-4-fluorophenyl]-N-{3-[(methylsulfonyl)methyl]phenyl}-1,3,5-triazin-2-amine | 130 nM | 3900 nM |
| 16 | N-{3-[(Methylsulfonyl)methyl]phenyl}-4-[2-(2,2,2-trifluoroethoxy)phenyl]-1,3,5-triazin-2-amine | 74 nM | 8300 nM |
| 17 | N-{3-[(tert-Butylsulfonyl)methyl]phenyl}-4-(4-fluoro-2-methoxyphenyl)-1,3,5-triazin-2-amine | 47 nM | 2000 nM |
| 18 | 4-(2,3-Dihydro-1,4-benzodioxin-5-yl)-N-{3-[(methylsulfonyl)methyl]phenyl}-1,3,5-triazin-2-amine | 8 nM | 840 nM |
| 19 | N-{3-[(Methylsulfonyl)methyl]phenyl}-4-(2,2,3,3-tetrafluoro-2,3-dihydro-1,4-benzodioxin-5-yl)-1,3,5-triazin-2-amine | 35 nM | 640 nM |
| 20 | 4-(2-Methoxypyridin-3-yl)-N-{3-[(methylsulfonyl)methyl]phenyl}-1,3,5-triazin-2-amine | 110 nM | 8200 nM |
| 21 | 4-[5-Fluoro-2-(tetrahydro-2H-pyran-4-ylmethoxy)phenyl]-N-{3-[(methylsulfonyl)methyl]phenyl}-1,3,5-triazin-2-amine | 110 nM | 8800 nM |
| 22 | 4-{2-[($^2$H$_3$)methyloxy]phenyl}-N-{3-[(methylsulfonyl)methyl]phenyl}-1,3,5-triazin-2-amine | 23 nM | 2500 nM |
| 23 | 4-(4-Fluoro-2-methoxyphenyl)-N-(3-{[(2-methoxyethyl)sulfonyl]methyl}phenyl)-1,3,5-triazin-2-amine | 12 nM | 1300 nM |
| 24 | 4-(4-Fluoro-2-methoxyphenyl)-N-{3-[(propan-2-ylsulfonyl)methyl]phenyl}-1,3,5-triazin-2-amine | 7 nM | 680 nM |
| 25 | 4-{2-[(4-Fluorobenzyl)oxy]phenyl}-N-{3-[(methylsulfonyl)methyl]phenyl}-1,3,5-triazin-2-amine | 7 nM | 1100 nM |
| 26 | 4-{2-[(3-Fluorobenzyl)oxy]phenyl}-N-{3-(methylsulfonyl)methyl]phenyl}-1,3,5-triazin-2-amine | 3 nM | 290 nM |
| 27 | 4-{2-[(2-Chlorobenzyl)oxy]phenyl}-N-{3-[(methylsulfonyl)methyl]phenyl}-1,3,5-triazin-2-amine | 87 nM | 8800 nM |
| 28 | 4-{2-[(3-Chlorobenzyl)oxy]phenyl}-N-{3-[(methylsulfonyl)methyl]phenyl}-1,3,5-triazin-2-amine | 3 nM | 500 nM |
| 29 | 4-[4-Chloro-2-(cyclopentyloxy)phenyl]-N-{3-[(methylsulfonyl)methyl]phenyl}-1,3,5-triazin-2-amine | 610 nM | 12000 nM |
| 30 | 4-{5-Fluoro-2-[(2-fluorobenzyl)oxy]phenyl}-N-{3-[(methylsulfonyl)methyl]phenyl}-1,3,5-triazin-2-amine | 32 nM | 6600 nM |
| 31 | 4-{5-Fluoro-2-[(3-fluorobenzyl)oxy]phenyl}-N-{3-[(methylsulfonyl)methyl]phenyl}-1,3,5-triazin-2-amine | 4 nM | 330 nM |
| 32 | 4-(4-Chloro-2-methoxyphenyl)-N-{3-[(methylsulfonyl)methyl]phenyl}-1,3,5-triazin-2-amine | 25 nM | 2300 nM |
| 33 | 4-(4-Fluoro-2-methoxyphenyl)-N-{4-fluoro-3-[(methylsulfonyl)methyl]phenyl}-1,3,5-triazin-2-amine | 6 nM | 360 nM |
| 34 | 4-{2-[(3-Chlorobenzyl)oxy]phenyl}-N-{3-[(propan-2-ylsulfonyl)methyl]phenyl}-1,3,5-triazin-2-amine | 10 nM | 800 nM |
| 35 | 4-(4-Fluoro-2-methoxyphenyl)-N-{3-[(phenylsulfonyl)methyl]phenyl}-1,3,5-triazin-2-amine | 30 nM | 2200 nM |
| 36 | N-{3-[(Cyclopentylsulfonyl)methyl]phenyl}-4-(4-fluoro-2-methoxyphenyl)-1,3,5-triazin-2-amine | 17 nM | 880 nM |
| 37 | 4-{2-[(4-Fluorobenzyl)oxy]phenyl}-N-{3-[(prop-2-ylsulfonyl)methyl]phenyl}-1,3,5-triazin-2-amine | 9 nM | 2500 nM |

TABLE 2-continued

Inhibition for CDK9 and CDK2 of compounds according to the present invention

| ① | Nomenclature | ② | ③ |
|---|---|---|---|
| 38 | 4-{5-Fluoro-2-[(3-fluorobenzyl)oxy]phenyl}-N-{3-[(prop-2-ylsulfonyl)methyl]phenyl}-1,3,5-triazin-2-amine | 6 nM | 320 nM |
| 39 | N-{5-Chloro-3-[(methylsulfonyl)methyl]phenyl}-4-(4-fluoro-2-methoxyphenyl)-1,3,5-triazin-2-amine | 9 nM | 190 nM |
| 40 | N-{3-[(Cyclopropylsulfonyl)methyl]phenyl}-4-(4-fluoro-2-methoxyphenyl)-1,3,5-triazin-2-amine | 14 nM | 1300 nM |
| 41 | 4-[2-(Cyclopropyloxy)-4-fluorophenyl]-N-{3-[(methylsulfonyl)methyl]phenyl}-1,3,5-triazin-2-amine | 29 nM | 1000 nM |
| 42 | 4-(2-Ethoxy-4-fluorophenyl)-N-{3-[(methylsulfonyl)-methyl]phenyl}-1,3,5-triazin-2-amine | 5 nM | 590 nM |
| 43 | 4-(4-Fluoro-2-propoxyphenyl)-N-{3-[(methylsulfonyl)-methyl]phenyl}-1,3,5-triazin-2-amine | 12 nM | 860 nM |
| 44 | 4-(2-Butoxy-4-fluorophenyl)-N-{3-[(methylsulfonyl)-methyl]phenyl}-1,3,5-triazin-2-amine | 9 nM | 910 nM |
| 45 | 4-[4-Fluoro-2-(pentyloxy)phenyl]-N-{3-[(methylsulfonyl)-methyl]phenyl}-1,3,5-triazin-2-amine | 4 nM | 990 nM |
| 46 | 4-[4-Fluoro-2-(hexyloxy)phenyl]-N-{3-[(methylsulfonyl)methyl]phenyl}-1,3,5-triazin-2-amine | 15 nM | 2700 nM |
| 47 | 4-{4-Fluoro-2-[(4-methylpentyl)oxy]phenyl}-N-{3-[(methylsulfonyl)-methyl]phenyl}-1,3,5-triazin-2-amine | 5 nM | 1200 nM |
| 48 | 4-[2-(2-Cyclopropylethoxy)-4-fluorophenyl]-N-{3-[(methylsulfonyl)methyl]phenyl}-1,3,5-triazin-2-amine | 29 nM | 1300 nM |
| 49 | 4-{4-Fluoro-2-[(1-methylcyclopropyl)methoxy]phenyl}-N-{3-[(methylsulfonyl)-methyl]phenyl}-1,3,5-triazin-2-amine | 11 nM | 640 nM |
| 50 | 4-[4-Fluoro-2-(2-methoxyethoxy)phenyl]-N-{3-[(methylsulfonyl)methyl]-phenyl}-1,3,5-triazin-2-amine | 38 nM | 490 nM |
| 51 | 4-[2-(2-Ethoxyethoxy)-4-fluorophenyl]-N-{3-[(methylsulfonyl)methyl]phenyl}-1,3,5-triazin-2-amine | 80 nM | 9400 nM |
| 52 | 4-[4-Fluoro-2-(3-methylbutoxy)phenyl]-N-{3-[(methylsulfonyl)methyl]phenyl}-1,3,5-triazin-2-amine | 16 nM | 4000 nM |
| 53 | 4-[2-(2-Cyclopentylethoxy)-4-fluorophenyl]-N-{3-[(methylsulfonyl)methyl]phenyl}-1,3,5-triazin-2-amine | 16 nM | 950 nM |
| 54 | 4-[4-Fluoro-2-(3-fluoropropoxy)phenyl]-N-{3-[(methylsulfonyl)methyl]phenyl}-1,3,5-triazin-2-amine | 29 nM | 1500 nM |
| 55 | 4-[2-(Cyclopropylmethoxy)-4-fluorophenyl]-N-{3-[(methylsulfonyl)methyl]phenyl}-1,3,5-triazin-2-amine | 15 nM | 1400 nM |
| 56 | 4-[2-(Cyclobutylmethoxy)-4-fluorophenyl]-N-{3-[(methylsulfonyl)methyl]phenyl}-1,3,5-triazin-2-amine | 27 nM | 1400 nM |
| 57 | 4-[2-(Cyclohexylmethoxy)-4-fluorophenyl]-N-{3-[(methylsulfonyl)methyl]phenyl}-1,3,5-triazin-2-amine | 7 nM | 2400 nM |
| 58 | 4-[4-Fluoro-2-(2-methylpropoxy)phenyl]-N-{3-[(methylsulfonyl)methyl]phenyl}-1,3,5-triazin-2-amine | 46 nM | 5100 nM |
| 59 | 4-[4-Fluoro-2-(4,4,4-trifluorobutoxy)phenyl]-N-{3-[(methylsulfonyl)methyl]phenyl}-1,3,5-triazin-2-amine | 5 nM | 710 nM |
| 60 | 4-[2-(2,2-Difluoroethoxy)-4-fluorophenyl]-N-{3-[(methylsulfonyl)methyl]phenyl}-1,3,5-triazin-2-amine | 22 nM | 1200 nM |
| 61 | 4-[4-Fluoro-2-(2-fluoroethoxy)phenyl]-N-{3-[(methylsulfonyl)methyl]phenyl}-1,3,5-triazin-2-amine | 8 nM | 640 nM |
| 62 | 4-[2-(But-2-yn-1-yloxy)-4-fluorophenyl]-N-{3-[(methylsulfonyl)methyl]phenyl}-1,3,5-triazin-2-amine | 3 nM | 540 nM |
| 63 | 4-[2-(2-Cyclohexylethoxy)-4-fluorophenyl]-N-{3-[(methylsulfonyl)methyl]phenyl}-1,3,5-triazin-2-amine | 170 nM | 7400 nM |
| 64 | 4-[2-(Cyclobutyloxy)-4-fluorophenyl]-N-{3-[(methylsulfonyl)methyl]phenyl}-1,3,5-triazin-2-amine | 34 nM | 1800 nM |
| 65 | 4-[2-(Cyclopentyloxy)-4-fluorophenyl]-N-{3-[(methylsulfonyl)methyl]phenyl}-1,3,5-triazin-2-amine | 36 nM | 2300 nM |
| 66 | 4-{4-Fluoro-2-[(1-fluorocyclohexyl)-methoxy]phenyl}-N-{3-[(methylsulfonyl)-methyl]phenyl}-1,3,5-triazin-2-amine | 22 nM | 6800 nM |
| 67 | 4-{4-Fluoro-2-[(1R)-1-(4-fluorophenyl)ethoxy]phenyl}-N-{3-[(methylsulfonyl)-methyl]phenyl}-1,3,5-triazin-2-amine | 8 nM | 1300 nM |
| 68 | rac-4-[4-Fluoro-2-(1-phenylethoxy)phenyl]-N-{3-[(methylsulfonyl)methyl]phenyl}-1,3,5-triazin-2-amine | 16 nM | 1100 nM |
| 69 | 4-(4-Fluoro-2-{[3-(trifluoromethyl)benzyl]oxy}phenyl)-N-{3-[(methylsulfonyl)-methyl]phenyl}-1,3,5-triazin-2-amine | 4 nM | 1300 nM |
| 70 | 4-{4-Fluoro-2-[(3-methoxybenzyl)oxy]phenyl}-N-{3-[(methylsulfonyl)-methyl]phenyl}-1,3,5-triazin-2-amine | 14 nM | 1100 nM |
| 71 | 4-{4-Fluoro-2-[(2-fluorobenzyl)oxy]phenyl}-N-{3-[(methylsulfonyl)methyl]phenyl}-1,3,5-triazin-2-amine | 12 nM | 2200 nM |
| 72 | 4-{4-Fluoro-2-[(2,3,4-trifluorobenzyl)oxy]-phenyl}-N-{3-[(methylsulfonyl)methyl]-phenyl}-1,3,5-triazin-2-amine | 7 nM | 20,000 nM |
| 73 | 4-(4-Fluoro-2-{[4-(trifluoromethyl)benzyl]oxy}phenyl)-N-{3-[(methylsulfonyl)--methyl]phenyl}-1,3,5-triazin-2-amine | 12 nM | 20,000 nM |
| 74 | 4-[4-Fluoro-2-(pyridin-3-ylmethoxy)phenyl]-N-{3-[(methylsulfonyl)methyl]phenyl}-1,3,5-triazin-2-amine | 7 nM | 570 nM |

TABLE 2-continued

Inhibition for CDK9 and CDK2 of compounds according to the present invention

| ① Nomenclature | ② | ③ |
|---|---|---|
| 75 4-{4-Fluoro-2-[(2,4,5-trifluorobenzyl)oxy]phenyl}-N-{3-[(methylsulfonyl)-methyl]phenyl}-1,3,5-triazin-2-amine | 6 nM | n.t. |
| 76 4-{2-[(4-Chlorobenzyl)oxy]-4-fluorophenyl}-N-{3-[(methylsulfonyl)methyl]phenyl}-1,3,5-triazin-2-amine | 6 nM | 710 nM |
| 77 4-{4-Fluoro-2-[(4-methylbenzyl)oxy]phenyl}-N-{3-[(methylsulfonyl)-methyl]phenyl}-1,3,5-triazin-2-amine | 13 nM | 1600 nM |
| 78 4-(4-Fluoro-2-{[3-fluoro-5-(trifluoromethyl)benzyl]oxy}phenyl)-N-{3-[(methylsulfonyl)-methyl]-phenyl}-1,3,5-triazin-2-amine | 4 nM | n.t. |
| 79 4-{4-Fluoro-2-[(1R)-1-phenylethoxy]phenyl}-N-{3-[(methylsulfonyl)methyl]phenyl}-1,3,5-triazin-2-amine | 3 nM | 440 nM |
| 80 4-{2-[(2,3-Difluorobenzyl)-oxy]-4-fluorophenyl}-N-{3-[(methylsulfonyl)-methyl]phenyl}-1,3,5-triazin-2-amine | 21 nM | 2000 nM |
| 81 4-{2-[(2,5-Difluorobenzyl)-oxy]-4-fluorophenyl}-N-{3-[(methylsulfonyl)methyl]phenyl}-1,3,5-triazin-2-amine | 5 nM | n.t. |
| 82 4-{4-Fluoro-2-[(2-fluoropyridin-4-yl)methoxy]-phenyl}-N-{3-[(methylsulfonyl)-methyl]-phenyl}-1,3,5-triazin-2-amine | 1 nM | 75 nM |
| 83 4-{4-Fluoro-2-[(3-methylbenzyl)oxy]phenyl}-N-{3-[(methylsulfonyl)-methyl]phenyl}-1,3,5-triazin-2-amine | 5 nM | 400 nM |
| 84 4-{4-Fluoro-2-[(2,3,5-trifluorobenzyl)oxy]phenyl}-N-{3-[(methylsulfonyl)methyl]-phenyl}-1,3,5-triazin-2-amine | 3 nM | n.t. |
| 85 4-{2-[(3-Chlorobenzyl)oxy]-4-fluorophenyl}-N-{3-[(methylsulfonyl)methyl]phenyl}-1,3,5-triazin-2-amine | 7 nM | 260 nM |
| 86 4-{2-[(3,4-Difluoro-benzyl)oxy]-4-fluorophenyl}-N-{3-[(methylsulfonyl)-methyl]phenyl}-1,3,5-triazin-2-amine | 6 nM | n.t. |
| 87 4-{4-Fluoro-2-[(2-methylpyridin-4-yl)methoxy]-phenyl}-N-{3-[(methylsulfonyl)methyl]phenyl}-1,3,5-triazin-2-amine | 6 nM | 370 nM |
| 88 4-{2-[(2-Chloropyridin-4-yl)methoxy]-4-fluorophenyl}-N-{3-[(methylsulfonyl)-methyl]phenyl}-1,3,5-triazin-2-amine | 4 nM | 130 nM |
| 89 4-[4-Fluoro-2-(pyridin-4-ylmethoxy)phenyl]-N-{3-[(methylsulfonyl)methyl]phenyl}-1,3,5-triazin-2-amine | 5 nM | 400 nM |
| 90 4-({5-Fluoro-2-[4-({3-[(methylsulfonyl)methyl]phenyl}amino)-1,3,5-triazin-2-yl]phenoxy}methyl)-benzonitrile | 3 nM | 680 nM |

The $IC_{50}$ (inhibitory concentration at 50% of maximal effect) values are indicated in nM or μM, "n.t." means that the compounds have not been tested in this assay.
①: Compound Number
②: CDK9 CDK9/CycT1 kinase assay as described under Method 1. of Materials and Methods
③: CDK2 CDK2/CycE kinase assay as described under Method 2. of Materials and Methods

TABLE 3

Inhibition of proliferation of MaTu/ADR, H460, DU145, CACO-2 and B16F10 cells by compounds according to the present invention.

| ① Nomenclature | ② | ③ | ④ | ⑤ | ⑥ | ⑦ |
|---|---|---|---|---|---|---|
| 1 4-(4,5-Difluoro-2-methoxyphenyl)-N-{3-[(methylsulfony)methyl]phenyl}-1,3,5-triazin-2-amine | 0.68 | 0.40 | 0.91 | 0.83 | 0.99 | 1.0 |
| 3 4-(4-Fluoro-2-methoxyphenyl)-N-{3-[(methylsulfonyl)methyl]phenyl}-1,3,5-triazin-2-amine | 1.5 | 0.92 | 1.2 | 1.2 | 1.5 | 1.7 |
| 4 4-[2-(Benzyloxy)-4-fluorophenyl]-N-{3-[(methylsulfonyl)methyl]phenyl}-1,3,5-triazin-2-amine | 0.1 | 0.1 | 0.15 | 0.14 | 0.14 | 0.13 |
| 8 4-(3-Methoxypyridin-4-yl)-N-{3-[(methylsulfonyl)methyl]phenyl}-1,3,5-triazin-2-amine | 1.5 | n.t | n.t | n.t | n.t | n.t |
| 9 N-{3-[(Cyclohexylsulfonyl)methyl]phenyl}-4-(4-fluoro-2-methoxyphenyl)-1,3,5-triazin-2-amine | 1.0 | 0.42 | 0.69 | 0.84 | 0.58 | 1.3 |
| 10 4-(4-Fluoro-2-methoxyphenyl)-N-{3-fluoro-5-[(methylsulfonyl)methyl]phenyl}-1,3,5-triazin-2-amine | 0.11 | 0.08 | 0.22 | 0.22 | 0.20 | 0.27 |
| 12 4-(3,4-Dihydro-2H-chromen-8-yl)-N-{3-[(methylsulfonyl)methyl]phenyl}-1,3,5-triazin-2-amine | 0.34 | 0.23 | 0.41 | 0.32 | 0.39 | 0.51 |
| 13 4-(2,3-Dihydro-1-benzofuran-7-yl)-N-{3-[(methylsulfonyl)methyl]phenyl}-1,3,5-triazin-2-amine | 0.95 | n.t | n.t | n.t | n.t | n.t |
| 14 2-[(3-{[4-(4-Fluoro-2-methoxyphenyl)-1,3,5-triazin-2-yl]amino}benzyl)sulfonyl]ethanol | 0.6 | n.t | n.t | n.t | n.t | n.t |

TABLE 3-continued

Inhibition of proliferation of MaTu/ADR, H460, DU145, CACO-2 and B16F10 cells by compounds according to the present invention.

| ① | Nomenclature | ② | ③ | ④ | ⑤ | ⑥ | ⑦ |
|---|---|---|---|---|---|---|---|
| 18 | 4-(2,3-Dihydro-1,4-benzodioxin-5-yl)-N-{3-[(methylsulfonyl)methyl]phenyl}-1,3,5-triazin-2-amine | 0.53 | 0.4 | 0.73 | 0.53 | 0.69 | 0.64 |
| 22 | 4-{2-[($^2$H$_3$)methyloxy]phenyl}-N-{3-[(methylsulfonyl)methyl]phenyl}-1,3,5-triazin-2-amine | 1.4 | n.t | n.t | n.t | n.t | n.t |
| 23 | 4-(4-Fluoro-2-methoxyphenyl)-N-(3-{[(2-methoxyethyl)sulfonyl]methyl}phenyl)-1,3,5-triazin-2-amine | 0.93 | n.t | n.t | n.t | n.t | n.t |
| 24 | 4-(4-Fluoro-2-methoxyphenyl)-N-{3-[(propan-2-ylsulfonyl)methyl]phenyl}-1,3,5-triazin-2-amine | 1.0 | n.t | n.t | n.t | n.t | n.t |
| 25 | 4-{2-[(4-Fluorobenzyl)oxy]phenyl}-N-{3-[(methylsulfonyl)methyl]phenyl}-1,3,5-triazin-2-amine | 0.76 | n.t | n.t | n.t | n.t | n.t |
| 26 | 4-{2-[(3-Fluorobenzyl)oxy]phenyl}-N-{3-[(methylsulfonyl)methyl]phenyl}-1,3,5-triazin-2-amine | 0.53 | n.t | n.t | n.t | n.t | n.t |
| 28 | 4-{2-[(3-Chlorobenzyl)oxy]phenyl}-N-{3-[(methylsulfonyl)methyl]phenyl}-1,3,5-triazin-2-amine | 0.36 | 0.35 | 0.37 | 0.42 | 0.32 | 0.39 |
| 29 | 4-[4-Chloro-2-(cyclopentyloxy)phenyl]-N-{3-[(methylsulfonyl)methyl]phenyl}-1,3,5-triazin-2-amine | 0.53 | 0.4 | 0.73 | 0.53 | 0.69 | 0.64 |
| 31 | 4-{5-Fluoro-2-[(3-fluorobenzyl)oxy]phenyl}-N-{3-[(methylsulfonyl)methyl]phenyl}-1,3,5-triazin-2-amine | 0.29 | 0.16 | 0.2 | 0.28 | 0.37 | 0.28 |
| 33 | 4-(4-Fluoro-2-methoxyphenyl)-N-{4-fluoro-3-[(methylsulfonyl)methyl]phenyl}-1,3,5-triazin-2-amine | 0.34 | 0.18 | 0.34 | 0.33 | 0.24 | 0.46 |
| 34 | 4-{2-[(3-Chlorobenzyl)oxy]phenyl}-N-{3-[(propan-2-ylsulfonyl)methyl]phenyl}-1,3,5-triazin-2-amine | 1.2 | n.t | n.t | n.t | n.t | n.t |
| 36 | N-{3-[(Cyclopentylsulfonyl)methyl]phenyl}-4-(4-fluoro-2-methoxyphenyl)-1,3,5-triazin-2-amine | 1.0 | n.t | n.t | n.t | n.t | n.t |
| 37 | 4-{2-[(4-Fluorobenzyl)oxy]phenyl}-N-{3-[(prop-2-ylsulfonyl)methyl]phenyl}-1,3,5-triazin-2-amine | 1.1 | n.t | n.t | n.t | n.t | n.t |
| 38 | 4-{5-Fluoro-2-[(3-fluorobenzyl)oxy]phenyl}-N-{3-[(prop-2-ylsulfonyl)methyl]phenyl}-1,3,5-triazin-2-amine | 0.84 | n.t | n.t | n.t | n.t | n.t |
| 39 | N-{5-Chloro-3-[(methylsulfonyl)methyl]phenyl}-4-(4-fluoro-2-methoxyphenyl)-1,3,5-triazin-2-amine | 0.28 | n.t | n.t | n.t | n.t | n.t |
| 40 | N-{3-[(Cyclopropylsulfonyl)methyl]phenyl}-4-(4-fluoro-2-methoxyphenyl)-1,3,5-triazin-2-amine | 0.64 | 0.51 | 0.6 | 0.6 | 0.84 | 0.82 |
| 41 | 4-[2-(Cyclopropyloxy)-4-fluorophenyl]-N-{3-[(methylsulfonyl)methyl]phenyl}-1,3,5-triazin-2-amine | 0.9 | n.t. | n.t. | n.t. | n.t. | n.t. |
| 42 | 4-(2-Ethoxy-4-fluorophenyl)-N-{3-[(methylsulfonyl)-methyl]phenyl}-1,3,5-triazin-2-amine | 0.33 | 0.22 | 0.29 | 0.26 | 0.42 | 0.37 |
| 43 | 4-(4-Fluoro-2-propoxyphenyl)-N-{3-[(methylsulfonyl)-methyl]phenyl}-1,3,5-triazin-2-amine | 1.1 | n.t. | n.t. | n.t. | n.t. | n.t. |
| 44 | 4-(2-Butoxy-4-fluorophenyl)-N-{3-[(methylsulfonyl)-methyl]phenyl}-1,3,5-triazin-2-amine | 0.34 | 0.32 | 0.44 | 0.52 | 1 | 0.57 |
| 45 | 4-[4-Fluoro-2-(pentyloxy)phenyl]-N-{3-[(methylsulfonyl)-methyl]phenyl}-1,3,5-triazin-2-amine | 1 | n.t. | n.t. | n.t. | n.t. | n.t. |
| 46 | 4-[4-Fluoro-2-(hexyloxy)phenyl]-N-{3-[(methylsulfonyl)methyl]phenyl}-1,3,5-triazin-2-amine | 2.8 | n.t. | n.t. | n.t. | n.t. | n.t. |
| 47 | 4-{4-Fluoro-2-[(4-methylpentyl)oxy]phenyl}-N-{3-[(methylsulfonyl)-methyl]phenyl}-1,3,5-triazin-2-amine | 1 | n.t. | n.t. | n.t. | n.t. | n.t. |
| 48 | 4-[2-(2-Cyclopropylethoxy)-4-fluorophenyl]-N-{3-[(methylsulfonyl)methyl]phenyl}-1,3,5-triazin-2-amine | 1 | n.t. | n.t. | n.t. | n.t. | n.t. |

TABLE 3-continued

Inhibition of proliferation of MaTu/ADR, H460, DU145, CACO-2 and B16F10 cells by compounds according to the present invention.

| ① Nomenclature | ② | ③ | ④ | ⑤ | ⑥ | ⑦ |
|---|---|---|---|---|---|---|
| 49 4-{4-Fluoro-2-[(1-methylcyclopropyl)-methoxy]phenyl}-N-{3-[(methylsulfonyl)-methyl]phenyl}-1,3,5-triazin-2-amine | 1.2 | n.t. | n.t. | n.t. | n.t. | n.t. |
| 50 4-[4-Fluoro-2-(2-methoxyethoxy)phenyl]-N-{3-[(methylsulfonyl)methyl]-phenyl}-1,3,5-triazin-2-amine | 2.9 | n.t. | n.t. | n.t. | n.t. | n.t. |
| 51 4-[2-(2-Ethoxyethoxy)-4-fluorophenyl]-N-{3-[(methylsulfonyl)methyl]phenyl}-1,3,5-triazin-2-amine | n.t. | n.t. | n.t. | n.t. | n.t. | n.t. |
| 52 4-[4-Fluoro-2-(3-methylbutoxy)phenyl]-N-{3-[(methylsulfonyl)methyl]phenyl}-1,3,5-triazin-2-amine | 1.2 | n.t. | n.t. | n.t. | n.t. | n.t. |
| 53 4-[2-(2-Cyclopentylethoxy)-4-fluorophenyl]-N-{3-[(methylsulfonyl)methyl]phenyl}-1,3,5-triazin-2-amine | 1.3 | n.t. | n.t. | n.t. | n.t. | n.t. |
| 54 4-[4-Fluoro-2-(3-fluoropropoxy)phenyl]-N-{3-[(methylsulfonyl)methyl]phenyl}-1,3,5-triazin-2-amine | 1.3 | n.t. | n.t. | n.t. | n.t. | n.t. |
| 55 4-[2-(Cyclopropylmethoxy)-4-fluorophenyl]-N-{3-[(methylsulfonyl)methyl]phenyl}-1,3,5-triazin-2-amine | 0.84 | 0.32 | 0.49 | 0.57 | 0.4 | 0.96 |
| 56 4-[2-(Cyclobutylmethoxy)-4-fluorophenyl]-N-{3-[(methylsulfonyl)methyl]phenyl}-1,3,5-triazin-2-amine | 1.1 | n.t. | n.t. | n.t. | n.t. | n.t. |
| 57 4-[2-(Cyclohexylmethoxy)-4-fluorophenyl]-N-{3-[(methylsulfonyl)methyl]phenyl}-1,3,5-triazin-2-amine | 1.1 | n.t. | n.t. | n.t. | n.t. | n.t. |
| 58 4-[4-Fluoro-2-(2-methylpropoxy)phenyl]-N-{3-[(methylsulfonyl)methyl]phenyl}-1,3,5-triazin-2-amine | 1.7 | n.t. | n.t. | n.t. | n.t. | n.t. |
| 59 4-[4-Fluoro-2-(4,4,4-trifluorobutoxy)phenyl]-N-{3-[(methylsulfonyl)methyl]phenyl}-1,3,5-triazin-2-amine | 0.47 | 0.22 | 0.35 | 0.22 | 0.57 | 0.33 |
| 60 4-[2-(2,2-Difluoroethoxy)-4-fluorophenyl]-N-{3-[(methylsulfonyl)methyl]phenyl}-1,3,5-triazin-2-amine | 1.1 | n.t. | n.t. | n.t. | n.t. | n.t. |
| 61 4-[4-Fluoro-2-(2-fluoroethoxy)phenyl]-N-{3-[(methylsulfonyl)methyl]phenyl}-1,3,5-triazin-2-amine | 0.59 | 0.38 | 0.61 | 0.48 | 1.1 | 0.74 |
| 62 4-[2-(But-2-yn-1-yloxy)-4-fluorophenyl]-N-{3-[(methylsulfonyl)methyl]phenyl}-1,3,5-triazin-2-amine | 0.11 | 0.18 | 0.16 | 0.17 | 0.21 | 0.24 |
| 63 4-[2-(2-Cyclohexylethoxy)-4-fluorophenyl]-N-{3-[(methylsulfonyl)methyl]phenyl}-1,3,5-triazin-2-amine | n.t. | n.t. | n.t. | n.t. | n.t. | n.t. |
| 64 4-[2-(Cyclobutyloxy)-4-fluorophenyl]-N-{3-[(methylsulfonyl)methyl]phenyl}-1,3,5-triazin-2-amine | n.t. | n.t. | n.t. | n.t. | n.t. | n.t. |
| 65 4-[2-(Cyclopentyloxy)-4-fluorophenyl]-N-{3-[(methylsulfonyl)methyl]phenyl}-1,3,5-triazin-2-amine | n.t. | n.t. | n.t. | n.t. | n.t. | n.t. |
| 66 4-{4-Fluoro-2-[(1-fluorocyclohexyl)-methoxy]phenyl}-N-{3-[(methylsulfonyl)-methyl]phenyl}-1,3,5-triazin-2-amine | n.t. | n.t. | n.t. | n.t. | n.t. | n.t. |
| 67 4-{4-Fluoro-2-[(1R)-1-(4-fluorophenyl)-ethoxy]phenyl}-N-{3-[(methylsulfonyl)-methyl]phenyl}-1,3,5-triazin-2-amine | 1.6 | n.t | n.t | n.t | n.t | n.t |
| 68 rac-4-[4-Fluoro-2-(1-phenylethoxy)phenyl]-N-{3-[(methylsulfonyl)methyl]phenyl}-1,3,5-triazin-2-amine | 1.4 | n.t. | n.t. | n.t. | n.t. | n.t. |
| 69 4-(4-Fluoro-2-{[3-(trifluoromethyl)benzyl]-oxy}phenyl)-N-{3-[(methylsulfonyl)-methyl]phenyl}-1,3,5-triazin-2-amine | 1.3 | n.t. | n.t. | n.t. | n.t. | n.t. |
| 70 4-{4-Fluoro-2-[(3-methoxybenzyl)-oxy]-phenyl}-N-{3-[(methylsulfonyl)-methyl]-phenyl}-1,3,5-triazin-2-amine | 1.3 | n.t. | n.t. | n.t. | n.t. | n.t. |
| 71 4-{4-Fluoro-2-[(2-fluorobenzyl)oxy]phenyl}-N-{3-[(methylsulfonyl)-methyl]phenyl}-1,3,5-triazin-2-amine | 1.17 | n.t. | n.t. | n.t. | n.t. | n.t. |
| 72 4-{4-Fluoro-2-[(2,3,4-trifluorobenzyl)oxy]-phenyl}-N-{3-[(methylsulfonyl)methyl]-phenyl}-1,3,5-triazin-2-amine | 1.16 | n.t. | n.t. | n.t. | n.t. | n.t. |

TABLE 3-continued

Inhibition of proliferation of MaTu/ADR, H460, DU145, CACO-2 and B16F10 cells by compounds according to the present invention.

| ① Nomenclature | ② | ③ | ④ | ⑤ | ⑥ | ⑦ |
|---|---|---|---|---|---|---|
| 73 4-(4-Fluoro-2-{[4-(trifluoromethyl)benzyl]-oxy}phenyl)-N-{3-[(methylsulfonyl)-methyl]phenyl}-1,3,5-triazin-2-amine | 1.1 | n.t. | n.t. | n.t. | n.t. | n.t. |
| 74 4-[4-Fluoro-2-(pyridin-3-ylmethoxy)phenyl]-N-{3-[(methylsulfonyl)methyl]phenyl}-1,3,5-triazin-2-amine | 1.1 | n.t. | n.t. | n.t. | n.t. | n.t. |
| 75 4-{4-Fluoro-2-[(2,4,5-trifluorobenzyl)oxy]-phenyl}-N-{3-[(methylsulfonyl)-methyl]phenyl}-1,3,5-triazin-2-amine | 1.1 | n.t. | n.t. | n.t. | n.t. | n.t. |
| 76 4-{2-[(4-Chlorobenzyl)oxy]-4-fluorophenyl}-N-{3-[(methylsulfonyl)methyl]phenyl}-1,3,5-triazin-2-amine | 1 | n.t. | n.t. | n.t. | n.t. | n.t. |
| 77 4-{4-Fluoro-2-[(4-methylbenzyl)oxy]-phenyl}-N-{3-[(methylsulfonyl)-methyl]phenyl}-1,3,5-triazin-2-amine | 1 | n.t. | n.t. | n.t. | n.t. | n.t. |
| 78 4-(4-Fluoro-2-{[3-fluoro-5-(trifluoromethyl)benzyl]oxy}phenyl)-N-{3-[(methylsulfonyl)-methyl]-phenyl}-1,3,5-triazin-2-amine | 0.95 | n.t. | n.t. | n.t. | n.t. | n.t. |
| 79 4-{4-Fluoro-2-[(1R)-1-phenylethoxy]phenyl}-N-{3-[(methylsulfonyl)methyl]phenyl}-1,3,5-triazin-2-amine | 0.92 | n.t. | n.t. | n.t. | n.t. | n.t. |
| 80 4-{2-[(2,3-Difluorobenzyl)-oxy]-4-fluorophenyl}-N-{3-[(methylsulfonyl)-methyl]phenyl}-1,3,5-triazin-2-amine | 0.89 | n.t. | n.t. | n.t. | n.t. | n.t. |
| 81 4-{2-[(2,5-Difluorobenzyl)-oxy]-4-fluorophenyl}-N-{3-[(methylsulfonyl)-methyl]phenyl}-1,3,5-triazin-2-amine | 0.82 | n.t. | n.t. | n.t. | n.t. | n.t. |
| 82 4-{4-Fluoro-2-[(2-fluoropyridin-4-yl)methoxy]-phenyl}-N-{3-[(methylsulfonyl)-methyl]-phenyl}-1,3,5-triazin-2-amine | n.t. | n.t. | n.t. | n.t. | n.t. | n.t. |
| 83 4-{4-Fluoro-2-[(3-methylbenzyl)oxy]phenyl}-N-{3-[(methylsulfonyl)-methyl]phenyl}-1,3,5-triazin-2-amine | 0.51 | 0.35 | 0.38 | 0.38 | 0.74 | 0.44 |
| 84 4-{4-Fluoro-2-[(2,3,5-trifluorobenzyl)oxy]phenyl}-N-{3-[(methylsulfonyl)methyl]-phenyl}-1,3,5-triazin-2-amine | 0.34 | 0.28 | 0.31 | 0.35 | 0.32 | 0.49 |
| 85 4-{2-[(3-Chlorobenzyl)oxy]-4-fluorophenyl}-N-{3-[(methylsulfonyl)methyl]phenyl}-1,3,5-triazin-2-amine | 0.32 | 0.35 | 0.36 | 0.41 | 0.56 | 0.45 |
| 86 4-{2-[(3,4-Difluoro-benzyl)oxy]-4-fluorophenyl}-N-{3-[(methylsulfonyl)-methyl]phenyl}-1,3,5-triazin-2-amine | 0.25 | 0.22 | 0.27 | 0.23 | 0.2 | 0.25 |
| 87 4-{4-Fluoro-2-[(2-methylpyridin-4-yl)methoxy]-phenyl}-N-{3-[(methylsulfonyl)methyl]phenyl}-1,3,5-triazin-2-amine | 0.32 | 0.74 | 0.34 | 0.3 | 0.73 | 0.37 |
| 88 4-{2-[(2-Chloropyridin-4-yl)methoxy]-4-fluorophenyl}-N-{3-[(methylsulfonyl)-methyl]phenyl}-1,3,5-triazin-2-amine | 0.19 | 0.27 | 0.21 | 0.17 | 0.31 | 0.23 |
| 89 4-[4-Fluoro-2-(pyridin-4-ylmethoxy)phenyl]-N-{3-[(methylsulfonyl)methyl]phenyl}-1,3,5-triazin-2-amine | 0.11 | 0.34 | 0.17 | 0.18 | 0.31 | 0.25 |
| 90 4-({5-Fluoro-2-[4-({3-[(methylsulfonyl)methyl]phenyl}amino)-1,3,5-triazin-2-yl]phenoxy}methyl)-benzonitrile | 0.11 | 0.33 | 0.06 | 0.28 | 0.31 | 0.32 |

All $IC_{50}$ (inhibitory concentration at 50% of maximal effect) values are indicated in μM,
"n.t." means that the compounds have not been tested in this assay.

① : Compound Number
② : Inhibition of HeLa cell proliferation
③ : Inhibition of HeLa/MaTu/ADR cell proliferation
④ : Inhibition of H460 cell proliferation (activity range)
⑤ : Inhibition of DU145 cell proliferation
⑥ : Inhibition of CACO-2 cell proliferation
⑦ : Inhibition of B16F10 cell proliferation

TABLE 4

Caco-2 permeation of compounds according to the present invention.

| ① | Nomenclature | ② | ③ | ④ | ⑤ |
|---|---|---|---|---|---|
| 1 | 4-(4,5-Difluoro-2-methoxyphenyl)-N-{3-[(methylsulfonyl)methyl]phenyl}-1,3,5-triazin-2-amine | 2 | 197 | 162 | 0.82 |
| 3 | 4-(4-Fluoro-2-methoxyphenyl)-N-{3-[(methylsulfonyl)methyl]phenyl}-1,3,5-triazin-2-amine | 2 | 143 | 170 | 1.2 |
| 4 | 4-[2-(Benzyloxy)-4-fluorophenyl]-N-{3-[(methylsulfonyl)methyl]phenyl}-1,3,5-triazin-2-amine | 2 | 179 | 84 | 0.47 |
| 6 | 4-(2,2-Difluoro-1,3-benzodioxol-4-yl)-N-{3-[(methylsulfonyl)methyl]phenyl}-1,3,5-triazin-2-amine | 2 | 213 | 92 | 0.43 |
| 8 | 4-(3-Methoxypyridin-4-yl)-N-{3-[(methylsulfonyl)methyl]phenyl}-1,3,5-triazin-2-amine | 2 | 30 | 226 | 7.4 |
| 10 | 4-(4-Fluoro-2-methoxyphenyl)-N-{3-fluoro-5-[(methylsulfonyl)methyl]phenyl}-1,3,5-triazin-2-amine | 2 | 135 | 147 | 1.1 |
| 13 | 4-(2,3-Dihydro-1-benzofuran-7-yl)-N-{3-[(methylsulfonyl)methyl]phenyl}-1,3,5-triazin-2-amine | 2 | 161 | 148 | 0.92 |
| 14 | 2-[(3-{[4-(4-Fluoro-2-methoxyphenyl)-1,3,5-triazin-2-yl]amino}benzyl)sulfonyl]ethanol | 2 | 16 | 227 | 14 |
| 25 | 4-{2-[(4-Fluorobenzyl)oxy]phenyl}-N-{3-[(methylsulfonyl)methyl]phenyl}-1,3,5-triazin-2-amine | 2 | 287 | 147 | 0.51 |
| 26 | 4-{2-[(3-Fluorobenzyl)oxy]phenyl}-N-{3-[(methylsulfonyl)methyl]phenyl}-1,3,5-triazin-2-amine | 2 | 169 | 72 | 0.43 |
| 27 | 4-{2-[(2-Chlorobenzyl)oxy]phenyl}-N-{3-[(methylsulfonyl)methyl]phenyl}-1,3,5-triazin-2-amine | 2 | 108 | 38 | 0.35 |
| 31 | 4-{5-Fluoro-2-[(3-fluorobenzyl)oxy]phenyl}-N-{3-[(methylsulfonyl)methyl]phenyl}-1,3,5-triazin-2-amine | 2 | 297 | 111 | 0.37 |
| 33 | 4-(4-Fluoro-2-methoxyphenyl)-N-{4-fluoro-3-[(methylsulfonyl)methyl]phenyl}-1,3,5-triazin-2-amine | 2 | 191 | 154 | 0.80 |
| 39 | N-{5-Chloro-3-[(methylsulfonyl)methyl]phenyl}-4-(4-fluoro-2-methoxyphenyl)-1,3,5-triazin-2-amine | 2 | 136 | 105 | 0.77 |
| 40 | N-{3-[(Cyclopropylsulfonyl)methyl]phenyl}-4-(4-fluoro-2-methoxyphenyl)-1,3,5-triazin-2-amine | 2 | 182 | 142 | 0.78 |
| 42 | 4-(2-Ethoxy-4-fluorophenyl)-N-{3-[(methylsulfonyl)-methyl]phenyl}-1,3,5-triazin-2-amine | 2 | 187 | 141 | 0.75 |
| 62 | 4-[2-(But-2-yn-1-yloxy)-4-fluorophenyl]-N-{3-[(methylsulfonyl)methyl]phenyl}-1,3,5-triazin-2-amine | 2 | 149 | 147 | 0.99 |
| 88 | 4-{2-[(2-Chloropyridin-4-yl)methoxy]-4-fluorophenyl}-N-{3-[(methylsulfonyl)-methyl]phenyl}-1,3,5-triazin-2-amine | 2 | 96 | 113 | 1.2 |

①: Compound Number
②: Concentration of test compound indicated in μM.
③: $P_{app}$ A-B ($M_{ari}$) indicated in [nm/s]
④: $P_{app}$ B-A ($M_{ari}$) indicated in [nm/s]
⑤: Efflux ratio

The invention claimed is:

1. A compound of general formula (I)

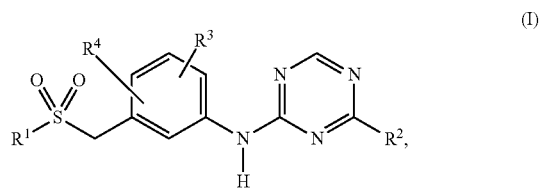

wherein $R^1$ represents a group selected from $C_1$-$C_6$-alkyl-, $C_3$-$C_7$-cycloalkyl-, heterocyclyl-, phenyl, heteroaryl, phenyl-$C_1$-$C_3$-alkyl- or heteroaryl-$C_1$-$C_3$-alkyl-, wherein said group is optionally substituted with one or two or three substituents, identically or differently, selected from the group consisting of hydroxy, cyano, halogen, halo-$C_1$-$C_3$-alkyl-, $C_1$-$C_6$-alkoxy-, $C_1$-$C_3$-fluoroalkoxy-, —$NH_2$, alkylamino-, dialkylamino-, acetylamino-, N-methyl-N-acetylamino-, cyclic amines;

$R^2$ represents a group selected from

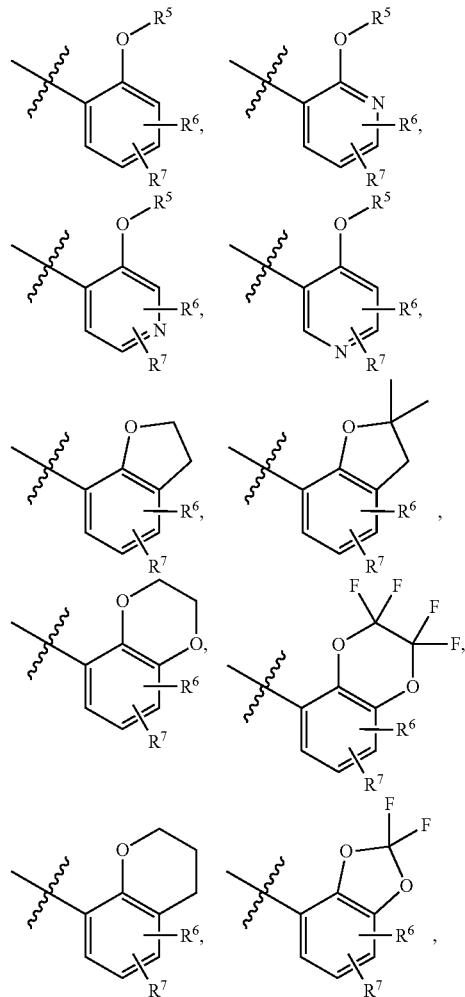

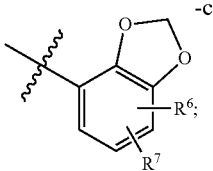

R³, R⁴ represent, independently from each other, a group selected from a hydrogen atom, fluoro atom, chloro atom, $C_1$-$C_3$-alkyl-, $C_1$-$C_3$-alkoxy-, halo-$C_1$-$C_3$-alkyl-, $C_1$-$C_3$-fluoroalkoxy-;

R⁵ represents a group selected from
- a) a $C_1$-$C_{10}$-alkyl group, which is optionally substituted with one or two or three substituents, identically or differently, selected from the group consisting of halogen, hydroxy, —NH₂, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-, $C_2$-$C_3$-alkenyl-, $C_2$-$C_3$-alkynyl-, $C_3$-$C_7$-cycloalkyl-, heterocycyl-, phenyl, heteroaryl, wherein said $C_3$-$C_7$-cycloalkyl-, heterocycyl-, phenyl or heteroaryl group is optionally substituted with one, two or three substituents, identically or differently, selected from halogen, hydroxy, $C_1$-$C_3$-alkyl-, $C_1$-$C_3$-alkoxy-, —NH₂, alkylamino-, dialkylamino-, acetylamino-, N-methyl-N-acetylamino-, cyclic amines, halo-$C_1$-$C_3$-alkyl-, $C_1$-$C_3$-fluoroalkoxy-;
- b) a $C_3$-$C_7$-cycloalkyl- group, which is optionally substituted with one or two or three substituents, identically or differently, selected from the group consisting of halogen, hydroxy, —NH₂, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-, $C_2$-$C_3$-alkenyl-, $C_2$-$C_3$-alkynyl-;
- c) a heterocyclyl- group, which is optionally substituted with one or two or three substituents, identically or differently, selected from the group consisting of halogen, hydroxy, —NH₂, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-, $C_2$-$C_3$-alkenyl-, $C_2$-$C_3$-alkynyl-;
- d) a phenyl group, which is optionally substituted with one or two or three substituents, identically or differently, selected from the group consisting of halogen, hydroxy, —NH₂, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-;
- e) a heteroaryl group, which is optionally substituted with one or two or three substituents, identically or differently, selected from the group consisting of halogen, hydroxy, —NH₂, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-;
- f) a phenyl-$C_1$-$C_3$-alkyl- group, which is optionally substituted with one or two or three substituents, identically or differently, selected from the group consisting of halogen, hydroxy, —NH₂, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-;
- g) a heteroaryl-$C_1$-$C_3$-alkyl- group, which is optionally substituted with one or two or three substituents, identically or differently, selected from the group consisting of halogen, hydroxy, —NH₂, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-;

R⁶, R⁷ represent, independently from each other, a group selected from a hydrogen atom, a fluoro atom, a chloro atom, $C_1$-$C_3$-alkyl-, $C_1$-$C_3$-alkoxy-, halo-$C_1$-$C_3$-alkyl-, $C_1$-$C_3$-fluoroalkoxy-;

or a salt, solvate or a salt of a solvate thereof.

2. The compound according to claim 1, wherein
R¹ represents a group selected from $C_1$-$C_6$-alkyl-, $C_3$-$C_7$-cycloalkyl-, phenyl,
   wherein said group is optionally substituted with one substituent selected from the group consisting of hydroxy, $C_1$-$C_6$-alkoxy-;
R² represents a group selected from

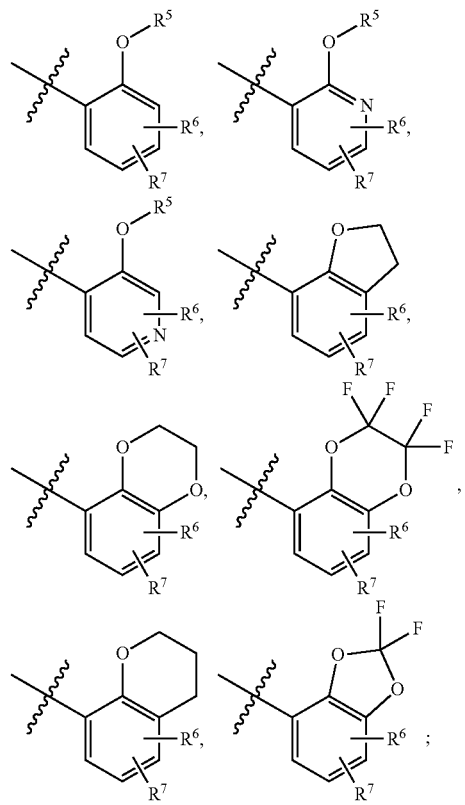

R³, R⁴ represent, independently from each other, a group selected from a hydrogen atom, fluoro atom, chloro atom;

R⁵ represents a group selected from
- a) a $C_1$-$C_{10}$-alkyl- group, which is optionally substituted with one or two or three substituents, identically or differently, selected from the group consisting of halogen atom, $C_1$-$C_3$-alkyl-, $C_2$-$C_3$-alkynyl-, $C_1$-$C_3$-alkoxy-, $C_3$-$C_7$-cycloalkyl-, heterocycyl-, phenyl,
   wherein said $C_3$-$C_7$-cycloalkyl- or phenyl group is optionally substituted with one halogen substituent;
- b) a $C_3$-$C_7$-cycloalkyl- group;
- c) a phenyl-$C_1$-$C_3$-alkyl- group, which phenyl group is optionally substituted with one or two or three substituents, identically or differently, selected from the group consisting of halogen, cyano, halo-$C_1$-$C_3$-alkyl-, $C_1$-$C_3$-alkyl, $C_1$-$C_3$-alkoxy-;
d) a heteroaryl-$C_1$-$C_3$-alkyl- group, which is optionally substituted with one substituent selected from the group consisting of halogen, $C_1$-$C_3$-alkyl-;

$R^7$ represent, independently from each other, a group selected from a hydrogen atom, fluoro atom or chloro atom;

or a salt, solvate or a salt of a solvate thereof.

3. The compound according to claim 1, which is a compound or 2 of general formula (Ia),

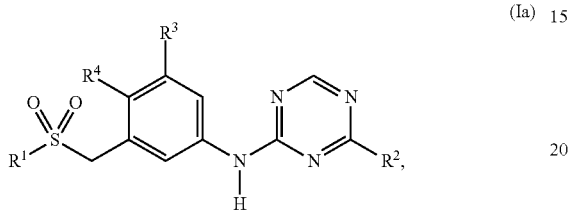

(Ia)

wherein
$R^1$ represents a group selected from $C_1$-$C_6$-alkyl-,
wherein said group is optionally substituted with one substituent selected from the group consisting of hydroxy, $C_1$-$C_6$-alkoxy-;
$R^2$ represents a group selected from

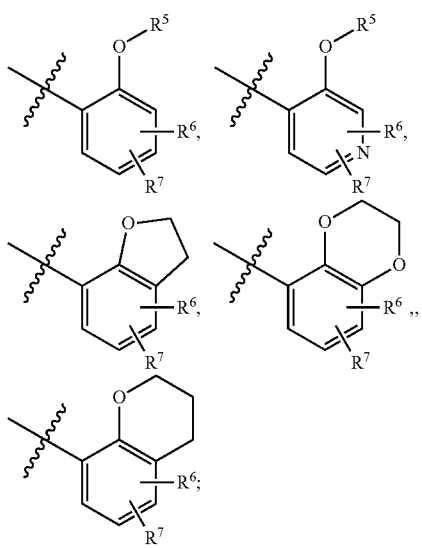

$R^3$, $R^4$ represent, independently from each other, a group selected from a hydrogen atom, fluoro atom, chloro atom;
$R^5$ represents a group selected from
a) a $C_1$-$C_{10}$-alkyl- group, which is optionally substituted with one or two or three substituents, identically or differently, selected from the group consisting of halogen atom, $C_1$-$C_3$-alkyl-, $C_2$-$C_3$-alkynyl-, $C_3$-$C_7$-cycloalkyl-, heterocycyl-, phenyl, wherein said $C_3$-$C_7$-cycloalkyl- or phenyl group is optionally substituted with one halogen substituent;
b) a $C_3$-$C_7$-cycloalkyl- group;
c) a phenyl-$C_1$-$C_3$-alkyl- group, which phenyl group is optionally substituted with one or two or three substituents, identically or differently, selected from the group consisting of halogen, cyano, halo-$C_1$-$C_3$-alkyl-, $C_1$-$C_3$-alkyl, $C_1$-$C_3$-alkoxy-;
d) a heteroaryl-$C_1$-$C_3$-alkyl- group, which is optionally substituted with one substituent selected from the group consisting of halogen, $C_1$-$C_3$-alkyl-;

$R^6$, $R^7$ represent, independently from each other, a group selected from a hydrogen atom or fluoro or chloro atom;

or a salt, solvate or a salt of a solvate thereof.

4. The compound according to claim 1, wherein
$R^1$ represents a group selected from $C_1$-$C_6$-alkyl-, $C_3$-$C_7$-cycloalkyl-,
wherein said group is optionally substituted with one substituent selected from the group consisting of hydroxy;
$R^2$ represents a group selected from

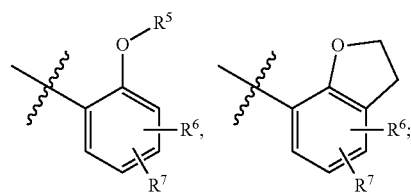

$R^3$, $R^4$ represent, independently from each other, a group selected from a hydrogen atom, fluoro atom, chloro atom;
$R^5$ represents a group selected from
a) a $C_1$-$C_{10}$-alkyl- group, which is optionally substituted with one substituent, selected from the group consisting of $C_2$-$C_3$-alkynyl-, phenyl, wherein said phenyl group is optionally substituted with one halogen substituent;
b) a phenyl-$C_1$-$C_3$-alkyl- group, which phenyl group is optionally substituted with one or two substituents, identically or differently, selected from the group consisting of halogen;
c) a heteroaryl-$C_1$-$C_3$-alkyl- group, which is optionally substituted with one substituent selected from the group consisting of halogen, $R^6$, $R^7$ represent, independently from each other, a group selected from a hydrogen atom or fluoro atom;

or a salt, solvate or a salt of a solvate thereof.

5. The compound according to claim 1, wherein
$R^1$ represents a group selected from methyl, hydroxyethyl-, propan-2-yl-, cyclopropyl, cyclopentyl; cyclohexyl;
$R^2$ represents a group selected from
4,5-difluoro-2-methoxyphenyl-4-fluoro-2-methoxyphenyl-, 2-(benzyloxy)-4-fluorophenyl-, 3-methoxypyridin-4-yl, 2-[(4-fluorobenzyl)oxy]phenyl-, 2-[(3-fluorobenzyl)oxy]phenyl-, 2-[(3-chlorobenzyl)oxy]phenyl-, 4-chloro-2-(cyclopentyloxy)phenyl-, 5-fluoro-2-[(3-fluorobenzyl)oxy]phenyl-, 2-(cyclopropyloxy)-4-fluorophenyl-, 2-ethoxy-4-fluorophenyl-, 4-fluoro-2-propoxyphenyl-, 2-butoxy-4-fluorophenyl-, 4-fluoro-2-(pentyloxy)phenyl-, 4-fluoro-2-[(4-methylpentyl)oxy]phenyl, 2-(2-cyclopropylethoxy)-4-fluorophenyl-, 4-fluoro-2-[(1-methylcyclopropyl)methoxy]phenyl-, 4-fluoro-2-(3-methylbutoxy)phenyl-, 2-(2-cyclopentylethoxy)-4-fluorophenyl-, 4-fluoro-2-(3-fluoropropoxy)phenyl-, 2-(cyclopropylmethoxy)-4-fluorophenyl-, 2-(cyclobutylmethoxy)-4-fluorophenyl-, 2-(cyclohexylmethoxy)-4-fluorophenyl-, 4-fluoro-2-(4,4,4-trifluorobutoxy)phenyl-, 2-(2,2-difluoroethoxy)-4-fluorophenyl-, 4-fluoro-2-(2-fluoroethoxy)phenyl-, 2-(but-2-yn-1-yloxy)-4-fluorophenyl-, 4-fluoro-2-(1-phenylethoxy)phenyl-, 4-fluoro-2-{[3-(trifluoromethyl)benzyl]oxy}phenyl-, 4-fluoro-2-[(3-methoxybenzyl)oxy]phenyl-, 4-fluoro-2-[(2-fluorobenzyl)oxy]phenyl-, 4-fluoro-2-[(2,3,4-trifluorobenzyl)oxy]phenyl-, 4-fluoro-2-{[4-(trifluoromethyl)benzyl]oxy}phenyl-, 4-fluoro-2-(pyridin-3-ylmethoxy)phenyl-, 4-fluoro-2-[(2,4,5-trifluorobenzyl)oxy]phenyl-, 2-[(4-chlorobenzyl)oxy]-4-fluorophenyl-, 4-fluoro-2-[(4-methylbenzyl)oxy]phenyl-, 4-fluoro-2-{[3-fluoro-5-(trifluoromethyl)benzyl]oxy}phenyl-, 4-fluoro-2-[(1R)-1-phenylethoxy]phenyl-, 2-[(2,3-difluorobenzyl)-oxy]-4-fluorophenyl-, 2-[(2,5-difluorobenzyl)-oxy]-4-fluorophenyl-, 4-fluoro-2-[(3-methylbenzyl)oxy]phenyl-, 4-fluoro-2-[(2,3,5-trifluorobenzyl)oxy]phenyl-, 2-[(3-chlorobenzyl)oxy]-4-fluorophenyl-, 2-[(3,4-difluorobenzyl)oxy]-4-fluorophenyl-, 4-fluoro-2-[(2-methylpyridin-4-yl)methoxy]-phenyl-, 2-[(2-chloropyridin-4-yl)methoxy]-4-fluorophenyl-, 4-fluoro-2-(pyridin-4-ylmethoxy)phenyl-, 2-[(4-cyanobenzyl)oxy]-4-fluorophenyl-;

R³ represents a group selected from a hydrogen atom, chloro atom, fluoro atom;

R⁴ represents a group selected from a hydrogen atom, fluoro atom;

or a salt, solvate or a salt of a solvate thereof.

6. The compound according to claim 1, which is a compound of general formula (Ia)

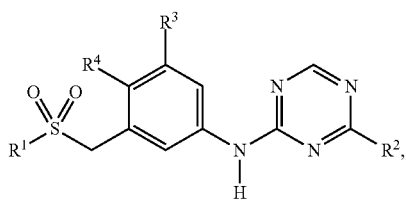

(Ia)

wherein
R¹ represents a group selected from methyl, hydroxyethyl-, propan-2-yl, cyclopentyl;
R² represents a group selected from
4,5-difluoro-2-methoxyphenyl-, 4-fluoro-2-methoxyphenyl-, 2-(benzyloxy)-4-fluorophenyl-, 3-methoxypyridin-4-yl, 2-[(4-fluorobenzyl)oxy]phenyl-, 2-[(3-fluorobenzyl)oxy]phenyl-, 2-[(3-chlorobenzyl)oxy]phenyl-, 4-chloro-2-(cyclopentyloxy)phenyl-, 5-fluoro-2-[(3-fluorobenzyl)oxy]phenyl-;
R³ represents a group selected from a hydrogen atom, chloro atom, fluoro atom;
R⁴ represents a group selected from a hydrogen atom, fluoro atom;
or a salt, solvate or a salt of a solvate thereof.

7. The compound according to claim 1, wherein
R¹ represents a group selected from methyl, hydroxyethyl-;
R² represents a group selected from
4-fluoro-2-methoxyphenyl-, 2-(benzyloxy)-4-fluorophenyl-, 2-[(3-fluorobenzyl)oxy]phenyl-, 4-chloro-2-(cyclopentyloxy)phenyl-, 5-fluoro-2-[(3-fluorobenzyl)oxy]phenyl-;

R³ represents a group selected from a hydrogen atom, fluoro atom;
R⁴ represents a group selected from a hydrogen atom, fluoro atom;
or a salt, solvate or a salt of a solvate thereof.

8. The compound according to claim 1, which is selected from 4-(4,5-Difluoro-2-methoxyphenyl)-N-{3-[(methylsulfonyl)methyl]phenyl}-1,3,5-triazin-2-amine, 4-(3,4-Difluoro-2-methoxyphenyl)-N-{3-[(methylsulfonyl)methyl]phenyl}-1,3,5-triazin-2-amine, 4-(4-Fluoro-2-methoxyphenyl)-N-{3-[(methylsulfonyl)methyl]phenyl}-1,3,5-triazin-2-amine, 4-[2-(Benzyloxy)-4-fluorophenyl]-N-{3-[(methylsulfonyl)methyl]phenyl}-1,3,5-triazin-2-amine, 4-[4-Fluoro-2-(propan-2-yloxy)phenyl]-N-{3-[(methylsulfonyl)methyl]phenyl}-1,3,5-triazin-2-amine, 4-(2,2-Difluoro-1,3-benzodioxol-4-yl)-N-{3-[(methylsulfonyl)methyl]phenyl}-1,3,5-triazin-2-amine, N-{3-[(Methylsulfonyl)methyl]phenyl}-4-[2-(trifluoromethoxy)phenyl]-1,3,5-triazin-2-amine, 4-(3-Methoxypyridin-4-yl)-N-{3-[(methylsulfonyl)methyl]phenyl}-1,3,5-triazin-2-amine, N-{3-[(Cyclohexylsulfonyl)methyl]phenyl}-4-(4-fluoro-2-methoxyphenyl)-1,3,5-triazin-2-amine, 4-(4-Fluoro-2-methoxyphenyl)-N-{3-fluoro-5-[(methylsulfonyl)methyl]phenyl}-1,3,5-triazin-2-amine, 4-(5-Fluoro-2-methoxyphenyl)-N-{3-[(methylsulfonyl)methyl]phenyl}-1,3,5-triazin-2-amine, 4-(3,4-Dihydro-2H-chromen-8-yl)-N-{3-[(methylsulfonyl)methyl]phenyl}-1,3,5-triazin-2-amine, 4-(2,3-Dihydro-1-benzofuran-7-yl)-N-{3-[(methylsulfonyl)methyl]phenyl}-1,3,5-triazin-2-amine, 2-[(3-{[4-(4-Fluoro-2-methoxyphenyl)-1,3,5-triazin-2-yl]amino} benzyl)sulfonyl]ethanol, 4-[2-(Difluoromethoxy)-4-fluorophenyl]-N-{3-[(methylsulfonyl)methyl]phenyl}-1,3,5-triazin-2-amine, N-{3-[(Methylsulfonyl)methyl]phenyl}-4-[2-(2,2,2-trifluoroethoxy)phenyl]-1,3,5-triazin-2-amine, N-{3-[(tert-Butylsulfonyl)methyl]phenyl}-4-(4-fluoro-2-methoxyphenyl)-1,3,5-triazin-2-amine, 4-(2,3-Dihydro-1,4-benzodioxin-5-yl)-N-{3-[(methylsulfonyl)methyl]phenyl}-1,3,5-triazin-2-amine, N-{3-[(Methylsulfonyl)methyl]phenyl}-4-(2,2,3,3-tetrafluoro-2,3-dihydro-1,4-benzodioxin-5-yl)-1,3,5-triazin-2-amine, 4-(2-Methoxypyridin-3-yl)-N-{3-[(methylsulfonyl)methyl]phenyl}-1,3,5-triazin-2-amine, 4-[5-Fluoro-2-(tetrahydro-2H-pyran-4-ylmethoxy)phenyl]-N-{3-[(methylsulfonyl)methyl]phenyl}-1,3,5-triazin-2-amine, 4-{2-[(²H₃)methyloxy]phenyl}-N-{3-[(methylsulfonyl)methyl]phenyl}-1,3,5-triazin-2-amine, 4-(4-Fluoro-2-methoxyphenyl)-N-(3-{[(2-methoxyethyl)sulfonyl]methyl} phenyl)-1,3,5-triazin-2-amine, 4-(4-Fluoro-2-methoxyphenyl)-N-{3-[(propan-2-ylsulfonyl)methyl]phenyl}-1,3,5-triazin-2-amine, 4-{2-[(4-Fluorobenzyl)oxy]phenyl}-N-{3-[(methylsulfonyl)methyl]phenyl}-1,3,5-triazin-2-amine, 4-{2-[(3-Fluorobenzyl)oxy]phenyl}-N-{3-[(methylsulfonyl)methyl]phenyl}-1,3,5-triazin-2-amine, 4-{2-[(2-Chlorobenzyl)oxy]phenyl}-N-{3-[(methylsulfonyl)methyl]phenyl}-1,3,5-triazin-2-amine, 4-{2-[(3-Chlorobenzyl)oxy]phenyl}-N-{3-[(methylsulfonyl)methyl]phenyl}-1,3,5-triazin-2-amine, 4-[4-Chloro-2-(cyclopentyloxy)phenyl]-N-{3-[(methylsulfonyl)methyl]phenyl}-1,3,5-triazin-2-amine, 4-{5-Fluoro-2-[(2-fluorobenzyl)oxy]phenyl}-N-{3-[(methylsulfonyl)methyl]phenyl}-1,3,5-triazin-2-amine,
4-{5-Fluoro-2-[(3-fluorobenzyl)oxy]phenyl}-N-{3-[(methylsulfonyl)methyl]phenyl}-1,3,5-triazin-2-amine,
4-(4-Chloro-2-methoxyphenyl)-N-{3-[(methylsulfonyl)methyl]phenyl}-1,3,5-triazin-2-amine,
4-(4-Fluoro-2-methoxyphenyl)-N-{4-fluoro-3-[(methylsulfonyl)methyl]phenyl}-1,3,5-triazin-2-amine,
4-{2-[(3-Chlorobenzyl)oxy]phenyl}-N-{3-[(propan-2-ylsulfonyl)methyl]phenyl}-1,3,5-triazin-2-amine
4-(4-Fluoro-2-methoxyphenyl)-N-{3-[(phenylsulfonyl)methyl]phenyl}-1,3,5-triazin-2-amine,
N-{3-[(Cyclopentylsulfonyl)methyl]phenyl}-4-(4-fluoro-2-methoxyphenyl)-1,3,5-triazin-2-amine,
4-{2-[(4-Fluorobenzyl)oxy]phenyl}-N-{3-[(prop-2-ylsulfonyl)methyl]phenyl}-1,3,5-triazin-2-amine,
4-{5-Fluoro-2-[(3-fluorobenzyl)oxy]phenyl}-N-{3-[(prop-2-ylsulfonyl)methyl]phenyl}-1,3,5-triazin-2-amine,
N-{5-Chloro-3-[(methylsulfonyl)methyl]phenyl}-4-(4-fluoro-2-methoxyphenyl)-1,3,5-triazin-2-amine,
N-{3-[(Cyclopropylsulfonyl)methyl]phenyl}-4-(4-fluoro-2-methoxyphenyl)-1,3,5-triazin-2-amine,
4-[2-(Cyclopropyloxy)-4-fluorophenyl]-N-{3-[(methylsulfonyl)methyl]phenyl}-1,3,5-triazin-2-amine,
4-(2-Ethoxy-4-fluorophenyl)-N-{3-[(methylsulfonyl)methyl]phenyl}-1,3,5-triazin-2-amine,
4-(4-Fluoro-2-propoxyphenyl)-N-{3-[(methylsulfonyl)methyl]phenyl}-1,3,5-triazin-2-amine,
4-(2-Butoxy-4-fluorophenyl)-N-{3-[(methylsulfonyl)methyl]phenyl}-1,3,5-triazin-2-amine,
4-[4-Fluoro-2-(pentyloxy)phenyl]-N-{3-[(methylsulfonyl)-methyl]phenyl}-1,3,5-triazin-2-amine,
4-[4-Fluoro-2-(hexyloxy)phenyl]-N-{3-[(methylsulfonyl)methyl]phenyl}-1,3,5-triazin-2-amine,
4-{4-Fluoro-2-[(4-methylpentyl)oxy]phenyl}-N-{3-[(methylsulfonyl)-methyl]phenyl}-1,3,5-triazin-2-amine,
4-[2-(2-Cyclopropylethoxy)-4-fluorophenyl]-N-{3-[(methylsulfonyl)methyl]phenyl}-1,3,5-triazin-2-amine,
4-{4-Fluoro-2-[(1-methylcyclopropyl)methoxy]phenyl}-N-{3-[(methylsulfonyl)-methyl]phenyl}-1,3,5-triazin-2-amine,
4-[4-Fluoro-2-(2-methoxyethoxy)phenyl]-N-{3-[(methylsulfonyl)methyl]-phenyl}-1,3,5-triazin-2-amine,
4-[2-(2-Ethoxyethoxy)-4-fluorophenyl]-N-{3-[(methylsulfonyl)methyl]phenyl}-1,3,5-triazin-2-amine,
4-[4-Fluoro-2-(3-methylbutoxy)phenyl]-N-{3-[(methylsulfonyl)methyl]phenyl}-1,3,5-triazin-2-amine,
4-[2-(2-Cyclopentylethoxy)-4-fluorophenyl]-N-{3-[(methylsulfonyl)methyl]phenyl}-1,3,5-triazin-2-amine,
4-[4-Fluoro-2-(3-fluoropropoxy)phenyl]-N-{3-[(methylsulfonyl)methyl]phenyl}-1,3,5-triazin-2-amine,
4-[2-(Cyclopropylmethoxy)-4-fluorophenyl]-N-{3-[(methylsulfonyl)methyl]phenyl}-1,3,5-triazin-2-amine,
4-[2-(Cyclobutylmethoxy)-4-fluorophenyl]-N-{3-[(methylsulfonyl)methyl]phenyl}-1,3,5-triazin-2-amine,
4-[2-(Cyclohexylmethoxy)-4-fluorophenyl]-N-{3-[(methylsulfonyl)methyl]phenyl}-1,3,5-triazin-2-amine,
4-[4-Fluoro-2-(2-methylpropoxy)phenyl]-N-{3-[(methylsulfonyl)methyl]phenyl}-1,3,5-triazin-2-amine,
4-[4-Fluoro-2-(4,4,4-trifluorobutoxy)phenyl]-N-{3-[(methylsulfonyl)methyl]phenyl}-1,3,5-triazin-2-amine,
4-[2-(2,2-Difluoroethoxy)-4-fluorophenyl]-N-{3-[(methylsulfonyl)methyl]phenyl}-1,3,5-triazin-2-amine,
4-[4-Fluoro-2-(2-fluoroethoxy)phenyl]-N-{3-[(methylsulfonyl)methyl]phenyl}-1,3,5-triazin-2-amine,
4-[2-(But-2-yn-1-yloxy)-4-fluorophenyl]-N-{3-[(methylsulfonyl)methyl]phenyl}-1,3,5-triazin-2-amine,
4-[2-(2-Cyclohexylethoxy)-4-fluorophenyl]-N-{3-[(methylsulfonyl)methyl]phenyl}-1,3,5-triazin-2-amine,
4-[2-(Cyclobutyloxy)-4-fluorophenyl]-N-{3-[(methylsulfonyl)methyl]phenyl}-1,3,5-triazin-2-amine,
4-[2-(Cyclopentyloxy)-4-fluorophenyl]-N-{3-[(methylsulfonyl)methyl]phenyl}-1,3,5-triazin-2-amine,
4-{4-Fluoro-2-[(1-fluorocyclohexyl)methoxy]phenyl}-N-{3-[(methylsulfonyl)methyl]phenyl}-1,3,5-triazin-2-amine,
4-{4-Fluoro-2-[(1R)-1-(4-fluorophenyl)ethoxy]phenyl}-N-{3-[(methylsulfonyl)-methyl]phenyl}-1,3,5-triazin-2-amine,
rac-4-[4-Fluoro-2-(1-phenylethoxy)phenyl]-N-{3-[(methylsulfonyl)methyl]phenyl}-1,3,5-triazin-2-amine,
4-(4-Fluoro-2-{[3-(trifluoromethyl)benzyl]oxy}phenyl)-N-{3-[(methylsulfonyl)-methyl]phenyl}-1,3,5-triazin-2-amine,
4-{4-Fluoro-2-[(3-methoxybenzyl)oxy]phenyl}-N-{3-[(methylsulfonyl)-methyl]phenyl}-1,3,5-triazin-2-amine,
4-{4-Fluoro-2-[(2-fluorobenzyl)oxy]phenyl}-N-{3-[(methylsulfonyl)-methyl]phenyl}-1,3,5-triazin-2-amine,
4-{4-Fluoro-2-[(2,3,4-trifluorobenzyl)oxy]phenyl}-N-{3-[(methylsulfonyl)methyl]-phenyl}-1,3,5-triazin-2-amine,
4-(4-Fluoro-2-{[4-(trifluoromethyl)benzyl]oxy}phenyl)-N-{3-[(methylsulfonyl)—methyl]phenyl}-1,3,5-triazin-2-amine,
4-[4-Fluoro-2-(pyridin-3-ylmethoxy)phenyl]-N-{3-[(methylsulfonyl)methyl]phenyl}-1,3,5-triazin-2-amine,
4-{4-Fluoro-2-[(2,4,5-trifluorobenzyl)oxy]phenyl}-N-{3-[(methylsulfonyl)-methyl]phenyl}-1,3,5-triazin-2-amine,
4-{2-[(4-Chlorobenzyl)oxy]-4-fluorophenyl}-N-{3-[(methylsulfonyl)methyl]phenyl}-1,3,5-triazin-2-amine,
4-{4-Fluoro-2-[(4-methylbenzyl)oxy]phenyl}-N-{3-[(methylsulfonyl)-methyl]phenyl}-1,3,5-triazin-2-amine,
4-(4-Fluoro-2-{[3-fluoro-5-(trifluoromethyl)benzyl]oxy}phenyl)-N-{3-[(methylsulfonyl)-methyl]-phenyl}-1,3,5-triazin-2-amine,
4-{4-Fluoro-2-[(1R)-1-phenylethoxy]phenyl}-N-{3-[(methylsulfonyl)methyl]phenyl}-1,3,5-triazin-2-amine,
4-{2-[(2,3-Difluorobenzyl)-oxy]-4-fluorophenyl}-N-{3-[(methylsulfonyl)-methyl]phenyl}-1,3,5-triazin-2-amine,
4-{2-[(2,5-Difluorobenzyl)-oxy]-4-fluorophenyl}-N-{3-[(methylsulfonyl)methyl]phenyl}-1,3,5-triazin-2-amine,
4-{4-Fluoro-2-[(2-fluoropyridin-4-yl)methoxy]phenyl}-N-{3-[(methylsulfonyl)-methyl]phenyl}-1,3,5-triazin-2-amine,
4-{4-Fluoro-2-[(3-methylbenzyl)oxy]phenyl}-N-{3-[(methylsulfonyl)-methyl]phenyl}-1,3,5-triazin-2-amine,
4-{4-Fluoro-2-[(2,3,5-trifluorobenzyl)oxy]phenyl}-N-{3-[(methylsulfonyl)methyl]-phenyl}-1,3,5-triazin-2-amine,
4-{2-[(3-Chlorobenzyl)oxy]-4-fluorophenyl}-N-{3-[(methylsulfonyl)methyl]phenyl}-1,3,5-triazin-2-amine,
4-{2-[(3,4-Difluoro-benzyl)oxy]-4-fluorophenyl}-N-{3-[(methylsulfonyl)methyl]phenyl}-1,3,5-triazin-2-amine, 4-{4-Fluoro-2-[(2-methylpyridin-4-yl)methoxy]-phenyl}-N-{3-[(methylsulfonyl)methyl]phenyl}-1,3,5-triazin-2-amine, 4-{2-[(2-Chloropyridin-4-yl)methoxy]-4-fluorophenyl}-N-{3-[(methylsulfonyl)-methyl]phenyl}-1,3,5-triazin-2-amine, 4-[4-Fluoro-2-(pyridin-4-ylmethoxy)phenyl]-N-{3-[(methylsulfonyl)methyl]phenyl}-1,3,5-triazin-2-amine, and 4-({5-Fluoro-2-[4-({3-[(methylsulfonyl)methyl]phenyl}amino)-1,3,5-triazin-2-yl]phenoxy}methyl)-benzonitrile, or a salt, solvate or a salt of a solvate thereof.

9. A pharmaceutical combination comprising a first active ingredient, which is a compound according to claim 1, in combination with one or more further active ingredients.

10. A pharmaceutical composition comprising a compound according to claim 1 in combination with an inert, nontoxic, pharmaceutically suitable adjuvant.

11. A method for the treatment of non-small cell lung cancer, prostate cancer, cervical cancer, colorectal cancer and melanoma in a patient in need thereof comprising administering to the patient a therapeutically effective amount of a compound according to claim 1.

12. A compound of general formula (3)

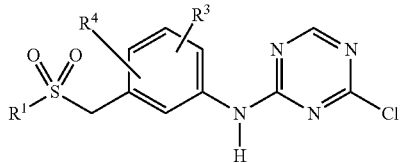

3 or of general formula (3a)

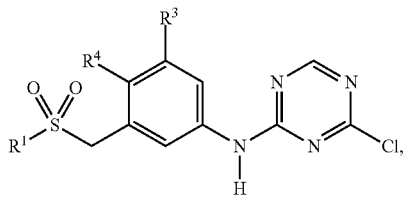

3a wherein $R^1$, $R^3$ and $R^4$ are as defined in claim 1.

13. The compound according to claim 3, wherein $R^1$ represents a group selected from $C_1$-$C_6$-alkyl-, $C_3$-$C_7$-cycloalkyl-,
  wherein said group is optionally substituted with one substituent selected from the group consisting of hydroxy;

$R^2$ represents a group selected from

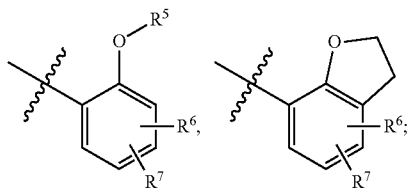

$R^3$, $R^4$ represent, independently from each other, a group selected from a hydrogen atom, fluoro atom, chloro atom;

$R^5$ represents a group selected from
  a) a $C_1$-$C_{10}$-alkyl- group, which is optionally substituted with one substituent, selected from the group consisting of $C_2$-$C_3$-alkynyl-, phenyl, wherein said phenyl group is optionally substituted with one halogen substituent;
  b) a phenyl-$C_1$-$C_3$-alkyl- group, which phenyl group is optionally substituted with one or two substituents, identically or differently, selected from the group consisting of halogen;
  c) a heteroaryl-$C_1$-$C_3$-alkyl- group, which is optionally substituted with one substituent selected from the group consisting of halogen, $R^6$, $R^7$ represent, independently from each other, a group selected from a hydrogen atom or fluoro atom;

or a salt, solvate or a salt of a solvate thereof.

14. The compound according to claim 3, wherein $R^1$ represents a group selected from methyl, hydroxyethyl-, propan-2-yl-, cyclopropyl, cyclopentyl; cyclohexyl;

$R^2$ represents a group selected from 4,5-difluoro-2-methoxyphenyl-4-fluoro-2-methoxyphenyl-, 2-(benzyloxy)-4-fluorophenyl-, 3-methoxypyridin-4-yl, 2-[(4-fluorobenzyl)oxy]phenyl-, 2-[(3-fluorobenzyl)oxy]phenyl-, 2-[(3-chlorobenzyl)oxy]phenyl-, 4-chloro-2-(cyclopentyloxy)phenyl-, 5-fluoro-2-[(3-fluorobenzyl)oxy]phenyl-, 2-(cyclopropyloxy)-4-fluorophenyl-, 2-ethoxy-4-fluorophenyl-, 4-fluoro-2-propoxyphenyl-, 2-butoxy-4-fluorophenyl-, 4-fluoro-2-(pentyloxy)phenyl-, 4-fluoro-2-[(4-methylpentyl)oxy]phenyl, 2-(2-cyclopropylethoxy)-4-fluorophenyl-, 4-fluoro-2-[(1-methylcyclopropyl)methoxy]phenyl-, 4-fluoro-2-(3-methylbutoxy)phenyl-, 2-(2-cyclopentylethoxy)-4-fluorophenyl-, 4-fluoro-2-(3-fluoropropoxy)phenyl-, 2-(cyclopropylmethoxy)-4-fluorophenyl-, 2-(cyclobutylmethoxy)-4-fluorophenyl-, 2-(cyclohexylmethoxy)-4-fluorophenyl-, 4-fluoro-2-(4,4,4-trifluorobutoxy)phenyl-, 2-(2,2-difluoroethoxy)-4-fluorophenyl-, 4-fluoro-2-(2-fluoroethoxy)phenyl-, 2-(but-2-yn-1-yloxy)-4-fluorophenyl-, 4-fluoro-2-(1-phenylethoxy)phenyl-, 4-fluoro-2-{[3-(trifluoromethyl)benzyl]oxy}phenyl-, 4-fluoro-2-[(3-methoxybenzyl)oxy]phenyl-, 4-fluoro-2-[(2-fluorobenzyl)oxy]phenyl-, 4-fluoro-2-[(2,3,4-trifluorobenzyl)oxy]phenyl-, 4-fluoro-2-{[4-(trifluoromethyl)benzyl]oxy}phenyl-, 4-fluoro-2-(pyridin-3-ylmethoxy)phenyl-, 4-fluoro-2-[(2,4,5-trifluorobenzyl)oxy]phenyl-, 2-[(4-chlorobenzyl)oxy]-4-fluorophenyl-, 4-fluoro-2-[(4-methylbenzyl)oxy]phenyl-, 4-fluoro-2-{[3-fluoro-5-(trifluoromethyl)benzyl]oxy}phenyl-, 4-fluoro-2-[(1R)-1-phenylethoxy]phenyl-, 2-[(2,3-difluorobenzyl)-oxy]-4-fluorophenyl-, 2-[(2,5-difluorobenzyl)-oxy]-4-fluorophenyl-, 4-fluoro-2-[(3-methylbenzyl)oxy]phenyl-, 4-fluoro-2-[(2,3,5-trifluorobenzyl)oxy]phenyl-, 2-[(3-chlorobenzyl)oxy]-4-fluorophenyl-, 2-[(3,4-difluorobenzyl)oxy]-4-fluorophenyl-, 4-fluoro-2-[(2-methylpyridin-4-yl)methoxy]-phenyl-, 2-[(2-chloropyridin-4-yl)methoxy]-4-fluorophenyl-, 4-fluoro-2-(pyridin-4-ylmethoxy)phenyl-, 2-[(4-cyanobenzyl)oxy]-4-fluorophenyl-;

$R^3$ represents a group selected from a hydrogen atom, chloro atom, fluoro atom;

$R^4$ represents a group selected from a hydrogen atom, fluoro atom;

or a salt, solvate or a salt of a solvate thereof.

15. The compound according to claim 3, wherein
$R^1$ represents a group selected from methyl, hydroxyethyl-;
$R^2$ represents a group selected from
4-fluoro-2-methoxyphenyl-, 2-(benzyloxy)-4-fluorophenyl-, 2-[(3-fluorobenzyl)oxy]phenyl-, 4-chloro-2-(cyclopentyloxy)phenyl-, 5-fluoro-2-[(3-fluorobenzyl)oxy]phenyl-;
$R^3$ represents a group selected from a hydrogen atom, fluoro atom;
$R^4$ represents a group selected from a hydrogen atom, fluoro atom;
or a salt, solvate or a salt of a solvate thereof.

\* \* \* \* \*